United States Patent
Koepke et al.

(10) Patent No.: US 11,286,466 B2
(45) Date of Patent: Mar. 29, 2022

(54) KETOREDUCTASES

(71) Applicant: C-LEcta GmbH, Leipzig (DE)

(72) Inventors: Sabrina Koepke, Leipzig (DE); Sebastian Bartsch, Leipzig (DE); Andreas Vogel, Leipzig (DE)

(73) Assignee: C-LECTA GMBH, Leipzig (DE)

( * ) Notice: Subject to any disclaimer, the term of this patent is extended or adjusted under 35 U.S.C. 154(b) by 0 days.

(21) Appl. No.: 16/740,728

(22) Filed: Jan. 13, 2020

(65) Prior Publication Data

US 2020/0216821 A1 Jul. 9, 2020

Related U.S. Application Data

(63) Continuation of application No. PCT/EP2018/069058, filed on Jul. 13, 2018.

(30) Foreign Application Priority Data

Jul. 14, 2017 (EP) .................................... 17181418
Feb. 11, 2018 (EP) .................................... 18156201
Feb. 28, 2018 (EP) .................................... 18159099

(51) Int. Cl.
*C12N 9/04* (2006.01)

(52) U.S. Cl.
CPC .................................. *C12N 9/0006* (2013.01)

(58) Field of Classification Search
CPC ...... C12P 7/24; C12P 7/04; C12P 7/26; C12N 9/0006; C12Y 101/01184
See application file for complete search history.

(56) References Cited

U.S. PATENT DOCUMENTS

| | | |
|---|---|---|
| 6,255,092 B1 | 7/2001 | Kojima et al. |
| 6,645,746 B1 | 11/2003 | Kizaki et al. |
| 7,393,667 B2 | 7/2008 | Patel et al. |
| 7,629,157 B2 | 12/2009 | Davis et al. |
| 7,977,078 B2 | 7/2011 | Liang et al. |
| 8,257,952 B2 | 9/2012 | Campopiano et al. |
| 8,273,554 B2 | 9/2012 | Mundorff et al. |
| 8,288,131 B2 | 10/2012 | Voladri et al. |
| 8,426,178 B2 | 4/2013 | Savile et al. |
| 8,512,973 B2 | 8/2013 | Liang et al. |
| 8,617,853 B2 | 12/2013 | Liang et al. |
| 8,932,835 B2 * | 1/2015 | Gupta ...................... C12P 7/04 435/128 |
| 9,228,223 B2 * | 1/2016 | Mundorff ................ C40B 10/00 |
| 10,696,964 B2 * | 6/2020 | Zhang ..................... G16C 20/64 |
| 2002/0064847 A1 | 5/2002 | Yamamoto et al. |
| 2010/0014399 A1 | 1/2010 | Kudo et al. |
| 2010/0035317 A1 | 2/2010 | Kawano et al. |

FOREIGN PATENT DOCUMENTS

| | | | |
|---|---|---|---|
| DE | WO 2013/102619 | * 11/2013 | ............. C12P 33/00 |
| EP | 0645453 A3 | 3/1997 | |
| EP | 1553170 B1 | 6/2012 | |
| WO | 2005017135 A1 | 2/2005 | |
| WO | 2009040080 A1 | 4/2009 | |
| WO | 2011022548 A2 | 2/2011 | |
| WO | 2012046254 A2 | 4/2012 | |
| WO | 2013102619 A2 | 7/2013 | |

OTHER PUBLICATIONS

Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
O'Hare et al., High-Throughput Mutagenesis to Evaluate Models of Stereochemical Control in Ketoreductase Domains from the Erythromycin Polyketide Synthase. Chem & Biol., 2006, vol. 13: 287-296. (Year: 2006).*
Altschul SF et al. "Gapped BLAST and PSI-BLAST: a new generation of protein database search programs", Nucleic Acids Res. 25:3389-3402 (1997).
Altschul SF, "Protein database searches using compositionally adjusted substitution matrices." FEBS J. 272:5101-5109 (2005).
Lountos et al., Crystallization and preliminary analysis of a water-forming NADH oxidase from Lactobacillus sanfranciscensis, Acta Cryst. D60, 2044-2047 (2004).
Mallin et al., A self-sufficient Baeyer-Villiger biocatalysis system for the synthesis of epsilon-caprolactone from cyclohexanol, Enzyme Microb Technol.53(4): 283-7 (Sep. 10, 2013).
Paul et al., Transaminases Applied to the Synthesis of High Added-Value Enantiopure Amines, ChemCatChem.: 3875-3881 (2013).
Schmidt et al., An Enzyme Cascade Synthesis of e-Caprolactone and its Oligomers, Angew. Chem. Int. Ed, 54: 2784-7(2015).
Studier, Protein production by auto-induction in high-density shaking cultures, Protein Expression and Purification 41: 207-234 (2005).
Wulf et al., Protein engineering of a thermostable polyol dehydrogenase, Enzyme Microb Technol. 51:217-24 (2012).

* cited by examiner

*Primary Examiner* — Ganapathirama Raghu
(74) *Attorney, Agent, or Firm* — Agris & von Natzmer, LLP; Joyce von Natzmer

(57) ABSTRACT

Disclosed are ketoreductases and the use thereof. The disclosed ketoreductases are particularly useful for enzymatically catalyzing the reduction of ketones to chiral or non-chiral secondary alcohols and oxidation of chiral or non-chiral secondary alcohols to ketones.

41 Claims, 1 Drawing Sheet
Specification includes a Sequence Listing.

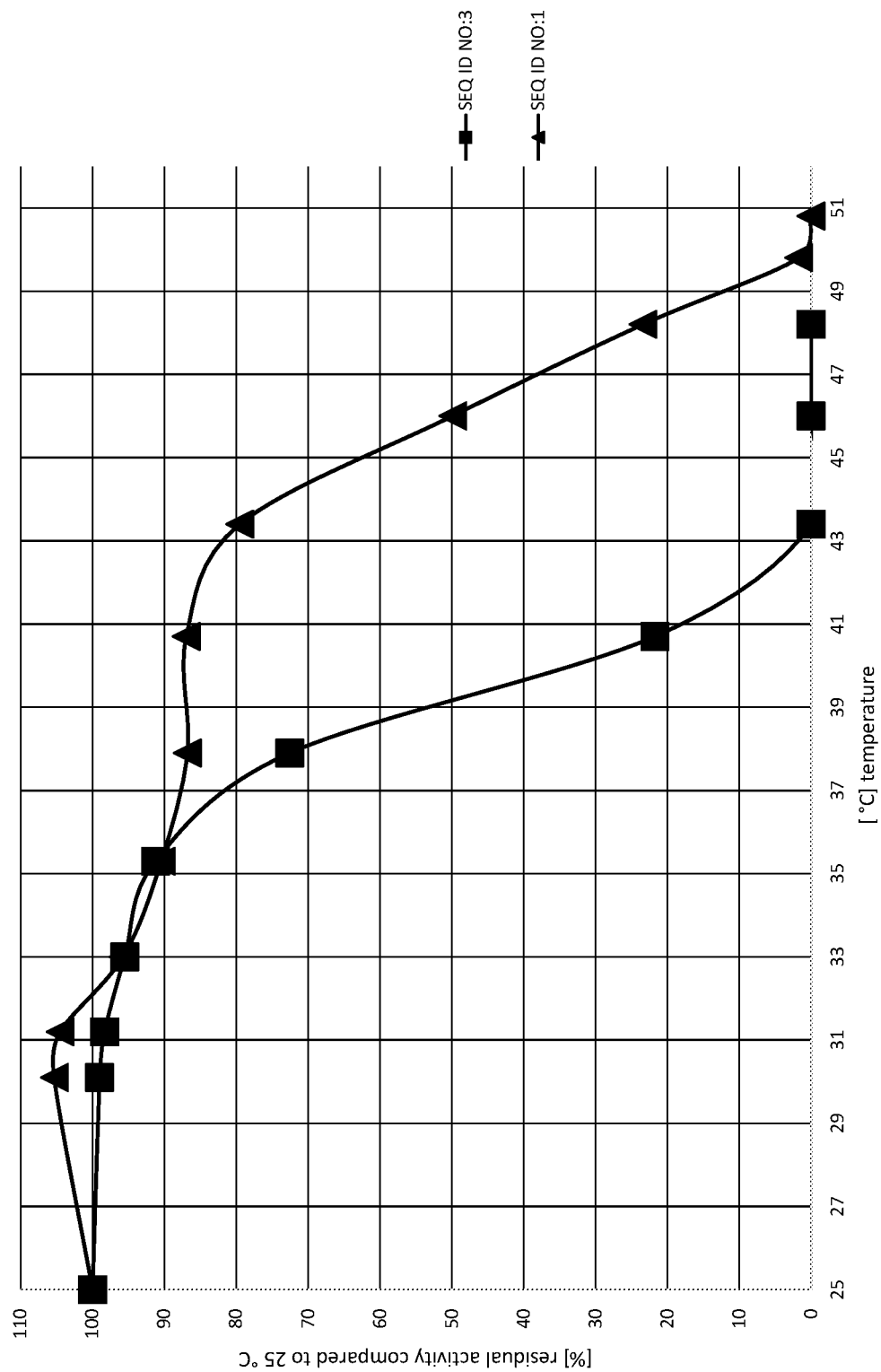

KETOREDUCTASES

CROSS REFERENCE TO RELATED APPLICATIONS

This application is a continuation application of international application PCT/EP2018/069058, filed Jul. 13, 2018, which is incorporated herein by reference in its entirety and which claims priority to European patent applications EP 17181418.9, filed Jul. 14, 2017, EP 18156201.8, filed Feb. 11, 2018 and EP 18159099.3, filed Feb. 28, 2018, which each are also incorporated herein by reference in their entireties.

STATEMENT REGARDING FEDERALLY SPONSORED RESEARCH OR DEVELOPMENT

The project leading to this application has received funding from the European Union's Horizon 2020 research and innovation program under Grant Agreement 635734.

INCORPORATION OF SEQUENCE LISTING

This application is filed electronically via EFS-Web and includes an electronically submitted sequence listing in .txt format. The .txt file contains a sequence listing entitled "3054-110_ST25" created on Mar. 30, 2020, and is 389 kilobytes in size. The sequence listing in this .txt file is part of the specification and is hereby incorporated by reference herein in its entirety.

FIELD OF THE INVENTION

The invention relates to ketoreductases and the use thereof. The ketoreductases of the invention are particularly useful for enzymatically catalyzing the reduction of ketones to chiral or non-chiral secondary alcohols and oxidation of chiral or non-chiral secondary alcohols to ketones.

BACKGROUND OF AND INTRODUCTION TO THE INVENTION

Ketoreductases (KREDs, also called 'alcohol dehydrogenases', 'ADHs', or 'carbonyl reductases') catalyze the reduction of aldehydes and ketones to the corresponding primary and secondary alcohols, respectively. These enzymes are also capable of catalyzing the reverse reaction, i.e. the oxidation of primary and secondary alcohols to the corresponding aldehydes and ketones, respectively.

Ketoreductases are ubiquitous enzymes found in all kingdoms of life. Well-known, commercially available ketoreductases are derived from horse liver (HLADH), baker's yeast (YADH) and from bacteria, such as *Thermoanaerobium brockii* (TBADH) and *Lactobacillus kefir* (LKADH).

Based on their sequence identity and biochemical properties, ketoreductases can be classified into different protein families. Members of the SDR-family (Short-Chain-Dehydrogenase/Reductase) exhibit short-chain enzymes, which do not contain any metal ions. In contrast, members of the MDR-family (Medium-Chain-Dehydrogenase/Reductase) exhibit medium-chain enzymes, which are dependent on $Zn^{2+}$. Another group of ketoreductases exhibits long-chain enzymes dependent on $Fe^{2+}$ (for review: K. Drauz, H. Gröger, O. May, Enzyme Catalysis in Organic Synthesis, Wiley VCH, Weinheim, 2012). Certain ketoreductases require dimerization or multimerization for providing full catalytic activity.

For industrial applications the stereoselective reduction of ketones to secondary alcohols is of great interest, in which prochiral carbonyl compounds are stereoselectively and/or regioselectively reduced to defined chiral alcohols. In some industrial applications, also the stereoselective conversion of secondary alcohols to ketones for chiral resolution of racemic compounds is desired, e.g. allowing the isolation of enantiomers. For alcohol compounds in which two or more hydroxyl groups are present, furthermore the regioselective oxidation of only one of such secondary alcohol groups to a ketone may be of great interest. In addition, the regioselective reduction of compounds with one or more keto group to may be of industrial relevance. The enzymatic oxidation of primary alcohols to aldehydes and the enzymatic reduction of aldehydes to primary alcohols are often considered of lower relevance in industrial applications, but are also catalyzed by ketoreductases. The use of one and a same ketoreductase for oxidation or reduction reaction, respectively, can be influenced through adjustment of the chemical equilibrium of the enzyme reaction.

It is desirable to employ ketoreductases with a high specific activity, stereoselectivity and regioselectivity. Another important criterion in the industrial use of ketoreductases is a long process stability, which often correlates with a high stability at elevated temperatures (also referred to as "thermal stability") and a high solvent stability. If the substrates are chiral already, it is further desirable to employ ketoreductases with a high stereospecificity.

The reduction catalyzed by ketoreductases requires a reduced cofactor as electron donor. Some ketoreductases use reduced nicotinamide adenine dinucleotide (NADH) as a cofactor, other ketoreductases use reduced nicotinamide adenine dinucleotide phosphate (NADPH) and some ketoreductases accept both, NADH and NADPH. The oxidation catalyzed by ketoreductases accordingly requires an oxidized cofactor as electron acceptor. For this reaction ketoreductases use oxidized nicotinamide adenine dinucleotide ($NAD^+$) or oxidized nicotinamide adenine dinucleotide phosphate ($NADP^+$) or both, $NAD^+$ and $NADP^+$.

The in vitro use of ketoreductases in reduction processes requires a regeneration system for NAD(P)H. Common regeneration systems are glucose dehydrogenase (GDH) or formate dehydrogenase, which are used in conjunction with ketoreductases. Cofactor regeneration can also be done by the ketoreductase itself by concomitant oxidation of a cosubstrate (often primary or secondary alcohols, e.g. oxidation of isopropanol to acetone). The concomitant use of ketoreductases as reduction catalysts and cofactor regeneration systems requires concurrent acceptance of a keto substrate and the cosubstrate for cofactor regeneration. The selection of a specific cosubstrate may depend on the specific activity of the ketoreductase for such cosubstrate and the ketoreductase stability under the specific cofactor regeneration conditions.

The in vitro use of ketoreductases in oxidation processes also need a regeneration system for the $NAD(P)^+$. Also here, a concomitant use of ketoreductases as oxidation catalyst and for cofactor regeneration can be used if a suitable ketone or aldehyde is available and accepted. Furthermore, NAD(P)H-oxidases (NOX) can be used for oxidation of NAD(P)H to NAD(P) using oxygen as a co-substrate. Side products of the NOX reactions may be either water or hydrogen peroxide, depending on the NOX enzyme class used. In industrial processes the water-forming NOX enzymes are usually preferred.

Various ketoreductases/alcohol dehydrogenases are known from the prior art. In this regard, reference can be made e.g. to the following patent applications and patents: U.S. Pat. Nos. 6,255,092, 6,645,746, 7,393,667, 7,629,157, 7,977,078, 8,257,952, 8,273,554, 8,288,131, 8,426,178, 8,512,973, 8,617,853, US 2002/0064847, US 2010/0035317, US 2010/014399, WO 2009/040080, WO 2011/022548, WO 2012/046254, WO 2013/102619, EP 0 645 453, and EP 1 553 170. In this regard, reference can also be made e.g. to the following scientific articles: Wulf et al. Enzyme Microb Technol. 2012 Sep. 10; 51(4):217-24; Paul et al., ChemCatChem. 2013 Sep. 23, 5(12):3875-3881; Mallin et al. Enzyme Microb Technol. 2013 Sep. 10; 53(4): 283-7; and Schmidt et al., Angew Chem Int Ed Engl. 2015 Feb. 23; 54(9):2784-7. Database Protein online, accession no. WP_022887115, relates to a short-chain dehydrogenase of *Glaciibacter superstes*. A majority of these ketoreductases described in the prior art are selected or improved for the reductive conversion of rather specific ketone substrates to secondary alcohol compounds in the realm of chemo-enzymatic synthesis of intermediates in pharmaceutical applications, e.g. the enzymes disclosed in WO 2009/040080.

The ketoreductases of the prior art, however, are not satisfactory in every respect and there is a demand for ketoreductases having advantages compared to conventional ketoreductases. In particular there is a demand for ketoreductases with high stereoselectivity, regioselectivity, and specific activity in both the oxidation of alcohol substrates to ketone or aldehyde products, and the reduction of ketone or aldehyde substrates to alcohol products, and a high process stability of such ketoreductases in the corresponding industrial production processes, respectively. In this regard, high process stabilities in industrial applications may encompass chemical and physical stability and enzymatic activity in aqueous, non-aqueous environments and/or at biphasic systems, and/or at high substrate concentrations and/or at elevated temperatures and/or with the addition of water miscible solvents and/or at a broad pH range from 4-11 and/or on solid supports (i.e. when being immobilized) and/or under high shear forces (e.g. produced by stirring, pumping, membrane filtration). Other factors, such as substrate selectivity, $K_M$, specific activity, stereospecificity, diastereoselectivity, substrate inhibition, product inhibition, inhibition by other factors e. g. crude extract components, substrate contaminants or side products, and recombinant soluble expressability in suitable hosts may play an important role. When the substrate is a chiral substrate, i.e. already contains one or more chiral centers and/or axes itself, it may be desirable that the stereoselectivity of the enzymatic reduction of a prochiral carbonyl group contained in said chiral substrate is not substantially influenced by said one or more chiral centers and/or axes.

BRIEF SUMMARY OF THE INVENTION

It is an objective of the present invention to provide improved ketoreductases.

This problem has been solved by the subject-matter of the patent claims.

SEQ ID NO:1 is the amino acid sequence of a preferred ketoreductase according to the invention. SEQ ID NO: 101, SEQ ID NO: 113 and SEQ ID NO: 149 are identical to SEQ ID NO: 1.

SEQ ID NO:2 is a DNA sequence encoding for the amino acid sequence according to inventive SEQ ID NO: 1.

SEQ ID NO:3 is a comparative amino acid sequence known from WO 2013/102619 wherein it is referred to as the sequence with the identification no. 10. Said comparative SEQ ID NO:3 has an identity of 91.1% to the amino acid sequence of inventive SEQ ID NO: 1.

SEQ ID NO:4 is a DNA sequence encoding for the amino acid sequence according to comparative SEQ ID NO:3 as disclosed in WO 2013/102619 wherein it is referred to as the sequence with the identification no. 9.

SEQ ID NO:5 is a DNA sequence, which is a codon-optimized variant of SEQ ID NO:4, encoding for the amino acid sequence of SEQ ID NO:3.

SEQ ID NO:6 up to SEQ ID NO:100, SEQ ID NO:102 up to SEQ ID NO:112, SEQ ID NO:114 up to SEQ ID NO: 148, and SEQ ID NO: 150 up to SEQ ID NO: 182 are variant ketoreductases from SEQ ID NO:1 with furthermore improved functional characteristics, for example an increased thermal stability, and an increased activity, in particular specific activity, in both the oxidation of alcohol substrates to ketone or aldehyde products, and the reduction of ketone or aldehyde substrates to alcohol products.

Specifically, the variant ketoreductases carry the following substitutions in one or more of the following positions with the numbering referring to the comparative SEQ ID NO: 1 of the invention:

| | Mutation Position compared to SEQ ID NO: 1 | | | | | | |
| --- | --- | --- | --- | --- | --- | --- | --- |
| SEQ ID. NO: | 1st mutation | 2nd Mutation | 3rd mutation | 4th mutation | 5th mutation | 6th mutation | 7th mutation |
| SEQ ID NO: 6 | I220V | | | | | | |
| SEQ ID NO: 7 | Y244F | | | | | | |
| SEQ ID NO: 8 | P204L | | | | | | |
| SEQ ID NO: 9 | D208H | | | | | | |
| SEQ ID NO: 10 | G213D | | | | | | |
| SEQ ID NO: 11 | D208C | | | | | | |
| SEQ ID NO: 12 | T194V | | | | | | |
| SEQ ID NO: 13 | A199C | | | | | | |
| SEQ ID NO: 14 | V217N | | | | | | |
| SEQ ID NO: 15 | E200P | | | | | | |
| SEQ ID NO: 16 | I202V | | | | | | |
| SEQ ID NO: 17 | M206T | | | | | | |
| SEQ ID NO: 18 | M206D | | | | | | |
| SEQ ID NO: 19 | M206G | T225M | | | | | |
| SEQ ID NO: 20 | M206A | | | | | | |
| SEQ ID NO: 21 | E200V | | | | | | |
| SEQ ID NO: 22 | E200A | | | | | | |
| SEQ ID NO: 23 | V217P | | | | | | |
| SEQ ID NO: 24 | T225I | | | | | | |

-continued

| SEQ ID. NO: | 1st mutation | 2nd Mutation | 3rd mutation | 4th mutation | 5th mutation | 6th mutation | 7th mutation |
|---|---|---|---|---|---|---|---|
| SEQ ID NO: 25 | L227V | | | | | | |
| SEQ ID NO: 26 | N232Y | | | | | | |
| SEQ ID NO: 27 | N232F | | | | | | |
| SEQ ID NO: 28 | T236S | | | | | | |
| SEQ ID NO: 29 | S100E | N112T | | | | | |
| SEQ ID NO: 30 | S100Q | | | | | | |
| SEQ ID NO: 31 | D109G | | | | | | |
| SEQ ID NO: 32 | S100R | | | | | | |
| SEQ ID NO: 33 | P101F | | | | | | |
| SEQ ID NO: 34 | P101H | | | | | | |
| SEQ ID NO: 35 | P101W | | | | | | |
| SEQ ID NO: 36 | F99R | | | | | | |
| SEQ ID NO: 37 | I132V | | | | | | |
| SEQ ID NO: 38 | G149C | | | | | | |
| SEQ ID NO: 39 | G149V | | | | | | |
| SEQ ID NO: 40 | G149S | | | | | | |
| SEQ ID NO: 41 | I132W | | | | | | |
| SEQ ID NO: 42 | S100V | | | | | | |
| SEQ ID NO: 43 | S100C | | | | | | |
| SEQ ID NO: 44 | D109R | | | | | | |
| SEQ ID NO: 45 | L9G | | | | | | |
| SEQ ID NO: 46 | L9M | | | | | | |
| SEQ ID NO: 47 | N10G | | | | | | |
| SEQ ID NO: 48 | L9C | | | | | | |
| SEQ ID NO: 49 | L9R | | | | | | |
| SEQ ID NO: 50 | L9K | | | | | | |
| SEQ ID NO: 51 | L9Q | | | | | | |
| SEQ ID NO: 52 | S25A | | | | | | |
| SEQ ID NO: 53 | E22K | | | | | | |
| SEQ ID NO: 54 | M26R | | | | | | |
| SEQ ID NO: 55 | A30R | | | | | | |
| SEQ ID NO: 56 | E31N | | | | | | |
| SEQ ID NO: 57 | A38M | | | | | | |
| SEQ ID NO: 58 | S39G | | | | | | |
| SEQ ID NO: 59 | L42Y | | | | | | |
| SEQ ID NO: 60 | S39A | | | | | | |
| SEQ ID NO: 61 | I54R | | | | | | |
| SEQ ID NO: 62 | I54V | | | | | | |
| SEQ ID NO: 63 | V55I | | | | | | |
| SEQ ID NO: 64 | S92M | | | | | | |
| SEQ ID NO: 65 | S92G | | | | | | |
| SEQ ID NO: 66 | I132F | | | | | | |
| SEQ ID NO: 67 | P121V | | | | | | |
| SEQ ID NO: 68 | Q98E | | | | | | |
| SEQ ID NO: 69 | T119L | | | | | | |
| SEQ ID NO: 70 | P121A | | | | | | |
| SEQ ID NO: 71 | P121A | S133M | | | | | |
| SEQ ID NO: 72 | M157F | | | | | | |
| SEQ ID NO: 73 | M157R | | | | | | |
| SEQ ID NO: 74 | M157G | | | | | | |
| SEQ ID NO: 75 | S151A | | | | | | |
| SEQ ID NO: 76 | M157G | I215T | G243V | C245F | A246F | | |
| SEQ ID NO: 77 | L9G | V13G | | | | | |
| SEQ ID NO: 78 | W214G | | | | | | |
| SEQ ID NO: 79 | S25A | D208N | | | | | |
| SEQ ID NO: 80 | M26R | G235F | T237I | V238F | S239F | | |
| SEQ ID NO: 81 | M157C | | | | | | |
| SEQ ID NO: 82 | M157E | | | | | | |
| SEQ ID NO: 83 | M157K | | | | | | |
| SEQ ID NO: 84 | T148S | | | | | | |
| SEQ ID NO: 85 | A106C | | | | | | |
| SEQ ID NO: 86 | A106E | | | | | | |
| SEQ ID NO: 87 | A108P | | | | | | |
| SEQ ID NO: 88 | G159S | | | | | | |
| SEQ ID NO: 89 | S97A | | | | | | |
| SEQ ID NO: 90 | S97W | | | | | | |
| SEQ ID NO: 91 | S97V | | | | | | |
| SEQ ID NO: 92 | S97C | | | | | | |
| SEQ ID NO: 93 | S97M | | | | | | |
| SEQ ID NO: 94 | V55C | | | | | | |
| SEQ ID NO: 95 | S4N | | | | | | |
| SEQ ID NO: 96 | E43K | | | | | | |
| SEQ ID NO: 97 | A11V | | | | | | |
| SEQ ID NO: 98 | S3I | | | | | | |

| SEQ ID. NO: | 1st mutation | 2nd Mutation | 3rd mutation | 4th mutation | 5th mutation | 6th mutation | 7th mutation |
|---|---|---|---|---|---|---|---|
| SEQ ID NO: 99 | S8A | | | | | | |
| SEQ ID NO: 100 | A11C | | | | | | |
| SEQ ID NO: 102 | Q44T | | | | | | |
| SEQ ID NO: 103 | K49R | | | | | | |
| SEQ ID NO: 104 | Q44E | | | | | | |
| SEQ ID NO: 105 | A50K | | | | | | |
| SEQ ID NO: 106 | Q44R | | | | | | |
| SEQ ID NO: 107 | K56M | | | | | | |
| SEQ ID NO: 108 | Q57P | | | | | | |
| SEQ ID NO: 109 | Q57A | | | | | | |
| SEQ ID NO: 110 | T60C | | | | | | |
| SEQ ID NO: 111 | T60N | | | | | | |
| SEQ ID NO: 112 | T60A | | | | | | |
| SEQ ID NO: 114 | S69V | | | | | | |
| SEQ ID NO: 115 | D70C | | | | | | |
| SEQ ID NO: 116 | D70S | | | | | | |
| SEQ ID NO: 117 | S69A | | | | | | |
| SEQ ID NO: 118 | S76M | | | | | | |
| SEQ ID NO: 119 | S76C | | | | | | |
| SEQ ID NO: 120 | S76L | | | | | | |
| SEQ ID NO: 121 | S76G | | | | | | |
| SEQ ID NO: 122 | F77L | | | | | | |
| SEQ ID NO: 123 | G75L | | | | | | |
| SEQ ID NO: 124 | L209C | | | | | | |
| SEQ ID NO: 125 | N212K | | | | | | |
| SEQ ID NO: 126 | N212P | | | | | | |
| SEQ ID NO: 127 | N212A | | | | | | |
| SEQ ID NO: 128 | A127K | | | | | | |
| SEQ ID NO: 129 | A127C | | | | | | |
| SEQ ID NO: 130 | A127G | | | | | | |
| SEQ ID NO: 131 | M113V | | | | | | |
| SEQ ID NO: 132 | A127Q | | | | | | |
| SEQ ID NO: 133 | S133L | | | | | | |
| SEQ ID NO: 134 | S133A | | | | | | |
| SEQ ID NO: 135 | S133Q | | | | | | |
| SEQ ID NO: 136 | S133M | | | | | | |
| SEQ ID NO: 137 | S133V | | | | | | |
| SEQ ID NO: 138 | P136V | | | | | | |
| SEQ ID NO: 139 | Q138A | | | | | | |
| SEQ ID NO: 140 | Q138T | | | | | | |
| SEQ ID NO: 141 | P136G | | | | | | |
| SEQ ID NO: 142 | Q138S | | | | | | |
| SEQ ID NO: 143 | A155W | | | | | | |
| SEQ ID NO: 144 | V158M | | | | | | |
| SEQ ID NO: 145 | G159A | | | | | | |
| SEQ ID NO: 146 | K152A | | | | | | |
| SEQ ID NO: 147 | D169E | | | | | | |
| SEQ ID NO: 148 | M172C | | | | | | |
| SEQ ID NO: 150 | P181V | | | | | | |
| SEQ ID NO: 151 | P181W | | | | | | |
| SEQ ID NO: 152 | P181L | | | | | | |
| SEQ ID NO: 153 | K182I | | | | | | |
| SEQ ID NO: 154 | L114V | | | | | | |
| SEQ ID NO: 155 | L114I | | | | | | |
| SEQ ID NO: 156 | A120G | | | | | | |
| SEQ ID NO: 157 | T139V | | | | | | |
| SEQ ID NO: 158 | T139F | | | | | | |
| SEQ ID NO: 159 | T139K | | | | | | |
| SEQ ID NO: 160 | A141S | | | | | | |
| SEQ ID NO: 161 | N185R | | | | | | |
| SEQ ID NO: 162 | G149M | | | | | | |
| SEQ ID NO: 163 | Y244L | | | | | | |
| SEQ ID NO: 164 | G149I | | | | | | |
| SEQ ID NO: 165 | P210C | | | | | | |
| SEQ ID NO: 166 | P210C | G149M | | | | | |
| SEQ ID NO: 167 | P210C | G147C | | | | | |
| SEQ ID NO: 168 | E200A | M206D | P210C | | | | |
| SEQ ID NO: 169 | S100R | P210C | | | | | |
| SEQ ID NO: 170 | M206D | P210C | | | | | |
| SEQ ID NO: 171 | S100R | G149M | E200A | P210C | N232F | | |
| SEQ ID NO: 172 | S100R | P121V | G149M | M157D | P210C | | |
| SEQ ID NO: 173 | S100R | P121V | P210C | | | | |
| SEQ ID NO: 174 | S97C | M206D | P210C | | | | |
| SEQ ID NO: 175 | S97C | E200A | M206D | P210C | | | |

-continued

| SEQ ID. NO: | 1st mutation | 2nd Mutation | 3rd mutation | 4th mutation | 5th mutation | 6th mutation | 7th mutation |
| --- | --- | --- | --- | --- | --- | --- | --- |
| | | | Mutation Position compared to SEQ ID NO: 1 | | | | |
| SEQ ID NO: 176 | S97C | P121V | G149M | M157D | M206D | P210C | N232F |
| SEQ ID NO: 177 | S97F | G149M | M157D | M206D | N232F | | |
| SEQ ID NO: 178 | S97C | P210C | | | | | |
| SEQ ID NO: 179 | E43K | S97C | T148S | T194V | P210C | L227V | |
| SEQ ID NO: 180 | S97C | T148S | A155H | P210C | L227V | | |
| SEQ ID NO: 181 | S97C | T148S | A155H | P210C | L227V | Y244F | |
| SEQ ID NO: 182 | E43K | S97C | T148S | A155H | P210C | L227V | Y244F |

When aligning inventive SEQ ID NO: 1 with comparative SEQ ID NO:3, position 1 of comparative SEQ ID NO:3 corresponds to position 9 of inventive SEQ ID NO: 1. Inventive SEQ ID NO: 1 contains at its N-terminus 8 positions that are missing in comparative SEQ ID NO:3, namely M, T2, S3, S4, S5, S6, P7, and S8. Accordingly, in the alignment, positions N2, A3, LA, V5, T6, G7, G8, S9, R10, G1, I12, G13, E14, and A15 of comparative SEQ ID NO:3 correspond to positions N10, A11, L12, V13, T14, G15, G16, S17, R18, G19, I120, G21, E22, and A23, respectively, of inventive SEQ ID NO: 1.

BRIEF DESCRIPTION OF THE FIGURE

FIG. 1 shows experimental results comparing the $Tm_{50}$ values of the ketoreductase of inventive SEQ ID NO: 1 with the ketoreductase of comparative SEQ ID NO:3.

DESCRIPTION OF VARIOUS AND PREFERRED EMBODIMENTS

The invention provides new ketoreductases, particularly ketoreductases exhibiting improved properties as compared to the ketoreductase of comparative SEQ ID NO:3. Further, the invention provides new ketoreductases, particularly ketoreductases exhibiting improved properties as compared to the ketoreductase of comparative SEQ ID NO: 1.

It has been surprisingly found that ketoreductases according to the invention have a superior
- specific activity, especially reduction activity (see Example 3), and/or oxidation activity (see Example 4), and/or
- pH profile in oxidation ("pH-related activity"), specifically a superior oxidation activity at neutral pH values (Example 4), and/or
- stereoselectivity (see Example 5), and/or
- temperature stability, i.e. residual activity at higher temperatures (half maximum melting temperatures, $Tm_{50\,(40)}$; see Example 6, FIG. 1; $Tm_{50(10)}$; see Example 12), and/or
- regioselectivity; and/or
- increased ratio of reduction activity over oxidation activity for the conversion of ketone or aldehyde substrates to alcohol products or vice versa; or
- decreased ratio of reduction activity over oxidation activity for the conversion of ketone or aldehyde substrates to alcohol products or vice versa; and/or
- a high cofactor preference.

A first aspect of the invention relates to a ketoreductase comprising an amino acid sequence with an identity of at least 92% to the amino acid sequence of inventive SEQ ID NO: 1.

The ketoreductase according to the invention comprises such an amino acid sequence with a defined identity to the amino acid sequence of inventive SEQ ID NO: 1. This means that the ketoreductase according to the invention may comprise said amino acid sequence as a subsequence of its overall amino acid sequence, or that the ketoreductase according to the invention may essentially consist of said amino acid sequence. When the ketoreductase according to the invention comprises said amino acid sequence as a subsequence of its overall amino acid sequence, said overall amino acid sequence may be extended, i.e. may comprise additional amino acid residues, at the N-terminus and/or at the C-terminus of said subsequence. Such extension may be advantageous, for example, when the ketoreductase is to be immobilized on a solid support, e.g. for purification purposes.

For the purpose of this invention, homology and identity are understood as synonyms. Percent identity is calculated as: Sequence Identity [%]=number of Matches/L×100, wherein L is the number of aligned positions, i.e. identities and nonidentities (including gaps, if any). Identity is preferably calculated using BLASTP (see, for example, Altschul SF et al. (1997) "Gapped BLAST and PSI-BLAST: a new generation of protein database search programs", Nucleic Acids Res. 25:3389-3402; or Altschul SF (2005) "Protein database searches using compositionally adjusted substitution matrices." FEBS J. 272:5101-5109), preferably with the following algorithm parameters: Matrix: BLOSUM62; Gap Costs: Existence: 11 Extension: 1, Expect threshold: 10 and Word size: 6. Results are filtered for sequences with more than 35% query coverage. BlastP can be accessed online at the NCBI Homepage Other program settings can be adjusted as desired, for example using the following settings:

Field "Enter Query Sequence": Query subrange: none
Field "Choose Search Set": Database: non-redundant protein sequences (nr); optional parameters: none
Field "Program Selection": Algorithm: blastp (protein-protein BLAST)
Algorithm parameters: Field "General parameters": Max target sequences: 20000; Short queries: Automatically adjust parameters for short input sequences; Expect threshold: 10; Word size: 6; Max matches in a query range: 0
Algorithm parameters: Field "Scoring parameters": Matrix: BLOSUM62; Gap Costs: Existence: 11 Extension: 1; Compositional adjustments: Conditional compositional score matrix adjustment
Algorithm parameters: Field "Filters and Masking": Filter: none; Mask: none.

Preferably, the ketoreductase comprises an amino acid sequence with an identity of at least 92.0%, at least 92.1%, at least 92.2%, at least 92.3%, at least 92.4%, at least 92.5%, at least 92.6%, at least 92.7%, at least 92.8%, at least 92.9%, at least 93%, at least 93.1%, at least 93.2%, at least 93.3%, at least 93.4%, at least 93.5%, at least 93.6%, at least 93.7%, at least 93.8%, at least 93.9%, more preferably at least 94%, at least 94.1%, at least 94.2%, at least 94.3%, at least 94.4%, at least 94.5%, at least 94.6%, at least 94.7%, at least 94.8%, at least 94.9%, still more preferably at least 95%, at least 95.1%, at least 95.2%, at least 95.3%, at least 95.4%, at least 95.5%, at least 95.6%, at least 95.7%, at least 95.8%, at least 95.9%, yet more preferably at least 96%, at least 96.1%, at least 96.2%, at least 96.3%, at least 96.4%, at least 96.5%, at least 96.6%, at least 96.7%, at least 96.8%, at least 96.9%, even more preferably at least 97%, at least 97.1%, at least 97.2%, at least 97.3%, at least 97.4%, at least 97.5%, at least 97.6%, at least 97.7%, at least 97.8%, at least 97.9%, most preferably at least 98%, at least 98.1%, at least 98.2%, at least 98.3%, at least 98.4%, at least 98.5%, at least 98.6%, at least 98.7%, at least 98.8%, at least 98.9%, and in particular at least 99%, at least 99.1%, at least 99.2%, at least 99.3%, at least 99.4%, at least 99.5%, at least 99.6%, at least 99.7%, at least 99.8%, at least 99.9%, to the amino acid sequence of inventive SEQ ID NO: 1. In a preferred embodiment, the ketoreductase comprises an amino acid sequence that essentially consists of the amino acid sequence of inventive SEQ ID NO:1. In another preferred embodiment, the ketoreductase consists of the amino acid sequence of inventive SEQ ID NO: 1.

In a preferred embodiment, the ketoreductase according to the invention is a fusion protein of the amino acid sequence of inventive SEQ ID NO: 1 with any other amino acid, oligo- or polypeptide, which is fused to the N-terminus and/or the C-terminus.

In a preferred embodiment, the ketoreductase according to the invention comprises the amino acid sequence of inventive SEQ ID NO: 1 and additionally, at least 10 amino acid residues, more preferably at least 20 amino acid residues, even more preferably at least 30 amino acid residues, and most preferably at least 40 amino acid residues, independently selected from the group consisting of Ala, Arg, Asn, Asp, Cys, Gln, Glu, Gly, His, Ile, Leu, Lys, Met, Phe, Pro, Ser, Thr, Trp Tyr, and Val.

In a preferred embodiments, the ketoreductase with improved properties according to the invention differs with respect to comparative SEQ ID NO:3, i.e. differs from the ketoreductase of comparative SEQ ID NO:3 by at least one residue change, preferably 1 to 23 residue changes, more preferably by 2 to 23 residue changes, more preferably by 3 to 23 residue changes, more preferably by 4 to 23 residue changes, more preferably by 5 to 23 residue changes, more preferably by 6 to 23 residue changes, more preferably by 7 to 23 residue changes, more preferably by 8 to 23 residue changes, more preferably by 9 to 23 residue changes, more preferably by 10 to 23 residue changes, more preferably by 1 to 23 residue changes, more preferably by 12 to 23 residue changes, more preferably by 13 to 23 residue changes, more preferably by 14 to 23 residue changes, even more preferably by 15 to 23 residue changes, even more preferably by 16 to 23 residue changes, even more preferably by 17 to 23 residue changes, even more preferably by 18 to 23 residue changes, more preferably by 19 to 23 residue changes, even more preferably by 20 to 23 residue changes, even more preferably by 21 to 23 residue changes, even more preferably by 22 to 23 residue changes, and most preferably by 23 residue changes.

Thus, the ketoreductase according to the invention preferably satisfies two requirements, one requirement with respect to a minimum identity to inventive SEQ ID NO:1, and another requirement with respect to certain differences from comparative SEQ ID NO:3.

Regarding the sequence variations between comparative SEQ ID NO:3 and the inventive SEQ ID NO:1, differing means that one or more amino acids in a given position of comparative SEQ ID NO:3 are substituted with any other proteinogenic amino acid selected from the group consisting of Ala, Arg, Asn, Asp, Cys, Gln, Glu, Gly, His, Ile, Leu, Lys, Met, Phe, Pro, Ser, Thr, Trp, Tyr, and Val. In a preferred embodiment, the substitution does not alter the sequence length, i.e. a single amino acid residue is replaced by another single amino acid residue. However, it is also possible to delete one or more amino acid residues without replacement and/or to insert one or more amino acid residues.

In principle, a substitution in any position of an enzyme may be a conservative substitution where such amino acid is substituted with an amino acid of comparable characteristics (e.g. substitution of a hydrophobic amino acid with another hydrophobic amino acid). In addition, a substitution in any position of an enzyme may be a non-conservative substitution where such amino acid is substituted with an amino acid of other characteristics (e.g. substitution of a hydrophobic amino acid with a hydrophilic amino acid).

For the purpose of the description, specific substitutions disclosed herein are described in accordance with common practice in the field of amino acid substitutions, wherein the format [non-substituted amino acid-sequence position—substituted amino acid] is chosen and the sequence position is directly flanked with the amino acids letter (one letter code) on the left or right side. In case where a single amino acid shall be substituted by more than one amino acid, or where more than a single amino acid shall be replaced by a single amino acid, the positions of said more than a single amino acid are listed in an order from left to right corresponding to the N-terminus to C-terminus. For clarification only, substitution "I190V" describes the substitution of the amino acid isoleucine (I) in sequence position 190 by the amino acid valine (V), i.e. I is replaced by V. Analogously, substitution "M1MTS" describes the substitution of the amino acid methionine (M) in sequence position 1 by the amino acids (N-terminus)-methionine(M)-threonine(T)-serine(S)-(C-terminus), i.e. M is replaced by MTS. Analogously, substitution "MTS1M" describes the substitution of the amino acids (N-terminus)-methionine(M)-threonine(T)-serine(S)-(C-terminus) in sequence position 1 by the amino acid methionine (M), i.e. MTS is replaced by M.

In the following, for the purpose of the specification regarding the first and second aspect of the invention, unless expressly stated otherwise, position numbers refer to the positions of comparative SEQ ID NO:3 commencing with M1, T2, S3, S4, S5, S6, P7, and S8.

Preferably, the ketoreductase according to the invention differs from the ketoreductase of comparative SEQ ID NO:3 by at least one residue change, preferably at least 2, at least 3, at least 4, or at least 5 residue changes, in a sequence section A of comparative SEQ ID NO:3, wherein said sequence section A ranges from position 14 of comparative SEQ ID NO:3 to position 28 of comparative SEQ ID NO:3; preferably wherein said sequence section A ranges from position 16 of comparative SEQ ID NO:3 to position 26 of comparative SEQ ID NO:3; preferably in one or more or all positions selected from V16, I18, S22, Q23, and G26; and/or at least one residue change in a sequence section B of comparative SEQ ID NO:3, wherein said sequence section B ranges from position 29 of comparative SEQ ID NO:3 to position 43 of comparative SEQ ID NO:3; preferably wherein said sequence section B ranges from position 33 of comparative SEQ ID NO:3 to position 35 of comparative SEQ ID NO:3; preferably in position V34; and/or at least one residue change in a sequence section C of comparative SEQ ID NO:3, wherein said sequence section C ranges from position 44 of comparative SEQ ID NO:3 to position 58 of comparative SEQ ID NO:3; preferably wherein said sequence section C ranges from position 45 of comparative SEQ ID NO:3 to position 47 of comparative SEQ ID NO:3; preferably in position V46; and/or at least one residue change in a sequence section D of comparative SEQ ID NO:3, wherein said sequence section D ranges from position 82 of comparative SEQ ID NO:3 to position 96 of comparative SEQ ID NO:3; preferably wherein said sequence section D ranges from position 88 of comparative SEQ ID NO:3 to position 90 of comparative SEQ ID NO:3; preferably in position A89; and/or at least one residue change in a sequence section E of comparative SEQ ID NO:3, wherein said sequence section E ranges from position 123 of comparative SEQ ID NO:3 to position 137 of comparative SEQ ID NO:3; preferably wherein said sequence section E ranges from position 129 of comparative SEQ ID NO:3 to position 131 of comparative SEQ ID NO:3; preferably in position E130; and/or at least one residue change, preferably at least 2, at least 3, at least 4, or at least 5 residue changes, in a sequence section F of comparative SEQ ID NO:3, wherein said sequence section F ranges from position 185 of comparative SEQ ID NO:3 to position 199 of comparative SEQ ID NO:3; preferably wherein said sequence section F ranges from position 188 of comparative SEQ ID NO:3 to position 195 of comparative SEQ ID NO:3; preferably in one or more or all positions selected from A189, I190, S191, D192, and V194; and/or at least one residue change in a sequence section G of comparative SEQ ID NO:3, wherein said sequence section G ranges from position 200 of comparative SEQ ID NO:3 to position 214 of comparative SEQ ID NO:3; preferably wherein said sequence section G ranges from position 203 of comparative SEQ ID NO:3 to position 205 of comparative SEQ ID NO:3; preferably in position S204; and/or at least one residue change, preferably at least 2, at least 3, at least 4 residue changes, in a sequence section H of comparative SEQ ID NO:3, wherein said sequence section H ranges from position 221 of comparative SEQ ID NO:3 to position 233 of comparative SEQ ID NO:3; preferably wherein said sequence section H ranges from position 227 of comparative SEQ ID NO:3 to position 232 of comparative SEQ ID NO:3; preferably in one or more or all positions selected from A228, I1229, L230, and V231; and/or at least one residue change, preferably at least 2, at least 3 residue changes, in a sequence section I of comparative SEQ ID NO:3, wherein said sequence section I ranges from position 234 of comparative SEQ ID NO:3 to position 238 of comparative SEQ ID NO:3; preferably wherein said sequence section I ranges from position 236 of comparative SEQ ID NO:3 to position 238 of comparative SEQ ID NO:3; preferably in one or more or all positions selected from F236, S237 and T238.

Preferably, residue changes in the inventive ketoreductase compared to the ketoreductase of comparative SEQ ID NO:3 include one or more, preferably at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, or at least 23 of the following positions of comparative SEQ ID NO:3: M1, V16, I18, S22, Q23, G26, V34, V46, A89, E130, A189, I190, S191, D192, V194, S204, A228, I1229, L230, V231, F236, S237, and T238.

In particularly preferred embodiments, the ketoreductase according to the invention differs from comparative SEQ ID NO:3 in at least one or more, preferably at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, or at least 23 positions such that it comprises at least one or more or all substitutions selected from the group consisting of:

at position M1 substitution to
M1A, M1R, M1N, M1D, M1C, M1Q, M1E, M1G, M1H, M1I, M1L, M1K, M1F, M1P, M1S, M1T, M1W, M1Y, or M1V; preferably M1L, M1P, M1G, M1S, M1Q, M1H, M1K, or M1R; more preferably M1K, M1L, or M1R; and most preferably M1L; or M1MSSSSPSM, M1MTSSSSPSA, M1MTSSSSPSR, M1MTSSSSPSN, M1MTSSSSPSD, M1MTSSSSPSC, M1MTSSSSPSQ, M1MTSSSSPSE, M1MTSSSSPSG, M1MTSSSSPSH, M1MTSSSSPSI, M1MTSSSSPSL, M1MTSSSSPSK, M1MTSSSSPSF, M1MTSSSSPSP, M1MTSSSSPSS, M1MTSSSSPST, M1MTSSSSPSW, M1MTSSSSPSY, or M1MTSSSSPSV; preferably M1MTSSSSPSL, M1MTSSSSPSP, M1MTSSSSPSG, M1MTSSSSPSS, M1MTSSSSPSQ, M1MTSSSSPSH, M1MTSSSSPSK, or M1MTSSSSPSR; more preferably M1MTSSSSPSK, M1MTSSSSPSL, or M1MTSSSSPSR; and most preferably M1MTSSSSPSL; and/or at position V16 substitution to V16A, V16R, V16N, V16D, V16C, V16Q, V16E, V16G, V16H, V16I, V16L, V16K, V16M, V16F, V16P, V16S, V16T, V16W, or V16Y; preferably V16A, V16I, V16L, V16M, V16Y, V16S, or V16T; more preferably V16I, V16V, V16M, or V16L; and most preferably V16I; and/or at position I18 substitution to I18A, I18R, I18N, I18D, I18C, I18Q, I18E, I18G, I18H, I18L, I18K, I18M, I18F, I18P, I18S, I18T, I18W, I18Y, or I18V; preferably I18A, I18V, I18L, I18M, I18S, I18T, I18Q, I18D, I18E, I18H, I18K, or I18R; more preferably I18M, I18R, I18K, or I18L; even more preferably I18M or I18R; and most preferably I18M; and/or at position S22 substitution to S22A, S22R, S22N, S22D, S22C, S22Q, S22E, S22G, S22H, S22I, S22L, S22K, S22M, S22F, S22P, S22T, S22W, S22Y, or S22V; preferably S22A, S22G, S22T, S22N, S22Q, S22D, S22E, S22K, or S22R; more preferably S22A, S22G, S22T, S22D, S22E, S22H, S22K, or S22R; even more preferably S22R, or S22A; and most preferably S22A; and/or at position Q23 substitution to Q23A, Q23R, Q23N, Q23D, Q23C, Q23E, Q23G, Q23H, Q23I, Q23L, Q23K, Q23M, Q23F, Q23P, Q23S, Q23T, Q23W, Q23Y, or Q23V; preferably Q23A, Q23L, Q23S, Q23C, Q23N, Q23D, Q23E, Q23H, Q23K, or Q23R; more preferably Q23N, Q23A, Q23E, or Q23D; even more preferably Q23N, or Q23E; and most preferably Q23E; and/or at position G26 substitution to G26A, G26R, G26N, G26D, G26C, G26Q, G26E, G26H, G26I, G26L, G26K, G26M, G26F, G26P, G26S, G26T, G26W, G26Y, or G26V; preferably G26I, G26F, G26S, G26T, G26N, G26D, G26H, G26K, or G26R; more preferably G26T, G26S, or G26N; and most preferably G26S; and/or at position V34 substitution to V34A, V34R, V34N, V34D, V34C, V34Q, V34E, V34G, V34H, V34I, V34L, V34K, V34M, V34F, V34P, V34S, V34T, V34W, or V34Y; preferably V34A, V34L, V34I, V34P, V34G, V34S, V34T, V34D, V34E. V34K, or V34Y; more preferably V34L, V34A, V34T, V34E, or V34Y; even more preferably V34L, V34E, or V34Y; even more preferably V34L, or V34Y; and most preferably V34L; and/or at position V46 substitution to V46A, V46R, V46N, V46D, V46C, V46Q, V46E, V46G, V46H, V46I, V46L, V46K, V46M, V46F, V46P, V46S, V46T, V46W, or V46Y; preferably V46A, V46I, V46L, V46G, V46T, V46Q, V46H, V46R, or V46K; more preferably V46I, V46A, V46G, V46R, or V46T; even more preferably V46I, or V46R; and most preferably V46I; and/or at position A89 substitution to A89R. A89N, A89D, A89C, A89Q, A89E, A89G, A89H, A89I, A89L, A89K, A89M, A89F, A89P, A89S, A89T, A89W, A89Y, or A89V; preferably A89V, A89I, A89L, A89F, A89W, A89M, A89G, A89S, A89T, A89N, A89D, A89R, or A89C; more preferably A89S, A89T, A89V, A89M, A89W, A89I, or A89C; even more preferably A89V, A89M, A89W, A89M, A89C, A89S or A89T; even more preferably A89V, A89M, A89W, A89M, A89C, or A89S; and most preferably A89S; and/or at position E130 substitution to E130A, E130R, E130N, E130D, E130C, E130Q, E130G, E130H, E130I, E130L, E130K, E130M, E130F, E130P, E130S, E130T, E130W, E130Y, or E130V; preferably E130A, E130L, E130P, E130G, E130S, E130N, E130Q, E130D, E130H, E130K, E130T, or E130R; more preferably E130A, E130T, E130S, E30S, E30Q, E130N, E130D, E130H, E130K, or E130R; even more preferably E130A, E130T, E130S, E130D, E130Q, or E130N; even more preferably E130A, E130T, E130S, or E130Q; and most preferably E130Q and/or at position A189 substitution to A189R, A189N, A189D, A189C, A189Q, A189E, A189G, A189H, A189I, A189L, A189K, A189M, A189F, A189P, A189S, A189T, A189W, A189Y, or A189V; preferably A189P, A189S, A189N, A189Q, A189D, A189E, A189K, A189R, or A189H; more preferably A189D, A189E, A189S, or A189P; even more preferably A189S, A189D, or A189E; and most preferably A189S; and/or at position I190 substitution to I190A, I190R, I190N, I190D, I190C, I190Q, I190E, I190G, I190H, I190L, I190K, I190M, I190F, I190P, I190S, I190T, I190W, I190Y, or I190V; preferably I190A, I190L, I190M, I190T, I190N, I190Q, or I190D; more preferably I190M, I190N, or I190L; and most preferably I190M; and/or at position S191 substitution to S191A, S191R, S191N, S191D, S191C, S191Q, S191E, S191G, S191H, S191I, S191L, S191K, S191M, S191F, S191P, S191T, S191W, S191Y, or S191V; preferably S191A, S191V, S191I, S191L, S191G, S191T, S191N, or S191C; more preferably S191C, S191A, S191T, or S191G; even more preferably S191C, S191A, or S191T, even more preferably S191C, or S191A; and most preferably S191A; and/or at position D192 substitution to D192A, D192R. D192N, D192C, D192Q, D192E, D192G, D192H, D192I, D192L, D192K, D192M, D192F, D192P, D192S, D192T, D192W, D192Y, or D192V; preferably D192A, D192V, D192I, D192L, D192P, D192G, D192S, D192T, D192N, D192Q, D192E, D192K, or D192R; more preferably D192V, D192E, D192K, D192R, D192A, D192P, D192S, or D192Q; even more preferably D192P, D192V, D192E or D192A; even more preferably D192P, D192V, D192A, or D192E; and most preferably D192E; and/or at position V194 substitution to V194A, V194R, V194N, V194D, V194C, V194Q, V194E, V194G, V194H, V194I, V194L, V194K, V194M, V194F, V194P, V194S, V194T, V194W, or V194Y; preferably V194A, V194I, V194L, V194M, V194F, V194G, V194Y, V194S, V194T, V194N, V194Q, or V194D; more preferably V194 L, V194I, V194A, V194M, or V194S; even more preferably V194L, or V194I; and most preferably V194I; and/or at position S204 substitution to S204A, S204R, S204N, S204D, S204C, S204Q, S204E, S204G, S204H, S204I, S204L, S204K, S204M, S204F, S204P, S204T, S204W, S204Y, or S204V; preferably S204A, S204M, S204P, S204G, S204C, S204N, S204Q, S204E, S204D, S204H, S204K, S204R, or S204T; more preferably S204N, S204G, S204K, S204P, or S204A; even more preferably S204A, S204K, S204P, S204N or S204G; even more preferably S204A, S204K, S204P; or S204N; and most preferably S204N; and/or at position A228 substitution to A228R, A228N, A228D, A228C, A228Q, A228E, A228G, A228H, A228I, A228L, A228K, A228M, A228F, A228P, A228S, A228T, A228W, A228Y, or A228V; preferably A228V, A228I, A228S, A228T, A228N, A228Q, A228D, A228E, A228H, or A228R; more preferably A228S, A228Q or A228T; and most preferably A228T; and/or at position I229 substitution to I229A, I229R, I229N, I229D, I229C, I229Q, I229E, I229G, I229H, I229L, I229K, I229M, I229F, I229P, I229S, I229T, I229W, I229Y, or I229V; preferably I229A, I229V, I229L, I229M, I229G, I229S, I229T, I229C, I229N, I229D, I229E, or I229H; more preferably I229T, I229S, I229A, or I229V; and most preferably I229T; and/or at position L230 substitution to L230A, L230R, L230N, L230D, L230C, L230Q, L230E, L230G, L230H, L230I, L230K, L230M, L230F, L230P, L230S, L230T, L230W, L230Y, or L230V; preferably L230V, L230I, L230M, L230F, L230T, L230S, L230G, or L230A; more preferably L230A, L230V, L230I, or L230F; even more preferably L230F, L230V or L230I; and most preferably L230V; and/or at position V231 substitution to V231A, V231R, V231N, V231D, V231C, V231Q, V231E, V231G, V231H, V231I, V231L, V231K, V231M, V231F, V231P, V231S, V231T, V231W, or V231Y; preferably V231A, V231I, V231L, V231P, V231G, V231S, V231T, V231N, V231Q, V231D, V231E, V231H, V231F, V231K, or V231R; more preferably V231F, V231S, or V231T; even more preferably V231F, V231S or V231H; even more preferably V231F, or V231S; and most preferably V231S; and/or at position F236 substitution to F236A, F236R, F236N, F236D, F236C, F236Q, F236E, F236G, F236H, F236I, F236L, F236K, F236M, F236P, F236S, F236T, F236W, F236Y, or F236V; preferably F236A, F236V, F236I, F236L, F236M, F236W, F236G, F236Y, F236S, F236T, F236N, F236Q, F236D, F236E, or F236R; more preferably F236Y, F236W, or F236M; even more preferably F236Y, or F236M, and most preferably F236Y; and/or at position S237 substitution to S237A, S237R, S237N, S237D, S237C, S237Q, S237E, S237G, S237H, S237I, S237L, S237K, S237M, S237F, S237P, S237T, S237W, S237Y, or S237V; preferably S237A, S237V, S237I, S237L, S237M, S237F, S237G, S237Y, S237T, S237C, S237N, S237Q, S237D, S237E, S237H, S237K, or S237R; more preferably S237F, S237A, S237V, or S237C; even more preferably S237F, S237A or S237C; even more preferably S237F, or S237C; and most preferably S237C; and/or at position T238 substitution to T238A, T238R, T238N, T238D, T238C, T238Q, T238E, T238G, T238H, T238I, T238L, T238K, T238M, T238F, T238P, T238S, T238W, T238Y, or T238V; preferably T238F, T238A, T238V, T238I, T238L, T238M, T238P, T238G, T238A, T238C, T238N, or T238Q; more preferably T238F, T238A, T238V, T238I, T238L, T238M, or T238G; even more preferably T238F, T238M or T238A; even more preferably T238F, T238A; and most preferably T238A.

Preferably, the ketoreductase according to the invention differs from comparative SEQ ID NO:3 in at least one or more, preferably at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, or at least 22 positions such that it comprises at least one or more or all substitutions selected from the group consisting of V16I, I18M, S22A, Q23E, G26S, V34L, V46I, A89S, E130Q, A189S, I190M, S191A, D192E, V194I, S204N, A228T, I229T, L230V, V231S, F236Y, S237C, and T238A.

Preferably, the ketoreductase according to the invention differs from comparative SEQ ID NO:3 in at least one or more, preferably at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, or at least 23 positions such that it comprises at least one or more or all substitutions selected from the group consisting of M1MTSSSSPSL, V16I, I18M, S22A, Q23E, G26S, V34L, V46I, A89S, E130Q, A189S, I190M, S191A, D192E, V194I, S204N, A228T, I229T, L230V, V231S, F236Y, S237C, and T238A.

Preferably, the ketoreductase according to the invention differs from comparative SEQ ID NO:3 in at least one or more, preferably at least 2, at least 3, at least 4, at least 5, at least 6, at least 7, or at least 8 positions such that it comprises at least one or more or all substitutions selected from the group consisting of M1MTSSSSPSL, V16I, S22A, Q23E, V46I, I190M, A228T, I229T, and may in addition furthermore differ from comparative SEQ ID NO:3 in at least one or more, preferably at least 2, at least 3, at least 4, at least 5, at least 6, at least 7, at least 8, at least 9, at least 10, at least 11, at least 12, at least 13, at least 14, or at least 15 positions such that it comprises furthermore at least one or more or all substitutions selected from the group consisting of I18M, G26S, V34L, A89S, E130Q, A189S, S191A, V194I, D192E, S204N, L230V, V231S, F236Y, S237C, and T238A.

Preferably, the ketoreductase according to the invention differs from comparative SEQ ID NO:3 in at least one or more, preferably at least 2, at least 3, at least 4, at least 5, at least 6, or at least 7 positions such that it comprises at least one or more or all substitutions selected from the group consisting of M1MTSSSSPSL, V16I, S22A, Q23E, V46I, A228T, I229T, and may in addition furthermore differ from comparative SEQ ID NO:3 in at least one or more, preferably at least 2, at least 3, at least 4, at least 5, at least 6, at least 7, at least 8, at least 9, at least 10, at least 11, at least 12, at least 13, at least 14, at least 15, or at least 16 positions such that it comprises furthermore at least one or more or all substitutions selected from the group consisting of I18M, G26S, V34L, A89S, E130Q, A189S, I190M, S191A, V194I, D192E, S204N, L230V, V231S, F236Y, S237C, and T238A.

Preferably, the ketoreductase according to the invention differs from comparative SEQ ID NO:3 in at least one or more, preferably at least 2, at least 3, at least 4, at least 5, at least 6, at least 7, at least 8, or at least 9 positions such that it comprises at least one or more or all substitutions selected from the group consisting of M1MTSSSSPSL, I18M, A89S, E130Q, A189S, D192E, S204N, V231S, S237C, and may in addition furthermore differ from comparative SEQ ID NO:3 in at least one or more, preferably at least 2, at least 3, at least 4, at least 5, at least 6, at least 7, at least 8, at least 9, at least 10, at least 11, at least 12, at least 13, or at least 14 positions such that it comprises furthermore at least one or more or all substitutions selected from the group consisting of V16I, S22A, Q23E, G26S, V34L, V46I, I190M, S191A, V194I, A228T, I229T, L230V, F236Y, and T238A.

Preferably, the ketoreductase according to the invention differs from comparative SEQ ID NO:3 in at least one or more, preferably at least 2, at least 3, at least 4, at least 5, at least 6, at least 7, or at least 8 positions such that it comprises at least one or more or all substitutions selected from the group consisting of M1MTSSSSPSL, I18M, E130Q, A189S, D192E, S204N, V231S, S237C, and may in addition furthermore differ from comparative SEQ ID NO:3 in at least one or more, preferably at least 2, at least 3, at least 4, at least 5, at least 6, at least 7, at least 8, at least 9, at least 10, at least 11, at least 12, at least 13, at least 14, or at least 15 positions such that it comprises furthermore at least one or more or all substitutions selected from the group consisting of V16I, S22A, Q23E, G26S, V34L, V46I, A89S, I190M, S191A, V194I, A228T, I229T, L230V, F236Y, and T238A.

A second aspect of the invention relates to a ketoreductase comprising an amino acid sequence with an identity of at least 70% to the amino acid sequence of comparative SEQ ID NO:3 but differs from comparative SEQ ID NO:3 by at least one residue change.

In preferred embodiments of this second aspect according to the invention, the ketoreductase comprises an amino acid sequence having an identity of at least 70%, or at least 71%, or at least 72%, or at least 73%, or at least 74%, or at least 75%, or at least 76%, or at least 77%, or at least 78%, or at least 79%, or at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99% to the amino acid sequence of comparative SEQ ID NO:3; and differing from comparative SEQ ID NO:3 by 1 to 23 residue changes, or 2 to 23 residue changes, or 3 to 23 residue changes, or 4 to 23 residue changes, or 5 to 23 residue changes, or 6 to 23 residue changes, or 7 to 23 residue changes, or 8 to 23 residue changes, or 9 to 23 residue changes, or 10 to 23 residue changes, or 11 to 23 residue changes, or 12 to 23 residue changes, or 13 to 23 residue changes, or 14 to 23 residue changes, or 15 to 23 residue changes, or 16 to 23 residue changes, or 17 to 23 residue changes, or 18 to 23 residue changes, or 19 to 23 residue changes, or 20 to 23 residue changes, or 21 to 23 residue changes, or 22 to 23 residue changes, or 23 residue changes.

Thus, the ketoreductase of this second aspect according to the invention preferably satisfies two requirements, one requirement with respect to a minimum identity to comparative SEQ ID NO:3, and another requirement with respect to certain differences from comparative SEQ ID NO:3.

The preferred differences of the ketoreductase of this second aspect according to the invention from comparative SEQ ID NO:3 have already been specified above in connection with the first aspect of the invention, i.e. the ketoreductase comprising an amino acid sequence with an identity of at least 92% to the amino acid sequence of inventive SEQ ID NO: 1, and analogously apply to this second aspect of the invention, i.e. the ketoreductase comprising an amino acid sequence with an identity of at least 70% to the amino acid sequence of comparative SEQ ID NO:3 but differs from comparative SEQ ID NO:3 by at least one residue change. Thus, said preferred differences and specific substitutions are not repeated hereinafter.

A third aspect of the invention relates to a ketoreductase comprising an amino acid sequence with an identity of at least 70% to the amino acid sequence of comparative SEQ ID NO: 1, wherein the amino acid sequence in comparison to comparative SEQ ID NO: 1
(i) differs by at least one amino acid residue change, and
(ii) exhibits an improved thermal stability, and/or
(iii) exhibits an increased activity, in particular specific activity, in the oxidation of alcohol substrates to ketone or aldehyde products, and/or
(iv) exhibits an increased activity, in particular specific activity, in the reduction of ketone or aldehyde substrates to alcohol products; and/or
(v) exhibits an increased ratio of oxidation activity over reduction activity for the conversion of ketone or aldehyde substrates to alcohol products or vice versa; and/or
(vi) exhibits an increased ratio of reduction activity over oxidation activity for the conversion of ketone or aldehyde substrates to alcohol products or vice versa; or
(vii) exhibits a decreased ratio of reduction activity over oxidation activity for the conversion of ketone or aldehyde substrates to alcohol products or vice versa.

Preferably, the ketoreductase comprises an amino acid sequence with a identity of at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, more preferably at least 91.0%, at least 91.5%, at least 92.0%, at least 92.1%, at least 92.2%, at least 92.3%, at least 92.4%, at least 92.5%, at least 92.6%, at least 92.7%, at least 92.8%, at least 92.9%, at least 93%, at least 93.1%, at least 93.2%, at least 93.3%, at least 93.4%, at least 93.5%, at least 93.6%, at least 93.7%, at least 93.8%, at least 93.9%, more preferably at least 94%, at least 94.1%, at least 94.2%, at least 94.3%, at least 94.4%, at least 94.5%, at least 94.6%, at least 94.7%, at least 94.8%, at least 94.9%, still more preferably at least 95%, at least 95.1%, at least 95.2%, at least 95.3%, at least 95.4%, at least 95.5%, at least 95.6%, at least 95.7%, at least 95.8%, at least 95.9%, yet more preferably at least 96%, at least 96.1%, at least 96.2%, at least 96.3%, at least 96.4%, at least 96.5%, at least 96.6%, at least 96.7%, at least 96.8%, at least 96.9%, even more preferably at least 97%, at least 97.1%, at least 97.2%, at least 97.3%, at least 97.4%, at least 97.5%, at least 97.6%, at least 97.7%, at least 97.8%, at least 97.9%, most preferably at least 98%, at least 98.1%, at least 98.2%, at least 98.3%, at least 98.4%, at least 98.5%, at least 98.6%, at least 98.7%, at least 98.8%, at least 98.9%, and in particular at least 99%, at least 99.1%, at least 99.2%, at least 99.3%, at least 99.4%, at least 99.5%, at least 99.6%, at least 99.7%, at least 99.8%, or at least 99.9%, to the amino acid sequence of inventive SEQ ID NO: 1.

In the following, for the purpose of the specification regarding the third aspect of the invention, unless expressly stated otherwise, position numbers refer to the positions of inventive SEQ ID NO: 1.

In preferred embodiments, the ketoreductase according to the invention differs from the ketoreductase of inventive SEQ ID NO:1 by at least one residue change in a sequence section SS-01 of inventive SEQ ID NO:1, wherein said sequence section SS-01 ranges from position 1 of inventive SEQ ID NO: 1 to position 10 of inventive SEQ ID NO: 1; preferably wherein said sequence section SS-01 ranges from position 3 of inventive SEQ ID NO:1 to position 10 of inventive SEQ ID NO: 1; preferably in one or more or all positions selected from S3, S4, S8, L9, and N10.

Preferred mutations in position S3 of inventive SEQ ID NO: 1 are preferably selected from S3A, S3R, S3N, S3D, S3C, S3Q, S3E, S3G, S3H, S3I, S3L, S3K, S3M, S3F, S3P, S3T, S3W, S3Y, and S3V; more preferably S3I; and/or preferred mutations in position S4 of inventive SEQ ID NO: 1 are preferably selected from S4A, S4R, S4N, S4D, S4C, S4Q, S4E, S4G, S4H, S41, S4L, S4K, S4M, S4F, S4P, S4T, S4W, S4Y, and S4V; more preferably S4N; and/or preferred mutations in position S8 of inventive SEQ ID NO: 1 are preferably selected from S8A, S8R, S8N, S8D, S8C, S8Q, S8E, S8G, S8H, S8I, S8L, S8K, S8M, S8F, S8P, S8T, S8W, S8Y, and S8V; more preferably S8A; and/or preferred mutations in position L9 of inventive SEQ ID NO: 1 are preferably selected from L9A, L9R, L9N, L9D, L9C, L9Q, L9E, L9G, L9H, L91, L9K, L9M, L9F, L9P, L9S, L9T, L9W, L9Y, and L9V; more preferably selected from L9C, L9M, L9R, L9K, L9Q, and L9G; and/or preferred mutations in position N10 of inventive SEQ ID NO: 1 are preferably selected from N10A, N I0R, N10D, N10C, N10Q, N10E, N10G, N10H, N10I, N10L, N10K, N10M, N10F, N10P, N10S, N10T, N10W, N10Y, and N10V; more preferably N10G.

In preferred embodiments, the ketoreductase according to the invention differs from the ketoreductase of inventive SEQ ID NO:1 by at least one residue change in a sequence section SS-02 of inventive SEQ ID NO: 1, wherein said sequence section SS-02 ranges from position 11 of inventive SEQ ID NO: 1 to position 20 of inventive SEQ ID NO: 1; preferably wherein said sequence section SS-02 ranges from position 11 of inventive SEQ ID NO: 1 to position 16 of inventive SEQ ID NO: 1; preferably in one or more or all positions selected from A11 and V13.

Preferred mutations in position A11 of inventive SEQ ID NO: 1 are preferably selected from A11R, A11N, A11D, A11C, A11Q, A11E, A11G, A11H, A11I, A11L, A11K, A11M, A11F, A11P, A11S, A11T, A11W, A11Y, and A11V; more preferably selected from A11V and A11C; and/or preferred mutations in position V13 of inventive SEQ ID NO: 1 are preferably selected from V13A, V13R, V13N, V13D, V13C, V13Q, V13E, V13G, V13H, V13I, V13L, V13K, V13M, V13F, V13P, V13S, V13T, V13W, and V13Y; more preferably V13G.

In preferred embodiments, the ketoreductase according to the invention differs from the ketoreductase of inventive SEQ ID NO:1 by at least one residue change in a sequence section SS-03 of inventive SEQ ID NO: 1, wherein said sequence section SS-03 ranges from position 21 of inventive SEQ ID NO: 1 to position 30 of inventive SEQ ID NO: 1; preferably wherein said sequence section SS-03 ranges from position 22 of inventive SEQ ID NO: 1 to position 30 of inventive SEQ ID NO: 1; preferably in one or more or all positions selected from E22, S25, M26, and A30.

Preferred mutations in position E22 of inventive SEQ ID NO: 1 are preferably selected from E22A, E22R, E22N, E22D, E22C, E22Q, E22G, E22H, E22I, E22L, E22K, E22M, E22F, E22P, E22S, E22T, E22W, E22Y, and E22V; more preferably E22K; and/or
preferred mutations in position S25 of inventive SEQ ID NO: 1 are preferably selected from S25A, S25R, S25N, S25D, S25C, S25Q, S25E, S25G, S25H, S25I, S25L, S25K, S25M, S25F, S25P, S25T, S25W, S25Y, and S25V; more preferably S25A; and/or
preferred mutations in position M26 of inventive SEQ ID NO:1 are preferably selected from M26A, M26R, M26N, M26D, M26C, M26Q, M26E, M26G, M26H, M26I, M26L, M26K, M26F, M26P, M26S, M26T, M26W, M26Y, and M26V; more preferably M26R; and/or
preferred mutations in position A30 of inventive SEQ ID NO: 1 are preferably selected from A30R, A30N, A30D, A30C, A30Q, A30E, A30G, A30H, A30I, A30L, A30K, A30M, A30F, A30P, A30S, A30T, A30W, A30Y, and A30V; more preferably A30R.

In preferred embodiments, the ketoreductase according to the invention differs from the ketoreductase of inventive SEQ ID NO:1 by at least one residue change in a sequence section SS-04 of inventive SEQ ID NO: 1, wherein said sequence section SS-04 ranges from position 31 of inventive SEQ ID NO: 1 to position 40 of inventive SEQ ID NO: 1; preferably wherein said sequence section SS-04 ranges from position 31 of inventive SEQ ID NO: 1 to position 39 of inventive SEQ ID NO: 1; preferably in one or more or all positions selected from E31, A38, and S39.

Preferred mutations in position E31 of inventive SEQ ID NO: 1 are preferably selected from E31A, E31R, E31N, E31D, E31C, E31Q, E31G, E31H, E31I, E31L, E31K, E31M, E31F, E31P, E31, E31T, E31W, E31Y, and E31V; more preferably E31N; and/or
preferred mutations in position A38 of inventive SEQ ID NO: 1 are preferably selected from A38R, A38N, A38D, A38C, A38Q, A38E, A38G, A38H, A38I, A38L, A38K, A38M, A38F, A38P, A38S, A38T, A38W, A38Y, and A38V; more preferably A38M; and/or
preferred mutations in position S39 of inventive SEQ ID NO: 1 are preferably selected from S39A, S39R, S39N, S39D, S39C, S39Q, S39E, S39G, S39H, S39I, S39L, S39K, S39M, S39F, S39P, S39T, S39W, S39Y, and S39V; more preferably selected from S39G and S39A.

In preferred embodiments, the ketoreductase according to the invention differs from the ketoreductase of inventive SEQ ID NO:1 by at least one residue change in a sequence section SS-05 of inventive SEQ ID NO: 1, wherein said sequence section SS-05 ranges from position 41 of inventive SEQ ID NO:1 to position 50 of inventive SEQ ID NO: 1; preferably wherein said sequence section SS-05 ranges from position 42 of inventive SEQ ID NO: 1 to position 50 of inventive SEQ ID NO: 1; preferably in one or more or all positions selected from L42, E43, Q44, K49, and A50.

Preferred mutations in position L42 of inventive SEQ ID NO: 1 are preferably selected from L42A, L42R, L42N, L42D, L42C, L42Q, L42E, L42G, L42H, L42I, L42K, L42M, L42F, L42P, L42S, L42T, L42W, L42Y, and L42V; more preferably L42Y; and/or
preferred mutations in position E43 of inventive SEQ ID NO: 1 are preferably selected from E43A, E43R, E43N, E43D, E43C, E43Q, E43G, E43H, E43I, E43L, E43K, E43M, E43F, E43P, E43S, E43T, E43W, E43Y, and E43V; more preferably E43K; and/or
preferred mutations in position Q44 of inventive SEQ ID NO: 1 are preferably selected from Q44A, Q44R, Q44N, Q44D, Q44C, Q44E, Q44G, Q44H, Q44I, Q44L, Q44K, Q44M, Q44F, Q44P, Q44S, Q44T, Q44W, Q44Y, and Q44V; more preferably selected from Q44T, Q44E, and Q44R; and/or
preferred mutations in position K49 of inventive SEQ ID NO: 1 are preferably selected from K49A, K49R, K49N, K49D, K49C, K49Q, K49E, K49G, K49H, K49I, K49L, K49M, K49F, K49P, K49S, K49T, K49W, K49Y, and K49V; more preferably K49R; and/or
preferred mutations in position A50 of inventive SEQ ID NO: 1 are preferably selected from A50R, A50N, A50D, A50C, A50Q, A50E, A50G, A50H, A50I, A50L, A50K, A50M, A50F, A50P, A50S, A50T, A50W, A50Y, and A50V; more preferably A50K.

In preferred embodiments, the ketoreductase according to the invention differs from the ketoreductase of inventive SEQ ID NO:1 by at least one residue change in a sequence section SS-06 of inventive SEQ ID NO: 1, wherein said sequence section SS-06 ranges from position 51 of inventive SEQ ID NO:1 to position 60 of inventive SEQ ID NO: 1; preferably wherein said sequence section SS-06 ranges from position 54 of inventive SEQ ID NO:1 to position 60 of inventive SEQ ID NO: 1; preferably in one or more or all positions selected from I54, V55, K56, Q57, and T60.

Preferred mutations in position I54 of inventive SEQ ID NO: 1 are preferably selected from I54A, I54R, I54N, I54D, I54C, I54Q, I54E, I54G, I54H, I54L, I54K, I54M, I54F, I54P, I54S, I54T, I54W, I54Y, and I54V; more preferably selected from I54R and I54V; and/or
preferred mutations in position V55 of inventive SEQ ID NO:1 are preferably selected from V55A, V55R, V55N, V55D, V55C, V55Q, V55E, V55G, V55H, V55I, V55L, V55K, V55M, V55F, V55P, V55S, V55T, V55W, and V55Y; more preferably selected from V55I and V55C; and/or
preferred mutations in position K56 of inventive SEQ ID NO: 1 are preferably selected from K56A, K56R, K56N, K56D, K56C, K56Q, K56E, K56G, K56H, K56I, K56L, K56M, K56F, K56P, K56S, K56T, K56W, K56Y, and K56V; more preferably K56M; and/or
preferred mutations in position Q57 of inventive SEQ ID NO: 1 are preferably selected from Q57A, Q57R, Q57N, Q57D, Q57C, Q57E, Q57G, Q57H, Q57I, Q57L, Q57K, Q57M, Q57F, Q57P, Q57S, Q57T, Q57W, Q57Y, and Q57V; more preferably selected from Q57P and Q57A; and/or
preferred mutations in position T60 of inventive SEQ ID NO: 1 are preferably selected from T60A, T60R, T60N, T60D, T60C, T60Q, T60E, T60G, T60H, T60I, T60L, T60K, T60M, T60F, T60P, T60S, T60W, T60Y, and T60V; more preferably selected from T60C, T60N, and T60A.

In preferred embodiments, the ketoreductase according to the invention differs from the ketoreductase of inventive SEQ ID NO:1 by at least one residue change in a sequence section SS-07 of inventive SEQ ID NO: 1, wherein said sequence section SS-07 ranges from position 61 of inventive SEQ ID NO:1 to position 70 of inventive SEQ ID NO: 1; preferably wherein said sequence section SS-07 ranges from position 63 of inventive SEQ ID NO: 1 to position 70 of inventive SEQ ID NO: 1; preferably in one or more or all positions selected from S69 and D70.

Preferred mutations in position S69 of inventive SEQ ID NO: 1 are preferably selected from S69A, S69R, S69N, S69D, S69C, S69Q, S69E, S69G, S69H, S69I, S69L, S69K, S69M, S69F, S69P, S69T, S69W, S69Y, and S69V; more preferably selected from S69V and S69A; and/or
preferred mutations in position D70 of inventive SEQ ID NO: 1 are preferably selected from D70A, D70R, D70N, D70C, D70Q, D70E, D70G, D70H, D70I, D70L, D70K, D70M, D70F, D70P, D70S, D70T, D70W, D70Y, and D70V; more preferably selected from D70C and D70S.

In preferred embodiments, the ketoreductase according to the invention differs from the ketoreductase of inventive SEQ ID NO:1 by at least one residue change in a sequence section SS-08 of inventive SEQ ID NO: 1, wherein said sequence section SS-08 ranges from position 71 of inventive SEQ ID NO:1 to position 80 of inventive SEQ ID NO: 1; preferably wherein said sequence section SS-08 ranges from position 75 of inventive SEQ ID NO: 1 to position 77 of inventive SEQ ID NO: 1; preferably in one or more or all positions selected from G75, S76, and F77.

Preferred mutations in position G75 of inventive SEQ ID NO: 1 are preferably selected from G75A, G75R, G75N, G75D, G75C, G75Q, G75E, G75H, G75I, G75L, G75K, G75M, G75F, G75P, G75S, G75T, G75W, G75Y, and G75V; more preferably G75L; and/or
preferred mutations in position S76 of inventive SEQ ID NO: 1 are preferably selected from S76A, S76R, S76N, S76D, S76C, S76Q, S76E, S76G, S76H, S76I, S76L, S76K, S76M, S76F, S76P, S76T, S76W, S76Y, and S76V; more preferably selected from S76M, S76C, S76L, and S76G; and/or
preferred mutations in position F77 of inventive SEQ ID NO: 1 are preferably selected from F77A, F77R, F77N, F77D, F77C, F77Q, F77E, F77G, F77H, F77I, F77L, F77K, F77M, F77P, F77S, F77T, F77W, F77Y, and F77V; more preferably F77L.

In preferred embodiments, the ketoreductase according to the invention differs from the ketoreductase of inventive SEQ ID NO:1 by at least one residue change in a sequence section SS-09 of inventive SEQ ID NO: 1, wherein said sequence section SS-09 ranges from position 81 of inventive SEQ ID NO:1 to position 90 of inventive SEQ ID NO: 1; preferably wherein said sequence section SS-09 ranges from position 82 of inventive SEQ ID NO: 1 to position 89 of inventive SEQ ID NO: 1.

In preferred embodiments, the ketoreductase according to the invention differs from the ketoreductase of inventive SEQ ID NO:1 by at least one residue change in a sequence section SS-10 of inventive SEQ ID NO: 1, wherein said sequence section SS-10 ranges from position 91 of inventive SEQ ID NO:1 to position 100 of inventive SEQ ID NO: 1; preferably wherein said sequence section SS-10 ranges from position 92 of inventive SEQ ID NO: 1 to position 100 of inventive SEQ ID NO: 1; preferably in one or more or all positions selected from S92, S97, Q98, F99, and S100.

Preferred mutations in position S92 of inventive SEQ ID NO: 1 are preferably selected from S92A, S92R, S92N, S92D, S92C, S92Q, S92E, S92G, S92H, S92I, S92L, S92K, S92M, S92F, S92P, S92T, S92W, S92Y, and S92V; more preferably selected from S92M and S92G; and/or preferred mutations in position S97 of inventive SEQ ID NO: 1 are preferably selected from S97A, S97R, S97N, S97D, S97C, S97Q, S97E, S97G, S97H, S97I, S97L, S97K, S97M, S97F, S97P, S97T, S97W, S97Y, and S97V; more preferably selected from S97A, S97W, S97V, S97C, S97F, and S97M; more preferably selected from S97V and S97C; most preferably selected from S97C; and/or
preferred mutations in position Q98 of inventive SEQ ID NO: 1 are preferably selected from Q98A, Q98R, Q98N, Q98D, Q98C, Q98E, Q98G, Q98H, Q98I, Q98L, Q98K, Q98M, Q98F, Q98P, Q98S, Q98T, Q98W, Q98Y, and Q98V; more preferably Q98E; and/or
preferred mutations in position F99 of inventive SEQ ID NO: 1 are preferably selected from F99A, F99R, F99N, F99D, F99C, F99Q, F99E, F99G, F99H, F99I, F99L, F99K, F99M, F99P, F99S, F99T, F99W, F99Y, and F99V; more preferably F99R; and/or
preferred mutations in position S100 of inventive SEQ ID NO:1 are preferably selected from S100A, S100R, S100N, S100D, S100C, S100Q, S100E, S100G, S100H, S100I, S100L, S100K, S100M, S100F, S100P, S100T, S100W, S100Y, and S100V; more preferably selected from S100E, S100Q, S100R, S100V, and S100C; most preferably selected from S100R.

In preferred embodiments, the ketoreductase according to the invention differs from the ketoreductase of inventive SEQ ID NO:1 by at least one residue change in a sequence section SS-11 of inventive SEQ ID NO: 1, wherein said sequence section SS-1 ranges from position 101 of inventive SEQ ID NO:1 to position 110 of inventive SEQ ID NO: 1; preferably wherein said sequence section SS-11 ranges from position 101 of inventive SEQ ID NO: 1 to position 109 of inventive SEQ ID NO: 1; preferably in one or more or all positions selected from P101, A106, A108, and D109.

Preferred mutations in position P101 of inventive SEQ ID NO:1 are preferably selected from P101A, P101R, P101N, P101D, P101C, P101Q, P101E, P101G, P101H, P101I, P101L, P101K, P101M, P101F, P101S, P101T, P101W, P101Y, and P101V; more preferably selected from P101F, P101H, and P101W; and/or
preferred mutations in position A106 of inventive SEQ ID NO:1 are preferably selected from A106R, A106N, A106D, A106C, A106Q, A106E, A106G, A106H, A106I, A106L, A106K, A106M, A106F, A106P, A106S, A106T, A106W, A106Y, and A106V; more preferably selected from A106C and A106E; and/or
preferred mutations in position A108 of inventive SEQ ID NO:1 are preferably selected from A108R, A108N, A108D, A108C, A108Q, A108E, A108G, A108H, A108I, A108L, A108K, A108M, A108F, A108P, A108S, A108T, A108W, A108Y, and A108V; more preferably A108P; and/or
preferred mutations in position D109 of inventive SEQ ID NO:1 are preferably selected from D109A, D109R, D109N, D109C, D109Q, D109E, D109G, D109H, D109I, D109L, D109K, D109M, D109F, D109P, D109S, D109T, D109W, D109Y, and D109V; more preferably selected from D109G and D109R.

In preferred embodiments, the ketoreductase according to the invention differs from the ketoreductase of inventive SEQ ID NO:1 by at least one residue change in a sequence section SS-12 of inventive SEQ ID NO: 1, wherein said sequence section SS-12 ranges from position 111 of inventive SEQ ID NO:1 to position 120 of inventive SEQ ID NO: 1; preferably wherein said sequence section SS-12 ranges from position 112 of inventive SEQ ID NO: 1 to position 120 of inventive SEQ ID NO: 1; preferably in one or more or all positions selected from N112, M113, L114, T119, and A120.

Preferred mutations in position N112 of inventive SEQ ID NO:1 are preferably selected from N112A, N112R, N112D, N112C, N112Q, N112E, N112G, N112H, N112I, N112L, N112K, N112M, N112F, N112P, N112S, N112T, N112W, N112Y, and N112V; more preferably N112T; and/or
preferred mutations in position M113 of inventive SEQ ID NO:1 are preferably selected from M113A, M113R, M113N, M113D, M113C, M113Q, M113E, M113G, M113H, M113I, M113L, M113K, M113F, M113P, M113S, M113T, M113W, M113Y, and M113V; more preferably M113V; and/or
preferred mutations in position L114 of inventive SEQ ID NO:1 are preferably selected from L114A, L114R, L114N, L114D, L114C, L114Q, L114E, L114G, L114H, L114I, L114K, L114M, L114F, L114P, L114S, L114T, L114W, L114Y, and L114V; more preferably selected from L114V and L114I; and/or
preferred mutations in position T119 of inventive SEQ ID NO:1 are preferably selected from T119A, T119R, T119N, T119D, T119C, T119Q, T119E, T119G, T119H, T119I, T119L, T119K, T119M, T119F, T119P, T119S, T119W, T119Y, and T119V; more preferably T119L; and/or
preferred mutations in position A120 of inventive SEQ ID NO:1 are preferably selected from A120R, A120N, A120D, A120C, A120Q, A120E, A120G, A120H, A120I, A120L, A120K, A120M, A120F, A120P, A120S, A120T, A120W, A120Y, and A120V; more preferably A120G.

In preferred embodiments, the ketoreductase according to the invention differs from the ketoreductase of inventive SEQ ID NO:1 by at least one residue change in a sequence section SS-13 of inventive SEQ ID NO: 1, wherein said sequence section SS-13 ranges from position 121 of inventive SEQ ID NO:1 to position 130 of inventive SEQ ID NO: 1; preferably wherein said sequence section SS-13 ranges from position 121 of inventive SEQ ID NO: 1 to position 127 of inventive SEQ ID NO: 1; preferably in one or more or all positions selected from P121, and A127.

Preferred mutations in position P121 of inventive SEQ ID NO:1 are preferably selected from P121A, P121R, P121N, P121D, P121C, P121Q, P121E, P121G, P121H, P121I, P121L, P121K, P121M, P121F, P121S, P121T, P121W, P121Y, and P121V; more preferably selected from P121V, and P121A; most preferably selected from P121V; and/or
preferred mutations in position A127 of inventive SEQ ID NO:1 are preferably selected from A127R, A127N, A127D, A127C, A127Q, A127E, A127G, A127H, A127I, A127L, A127K, A127M, A127F, A127P, A127S, A127T, A127W, A127Y, and A127V; more preferably selected from A127K, A127C, A127G, and A127Q.

In preferred embodiments, the ketoreductase according to the invention differs from the ketoreductase of inventive SEQ ID NO:1 by at least one residue change in a sequence section SS-14 of inventive SEQ ID NO: 1, wherein said sequence section SS-14 ranges from position 131 of inventive SEQ ID NO:1 to position 140 of inventive SEQ ID NO: 1; preferably wherein said sequence section SS-14 ranges from position 132 of inventive SEQ ID NO: 1 to position 139 of inventive SEQ ID NO: 1; preferably in one or more or all positions selected from I132, S133, P136, Q138, and T139.

Preferred mutations in position I132 of inventive SEQ ID NO:1 are preferably selected from I132A, I132R, I132N, I132D, I132C, I132Q, I132E, I132G, I132H, I132L, I132K, I132M, I132F, I132P, I132S, I132T, I132W, I132Y, and I132V; more preferably selected from I132V, I132W, and I132F; and/or
preferred mutations in position S133 of inventive SEQ ID NO:1 are preferably selected from S133A, S133R, S133N, S133D, S133C, S133Q, S133E, S133G, S133H, S133I, S133L, S133K, S133M, S133F, S133P, S133T, S133W, S133Y, and S133V; more preferably selected from S133M, S133L, S133A, S133Q, and S133V; and/or
preferred mutations in position P136 of inventive SEQ ID NO:1 are preferably selected from P136A, P136R, P136N, P136D, P136C, P136Q, P136E, P136G, P136H, P136I, P136L, P136K, P136M, P136F, P136S, P136T, P136W, P136Y, and P136V; more preferably selected from P136V and P136G; and/or
preferred mutations in position Q138 of inventive SEQ ID NO:1 are preferably selected from Q138A, Q138R, Q138N, Q138D, Q138C, Q138E, Q138G, Q138H, Q138I, Q138L, Q138K, Q138M, Q138F, Q138P, Q138S, Q138T, Q138W, Q138Y, and Q138V; more preferably selected from Q138A, Q138T, and Q138S; and/or
preferred mutations in position T139 of inventive SEQ ID NO:1 are preferably selected from T139A, T139R, T139N, T139D, T139C, T139Q, T139E, T139G, T139H, T139I, T139L, T139K, T139M, T139F, T139P, T139S, T139W, T139Y, and T139V; more preferably selected from T139V, T139F, and, T139K.

In preferred embodiments, the ketoreductase according to the invention differs from the ketoreductase of inventive SEQ ID NO:1 by at least one residue change in a sequence section SS-15 of inventive SEQ ID NO: 1, wherein said sequence section SS-15 ranges from position 141 of inventive SEQ ID NO:1 to position 150 of inventive SEQ ID NO: 1; preferably wherein said sequence section SS-15 ranges from position 141 of inventive SEQ ID NO: 1 to position 149 of inventive SEQ ID NO: 1; preferably in one or more or all positions selected from A141, G147, T148, and G149.

Preferred mutations in position A141 of inventive SEQ ID NO:1 are preferably selected from A141R, A141N, A141D, A141C, A141Q, A141E, A141G, A141H, A141I, A141L, A141K, A141M, A141F, A141P, A141S, A141T, A141W, A141Y, and A141V; more preferably A141S; and/or
preferred mutations in position G147 of inventive SEQ ID NO:1 are preferably selected from G147A, G147R, G147N, G147D, G147C, G147Q, G147E, G147H, G147I, G147L, G147K, G147M, G147F, G147P, G147S, G147T, G147W, G147Y, and G147V; more preferably G147C; and/or
preferred mutations in position T148 of inventive SEQ ID NO:1 are preferably selected from T148A, T148R, T148N, T148D, T148C, T148Q, T148E, T148G, T148H, T148I, T148L, T148K, T148M, T148F, T148P, T148S, T148W, T148Y, and T148V; more preferably T148S; and/or
preferred mutations in position G149 of inventive SEQ ID NO:1 are preferably selected from G149A, G149R, G149N, G149D, G149C, G149Q, G149E, G149H, G149I, G149L, G149K, G149M, G149F, G149P, G149S, G149T, G149W, G149Y, and G149V; more preferably selected from G149C, G149V, G149M, G149I and G149S, most preferably selected from G149C, G149V, G149M and G149I.

In preferred embodiments, the ketoreductase according to the invention differs from the ketoreductase of inventive SEQ ID NO:1 by at least one residue change in a sequence section SS-16 of inventive SEQ ID NO: 1, wherein said sequence section SS-16 ranges from position 151 of inventive SEQ ID NO:1 to position 160 of inventive SEQ ID NO: 1; preferably wherein said sequence section SS-16 ranges from position 151 of inventive SEQ ID NO: 1 to position 159 of inventive SEQ ID NO: 1; preferably in one or more or all positions selected from S151, K152, A155, M157, V158, and G159.

Preferred mutations in position S151 of inventive SEQ ID NO:1 are preferably selected from S151A, S151R, S151N, S151D, S151C, S151Q, S151E, S151G, S151H, S151I, S151L, S151K, S151M, S151F, S151P, S151T, S151W, S151Y, and S151V; more preferably S151A; and/or
preferred mutations in position K152 of inventive SEQ ID NO:1 are preferably selected from K152A, K152R, K152N, K152D, K152C, K152Q, K152E, K152G, K152H, K152I, K152L, K152M, K152F, K152P, K152S, K152T, K152W, K152Y, and K152V; more preferably K152A; and/or
preferred mutations in position A155 of inventive SEQ ID NO:1 are preferably selected from A155R, A155N, A155D, A155C, A155Q, A155E, A155G, A155H, A155I, A155L, A155K, A155M, A155F, A155P, A155S, A155T, A155W, A155Y, and A155V; more preferably A155W and A155H; and/or
preferred mutations in position M157 of inventive SEQ ID NO:1 are preferably selected from M157A, M157R, M157N, M157D, M157C, M157Q, M157E, M157G, M157H, M157I, M157L, M157K, M157F, M157P, M157S, M157T, M157W, M157Y, and M157V; more preferably selected from M157F, M157R, M157G, M157C, M157E, M157D and M157K; and/or
preferred mutations in position V158 of inventive SEQ ID NO:1 are preferably selected from V158A, V158R, V158N, V158D, V158C, V158Q, V158E, V158G, V158H, V158I, V158L, V158K, V158M, V158F, V158P, V158S, V158T, V158W, and V158Y; more preferably V158M; and/or
preferred mutations in position G159 of inventive SEQ ID NO:1 are preferably selected from G159A, G159R, G159N, G159D, G159C, G159Q, G159E, G159H, G159I, G159L, G159K, G159M, G159F, G159P, G159S, G159T, G159W, G159Y, and G159V; more preferably selected from G159S and G159A.

In preferred embodiments, the ketoreductase according to the invention differs from the ketoreductase of inventive SEQ ID NO:1 by at least one residue change in a sequence section SS-17 of inventive SEQ ID NO: 1, wherein said sequence section SS-17 ranges from position 161 of inventive SEQ ID NO:1 to position 170 of inventive SEQ ID NO: 1; preferably wherein said sequence section SS-17 ranges from position 168 of inventive SEQ ID NO: 1 to position 170 of inventive SEQ ID NO: 1; preferably in one or more or all positions selected from D169.

Preferred mutations in position D169 of inventive SEQ ID NO:1 are preferably selected from D169A, D1169R, D169N, D169C, D169Q, D169E, D169G, D169H, D169I, D169L, D169K, D169M, D169F, D169P, D169S, D169T, D169W, D169Y, and D169V; more preferably D169E.

In preferred embodiments, the ketoreductase according to the invention differs from the ketoreductase of inventive SEQ ID NO:1 by at least one residue change in a sequence section SS-18 of inventive SEQ ID NO: 1, wherein said sequence section SS-18 ranges from position 171 of inventive SEQ ID NO:1 to position 180 of inventive SEQ ID NO: 1; preferably wherein said sequence section SS-18 ranges from position 172 of inventive SEQ ID NO: 1 to position 177 of inventive SEQ ID NO: 1; preferably in one or more or all positions selected from M172.

Preferred mutations in position M172 of inventive SEQ ID NO:1 are preferably selected from M172A, M172R, M172N, M172D, M172C, M172Q, M172E, M172G, M172H, M172I, M172L, M172K, M172F, M172P, M172S, M172T, M172W, M172Y, and M172V; more preferably M172C.

In preferred embodiments, the ketoreductase according to the invention differs from the ketoreductase of inventive SEQ ID NO:1 by at least one residue change in a sequence section SS-19 of inventive SEQ ID NO: 1, wherein said sequence section SS-19 ranges from position 181 of inventive SEQ ID NO:1 to position 190 of inventive SEQ ID NO: 1; preferably wherein said sequence section SS-19 ranges from position 181 of inventive SEQ ID NO: 1 to position 185 of inventive SEQ ID NO: 1; preferably in one or more or all positions selected from P181, K182, and N185.

Preferred mutations in position P181 of inventive SEQ ID NO:1 are preferably selected from P181A, P181R, P181N, P181D, P181C, P181Q, P181E, P181G, P181H, P181I, P181L, P181K, P181M, P181F, P181S, P181T, P181W, P181Y, and P181V; more preferably selected from P181V, P181W, and P181L; and/or
preferred mutations in position K182 of inventive SEQ ID NO:1 are preferably selected from K182A, K182R, K182N, K182D, K182C, K182Q, K182E, K182G, K182H, K182I, K182L, K182M, K182F, K182P, K182S, K182T, K182W, K182Y, and K182V; more preferably K182I; and/or
preferred mutations in position N185 of inventive SEQ ID NO:1 are preferably selected from N185A, N185R, N185D, N185C, N185Q, N185E, N185G, N185H, N185I, N185L, N185K, N185M, N185F, N185P, N185S, N185T, N185W, N185Y, and N185V; more preferably N185R.

In preferred embodiments, the ketoreductase according to the invention differs from the ketoreductase of inventive SEQ ID NO:1 by at least one residue change in a sequence section SS-20 of inventive SEQ ID NO: 1, wherein said sequence section SS-20 ranges from position 191 of inventive SEQ ID NO:1 to position 200 of inventive SEQ ID NO: 1; preferably wherein said sequence section SS-20 ranges from position 194 of inventive SEQ ID NO: 1 to position 200 of inventive SEQ ID NO: 1; preferably in one or more or all positions selected from T194, A199, and E200.

Preferred mutations in position T194 of inventive SEQ ID NO:1 are preferably selected from T194A, T194R, T194N, T194D, T194C, T194Q, T194E, T194G, T194H, T194I, T194L, T194K, T194M, T194F, T194P, T194S, T194W, T194Y, and T194V; more preferably T194V; and/or
preferred mutations in position A199 of inventive SEQ ID NO:1 are preferably selected from A199R, A199N, A199D, A199C, A199Q, A199E, A199G, A199H, A199I, A199L, A199K, A199M, A199F, A199P, A199S, A199T, A199W, A199Y, and A199V; more preferably A199C; and/or
preferred mutations in position E200 of inventive SEQ ID NO:1 are preferably selected from E200A, E200R, E200N, E200D, E200C, E200Q, E200G, E200H, E200I, E200L, E200K, E200M, E200F, E200P, E200S, E200T, E200W, E200Y, and E200V; more preferably selected from E200P, E200V, and E200A.

In preferred embodiments, the ketoreductase according to the invention differs from the ketoreductase of inventive SEQ ID NO:1 by at least one residue change in a sequence section SS-21 of inventive SEQ ID NO: 1, wherein said sequence section SS-21 ranges from position 201 of inventive SEQ ID NO:1 to position 210 of inventive SEQ ID NO: 1; preferably wherein said sequence section SS-21 ranges from position 202 of inventive SEQ ID NO: 1 to position 210 of inventive SEQ ID NO: 1; preferably in one or more or all positions selected from I202, P204, M206, D208, L209 and P210.

Preferred mutations in position I202 of inventive SEQ ID NO:1 are preferably selected from I202A, I202R, I202N, I202D, I202C, I202Q, I202E, I202G, I202H, I202L, I202K, I202M, I202F, I202P, I202S, I202T, I202W, I202Y, and I202V; more preferably I202V; and/or preferred mutations in position P204 of inventive SEQ ID NO:1 are preferably selected from P204A, P204R, P204N, P204D, P204C, P204Q, P204E, P204G, P204H, P204I, P204L, P204K, P204M, P204F, P204S, P204T, P204W, P204Y, and P204V; more preferably P204L; and/or preferred mutations in position M206 of inventive SEQ ID NO:1 are preferably selected from M206A, M206R, M206N, M206D, M206C, M206Q, M206E, M206G, M206H, M2061, M206L, M206K, M206F, M206P, M206S, M206T, M206W, M206Y, and M206V; more preferably selected from M206T, M206D, M206G, and M206A; most preferably selected from M206D; and/or preferred mutations in position D208 of inventive SEQ ID NO: 1 are preferably selected from D208A, D208R, D208N, D208C, D208Q, D208E, D208G, D208H, D208I, D208L, D208K, D208M, D208F, D208P, D208S, D208T, D208W, D208Y, and D208V; more preferably selected from D208H, D208C, and D208N; and/or preferred mutations in position L209 of inventive SEQ ID NO:1 are preferably selected from L209A, L209R, L209N, L209D, L209C, L209Q, L209E, L209G, L209H, L209I, L209K, L209M, L209F, L209P, L209S, L209T, L209W, L209Y, and L209V; more preferably L209C; and/or preferred mutations in position P210 of inventive SEQ ID NO:1 are preferably selected from P210A, P210R, P210N, P210D, P210C, P210Q, P210E, P210G, P210H, P210I, P210L, P210K, P210M, P210F, P210S, P210T, P210W, P210Y, and P210V; more preferably P210C.

In preferred embodiments, the ketoreductase according to the invention differs from the ketoreductase of inventive SEQ ID NO:1 by at least one residue change in a sequence section SS-22 of inventive SEQ ID NO: 1, wherein said sequence section SS-22 ranges from position 211 of inventive SEQ ID NO:1 to position 220 of inventive SEQ ID NO: 1; preferably wherein said sequence section SS-22 ranges from position 212 of inventive SEQ ID NO: 1 to position 220 of inventive SEQ ID NO: 1; preferably in one or more or all positions selected from N212, G213, W214, I1215, V217, and I220.

Preferred mutations in position N212 of inventive SEQ ID NO:1 are preferably selected from N212A, N212R, N212D, N212C, N212Q, N212E, N212G, N212H, N212I, N212L, N212K, N212M, N212F, N212P, N212S, N212T, N212W, N212Y, and N212V; more preferably selected from N212K, N212P, and N212A; and/or preferred mutations in position G213 of inventive SEQ ID NO: 1 are preferably selected from G213A, G213R, G213N, G213D, G213C, G213Q, G213E, G213H, G213I, G213L, G213K, G213M, G213F, G213P, G213S, G213T, G213W, G213Y, and G213V; more preferably G213D; and/or preferred mutations in position W214 of inventive SEQ ID NO: 1 are preferably selected from W214A, W214R, W214N, W214D, W214C, W214Q, W214E, W214G, W214H, W214I, W214L, W214K, W214M, W214F, W214P, W214S, W214T, W214Y, and W214V; more preferably W214G; and/or preferred mutations in position I215 of inventive SEQ ID NO: 1 are preferably selected from I215A, I215R, I215N, I215D, I215C, I215Q, I215E, I215G, I215H, I215L, I215K, I215M, I215F, I215P, I215S, I215T, I215W, I215Y, and I215V; more preferably I215T; and/or preferred mutations in position V217 of inventive SEQ ID NO: 1 are preferably selected from V217A, V217R, V217N, V217D, V217C, V217Q, V217E, V217G, V217H, V217I, V217L, V217K, V217M, V217F, V217P, V217S, V217T, V217W, and V217Y; more preferably selected from V217N and V217P; and/or preferred mutations in position I220 of inventive SEQ ID NO: 1 are preferably selected from I220A, I220R, I220N, I220D, I220C, I220Q, I220E, I220G, I220H, I220L, I220K, I220M, I220F, I220P, I220S, I220T, I220W, I220Y, and I220V; more preferably I220V.

In preferred embodiments, the ketoreductase according to the invention differs from the ketoreductase of inventive SEQ ID NO:1 by at least one residue change in a sequence section SS-23 of inventive SEQ ID NO: 1, wherein said sequence section SS-23 ranges from position 221 of inventive SEQ ID NO:1 to position 230 of inventive SEQ ID NO: 1; preferably wherein said sequence section SS-23 ranges from position 225 of inventive SEQ ID NO: 1 to position 227 of inventive SEQ ID NO: 1; preferably in one or more or all positions selected from T225, and L227.

Preferred mutations in position T225 of inventive SEQ ID NO:1 are preferably selected from T225A, T225R, T225N, T225D, T225C, T225Q, T225E, T225G, T225H, T225I, T225L, T225K, T225M, T225F, T225P, T225S, T225W, T225Y, and T225V; more preferably selected from T225M and T225I; and/or preferred mutations in position L227 of inventive SEQ ID NO:1 are preferably selected from L227A, L227R, L227N, L227D, L227C, L227Q, L227E, L227G, L227H, L2271, L227K, L227M, L227F, L227P, L227S, L227T, L227W, L227Y, and L227V; more preferably L227V.

In preferred embodiments, the ketoreductase according to the invention differs from the ketoreductase of inventive SEQ ID NO:1 by at least one residue change in a sequence section SS-24 of inventive SEQ ID NO: 1, wherein said sequence section SS-24 ranges from position 231 of inventive SEQ ID NO:1 to position 240 of inventive SEQ ID NO: 1; preferably wherein said sequence section SS-24 ranges from position 232 of inventive SEQ ID NO: 1 to position 239 of inventive SEQ ID NO: 1; preferably in one or more or all positions selected from N232, G235, T236, T237, V238, and S239.

Preferred mutations in position N232 of inventive SEQ ID NO:1 are preferably selected from N232A, N232R, N232D, N232C, N232Q, N232E, N232G, N232H, N232I, N232L, N232K, N232M, N232F, N232P, N232S, N232T, N232W, N232Y, and N232V; more preferably selected from N232Y and N232F; and/or preferred mutations in position G235 of inventive SEQ ID NO: 1 are preferably selected from G235A, G235R, G235N, G235D, G235C, G235Q, G235E, G235H, G235I, G235L, G235K, G235M, G235F, G235P, G235S, G235T, G235W, G235Y, and G235V; more preferably G235F; and/or preferred mutations in position T236 of inventive SEQ ID NO:1 are preferably selected from T236A, T236R, T236N, T236D, T236C, T236Q, T236E, T236G, T236H, T236I, T236L, T236K, T236M, T236F, T236P, T236S, T236W, T236Y, and T236V; more preferably T236S; and/or preferred mutations in position T237 of inventive SEQ ID NO:1 are preferably selected from T237A, T237R, T237N, T237D, T237C, T237Q, T237E, T237G, T237H, T237I, T237L, T237K, T237M, T237F, T237P, T237S, T237W, T237Y, and T237V; more preferably T237I; and/or preferred mutations in position V238 of inventive SEQ ID NO: 1 are preferably selected from V238A, V238R, V238N, V238D, V238C, V238Q, V238E, V238G, V238H, V238I, V238L, V238K, V238M, V238F, V238P, V238S, V238T, V238W, and V238Y; more preferably V238F; and/or
preferred mutations in position S239 of inventive SEQ ID NO:1 are preferably selected from S239A, S239R, S239N, 5239D, S239C, S239Q, S239E, S239G, S239H, S239I, S239L, S239K, S239M, 5239F, S239P, S239T, S239W, S239Y, and S239V; more preferably S239F.

In preferred embodiments, the ketoreductase according to the invention differs from the ketoreductase of inventive SEQ ID NO:1 by at least one residue change in a sequence section SS-25 of inventive SEQ ID NO: 1, wherein said sequence section SS-25 ranges from position 241 of inventive SEQ ID NO:1 to position 246 of inventive SEQ ID NO: 1; preferably wherein said sequence section SS-25 ranges from position 243 of inventive SEQ ID NO: 1 to position 246 of inventive SEQ ID NO: 1; preferably in one or more or all positions selected from G243, Y244, C245, and A246.

Preferred mutations in position G243 of inventive SEQ ID NO:1 are preferably selected from G243A, G243R, G243N, G243D, G243C, G243Q, G243E, G243H, G243I, G243L, G243K, G243M, G243F, G243P, G2435, G243T, G243W, G243Y, and G243V; more preferably G243V; and/or
preferred mutations in position Y244 of inventive SEQ ID NO: 1 are preferably selected from Y244A, Y244R, Y244N, Y244D, Y244C, Y244Q, Y244E, Y244G, Y244H, Y244I, Y244L, Y244K, Y244M, Y244F, Y244P, Y244S, Y244T, Y244W, and Y244V; more preferably Y244F and Y244L; most preferably Y244L; and/or
preferred mutations in position C245 of inventive SEQ ID NO: 1 are preferably selected from C245A, C245R, C245N, C245D, C245Q, C245E, C245G, C245H, C245I, C245L, C245K, C245M, C245F, C245P, C2455, C245T, C245W, C245Y, and C245V; more preferably C245F; and/or
preferred mutations in position A246 of inventive SEQ ID NO: 1 are preferably selected from A246R, A246N, A246D, A246C, A246Q, A246E, A246G, A246H, A246I, A246L, A246K, A246M, A246F, A246P, A246S, A246T, A246W, A246Y, and A246V; more preferably A246F.

In a further embodiment of the third aspect of the inventions, which is also an embodiment of all previous embodiments of the third aspect, the ketoreductase according to the invention differs from the ketoreductase of inventive SEQ ID NO: 1 by at least two residue changes, by at least three residue changes, by at least four residue changes, or by at least six residue changes in one or more sequence sections SS-01 to SS-25.

In a further embodiment of the third aspect of the inventions, which is also an embodiment of all previous embodiments of the third aspect, the ketoreductase according to the invention differs from the ketoreductase of inventive SEQ ID NO: 1 by at least two residue changes, by at least three residue changes, by at least four residue changes, or by at least six residue changes of the sequences positions selected from the group consisting of S3, S4, S8, L9, N10, A11, V13, E22, S25, M26, A30, E31, A38, S39, L42, E43, Q44, K49, A50, 154, V55, K56, Q57, T60, S69, D70, G75, S76, F77, S92, S97, Q98, F99, S100, P101, A106, A108, D109, N112, M113, L114, T119, A120, P121, A127, I132, S133, P136, Q138, T139, A141, G147, T148, G149, S151, K152, A155, M157, V158, G159, D169, M172, P181, K182, N185, T194, A199, E200, I202, P204, M206, D208, L209, P210, N212, G213, W214, I1215, V217, I220, T225, L227, N232, G235, T236, T237, V238, S239, G243, Y244, C245, and A246, and preferably consisting of S97, F99, S100, P121, G147, G149, M206, P210, and Y244.

In a further embodiment of the third aspect of the inventions, which is also an embodiment of all previous embodiments of the third aspect, the ketoreductase according to the invention differs from the ketoreductase of inventive SEQ ID NO: 1 by at least two residue changes, by at least three residue changes, by at least four residue changes, or by at least six residue changes of the sequences positions selected from the group consisting of S3I, S4N, S8A, L9G, L9M, L9C, L9R, L9K, L9Q, N10G, A11V, A11C, V13G, E22K, S25A, M26R. A30R, E31N, A38M, S39G, S39A, L42Y, E43K, Q44T, Q44E, Q44R, K49R, A50K, I54R. 154V, V55I, V55C, K56M, Q57P, Q57A, T60C, T60N, T60A, S69V, S69A, D70C, D70S, G75L, S76M, S76C, S76L, S76G, F77L, S92M, S92G, S97A, S97W, S97V, S97C, S97M, S97F, Q98E, F99R, S100E, S100Q, S100R, S100V, S100C, P101F, P101H, P101W, A106C, A106E, A108P, D109G, D109R, N112T, M113V, L114V, L114I, T119L, A120G, P121V, P121A, A127K, A127C, A127G, A127Q, I132V, I132W, I132F, S133L, S133A, S133Q, S133M, S133V, P136V, P136G, Q138A, Q138T, Q138S, T139V, T139F, T139K, A141S, G147C, T148S, G149C, G149V, G149S, G149M, G149I, S151A, K152A, A155W, A155H, M157F, M157R, M157G, M157C, M157E, M157K, M157D, V158M, G159S, G159A, D169E, M172C, P181V, P181W, P181L, K182I, N185R, T194V, A199C, E200P, E200V, E200A, I202V, P204L, M206T, M206D, M206G, M206A, D208H, D208C, D208N, L209C, P210C, N212K, N212P, N212A, G213D, W214G, I215T, V217N, V217P, I220V, T225I, T225M, L227V, N232Y, N232F, G235F, T236S, T237I, V238F, S239F, G243V, Y244F, Y244L, C245F, and A246F, and preferably consisting of S97V, S97C, F99R, S100R, P121V, G147C, G1491, G149M, G149C, G149V, Y244L, M206D, and P210C.

In a preferred embodiment of the third aspect which is also an embodiment of all previous embodiments of the third aspect, the ketoreductase according to the invention differs from the ketoreductase of inventive SEQ ID NO: 1 by at least two residue change in one or more sequence sections SS-01 to SS-25.

In a preferred embodiment of the third aspect which is also an embodiment of all previous embodiments of the third aspect, the at least two amino acid positions comprises a pair of two amino acid positions, wherein the pair of two amino acid positions is selected from the group consisting of S97 and F99, S97 and S100, S97 and P121, S97 and G147, S97 and G149, S97 and M206, S97 and P210, S97 and Y244, F99 and S100, F99 and P121, F99 and G147, F99 and G149, F99 and M206, F99 and P210, F99 and Y244, S100 and P121, S100 and G147, S100 and G149, S100 and M206, S100 and P210, S100 and Y244, P121 and G147, P121 and G149, P121 and M206, P121 and P210, P121 and Y244, G147 and G149, G147 and M206, G147 and P210, G147 and Y244, G149 and M206, G149 and P210, G149 and Y244, M206 and P210, M206 and Y244 or P210 and Y244, more preferably S97 and S100, S97 and G147, S97 and G149, S97 and P210, S97 and Y244, S100 and G147, S100 and G149, S100 and P210, S100 and Y244, G147 and G149, G147 and P210, G147 and Y244, G149 and P210, G149 and Y244 or P210 and Y244, and most preferably S97 and G149, S97 and P210, S97 and Y244, G149 and P210, G149 and Y244, P210 and Y244.

Even more preferably, the at least two amino acid positions comprises a pair of two amino acid positions, wherein the pair of two amino acid positions is selected from the group consisting of S97V and F99R, S97V and S100R, S97V and P121V, S97V and G147C, S97V and G149I, S97V and G149M, S97V and G149C, S97V and G149V, S97V and Y244L, S97V and M206D, S97V and P210C, S97C and F99R, S97C and S100R, S97C and P121V, S97C and G147C, S97C and G149I, S97C and G149M, S97C and G149C, S97C and G149V, S97C and Y244L, S97C and M206D, S97C and P210C, F99R and S100R, F99R and P121V, F99R and G147C, F99R and G149I, F99R and G149M, F99R and G149C, F99R and G149V, F99R and Y244L, F99R and M206D, F99R and P210C, S100R and P121V, S100R and G147C, S100R and G149I, S100R and G149M, S100R and G149C, S100R and G149V, S100R and Y244L, S100R and M206D, S100R and P210C, P121V and G147C, P121V and G149I, P121V and G149M, P121V and G149C, P121V and G149V, P121V and Y244L, P121V and M206D, P121V and P210C, G147C and G149I, G147C and G149M, G147C and G149C, G147C and G149V, G147C and Y244L, G147C and M206D, G147C and P210C, G149I and Y244L, G149I and M206D, G149I and P210C, G149M and Y244L, G149M and M206D, G149M and P210C, G149C and Y244L, G149C and M206D, G149C and P210C, G149V and Y244L, G149V and M206D, G149V and P210C, Y244L and M206D, Y244L and P210C, or M206D and P210C, more preferably S97C and S100R, S97C and G147C, S97C and G149I, S97C and G149C, S97C and G149M, S97C and G149V, S97C and P210C, S97C and Y244L, S100R and G147C, S100R and G149I, S100R and G149C, S100R and G149M, S100R and G149V, S100R and P210C, S100R and Y244L, G147C and G149I, G147C and G149C, G147C and G149M, G147C and G149V, G147C and P210C, G147C and Y244L, G149I and P210C, G149I and Y244L, G149C and P210C, G149C and Y244L, G149M and P210C, G149M and Y244L, G149V and P210C, G149V and Y244L, or P210C and Y244L, and most preferably S97C and G149I, S97C and G149C, S97C and G149M, S97C and G149V, S97C and P210C, S97C and Y244L, G149I and P210C, G149I and Y244L, G149C and P210C, G149C and Y244L, G149M and P210C, G149M and Y244L, G149V and P210C, G149V and Y244L, or P210C and Y244L.

In another preferred embodiment of the third aspect which is also an embodiment of all previous embodiments of the third aspect, the ketoreductase according to the invention differs from the ketoreductase of inventive SEQ ID NO: 1 by at least three residue change in one or more sequence sections SS-01 to SS-25.

In a preferred embodiment of the third aspect which is also an embodiment of all previous embodiments of the third aspect, the at least three amino acid positions comprise a triplet of three amino acid positions, wherein the triplet of three amino acid positions is selected from the group consisting of S97 and F99 and S100, S97 and F99 and P121, S97 and F99 and G147, S97 and F99 and G149, S97 and F99 and M206, S97 and F99 and P210, S97 and F99 and Y244, S97 and S100 and P121, S97 and S100 and G147, S97 and S100 and G149, S97 and S100 and M206, S97 and S100 and P210, S97 and S100 and Y244, S97 and P121 and G147, S97 and P121 and G149, S97 and P121 and M206, S97 and P121 and P210, S97 and P121 and Y244, S97 and G147 and G149, S97 and G147 and M206, S97 and G147 and P210, S97 and G147 and Y244, S97 and G149 and M206, S97 and G149 and P210, S97 and G149 and Y244, S97 and M206 and P210, S97 and M206 and Y244, S97 and P210 and Y244, F99 and S100 and P121, F99 and S100 and G147, F99 and S100 and G149, F99 and S100 and M206, F99 and S100 and P210, F99 and S100 and Y244, F99 and P121 and G147, F99 and P121 and G149, F99 and P121 and M206, F99 and P121 and P210, F99 and P121 and Y244, F99 and G147 and G149, F99 and G147 and M206, F99 and G147 and P210, F99 and G147 and Y244, F99 and G149 and M206, F99 and G149 and P210, F99 and G149 and Y244, F99 and M206 and P210, F99 and M206 and Y244, F99 and P210 and Y244, S100 and P121 and G147, S100 and P121 and G149, S100 and P121 and M206, S100 and P121 and P210, S100 and P121 and Y244, S100 and G147 and G149, S100 and G147 and M206, S100 and G147 and P210, S100 and G147 and Y244, S100 and G149 and M206, S100 and G149 and P210, S100 and G149 and Y244, S100 and M206 and P210, S100 and M206 and Y244, S100 and P210 and Y244, P121 and G147 and G149, P121 and G147 and M206, P121 and G147 and P210, P121 and G147 and Y244, P121 and G149 and M206, P121 and G149 and P210, P121 and G149 and Y244, P121 and M206 and P210, P121 and M206 and Y244, P121 and P210 and Y244, G147 and G149 and M206, G147 and G149 and P210, G147 and G149 and Y244, G147 and M206 and P210, G147 and M206 and Y244, G147 and P210 and Y244, G149 and M206 and P210, G149 and M206 and Y244, G149 and P210 and Y244, or M206 and P210 and Y244, more preferably S97 and S100 and G147, S97 and S100 and G149, S97 and S100 and P210, S97 and S100 and Y244, S97 and G147 and G149, S97 and G147 and P210, S97 and G147 and Y244, S97 and G149 and P210, S97 and G149 and Y244, S97 and P210 and Y244, S100 and G147 and G149, S100 and G147 and P210, S100 and G147 and Y244, S100 and G149 and P210, S100 and G149 and Y244, S100 and P210 and Y244, G147 and G149 and P210, G147 and G149 and Y244, G147 and P210 and Y244, or G149 and P210 and Y244 and most preferably S97 and G149 and P210, S97 and G149 and Y244, S97 and P210 and Y244, or G149 and P210 and Y244.

Even more preferably, the at least three amino acid positions comprise a triplet of three amino acid positions, wherein the triplet of three amino acid positions is selected from the group consisting of S97V and F99R and S100R, S97V and F99R and P121V, S97V and F99R and G147C, S97V and F99R and G149I, S97V and F99R and G149M, S97V and F99R and G149C, S97V and F99R and G149V, S97V and F99R and Y244L, S97V and F99R and M206D, S97V and F99R and P210C, S97V and S100R and P121V, S97V and S100R and G147C, S97V and S100R and G149I, S97V and S100R and G149M, S97V and S100R and G149C, S97V and S100R and G149V, S97V and S100R and Y244L, S97V and S100R and M206D, S97V and S100R and P210C, S97V and P121V and G147C, S97V and P121V and G149I, S97V and P121V and G149M, S97V and P121V and G149C, S97V and P121V and G149V, S97V and P121V and Y244L, S97V and P121V and M206D, S97V and P121V and P210C, S97V and G147C and G149I, S97V and G147C and G149M, S97V and G147C and G149C, S97V and G147C and G149V, S97V and G147C and Y244L, S97V and G147C and M206D, S97V and G147C and P210C, S97V and G149I and Y244L, S97V and G149I and M206D, S97V and G149I and P210C, S97V and G149M and Y244L, S97V and G149M and M206D, S97V and G149M and P210C, S97V and G149C and Y244L, S97V and G149C and M206D, S97V and G149C and P210C, S97V and G149V and Y244L, S97V and G149V and M206D, S97V and G149V and P210C, S97V and Y244L and M206D, S97V and Y244L and P210C, S97V and M206D and P210C, S97C and F99R and S100R, S97C and F99R and P121V, S97C and F99R and G147C, S97C and F99R and G149I, S97C and F99R and G149M, S97C and F99R and G149C, S97C and F99R and G149V, S97C and F99R and Y244L, S97C and F99R and M206D, S97C and F99R and P210C, S97C and S100R and P121V, S97C and S100R and G147C, S97C and S100R and G149I, S97C and S100R and G149M, S97C and S100R and G149C, S97C and S100R and G149V, S97C and S100R and Y244L, S97C and S100R and M206D, S97C and S100R and P210C, S97C and P121V and G147C, S97C and P121V and G149I, S97C and P121V and G149M, S97C and P121V and G149C, S97C and P121V and G149V, S97C and P121V and Y244L, S97C and P121V and M206D, S97C and P121V and P210C, S97C and G147C and G149I, S97C and G147C and G149M, S97C and G147C and G149C, S97C and G147C and G149V, S97C and G147C and Y244L, S97C and G147C and M206D, S97C and G147C and P210C, S97C and G149I and Y244L, S97C and G149I and M206D, S97C and G149I and P210C, S97C and G149M and Y244L, S97C and G149M and M206D, S97C and G149M and P210C, S97C and G149C and Y244L, S97C and G149C and M206D, S97C and G149C and P210C, S97C and G149V and Y244L, S97C and G149V and M206D, S97C and G149V and P210C, S97C and Y244L and M206D, S97C and Y244L and P210C, S97C and M206D and P210C, F99R and S100R and P121V, F99R and S100R and G147C, F99R and S100R and G149I, F99R and S100R and G149M, F99R and S100R and G149C, F99R and S100R and G149V, F99R and S100R and Y244L, F99R and S100R and M206D, F99R and S100R and P210C, F99R and P121V and G147C, F99R and P121V and G149I, F99R and P121V and G149M, F99R and P121V and G149C, F99R and P121V and G149V, F99R and P121V and Y244L, F99R and P121V and M206D, F99R and P121V and P210C, F99R and G147C and G149I, F99R and G147C and G149M, F99R and G147C and G149C, F99R and G147C and G149V, F99R and G147C and Y244L, F99R and G147C and M206D, F99R and G147C and P210C, F99R and G149I and Y244L, F99R and G149I and M206D, F99R and G149I and P210C, F99R and G149M and Y244L, F99R and G149M and M206D, F99R and G149M and P210C, F99R and G149C and Y244L, F99R and G149C and M206D, F99R and G149C and P210C, F99R and G149V and Y244L, F99R and G149V and M206D, F99R and G149V and P210C, F99R and Y244L and M206D, F99R and Y244L and P210C, F99R and M206D and P210C, S100R and P121V and G147C, S100R and P121V and G149I, S100R and P121V and G149M, S100R and P121V and G149C, S100R and P121V and G149V, S100R and P121V and Y244L, S100R and P121V and M206D, S100R and P121V and P210C, S100R and G147C and G149I, S100R and G147C and G149M, S100R and G147C and G149C, S100R and G147C and G149V, S100R and G147C and Y244L, S100R and G147C and M206D, S100R and G147C and P210C, S100R and G149I and Y244L, S100R and G149I and M206D, S100R and G149I and P210C, S100R and G149M and Y244L, S100R and G149M and M206D, S100R and G149M and P210C, S100R and G149C and Y244L, S100R and G149C and M206D, S100R and G149C and P210C, S100R and G149V and Y244L, S100R and G149V and M206D, S100R and G149V and P210C, S100R and Y244L and M206D, S100R and Y244L and P210C, S100R and M206D and P210C, P121V and G147C and G149I, P121V and G147C and G149M, P121V and G147C and G149C, P121V and G147C and G149V, P121V and G147C and Y244L, P121V and G147C and M206D, P121V and G147C and P210C, P121V and G149I and Y244L, P121V and G149I and M206D, P121V and G149I and P210C, P121V and G149M and Y244L, P121V and G149M and M206D, P121V and G149M and P210C, P121V and G149C and Y244L, P121V and G149C and M206D, P121V and G149C and P210C, P121V and G149V and Y244L, P121V and G149V and M206D, P121V and G149V and P210C, P121V and Y244L and M206D, P121V and Y244L and P210C, P121V and M206D and P210C, G147C and G149I and Y244L, G147C and G149I and M206D, G147C and G149I and P210C, G147C and G149M and Y244L, G147C and G149M and M206D, G147C and G149M and P210C, G147C and G149C and Y244L, G147C and G149C and M206D, G147C and G149C and P210C, G147C and G149V and Y244L, G147C and G149V and M206D, G147C and G149V and P210C, G147C and Y244L and M206D, G147C and Y244L and P210C, G147C and M206D and P210C, G149I and Y244L and M206D, G149I and Y244L and P210C, G149I and M206D and P210C, G149M and Y244L and M206D, G149M and Y244L and P210C, G149M and M206D and P210C, G149C and Y244L and M206D, G149C and Y244L and P210C, G149C and M206D and P210C, G149V and Y244L and M206D, G149V and Y244L and P210C, G149V and M206D and P210C, or Y244L and M206D and P210C, more preferably S97C and S100R and G147C, S97C and S100R and G149I, S97C and S100R and G149C, S97C and S100R and G149M, S97C and S100R and G149V, S97C and S100R and P210C, S97C and S100R and Y244L, S97C and G147C and G149I, S97C and G147C and G149C, S97C and G147C and G149M, S97C and G147C and G149V, S97C and G147C and P210C, S97C and G147C and Y244L, S97C and G149I and P210C, S97C and G149I and Y244L, S97C and G149C and P210C, S97C and G149C and Y244L, S97C and G149M and P210C, S97C and G149M and Y244L, S97C and G149V and P210C, S97C and G149V and Y244L, S97C and P210C and Y244L, S100R and G147C and G149I, S100R and G147C and G149C, S100R and G147C and G149M, S100R and G147C and G149V, S100R and G147C and P210C, S100R and G147C and Y244L, S100R and G149I and P210C, S100R and G149I and Y244L, S100R and G149C and P210C, S100R and G149C and Y244L, S100R and G149M and P210C, S100R and G149M and Y244L, S100R and G149V and P210C, S100R and G149V and Y244L, S100R and P210C and Y244L, G147C and G149I and P210C, G147C and G149I and Y244L, G147C and G149C and P210C, G147C and G149C and Y244L, G147C and G149M and P210C, G147C and G149M and Y244L, G147C and G149V and P210C, G147C and G149V and Y244L, G147C and P210C and Y244L, G149I and P210C and Y244L, G149C and P210C and Y244L, G149M and P210C and Y244L, or G149V and P210C and Y244L and most preferably S97C and G149I and P210C, S97C and G149I and Y244L, S97C and G149C and G149M, S97C and G149C and P210C, S97C and G149C and Y244L, S97C and G149M and P210C, S97C and G149M and Y244L, S97C and G149V and P210C, S97C and G149V and Y244L, S97C and P210C and Y244L, G149I and P210C and Y244L, G149C and P210C and Y244L, G149M and P210C and Y244L, or G149V and P210C and Y244L In preferred embodiments of the third aspect of the inventions, which is also a preferred embodiment of all previous embodiments, the ketoreductase comprises or consists of the amino acid sequences selected from the group consisting of SEQ ID NO:6, SEQ ID NO:7, SEQ ID NO:8, SEQ ID NO:9, SEQ ID NO: 10, SEQ ID NO: 11, SEQ ID NO:12, SEQ ID NO:13, SEQ ID NO: 14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO: 24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO: 34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO: 44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO: 54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO: 64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO: 74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO: 84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO: 94, SEQ ID NO:95, SEQ ID NO:96, SEQ ID NO:97, SEQ ID NO:98, SEQ ID NO:99, SEQ ID NO: 100, SEQ ID NO: 102, SEQ ID NO: 103, SEQ ID NO: 104, SEQ ID NO: 105, SEQ ID NO:106, SEQ ID NO:107, SEQ ID NO:108, SEQ ID NO: 109, SEQ ID NO: 110, SEQ ID NO: 111, SEQ ID NO: 112, SEQ ID NO: 114, SEQ ID NO: 115, SEQ ID NO: 116, SEQ ID NO: 117, SEQ ID NO:118, SEQ ID NO:119, SEQ ID NO:120, SEQ ID NO:121, SEQ ID NO.122, SEQ ID NO:123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO:131, SEQ ID NO:132, SEQ ID NO:133, SEQ ID NO: 134, SEQ ID NO:135, SEQ ID NO:136, SEQ ID NO:137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 150, SEQ ID NO:151, SEQ ID NO:152, SEQ ID NO: 153, SEQ ID NO: 154, SEQ ID NO:155, SEQ ID NO:156, SEQ ID NO:157, SEQ ID NO:158, SEQ ID NO:159, SEQ ID NO:160, SEQ ID NO:161, SEQ ID NO:162, SEQ ID NO:163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO:171, SEQ ID NO:172, SEQ ID NO:173, SEQ ID NO:174, SEQ ID NO:175, SEQ ID NO:176, SEQ ID NO:177, SEQ ID NO:178, SEQ ID NO:179, SEQ ID NO:180, SEQ ID NO:181, and/or SEQ ID NO:182.

In other preferred embodiments of the third aspect of the inventions, the ketoreductase of the invention is at least 72%, 73%, 74%, 75%, 76%, 77%, 78%, 79%, 80%, 81%, 82%, 83%, 84%, 85%, 86%, 87%, 88%, 89%, 90%, 91%, 92%, preferably at least 92.1%, at least 92.2%, at least 92.3%, at least 92.4%, at least 92.5%, at least 92.6%, at least 92.7%, at least 92.8%, at least 92.9%, at least 93%, at least 93.1%, at least 93.2%, at least 93.3%, at least 93.4%, at least 93.5%, at least 93.6%, at least 93.7%, at least 93.8%, at least 93.9%, more preferably at least 94%, at least 94.1%, at least 94.2%, at least 94.3%, at least 94.4%, at least 94.5%, at least 94.6%, at least 94.7%, at least 94.8%, at least 94.9%, still more preferably at least 95%, at least 95.1%, at least 95.2%, at least 95.3%, at least 95.4%, at least 95.5%, at least 95.6%, at least 95.7%, at least 95.8%, at least 95.9%, yet more preferably at least 96%, at least 96.1%, at least 96.2%, at least 96.3%, at least 96.4%, at least 96.5%, at least 96.6%, at least 96.7%, at least 96.8%, at least 96.9%, even more preferably at least 97%, at least 97.1%, at least 97.2%, at least 97.3%, at least 97.4%, at least 97.5%, at least 97.6%, at least 97.7%, at least 97.8%, at least 97.9%, most preferably at least 98%, at least 98.1%, at least 98.2%, at least 98.3%, at least 98.4%, at least 98.5%, at least 98.6%, at least 98.7%, at least 98.8%, at least 98.9%, and in particular at least 99%, at least 99.1%, at least 99.2%, at least 99.3%, at least 99.4%, at least 99.5%, at least 99.6%, at least 99.7%, at least 99.8%, or at least 99.9% of one or more of the ketoreductases selected from the group consisting of SEQ ID NO:6, SEQ ID NO:7, SEQ ID NO:8, SEQ ID NO:9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO:20, SEQ ID NO:21, SEQ ID NO:22, SEQ ID NO:23, SEQ ID NO: 24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO: 34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO: 44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO: 54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO: 64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO: 74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO: 84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO: 94, SEQ ID NO:95, SEQ ID NO:96, SEQ ID NO:97, SEQ ID NO:98, SEQ ID NO:99, SEQ ID NO: 100, SEQ ID NO: 102, SEQ ID NO: 103, SEQ ID NO: 104, SEQ ID NO:105, SEQ ID NO:106, SEQ ID NO:107, SEQ ID NO:108, SEQ ID NO:109, SEQ ID NO: 110, SEQ ID NO:111, SEQ ID NO:112, SEQ ID NO: 114, SEQ ID NO: 115, SEQ ID NO:116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, SEQ ID NO: 134, SEQ ID NO:135, SEQ ID NO: 136, SEQ ID NO: 137, SEQ ID NO: 138, SEQ ID NO: 139, SEQ ID NO: 140, SEQ ID NO:141, SEQ ID NO: 142, SEQ ID NO: 143, SEQ ID NO: 144, SEQ ID NO:145, SEQ ID NO: 146, SEQ ID NO:147, SEQ ID NO: 148, SEQ ID NO:150, SEQ ID NO:151, SEQ ID NO:152, SEQ ID NO:153, SEQ ID NO: 154, SEQ ID NO:155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO:163, SEQ ID NO:164, SEQ ID NO:165, SEQ ID NO: 166, SEQ ID NO: 167, SEQ ID NO:168, SEQ ID NO:169, SEQ ID NO:170, SEQ ID NO:171, SEQ ID NO:172, SEQ ID NO:173, SEQ ID NO:174, SEQ ID NO: 175, SEQ ID NO: 176, SEQ ID NO: 177, SEQ ID NO: 178, SEQ ID NO: 179, SEQ ID NO: 180, SEQ ID NO:181, and/or SEQ ID NO: 182.

For the purpose of the invention the terms "differing by at least one residue change" or "differing by at least one amino acid residue change" of two amino acid sequences shall mean that the sequences differ in one, two, three, four five, six, seven, eight, nine, ten, eleven, twelve, 13, 14, 15, 16, 17, 18, 19, 20, 21, 22, 23, 24, 25, 26, 27, 28, 29, 30, or more amino acid residues.

For the purpose of the third aspect of the invention, an improved activity, in in particular specific activity, in the oxidation of alcohol substrates to ketone or aldehyde products, shall mean the activity improvement rate of the volumetric activity given as U/ml lysate, or U/mg lyophilized lysate, or U/mg purified or partially purified protein activity, of a certain ketoreductase variant in comparison to the ketoreductase of SEQ ID NO: 1.

The activity improvement of ketoreductases variants differing from the ketoreductase of inventive SEQ ID NO: 1 may be detected with any alcohol substrate known in the art, and preferably by use of either of the substrates ethyl acetoacetate (EAA), or cyclohexanol. The activity of the improved ketoreductases variants differing from the ketoreductase of inventive SEQ ID NO: 1 is increased in comparison to SEQ ID NO: 1, with an activity compared to SEQ ID NO: 1 of preferably at least 101% up to 2000%, at least 101% up to 1900%, at least 101% up to 1800%, at least 101% up to 1700%, at least 101% up to 1600%, at least 101% up to 1500%, at least 102% up to 1500%, at least 103% up to 1500%, at least 104% up to 1500%, at least 105% up to 1500%, at least 106% up to 1500%, at least 107% up to 1500%, at least 108% up to 1500%, at least 109% up to 1500%, at least 110% up to 1500%, at least 111% up to 1500%, at least 112% up to 1500%, at least 113% up to 1500%, at least 114% up to 1500%, at least 115% up to 1500%, at least 116% up to 1500%, at least 117% up to 1500%, at least 118% up to 1500%, at least 119% up to 1500%, at least 120% up to 1500%, at least 121% up to 1500%, at least 122% up to 1500%, at least 123% up to 1500%, at least 124% up to 1500%, at least 125% up to 1500%, at least 126% up to 1500%, at least 127% up to 1500%, at least 128% up to 1500%, at least 129% up to 1500%, at least 130% up to 1500%, at least 131% up to 1500%, at least 132% up to 1500%, at least 133% up to 1500%, at least 134% up to 1500%, at least 135% up to 1500%, at least 136% up to 1500%, at least 137% up to 1500%, at least 138% up to 1500%, at least 139% up to 1500%, at least 140% up to 1500%, at least 141% up to 1500%, at least 142% up to 1500%, at least 143% up to 1500%, at least 144% up to 1500%, at least 145% up to 1500%, at least 146% up to 1500%, at least 147% up to 1500%, at least 148% up to 1500%, at least 149% up to 1500%, at least 150% up to 1500%, at least 151% up to 1500%, at least 152% up to 1500%, at least 153% up to 1500%, at least 154% up to 1500%, at least 155% up to 1500%, at least 156% up to 1500%, at least 157% up to 1500%, at least 158% up to 1500%, at least 159% up to 1500%, at least 160% up to 1500%, at least 161% up to 1500%, at least 162% up to 1500%, at least 163% up to 1500%, at least 164% up to 1500%, at least 165% up to 1500%, at least 166% up to 1500%, at least 167% up to 1500%, at least 168% up to 1500%, at least 169% up to 1500%, at least 170% up to 1500%, at least 171% up to 1500%, at least 172% up to 1500%, at least 173% up to 1500%, at least 174% up to 1500%, at least 175% up to 1500%, at least 176% up to 1500%, at least 177% up to 1500%, at least 178% up to 1500%, at least 179% up to 1500%, at least 180% up to 1500%, at least 181% up to 1500%, at least 182% up to 1500%, at least 183% up to 1500%, at least 184% up to 1500%, at least 185% up to 1500%, at least 186% up to 1500%, at least 187% up to 1500%, at least 188% up to 1500%, at least 189% up to 1500%, at least 190% up to 1500%, at least 191% up to 1500%, at least 192% up to 1500%, at least 193% up to 1500%, at least 194% up to 1500%, at least 195% up to 1500%, at least 196% up to 1500%, at least 197% up to 1500%, at least 198% up to 1500%, at least 199% up to 1500%, at least 200% up to 1500%, at least 101% up to 1200%, at least 102% up to 1200%, at least 103% up to 1200%, and preferably of at least 104% up to 1200%, at least 105% up to 1200%, at least 106% up to 1200%, at least 107% up to 1200%, at least 108% up to 1200%, at least 109% up to 1200%, at least 110% up to 1200%, at least 111% up to 1200%, at least 112% up to 1200%, at least 113% up to 1200%, at least 114% up to 1200%, at least 115% up to 1200%, at least 116% up to 1200%, at least 117% up to 1200%, at least 118% up to 1200%, at least 119% up to 1200%, at least 120% up to 1200%, at least 121% up to 1200%, at least 122% up to 1200%, at least 123% up to 1200%, at least 124% up to 1200%, at least 125% up to 1200%, at least 126% up to 1200%, at least 127% up to 1200%, at least 128% up to 1200%, at least 129% up to 1200%, at least 130% up to 1200%, at least 131% up to 1200%, at least 132% up to 1200%, at least 133% up to 1200%, at least 134% up to 1200%, at least 135% up to 1200%, at least 136% up to 1200%, at least 137% up to 1200%, at least 138% up to 1200%, at least 139% up to 1200%, at least 140% up to 1200%, at least 141% up to 1200%, at least 142% up to 1200%, at least 143% up to 1200%, at least 144% up to 1200%, at least 145% up to 1200%, at least 146% up to 1200%, at least 147% up to 1200%, at least 148% up to 1200%, at least 149% up to 1200%, at least 150% up to 1200%, at least 151% up to 1200%, at least 152% up to 1200%, at least 153% up to 1200%, at least 154% up to 1200%, at least 155% up to 1200%, at least 156% up to 1200%, at least 157% up to 1200%, at least 158% up to 1200%, at least 159% up to 1200%, at least 160% up to 1200%, at least 161% up to 1200%, at least 162% up to 1200%, at least 163% up to 1200%, at least 164% up to 1200%, at least 165% up to 1200%, at least 166% up to 1200%, at least 167% up to 1200%, at least 168% up to 1200%, at least 169% up to 1200%, at least 170% up to 1200%, at least 171% up to 1200%, at least 172% up to 1200%, at least 173% up to 1200%, at least 174% up to 1200%, at least 175% up to 1200%, at least 176% up to 1200%, at least 177% up to 1200%, at least 178% up to 1200%, at least 179% up to 1200%, at least 180% up to 1200%, at least 181% up to 1200%, at least 182% up to 1200%, at least 183% up to 1200%, at least 184% up to 1200%, at least 185% up to 1200%, at least 186% up to 1200%, at least 187% up to 1200%, at least 188% up to 1200%, at least 189% up to 1200%, at least 190% up to 1200%, at least 191% up to 1200%, at least 192% up to 1200%, at least 193% up to 1200%, at least 194% up to 1200%, at least 195% up to 1200%, at least 196% up to 1200%, at least 197% up to 1200%, at least 198% up to 1200%, at least 199% up to 1200%, at least 200% up to 1200%.

The activity improvement of ketoreductases variants differing from the ketoreductase of inventive SEQ ID NO: 1 may be detected with any ketone substrate known in the art, and preferably by use of cyclohexanone. The activity of the improved ketoreductases variants differing from the ketoreductase of inventive SEQ ID NO:1 is increased in comparison to SEQ ID NO: 1, with an activity compared to SEQ ID NO: 1 of at least 101% up to 2000%, at least 101% up to 1900%, at least 101% up to 1800%, at least 101% up to 1700%, at least 101% up to 1600%, at least 101% up to 1500%, at least 102% up to 1500%, at least 103% up to 1500%, at least 104% up to 1500%, at least 105% up to 1500%, at least 101% up to 1000%, at least 101% up to 1000%, at least 102% up to 1000%, at least 103% up to 1000%, at least 104% up to 1000%, at least 105% up to 1000%, at least 101% up to 500%, at least 101% up to 500%, at least 102% up to 500%, at least 103% up to 500%, at least 104% up to 500%, at least 105% up to 500%, and at least 105% up to 479%.

The activity improvement of ketoreductases variants differing from the ketoreductase of inventive SEQ ID NO: 1 may be detected with any alcohol substrate known in the art, and preferably by use of either of the substrates ethyl acetoacetate (EAA), or cyclohexanol. The activity of the improved ketoreductases variants differing from the ketoreductase of inventive SEQ ID NO: 1 is increased in comparison to SEQ ID NO: 1, expressed as percentage, by preferably at least 1% up to 300%, at least 2% up to 300%, at least 3% up to 300%, at least 4% up to 300%, at least 5% up to 300%, at least 6% up to 300%, at least 7% up to 300%, at least 8% up to 300%, at least 9% up to 300%, at least 10% up to 300%, at least 11% up to 300%, at least 12% up to 300%, at least 13% up to 300%, at least 14% up to 300%, at least 15% up to 300%, at least 16% up to 300%, at least 17% up to 300%, at least 18% up to 300%, at least 19% up to 300%, at least 20% up to 300%, at least 21% up to 300%, at least 22% up to 300%, at least 23% up to 300%, at least 24% up to 300%, at least 25% up to 300%, at least 26% up to 300%, at least 27% up to 300%, at least 28% up to 300%, at least 29% up to 300%, at least 30% up to 300%, at least 31% up to 300%, at least 32% up to 300%, at least 33% up to 300%, at least 34% up to 300%, at least 35% up to 300%, at least 36% up to 300%, at least 37% up to 300%, at least 38% up to 300%, at least 39% up to 300%, at least 40% up to 300%, at least 41% up to 300%, at least 42% up to 300%, at least 43% up to 300%, at least 44% up to 300%, at least 45% up to 300%, at least 46% up to 300%, at least 47% up to 300%, at least 48% up to 300%, at least 49% up to 300%, at least 50% up to 300%, at least 51% up to 300%, at least 52% up to 300%, at least 53% up to 300%, at least 54% up to 300%, at least 55% up to 300%, at least 56% up to 300%, at least 57% up to 300%, at least 58% up to 300%, at least 59% up to 300%, at least 60% up to 300%, at least 61% up to 300%, at least 62% up to 300%, at least 63% up to 300%, at least 64% up to 300%, at least 65% up to 300%, at least 66% up to 300%, at least 67% up to 300%, at least 68% up to 300%, at least 69% up to 300%, at least 70% up to 300%, at least 71% up to 300%, at least 72% up to 300%, at least 73% up to 300%, at least 74% up to 300%, at least 75% up to 300%, at least 76% up to 300%, at least 77% up to 300%, at least 78% up to 300%, at least 79% up to 300%; or preferably by at least 1% up to 200%, at least 2% up to 200%, at least 3% up to 200%, at least 4% up to 200%, at least 5% up to 200%, at least 6% up to 200%, at least 7% up to 200%, at least 8% up to 200%, at least 9% up to 200%, at least 10% up to 200%, at least 11% up to 200%, at least 12% up to 200%, at least 13% up to 200%, at least 14% up to 200%, at least 15% up to 200%, at least 16% up to 200%, at least 17% up to 200%, at least 18% up to 200%, at least 19% up to 200%, at least 20% up to 200%, at least 21% up to 200%, at least 22% up to 200%, at least 23% up to 200%, at least 24% up to 200%, at least 25% up to 200%, at least 26% up to 200%, at least 27% up to 200%, at least 28% up to 200%, at least 29% up to 200%, at least 30% up to 200%, at least 31% up to 200%, at least 32% up to 200%, at least 33% up to 200%, at least 34% up to 200%, at least 35% up to 200%, at least 36% up to 200%, at least 37% up to 200%, at least 38% up to 200%, at least 39% up to 200%, at least 40% up to 200%, at least 41% up to 200%, at least 42% up to 200%, at least 43% up to 200%, at least 44% up to 200%, at least 45% up to 200%, at least 46% up to 200%, at least 47% up to 200%, at least 48% up to 200%, at least 49% up to 200%, at least 50% up to 200%, at least 51% up to 200%, at least 52% up to 200%, at least 53% up to 200%, at least 54% up to 200%, at least 55% up to 200%, at least 56% up to 200%, at least 57% up to 200%, at least 58% up to 200%, at least 59% up to 200%, at least 60% up to 200%, at least 61% up to 200%, at least 62% up to 200%, at least 63% up to 200%, at least 64% up to 200%, at least 65% up to 200%, at least 66% up to 200%, at least 67% up to 200%, at least 68% up to 200%, at least 69% up to 200%, at least 70% up to 200%, at least 71% up to 200%, at least 72% up to 200%, at least 73% up to 200%, at least 74% up to 200%, at least 75% up to 200%, at least 76% up to 200%, at least 77% up to 200%, at least 78% up to 200%, at least 79% up to 200%;

or preferably at least 1% up to 100%, at least 2% up to 100%, at least 3% up to 100%, at least 4% up to 100%, at least 5% up to 100%, at least 6% up to 100%, at least 7% up to 100%, at least 8% up to 100%, at least 9% up to 100%, at least 10% up to 100%, at least 11% up to 100%, at least 12% up to 100%, at least 13% up to 100%, at least 14% up to 100%, at least 15% up to 100%, at least 16% up to 100%, at least 17% up to 100%, at least 18% up to 100%, at least 19% up to 100%, at least 20% up to 100%, at least 21% up to 100%, at least 22% up to 100%, at least 23% up to 100%, at least 24% up to 100%, at least 25% up to 100%, at least 26% up to 100%, at least 27% up to 100%, at least 28% up to 100%, at least 29% up to 100%, at least 30% up to 100%, at least 31% up to 100%, at least 32% up to 100%, at least 33% up to 100%, at least 34% up to 100%, at least 35% up to 100%, at least 36% up to 100%, at least 37% up to 100%, at least 38% up to 100%, at least 39% up to 100%, at least 40% up to 100%, at least 41% up to 100%, at least 42% up to 100%, at least 43% up to 100%, at least 44% up to 100%, at least 45% up to 100%, at least 46% up to 100%, at least 47% up to 100%, at least 48% up to 100%, at least 49% up to 100%, at least 50% up to 100%, at least 51% up to 100%, at least 52% up to 100%, at least 53% up to 100%, at least 54% up to 100%, at least 55% up to 100%, at least 56% up to 100%, at least 57% up to 100%, at least 58% up to 100%, at least 59% up to 100%, at least 60% up to 100%, at least 61% up to 100%, at least 62% up to 100%, at least 63% up to 100%, at least 64% up to 100%, at least 65% up to 100%, at least 66% up to 100%, at least 67% up to 100%, at least 68% up to 100%, at least 69% up to 100%, at least 70% up to 100%, at least 71% up to 100%, at least 72% up to 100%, at least 73% up to 100%, at least 74% up to 100%, at least 75% up to 100%, at least 76% up to 100%, at least 77% up to 100%, at least 78% up to 100%, at least 79% up to 100%; and or preferably of preferably at least 1% up to 70%, at least 2% up to 70%, at least 3% up to 70%, at least 4% up to 70%, at least 5% up to 70%, at least 6% up to 70%, at least 7% up to 70%, at least 8% up to 70%, at least 9% up to 70%, at least 10% up to 70%, at least 11% up to 70%, at least 12% up to 70%, at least 13% up to 70%, at least 14% up to 70%, at least 15% up to 70%, at least 16% up to 70%, at least 17% up to 70%, at least 18% up to 70%, at least 19% up to 70%, at least 20% up to 70%, at least 21% up to 70%, at least 22% up to 70%, at least 23% up to 70%, at least 24% up to 70%, at least 25% up to 70%, at least 26% up to 70%, at least 27% up to 70%, at least 28% up to 70%, at least 29% up to 70%, at least 30% up to 70%, at least 31% up to 70%, at least 32% up to 70%, at least 33% up to 70%, at least 34% up to 70%, at least 35% up to 70%, at least 36% up to 70%, at least 37% up to 70%, at least 38% up to 70%, at least 39% up to 70%, at least 40% up to 70%, at least 41% up to 70%, at least 42% up to 70%, at least 43% up to 70%, at least 44% up to 70%, at least 45% up to 70%, at least 46% up to 70%, at least 47% up to 70%, at least 48% up to 70%, at least 49% up to 70%, at least 50% up to 70%, at least 51% up to 70%, at least 52% up to 70%, at least 53% up to 70%, at least 54% up to 70%, at least 55% up to 70%.

Alternatively, the improved activity, in particular specific activity, in the oxidation of alcohol substrates to ketone or aldehyde products or in the reduction of a ketone or aldehyde substrate to an alcohol product, may be expressed as a higher activity value of an improved variant over SEQ ID NO: 1 with a volumetric activity given as U/ml culture, U/ml lysate, or a specific activity given as U/mg lyophilized lysate, or U/mg purified or partially purified protein activity, wherein the oxidation activity of cyclohexanol to cyclohexanone of the improved variant in comparison to SEQ ID NO:1 will be increased by at least 1.1 up to 12-fold higher, at least 1.2 up to 12-fold higher, at least 1.3 up to 12-fold higher, at least 1.4 up to 12-fold higher, at least 1.5 up to 12-fold higher, at least 1.6 up to 12-fold higher, at least 1.7 up to 12-fold higher, at least 1.8 up to 12-fold higher, at least 1.9 up to 12-fold higher, at least 2 up to 12-fold higher, at least 2.5 up to 12-fold higher, at least 3 up to 12-fold higher, at least 3.5 up to 12-fold higher, at least 4 up to 12-fold higher, at least 4.5 up to 12-fold higher, at least 5 up to 12-fold higher, at least 5.5 up to 12-fold higher, at least 5 up to 10-fold higher, and/or preferably will be increased by at least 1.1 up to 15-fold, at least 1.2 up to 15-fold, at least 1.3 up to 15-fold, at least 1.4 up to 15-fold, at least 1.5 up to 15-fold, at least 1.6 up to 15-fold, at least 1.7 up to 15-fold, at least 1.8 up to 15-fold, at least 1.9 up to 15-fold, at least 2 up to 15-fold, at least 2.5 up to 15-fold, at least 3 up to 15-fold, at least 3.5 up to 15-fold, at least 4 up to 15-fold, at least 4.5 up to 15-fold, at least 5 up to 15-fold, at least 5.5 up to 15-fold, at least 5 up to 12-fold; and/or wherein the reduction activity of cyclohexanone to cyclohexanol of the improved variant in comparison to SEQ ID NO:1 will be increased by at least 20-fold up to 200-fold higher, at least 20-fold up to 190-fold higher, at least 20-fold up to 180-fold higher, at least 20-fold up to 170-fold higher, at least 20-fold up to 160-fold higher, at least 20-fold up to 150-fold higher, at least 22-fold up to 150-fold higher, more preferably at least 30-fold up to 150-fold higher, at least 40-fold up to 150-fold higher, at least 40-fold up to 140-fold higher at least 40-fold up to 130-fold higher, at least 40-fold up to 120-fold higher, at least 40-fold up to 110-fold higher, at least 40-fold up to 100-fold higher, and/or preferably will be increased by at least 1.1-fold up to 10-fold, at least 1.1-fold up to 9-fold, at least 1.1-fold up to 8-fold, at least 1.1-fold up to 7-fold, at least 1.5-fold up to 7-fold, more preferably at least 2-fold up to 7-fold, at least 2-fold up to 6.5-fold, at least 2-fold up to 6-fold, at least 2-fold up to 5.5-fold, at least 2-fold up to 5-fold, preferably at least 1.1-fold up to 4.8-fold; and/or wherein the ratio of reduction activity versus oxidation activity for cyclohexanone/cyclohexanol for the improved variant in comparison to SEQ ID NO: 1 will be increased by at least 20-fold up to 200-fold higher, at least 20-fold up to 190-fold higher, at least 20-fold up to 180-fold higher, at least 20-fold up to 170-fold higher, at least 20-fold up to 160-fold higher, at least 20-fold up to 150-fold higher, at least 30-fold up to 150-fold higher, at least 40-fold up to 150-fold higher, at least 45-fold up to 150-fold higher, at least 50-fold up to 150-fold higher, preferably at least 70-fold up to 120-fold higher, and/or preferably will be increased at least 1.1 up to 10-fold, at least 1.1 up to 9-fold, at least 1.1 up to 8-fold, at least 1.4 up to 7-fold, at least 1.6 up to 7-fold, preferably at least 1.4 up to 5; or wherein the ration of reduction activity versus oxidation activity cyclohexanone/cyclohexanol for the improved variant in comparison to SEQ ID NO: 1 will be decreased by at least 0.9 up to 0.05-fold, at least 0.9 up to 0.06-fold, at least 0.9 up to 0.07-fold, at least 0.9 up to 0.08-fold, at least 0.9 up to 0.09-fold, at least 0.8 up to 0.09-fold, 0.7 up to 0.09-fold, 0.6 up to 0.09-fold, 0.8 up to 0.1-fold, preferably at least 0.65 up to 0.13-fold.

Alternatively, the improved activity, in particular specific activity, in the oxidation of alcohol substrates to ketone or aldehyde products or in the reduction of a ketone or aldehyde substrate to an alcohol product, may be expressed as a higher activity value of an improved variant over SEQ ID NO: 1 with a volumetric activity given as U/ml culture, U/ml lysate, or a specific activity given as U/mg lyophilized lysate, or U/mg purified or partially purified protein activity, wherein the oxidation activity of cyclohexanol to cyclohexanone of the improved variant in comparison to SEQ ID NO:1 will be at least 1.1 up to 15-fold, at least 1.2 up to 15-fold, at least 1.3 up to 15-fold, at least 1.4 up to 15-fold, at least 1.5 up to 15-fold, at least 1.6 up to 15-fold, at least 1.7 up to 15-fold, at least 1.8 up to 15-fold, at least 1.9 up to 15-fold, at least 2 up to 15-fold, at least 2.5 up to 15-fold, at least 3 up to 15-fold, at least 3.5 up to 15-fold, at least 4 up to 15-fold, at least 4.5 up to 15-fold, at least 5 up to 15-fold, at least 5.5 up to 15-fold; and/or preferably will be increased by at least 1.1 up to 12-fold, at least 1.2 up to 12-fold, at least 1.3 up to 12-fold, at least 1.4 up to 12-fold, at least 1.5 up to 12-fold, at least 1.6 up to 12-fold, at least 1.7 up to 12-fold, at least 1.8 up to 12-fold, at least 1.9 up to 12-fold, at least 2 up to 12-fold, at least 2.5 up to 12-fold, at least 3 up to 12-fold, at least 3.5 up to 12-fold, at least 4 up to 12-fold, at least 4.5 up to 12-fold, at least 5 up to 12-fold, at least 5.5 up to 12-fold, at least 5 up to 12-fold higher than SEQ ID NO: 1; and/or wherein the reduction activity of cyclohexanone to cyclohexanol of the improved variant in comparison to SEQ ID NO:1 will be at least 1.1-fold up to 10-fold, at least 1.1-fold up to 9-fold, at least 1.1-fold up to 8-fold, at least 1.1-fold up to 7-fold, at least 1.5-fold up to 7-fold, more preferably at least 2-fold up to 7-fold, at least 2-fold up to 6.5-fold, at least 2-fold up to 6-fold, at least 2-fold up to 5.5-fold, at least 2-fold up to 5-fold, preferably at least 1.1-fold up to 4.8-fold higher than SEQ ID NO: 1; and/or wherein the ratio of reduction activity versus oxidation activity for cyclohexanone/cyclohexanol for the improved variant in comparison to SEQ ID NO:1 will be at least 1.1 up to 10-fold, at least 1.1 up to 9-fold, at least 1.1 up to 8-fold, at least 1.4 up to 7-fold, at least 1.6 up to 7-fold, preferably at least 1.4 up to 5-fold higher than SEQ ID NO: 1; or wherein the ration of reduction activity versus oxidation activity cyclohexanone/cyclohexanol for the improved variant in comparison to SEQ ID NO:1 will be at least 0.9 up to 0.05-fold, at least 0.9 up to 0.06-fold, at least 0.9 up to 0.07-fold, at least 0.9 up to 0.08-fold, at least 0.9 up to 0.09-fold, at least 0.8 up to 0.09-fold, 0.7 up to 0.09-fold, 0.6 up to 0.09-fold, 0.8 up to 0.1-fold, preferably at least 0.65 up to 0.13-fold lower than SEQ ID NO: 1.

In a preferred embodiment of the invention, the improved variants of SEQ ID NO:1 exhibiting an improved reduction activity of cyclohexanone to cyclohexanol compared to SEQ ID NO:1 differ from the ketoreductase of inventive SEQ ID NO: 1 by at least one residue changes, by at least two residue changes, by at least three residue changes, by at least four residue changes, or by at least six residue changes of the sequences positions selected from the group consisting of S3I, S4N, S8A, L9G, L9M, L9C, L9R, L9K, L9Q, N10G, A11V, A11C, V13G, E22K, S25A, M26R, A30R, E31N, A38M, S39G, 539A, L42Y, E43K, Q44T, Q44E, Q44R, K49R, A50K, I54R, I54V, V55I, V55C, K56M, Q57P, Q57A, T60C, T60N, T60A, S69V, S69A, D70C, D70S, G75L, 576M, 576C, 576L, S76G, F77L, 592M, 592G, 597A, S97W, 597V, 597C, 597M, 597F, Q98E, F99R, S100E, S100Q, S100R, S100V, S100C, P110F, P101H, P101W, A106C, A106E, A108P, D109G, D109R, N112T, M113V, L114V, L114I, T119L, A120G, P121V, P121A, A127K, A127C, A127G, A127Q, I132V, I132W, I132F, S133L, S133A, S133Q, S133M, S133V, P136V, P136G, Q138A, Q138T, Q138S, T139V, T139F, T39K, A41S, G147C, T148S, G149C, G149V, G149S, G149M, G149I, S151A, K152A, A155W, A155H, M157F, M157R, M157G, M157C, M157E, M157K, M157D, V158M, G159S, G159A, D169E, M172C, P181V, P181W, P181L, K182I, N185R, T194V, A199C, E200P, E200V, E200A, I202V, P204L, M206T, M206D, M206G, M206A, D208H, D208C, D208N, L209C, P210C, N212K, N212P, N212A, G213D, W214G, I215T, V217N, V217P, I220V, T2251, T225M, L227V, N232Y, N232F, G235F, T236S, T237I, V238F, S239F, G243V, Y244F, Y244L, C245F, and A246F, and preferably consisting of G149M, G149C, G149V, P210C, Y244L, and, and most preferably consisting of G149V, and Y244L.

In a preferred embodiment of the invention, the improved variants of SEQ ID NO:1 exhibiting an improved oxidation activity of cyclohexanol to cyclohexanone compared to SEQ ID NO:1 differ from the ketoreductase of inventive SEQ ID NO: 1 by at least one residue changes, by at least two residue changes, by at least three residue changes, by at least four residue changes, or by at least six residue changes of the sequences positions selected from the group consisting of S3I, S4N, S8A, L9G, L9M, L9C, L9R, L9K, L9Q, N10G, A11V, A11C, V13G, E22K, S25A, M26R, A30R, E31N, A38M, S39G, S39A, L42Y, E43K, Q44T, Q44E, Q44R, K49R, A50K, I54R, I54V, V55I, V55C, K56M, Q57P, Q57A, T60C, T60N, T60A, S69V, S69A, D70C, D70S, G75L, S76M, S76C, S76L, S76G, F77L, S92M, S92G, S97A, S97W, S97V, S97C, S97M, S97F, Q98E, F99R, S100E, S100Q, S100P, S100V, S100C, P101F, P101H, P101W, A106C, A106E, A108P, D109G, D109R, N112T, M113V, L114V, L114I, T119L, A120G, P121V, P121A, A127K, A127C, A127G, A127Q, I132V, I132W, I132F, S133L, S133A, S133Q, S133M, S133V, P136V, P136G, Q138A, Q138T, Q138S, T139V, T139F, T139K, A141S, G147C, T148S, G149C, G149V, G149S, G149M, G149I, S151A, K152A, A155W, A155H, M157F, M157R, M157G, M157C, M157E, M157K, M157D, V158M, G159S, G159A, D169E, M172C, P181V, P181W, P181L, K182I, N185R, T194V, A199C, E200P, E200V, E200A, I202V, P204L, M206T, M206D, M206G, M206A, D208H, D208C, D208N, L209C, P210C, N212K, N212P, N212A, G213D, W214G, I215T, V217N, V217P, I220V, T2251, T225M, L227V, N232Y, N232F, G235F, T236S, T237I, V238F, S239F, G243V, Y244F, Y244L, C245F, and A246F, and preferably consisting of S97V, G147C, G149M, G149V, G149I, M206D, P210C, Y244L, and most preferably consisting of G147C, G149M, P210C.

In a preferred embodiment of the invention, the improved variants of SEQ ID NO:1 exhibiting an increased ratio of reduction activity versus oxidation activity for cyclohexanone/cyclohexanol for the improved variant in comparison to SEQ ID NO:1 differ from the ketoreductase of inventive SEQ ID NO:1 by at least one residue changes, by at least two residue changes, by at least three residue changes, by at least four residue changes, or by at least six residue changes of the sequences positions selected from the group consisting of S3I, S4N, S8A, L9G, L9M, L9C, L9R, L9K, L9Q, N10G, A11V, A11C, V13G, E22K, S25A, M26R, A30R, E31N, A38M, S39G, S39A, L42Y, E43K, Q44T, Q44E, Q44R, K49R, A50K, I54R, 154V, V55I, V55C, K56M, Q57P, Q57A, T60C, T60N, T60A, S69V, S69A, D70C, D70S, G75L, S76M, S76C, S76L, S76G, F77L, S92M, S92G, S97A, S97W, S97V, S97C, S97M, S97F, Q98E, F99R, S100E, S100Q, S100R, S100V, S100C, P101F, P101H, P101W, A106C, A106E, A108P, D109G, D109R, N12T, M13V, L14V, L14I, T19L, A120G, P121V, P121A, A127K, A127C, A127G, A127Q, I132V, I132W, I132F, S133L, S133A, S133Q, S133M, S133V, P136V, P136G, Q138A, Q138T, Q138S, T139V, T139F, T139K, A141S, G147C, T148S, G149C, G149V, G149S, G149M, G149I, S151A, K152A, A155W, A155H, M157F, M157R, M157G, M157C, M157E, M157K, M157D, V158M, G159S, G159A, D169E, M172C, P181V, P181W, P181L, K182I, N185R, T194V, A199C, E200P, E200V, E200A, I202V, P204L, M206T, M206D, M206G, M206A, D208H, D208N, L209C, P210C, N212K, N212P, N212A, G213D, W214G, I215T, V217N, V217P, I220V, T2251, T225M, L227V, N232Y, N232F, G235F, T236S, T237I, V238F, S239F, G243V, Y244F, Y244L, C245F, and A246F, and preferably consisting of S100R, P121V, M206D, and P210C, and most preferably consisting of S100R, and P210C.

In a preferred embodiment of the invention, the improved variants of SEQ ID NO: 1 exhibiting a decreased ratio of reduction activity versus oxidation activity for cyclohexanone/cyclohexanol for the improved variant in comparison to SEQ ID NO:1 differ from the ketoreductase of inventive SEQ ID NO:1 by at least one residue changes, by at least two residue changes, by at least three residue changes, by at least four residue changes, or by at least six residue changes of the sequences positions selected from the group consisting of S3I, S4N, S8A, L9G, L9M, L9C, L9R, L9K, L9Q, N10G, A11V, A11C, V13G, E22K, S25A, M26R, A30R, E31N, A38M, S39G, S39A, L42Y, E43K, Q44T, Q44E, Q44R, K49R, A50K, 154R, 154V, V55I, V55C, K56M, Q57P, Q57A, T60C, T60N, T60A, S69V, S69A, D70C, D70S, G75L, S76M, S76C, S76L, S76G, F77L, S92M, S92G, S97A, S97W, S97V, S97C, S97M, S97F, Q98E, F99R, S100E, S100Q, S100R, S100V, S100C, P101F, P101H, P101W, A106C, A106E, A108P, D109G, D109R, N112T, M113V, L114V, L114I, T119L, A120G, P121V, P121A, A127K, A127C, A127G, A127Q, I132J, I132W, I132F, S133L, S133A, S133Q, S133M, S133V, P136V, P136G, Q138A, Q138T, Q138S, T139V, T139F, T139K, A141S, G147C, T148S, G149C, G149V, G149S, G149M, G149I, S151A, K152A, A155W, A155H, M157F, M157R, M157G, M157C, M157E, M157K, M157D, V158M, G159S, G159A, D169E, M172C, P181V, P181W, P181L, K182I, N185R, T194V, A199C, E200P, E200V, E200A, I202V, P204L, M206T, M206D, M206G, M206A, D208H, D208C, D208N, L209C, P210C, N212K, N212P, N212A, G213D, W214G, I215T, V217N, V217P, I220V, T225I, T225M, L227V, N232Y, N232F, G235F, T236S, T237I, V238F, S239F, G243V, Y244F, Y244L, C245F, and A246F, and preferably consisting of S97V, S97C, G147C, G149I, G149M, G149C, G149V, Y244L, and most preferably consisting of G147C, G149I, and G149M.

For the purpose of the third aspect of the invention, an improved thermal stability of an enzyme according to the invention is the property of such enzyme to retain enzymatic activity upon incubation at elevated temperatures for a given time. The ketoreductase activity thereby can be determined using any assay conditions. For the purpose of this invention improvements in thermal stability of a certain ketoreductase were determined by measuring one or more of the following characteristics:

The $Tm_{50(40)}$-value: For the purpose of this invention, the $Tm_{50(40)}$-value is the temperature at which after 15 min of incubation of a 40 mg/ml solution the ketoreductase enzyme possesses 50% of its initial activity. The initial activity is the activity of the respective enzyme without temperature treatment, i.e. with 15 min incubation at room temperature. The enzyme activity can be determined in principle by using any activity assay. In this invention the assays for the determination of oxidation or reduction activity as specified in the examples have been used, which are made part to the description.

The $Tm_{50(10)}$ value: For the purpose of this invention, the $Tm_{50(10)}$-value is the temperature at which after 15 min of incubation of a crude extract corresponding to an $OD_{600}$ of 10 the ketoreductase enzyme possesses 50% of its initial activity. The initial activity is the activity of the respective enzyme without temperature treatment, i.e. with 15 min incubation at room temperature. The enzyme activity can be determined in principle by using any activity assay. In this invention the assays for the determination of oxidation or reduction activity as specified in the examples have been used, which are made part to the description.

Residual activity: For the purpose of this invention, residual activity after 15 min/42° C. is defined as the activity of a ketoreductase enzyme after incubation for 15 min at 42° C. compared to its activity without incubation at 42° C. The residual activity is calculated by dividing the activity after incubation at 42° C. for 15 min by the activity without incubation at 42° C. and multiplying the value by 100 to obtain the residual activity value in percent. The enzyme activity can be determined in principle by using any activity assay. For the purpose of this invention the assays as described in the examples have been used, which are made part to the description.

The improved variants of SEQ ID NO:1 over SEQ ID NO:1 exhibit a thermal stability expressed as residual activity after 15 min incubation at 42° C. of at least 20% up to 100%, at least 21% up to 100%, at least 22% up to 100%, at least 23% up to 100%, at least 24% up to 100%, at least 25% up to 100%, at least 26% up to 100%, at least, and preferably exhibit a thermal stability expressed as residual activity after 15 min incubation at 42° C. of at least 27% up to 100%, at least 28% up to 100%, at least 29% up to 100%, at least 30% up to 100%, at least 31% up to 100%, at least 32% up to 100%, at least 33% up to 100%, at least 34% up to 100%, at least 35% up to 100%, at least 36% up to 100%, at least 37% up to 100%, at least 38% up to 100%, at least 39% up to 100%, at least 40% up to 100%, at least 41% up to 100%, at least 42% up to 100%, at least 43% up to 100%, at least 44% up to 100%, at least 45% up to 100%, at least 46% up to 100%, at least 47% up to 100%, at least 48% up to 100%, at least 49% up to 100%, at least 50% up to 100%, at least 51% up to 100%, at least 52% up to 100%, at least 53% up to 100%, at least 54% up to 100%, at least 55% up to 100%, at least 56% up to 100%, at least 57% up to 100%, at least 58% up to 100%, at least 59% up to 100%, 60% up to 100%, at least 61% up to 100%, at least 62% up to 100%, at least 63% up to 100%, at least 64% up to 100%, preferably at least 40% up to 100%, at least 41% up to 100%, at least 42% up to 100%, at least 43% up to 100%, at least 44% up to 100%, at least 45% up to 100%, at least 46% up to 100%, at least 47% up to 100%, at least 48% up to 100%, at least 49% up to 100%, at least 50% up to 100%, at least 51% up to 100%, at least 52% up to 100%, at least 53% up to 100%, at least 54% up to 100%, at least 55% up to 100%, at least 56% up to 100%, at least 57% up to 100%, at least 58% up to 100%, at least 59% up to 100%, 60% up to 100%, at least 61% up to 100%, at least 62% up to 100%, at least 63% up to 100%, at least 64% up to 100%, more preferably of at least 50% up to 100%, at least 51% up to 100%, at least 52% up to 100%, at least 53% up to 100%, at least 54% up to 100%, at least 55% up to 100%, at least 56% up to 100%, at least 57% up to 100%, at least 58% up to 100%, at least 59% up to 100%, 60% up to 100%, at least 61% up to 100%, at least 62% up to 100%, at least 63% up to 100%, at least 64% up to 100%, and most preferably of at least of at least 65% up to 100%, at least 66% up to 100%, at least 67% up to 100%, at least 68% up to 100%, at least 69% up to 100%, at least 70% up to 100%, at least 71% up to 100%, at least 72% up to 100%, at least 73% up to 100%, at least 74% up to 100%, at least 75% up to 100%, at least 76% up to 100%, at least 77% up to 100%, at least 78% up to 100%, at least 79% up to 100%, or 80% up to 100%.

The improved variants of SEQ ID NO: 1 over SEQ ID NO:1 exhibit a thermal stability of a $Tm_{50(40)}$-value of at least 47.0° C. up to 90° C., at least 47.0° C. up to 85° C., at least 47.0° C. up to 80° C., at least 47.0° C. up to 75° C., at least 47.0° C. up to 70° C., at least 47.5° C. up to 70° C., at least 48.0° C. up to 70° C., at least 48.5° C. up to 70° C., at least 49.0° C. up to 70° C., at least 49.5° C. up to 70° C., at least 50.0° C. up to 70° C., at least 50.5° C. up to 70° C., at least 51.0° C. up to 70° C., at least 51.5° C. up to 70° C., at least 52.0° C. up to 70° C., at least 52.5° C. up to 70° C., at least 53.0° C. up to 70° C., at least 53.5° C. up to 70° C., at least 54.0° C. up to 70° C., at least 54.5° C. up to 70° C., at least 55.0° C. up to 70° C., at least 55.5° C. up to 70° C., at least 56.0° C. up to 70° C., at least 56.5° C. up to 70° C., at least 57.0° C. up to 70° C., at least 57.5° C. up to 70° C., at least 58.0° C. up to 70° C., at least 58.0° C. up to 70° C., at least 58.0° C. up to 69° C., at least 58.0° C. up to 68° C., at least 58.0° C. up to 67° C., at least 58.0° C. up to 66° C., at least 58.0° C. up to 65° C., at least 58.0° C. up to 64° C., at least 58.0° C. up to 63° C., and at least 58.0° C. up to 62° C., and preferably, at least 47.0° C. up to 90° C., at least 47.0° C. up to 87.5° C., at least 47.0° C. up to 85° C., at least 47.0° C. up to 82.5° C., at least 47.0° C. up to 80° C., at least 47.5° C. up to 80° C., at least 48.0° C. up to 80° C., at least 48.5° C. up to 80° C., at least 49.0° C. up to 80° C., at least 49.5° C. up to 80° C., at least 50.0° C. up to 80° C., at least 50.5° C. up to 80° C., at least 51.0° C. up to 80° C., at least 51.5° C. up to 80° C., at least 52.0° C. up to 80° C., at least 52.5° C. up to 80° C., at least 53.0° C. up to 80° C., at least 53.5° C. up to 80° C., at least 54.0° C. up to 80° C., at least 54.5° C. up to 80° C., at least 55.0° C. up to 80° C., at least 55.5° C. up to 80° C., at least 56.0° C. up to 80° C., at least 56.5° C. up to 80° C., at least 57.0° C. up to 80° C., at least 57.5° C. up to 80° C., at least 58.0° C. up to 80° C., at least 58.0° C. up to 80° C., at least 58.0° C. up to 79° C., at least 58.0° C. up to 78° C., at least 58.0° C. up to 77° C., at least 58.0° C. up to 76° C., at least 58.0° C. up to 75° C., at least 58.0° C. up to 74° C., at least 58.0° C. up to 73° C., and at least 58.0° C. up to 72° C.

The improved variants of SEQ ID NO: 1 over SEQ ID NO:1 exhibit a thermal stability of a $Tm_{50(10)}$-value of at least 42.0° C. up to 90° C., at least 42.0° C. up to 85° C., at least 42.0° C. up to 80° C., at least 42.0° C. up to 75° C., at least 42.5° C. up to 75° C., at least 43.0° C. up to 75° C., at least 44° C. up to 75° C., at least 44.5° C. up to 75° C., at least 45° C. up to 75° C., at least 45.5° C. up to 75° C., at least 46° C. up to 75° C., at least 46.5° C. up to 75° C., at least 47° C. up to 75° C., at least 47.5° C. up to 75° C., at least 48° C. up to 75° C., at least 48.5° C. up to 75° C., at least 49° C. up to 75° C., at least 49.5° C. up to 75° C., at least 50° C. up to 75° C., at least 50.5° C. up to 75° C., at least 51° C. up to 75° C., at least 51.5° C. up to 75° C., at least 52° C. up to 75° C., at least 52.5° C. up to 75° C., at least 53° C. up to 75° C., at least 53.0° C. up to 74° C., at least 53.0° C. up to 73° C., at least 53.0° C. up to 72° C., at least 53.0° C. up to 71° C., at least 53.0° C. up to 70° C., at least 53.0° C. up to 69° C., at least 53.0° C. up to 68° C., at least 53.0° C. up to 67° C., at least 53.0° C. up to 66° C., and at least 53.0° C. up to 66.5° C.

In a preferred embodiment of the invention, the improved variants of SEQ ID NO:1 exhibiting an improved thermal stability compared to SEQ ID NO: 1 differs from the ketoreductase of inventive SEQ ID NO: 1 by at least one residue changes, by at least two residue changes, by at least three residue changes, by at least four residue changes, or by at least six residue changes of the sequences positions selected from the group consisting of S3I, S4N, S8A, L9G, L9M. L9C, L9R. L9K. L9Q, N10G, A11V, A11C, V13G, E22K. S25A, M26R. A30R. E31N, A38M, S39G, S39A, L42Y, E43K, Q44T, Q44E, Q44R. K49R, A50K, I54R, I54V, V55I, V55C, K56M, Q57P, Q57A, T60C, T60N, T60A, S69V, S69A, D70C, D70S, G75L, S76M, S76C, S76L, S76G, F77L, S92M, S92G, S97A, S97W, S97V, S97C, S97M, S97F, Q98E, F99R, S100E, S100Q, S100R, S100V, S100C, P101F, P101H, P101W, A106C, A106E, A108P, D109G, D109R, N112T, M113V, L114V, L114I, T119L, A120G, P121V, P121A, A127K, A127C, A127G, A127Q, I132V, I132W, I132F, S133L, S133A, S133Q, S133M, S133V, P136V, P136G, Q138A, Q138T, Q138S, T139V, T139F, T139K, A141S, G147C, T148S, G149C, G149V, G149S, G149M, G149I, S151A, K152A, A155W, A155H, M157F, M157R, M157G, M157C, M157E, M157K, M157D, V158M, G159S, G159A, D169E, M172C, P181V, P181W, P181L, K182I, N185R, T194V, A199C, E200P, E200V, E200A, I202V, P204L, M206T, M206D, M206G, M206A, D208H, D208C, D208N, L209C, P210C, N212K, N212P, N212A, G213D, W214G, I215T, V217N, V217P, I220V, T225I, T225M, L227V, N232Y, N232F, G235F, T236S, T237I, V238F, S239F, G243V, Y244F, Y244L, C245F, and A246F, and preferably consisting of S97V, S97C, F99R, P121V, G149C, G149M, Y244L, and most preferably consisting of S97C, G149C, and G149M.

The following parts of the description apply to all, the first aspect of the invention, the second aspect of the invention, and the third aspect of the invention.

Preferably, the ketoreductase according to the invention is capable of stereoselectively and/or regioselectively reducing keto substrates to secondary alcohols and/or capable of stereoselectively and/or regioselectively oxidizing secondary alcohols to keto products.

Preferably, the ketoreductases according to the invention are capable of oxidizing primary alcohols to aldehydes and/or capable of reducing aldehydes to primary alcohols.

In some embodiments, the ketoreductases according to the invention are capable of oxidizing an aldehyde compound to a carboxylic acid.

In a preferred embodiment, the ketoreductase according to the invention is capable of preferably stereoselectively and/or regioselectively reducing a keto substrate of general formula (I)

to a secondary alcohol;
or preferably regioselectively reducing an aldehyde substrate of general formula (I')

to a primary alcohol;
or preferably stereoselectively and/or regioselectively oxidizing a secondary alcohol of the general formula (II)

to a ketone;
or preferably regioselectively oxidizing a primary alcohol of the general formula (II')

to an aldehyde;
wherein X and Y are each independently selected from
saturated or unsaturated, unsubstituted or mono- or poly-substituted, branched or unbranched $C_1$-$C_{12}$ aliphatic residues;
saturated or unsaturated, unsubstituted or mono- or poly-substituted $C_3$-$C_{12}$ cycloaliphatic residues, optionally being bridged to the CO-moiety through a saturated or unsaturated, unsubstituted or mono- or polysubstituted $C_1$-$C_{12}$-aliphatic residue;

saturated or unsaturated, unsubstituted or mono- or polysubstituted $C_1$-$C_{12}$ heterocycloaliphatic residues, optionally being bridged to the CO-moiety through a saturated or unsaturated, unsubstituted or mono- or polysubstituted $C_1$-$C_{12}$-aliphatic residue;

unsubstituted or mono- or polysubstituted $C_6$-$C_{10}$-aromatic residues, optionally being bridged to the CO-moiety through a saturated or unsaturated, unsubstituted or mono- or polysubstituted $C_1$-$C_{12}$-aliphatic residue; or unsubstituted or mono- or polysubstituted $C_1$-$C_{12}$ heteroaromatic residues, optionally being bridged to the CO-moiety through a saturated or unsaturated, unsubstituted or mono- or polysubstituted $C_1$-$C_{12}$-aliphatic residue;

or wherein X and Y together with the carbon atom to which they are attached may form a saturated or unsaturated, unsubstituted or mono- or polysubstituted $C_3$-$C_{12}$ cycloaliphatic residue, or a saturated or unsaturated, unsubstituted or mono- or polysubstituted $C_1$-$C_{12}$ heterocycloaliphatic residue; and wherein mono- or polysubstituted means independently substituted with one or more functional groups selected from —F, —Cl, —Br, —$C_{1-12}$-alkyl, —$C_{1-12}$-alkyl-F, —$C_{1-12}$-alkyl-Cl, —$C_{1-12}$-alkyl-Br, —OH, =O, —O$C_{1-12}$-alkyl, —O$C_{6-10}$-aryl, —O-heteroaryl, —OCO$C_{1-12}$-alkyl, —OCO$C_{6-10}$-aryl, —OCO-heteroaryl, —SH, —S$C_{1-12}$-alkyl, —S$C_{6-10}$-aryl, —S-heteroaryl, —S(=O)$_{1-2}$OH, —NO, —NO$_2$, —N$_3$, —NH$_2$, —NH($C_{1-12}$-alkyl), —N($C_{1-12}$-alkyl)$_2$, —NH($C_{6-10}$-aryl), —N($C_{6-10}$-aryl)$_2$, —NH(heteroaryl), —N(heteroaryl)$_2$, —CN, —CHO, —CO$_2$H, CO—$C_{1-2}$-alkyl, —CO—$C_{6-10}$-aryl and —CO— heteroaryl;

and wherein heterocycloaliphatic or heteroaromatic means cyclic structures that have atoms of at least two different elements as members of its ring(s), whereas the heteroatoms are preferably selected from the group consisting of the elements S, O, N, and B.

In a preferred embodiment, X and Y together with the carbon atom to which they are attached form a ring selected from cyclopropyl, cyclobutyl, cyclopentyl, cyclohexyl, and cycloheptyl, in each case saturated or unsaturated, unsubstituted or mono- or polysubstituted.

In another preferred embodiment, X and Y together with the carbon atom to which they are attached form a ring selected from oxirane, oxetane, oxolane, oxole, azetidine, azolidine, pyrrolidine, piperidine, piperazine and morpholine, in each case saturated or unsaturated, unsubstituted or mono- or polysubstituted. Preferably, said ring is substituted with =O, more preferably in alpha position to a ring oxygen atom or a ring nitrogen atom such that the respective rings may be regarded as lactones and lactams, respectively, optionally further substituted, preferably with one or more hydroxyl groups. Preferably, said ring is substituted with —OH, more preferably in alpha position to a ring oxygen atom or a ring nitrogen atom such that the respective rings may be regarded as acetals, ketals and aminals, respectively, optionally further substituted, preferably with one or more hydroxyl groups. Preferred examples include aldopyranoses, ketopyranoses, and sugar alcohols.

In another preferred embodiment, X and Y together with the carbon atom to which they are attached form a heterocycloaliphatic ring, whereas one or more heteroatoms are preferably selected from the group consisting of the elements S, O, N, and B, more preferably the elements O and N. Preferably, at least one of said heteroatoms is directly adjacent to the carbonyl group of general formula (I) or (I'), so that the respective rings may be regarded as lactones or lactams and/or at least one of said heteroatoms is directly adjacent to the hydroxyl group of general formula (II) or (II'), so that the respective rings may be regarded as cyclic hemiacetals, hemiketals and the corresponding aminals, respectively.

In a preferred embodiment, the keto substrate of general formula (I) is a ketose, which may be present in open chain form or cyclic form (e.g. furanose form or pyranose form). Preferred ketoses include but are not limited to ketopentoses and ketohexoses, especially psicose, fructose, sorbose and tagatose. The ketose may also be part of a di- or polysaccharide.

In a preferred embodiment, the aldehyde substrate of general formula (I') is an aldose, which may be present in open chain form or cyclic form (e.g. furanose form or pyranose form). Preferred aldoses include but are not limited to aldopentoses and aldohexoses, especially ribose, arabinose, xylose, lyxose, allose, altrose, glucose, mannose, gulose, idose, galactose, talose, and the deoxyderivatives of any of the foregoing such as rhamnose. The aldose may also be part of a di- or polysaccharide.

In a preferred embodiment, the secondary alcohol of the general formula (II) or primary alcohol of the general formula (II') is a ketose, which may be present in open chain form or cyclic form (e.g. furanose form or pyranose form), or an aldose, which may be present in open chain form or cyclic form (e.g. furanose form or pyranose form), or a sugar alcohol of a ketose or and aldose, or another polyalcohol such as glycerol. The ketose may also be part of a di- or polysaccharide. The aldose may also be part of a di- or polysaccharide.

For the purpose of the description, saturated or unsaturated, unsubstituted or mono- or polysubstituted, branched or unbranched $C_1$-$C_{12}$ aliphatic residues include but are not limited to alkyl, alkenyl and alkynyl residues, such as —CH$_3$, —CH$_2$CH$_3$, —CH$_2$CH$_2$CH$_3$, —CH(CH$_3$)$_2$, —CH$_2$CH$_2$CH$_2$CH$_3$, —CH(CH$_3$)CH$_2$CH$_3$, —CH$_2$CH(CH$_3$)$_2$, —C(CH$_3$)$_3$, —CH=CH$_2$, —CH=CHCH=CH$_2$, —C≡CH, and —CH=CHC≡CH.

For the purpose of the description, saturated or unsaturated, unsubstituted or mono- or polysubstituted $C_3$-$C_{12}$ cycloaliphatic residues include but are not limited to $C_{3-12}$-cycloalkyl, such as cyclopentyl and cyclohexyl.

For the purpose of the description, saturated or unsaturated, unsubstituted or mono- or polysubstituted $C_1$-$C_{12}$ heterocycloaliphatic residues include but are not limited to $C_{3-12}$-cycloalkyl, wherein 1 or 2 carbon ring atoms are replaced by heteroatoms selected from N, O and S ($C_{1-12}$-heterocycloalkyl), such as oxirane, oxetane, oxolane, oxole, azetidine, azolidine, pyrrolidine, piperidine, piperazine and morpholine.

For the purpose of the description, unsubstituted or mono- or polysubstituted $C_6$-$C_{10}$-aromatic residues include but are not limited to phenyl and naphthyl.

For the purpose of the description, unsubstituted or mono- or polysubstituted $C_1$-$C_{12}$ heteroaromatic residues include but are not limited to monocyclic ring systems, bicyclic ring systems and tricyclic ring systems. Examples of monocyclic heteroaryls include but are not limited to azetidinyl, azepanyl, aziridinyl, diazepinyl, 1,3-dioxolanyl, dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, piperidinyl, pyranyl, pyrazinyl, pyrazolyl, pyrazolinyl, pyrazolidinyl, pyridinyl, pyrimidinyl, pyridazinyl, pyrrolyl, pyrrolinyl, pyrrolidinyl, tetrahydrofuranyl, tetrahydrothienyl, tetrazinyl, tetrazolyl, thiadiazolyl, thiadiazolinyl, thiadiazolidinyl, thiazolyl, thiazolinyl, thiazolidinyl, thienyl, thiomorpholinyl, 1,1-dioxidothiomorpholinyl (thiomorpholine sulfone), thiopyranyl, triazinyl, triazolyl, and trithianyl. Examples of bicyclic heteroaryls include but are not limited to benzimidazolyl, benzodioxinyl, benzothiazolyl, benzothienyl, benzotriazolyl, benzoxazolyl, benzofuranyl, benzopyranyl, benzothiopyranyl, cinnolinyl, indazolyl, indolyl, 2,3-dihydroindolyl, indolizinyl, naphthyridinyl, isobenzofuranyl, isobenzothienyl, isoindolyl, isoquinolinyl, phthalazinyl, 4H-pyrido(1,2-a)pyrimidin-4-one, pyranopyridinyl, quinolinyl, quinolizinyl, quinoxalinyl, quinazolinyl, tetrahydroisoquinolinyl, tetrahydro-quinolinyl, and thiopyranopyridinyl. Examples of tricyclic heteroaryls include but are not limited to acridinyl, carbazolyl, carbolinyl, dibenzo(b,d)furanyl, dibenzo(b,d)thienyl, naphtho(2,3-b)furan, naphtho(2,3-b)thienyl, phenazinyl, phenothiazinyl, phenoxazinyl, thianthrenyl, thioxanthenyl and xanthenyl.

For the purpose of the description, mono- or polysubstituted preferably independently means replacement of a hydrogen from the core by one or more functional groups selected from -halo (preferably —F, —Cl, —Br, —I), —OH, =O, —OC$_{1-12}$-alkyl, —OC$_{6-10}$-aryl, —O-heteroaryl, —OCOC$_{1-12}$-alkyl, —OCOC$_{6-10}$-aryl, —OCO-heteroaryl, —SH, —SC$_{1-12}$-alkyl, —SC$_{6-10}$-aryl, —S-heteroaryl, —S(=O)$_{1-2}$OH, —NO, —NO$_2$, —N$_3$, —NH$_2$, —NH(C$_{1-12}$-alkyl), —N(C$_{1-12}$-alkyl)$_2$, —NH(C$_{6-10}$-aryl), —N(C$_{6-10}$-aryl)$_2$, —NH(heteroaryl), —N(heteroaryl)$_2$, —CN, —CHO, —CO$_2$H, CO—C$_{1-2}$-alkyl, —CO—C$_{6-10}$-aryl and —CO-heteroaryl.

For the purpose of the description, sugar residues or desoxysugar residues in each case comprising mono-, di- or oligosaccharides means that the keto substrate of general formula (I) or the aldehyde substrate of general formula (I) may be a polyhydroxycarbonyl compound, optionally linked to other polyhydroxycarbonyl compounds through acetal and/or ketal bonds. For example, when X is C$_1$ alkyl monosubstituted with —OH and Y is C$_2$ alkyl polysubstituted with —OH, wherein every carbon atom bears a single —OH substituent, the keto substrate of general formula (I) is a ketotetrose encompassing both enantiomers, D-erythrulose as well as L-erythrulose. Analogously, the keto substrate of general formula (I) may be a ketopentose or a ketohexose which in turn may be linked to other sugar residues thus forming disaccharides or oligosaccharides. Correspondingly, when X is C$_2$ alkyl polysubstituted with —OH, wherein every carbon atom bears a single —OH substituent, the aldehyde substrate of general formula (I') is an aldotriose encompassing both enantiomers, D-glycerinaldehyde as well as L-glycerinaldehyde. Analogously, the aldehyde substrate of general formula (I) may be a aldotetrose, aldopentose or a aldohexose which in turn may be linked to other sugar residues thus forming disaccharides or oligosaccharides.

For the purpose of the description, capable of preferably stereoselectively and/or regioselectively reducing a keto substrate means that in the presence of a suitable cofactor under suitable conditions (preferably in water at pH 7.0 and 37° C.) the ketoreductase exhibits at least some activity against at least one keto substrate thereby yielding a secondary alcohol.

For the purpose of the description, capable of preferably setereoselectively oxidizing an alcohol substrate means that in the presence of a suitable cofactor under suitable conditions (preferably in water at pH 7.0 and 37° C.) the ketoreductase exhibits at least some activity against at least one primary or secondary alcohol substrate thereby yielding an aldehyde or ketone.

In some embodiments of the invention, the ketoreductases according to the invention are capable of preferably stereoselectively and/or regioselectively reducing acetophenone-derivatives according to general formula (III)

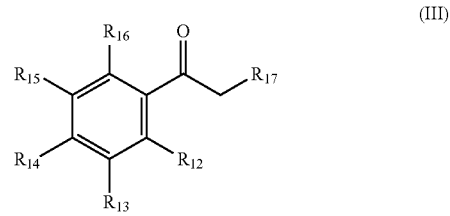

(III)

to the corresponding secondary alcohols,
wherein
$R_{12}$, $R_{13}$, $R_{14}$, $R_{15}$, and $R_{16}$ are each independently selected from the group consisting of —H; -halo (preferably chloro, bromo and iodo); unsubstituted or mono- or polysubstituted —C$_{1-12}$-alkyl; unsubstituted or mono- or polysubstituted —C$_{6-10}$-aryl, optionally being bridged through a saturated or unsaturated, unsubstituted or mono- or polysubstituted aliphatic C$_{1-12}$-hydrocarbon residue; unsubstituted or mono- or polysubstituted-heteroaryl, optionally being bridged through a saturated or unsaturated, unsubstituted or mono- or polysubstituted aliphatic C$_{1-12}$-hydrocarbon residue; and —OR$_{18}$, wherein R$_{18}$ is —H, unsubstituted or mono- or polysubstituted —C$_{1-12}$-alkyl, or unsubstituted or mono- or polysubstituted —C$_{6-10}$-aryl, optionally being bridged through a saturated or unsaturated, unsubstituted or mono- or polysubstituted aliphatic C$_{1-12}$-hydrocarbon residue;
preferably, $R_{12}$, $R_{13}$, $R_{14}$, $R_{15}$, and $R_{16}$ are independently —H, -halo, or OR$_{18}$; more preferably —H, —Cl, or OCH$_3$;
$R_{17}$ is —H; -halo (preferably chloro, bromo and iodo); unsubstituted or mono- or polysubstituted —C$_{1-12}$-alkyl; unsubstituted or mono- or polysubstituted —C$_{6-10}$-aryl, optionally being bridged through a saturated or unsaturated, unsubstituted or mono- or polysubstituted aliphatic C$_{1-12}$-hydrocarbon residue; unsubstituted or mono- or polysubstituted-heteroaryl, optionally being bridged through a saturated or unsaturated, unsubstituted or mono- or polysubstituted aliphatic C$_{1-12}$-hydrocarbon residue; —OR$_{19}$, —NH$_2$, —NHR$_{19}$, or —NR$_{19}$R$_{20}$, wherein R$_{19}$ and R$_{20}$ are each independently selected from unsubstituted or mono- or polysubstituted —C$_{1-12}$-alkyl; unsubstituted or mono- or polysubstituted —C$_{6-10}$-aryl, optionally being bridged through a saturated or unsaturated, unsubstituted or mono- or polysubstituted aliphatic C$_{1-12}$-hydrocarbon residue; or unsubstituted or mono- or polysubstituted-heteroaryl, optionally being bridged through a saturated or unsaturated, unsubstituted or mono- or polysubstituted aliphatic C$_{1-12}$-hydrocarbon residue;
preferably, $R_{17}$ is —H;
wherein a particularly preferred keto substrate of this type is 1-(4-chlorophenyl)ethanone (4-CAP),

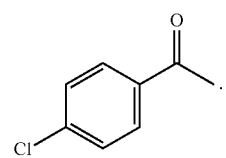

In some embodiments of the invention, the ketoreductases according to the invention are capable of preferably stereoselectively and/or regioselectively catalyzing the reverse reaction, i.e. oxidizing the corresponding secondary alcohol to the acetophenone-derivatives according to general formula (III).

In some embodiments of the invention, the ketoreductases according to the invention are capable of preferably stereoselectively and/or regioselectively reducing secodione-derivatives according to general formula (IV)

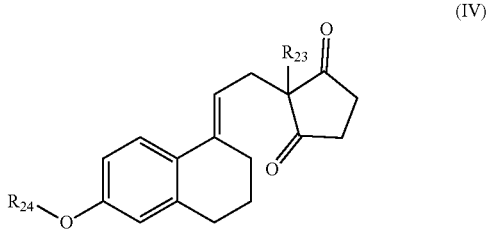

to the corresponding secondary alcohols,
wherein
$R_{23}$ and $R_{24}$ are each independently selected from the group consisting of —H and —$C_{1-12}$-alkyl; and
preferably $R_{23}$ is —$CH_2CH_3$ and $R_u$ is —$C_{1-12}$-alkyl; more preferably $R_{23}$ is —$CH_2CH_3$ and $R_u$ is —$CH_3$;
wherein a particularly preferred keto substrate of this type is ethylsecodion (ethyl-3-methoxy-8,14-seco-gona-1,3,5(10),9(11)-tetraen-14,17-dione)

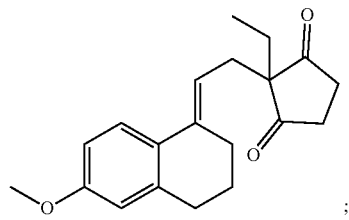 [SMILES: CCC1(C/C=C2\CCCc3cc(OC)ccc32)C(=O)CCC1=O ; ";"]

In some embodiments of the invention, the ketoreductases according to the invention are capable of preferably stereoselectively and/or regioselectively catalyzing the reverse reaction, i.e. oxidizing the corresponding secondary alcohol to the secodione-derivatives according to general formula (IV).

In some embodiments of the invention, the ketoreductases according to the invention are capable of preferably stereoselectively and/or regioselectively reducing ethyl-4-chloro-3-oxo-butanoate (COBE) to the corresponding secondary alcohol. In some embodiments of the invention, the ketoreductases according to the invention are capable of preferably stereoselectively and/or regioselectively catalyzing the reverse reaction, i.e. oxidizing the corresponding secondary alcohol to ethyl-4-chloro-3-oxo-butanoate (COBE).

In some embodiments of the invention, the ketoreductases according to the invention are capable of preferably stereoselectively and/or regioselectively reducing ethyl-3-oxo-3-phenyl-propanoate. to the corresponding secondary alcohol. In some embodiments of the invention, the ketoreductases according to the invention are capable of preferably stereoselectively and/or regioselectively catalyzing the reverse reaction, i.e. oxidizing the corresponding secondary alcohol to ethyl-3-oxo-3-phenyl-propanoate.

In some embodiments of the invention, the ketoreductases according to the invention are capable of preferably regioselectively reducing an aldehyde substrate selected from the group consisting of ketones of aliphatic alcohols like 2-butanal (synonymous to isobutyraldehyde), or preferably 2-heptanal to the corresponding primary alcohol. In some embodiments of the invention, the ketoreductases according to the invention are capable of preferably regioselectively catalyzing the reverse reaction, i.e. oxidizing the corresponding primary alcohol to ketones of aliphatic alcohols like 2-butanal or 2-heptanal.

In some embodiments, the ketoreductases according to the invention are capable of oxidizing an aldehyde compound to a carboxylic acid.

In some embodiments the ketoreductase according to the invention is capable of oxidizing aldehyde substrates to carboxylic acids, wherein the aldehyde substrates are preferably selected from the group consisting of aliphatic, aromatic and hetero-aromatic aldehyde substrates.

It has been surprisingly found that the ketoreductases according to the invention exhibit
- a high activity regarding both, oxidation and reduction; and/or
- a high oxidation activity at different pH values ("pH-related activity"); and/or
- a broad substrate tolerance; and/or
- a high cofactor preference; and/or
- a high stereoselectivity; and/or
- a high stereospecificity; and/or
- a high residual activity at elevated temperature; and/or
- a high regioselectivity.

In preferred embodiments of the ketoreductase according to the invention,
(i) the specific activity of the ketoreductase is higher than the specific activity of the amino acid sequence of comparative SEQ ID NO: 1 and/or SEQ ID NO:3; and/or
(ii) the thermal stability of the ketoreductase is higher than the thermal stability of the amino acid sequence of comparative SEQ ID NO: 1 and/or SEQ ID NO:3; and/or
(iii) the stereoselectivity of the ketoreductase is higher than the stereoselectivity of the amino acid sequence of comparative SEQ ID NO: 1 and/or SEQ ID NO:3; and/or
(iv) the pH-related activity ratio in terms of the specific activity at pH 7 versus pH 9 of the ketoreductase is higher than the stereoselectivity of the amino acid sequence of comparative SEQ ID NO: 1 and/or SEQ ID NO:3; and/or
(v) the oxidation-related activity for the conversion of primary alcohols to aldehydes and/or secondary alcohols to ketones by the ketoreductase is higher than the corresponding oxidation-related activity of the amino acid sequence of SEQ ID NO: 1 and/or SEQ ID NO:3.

In other preferred embodiments of the ketoreductase according to the invention, the ketoreductase variants of SEQ ID NO: 1
(i) exhibit a higher thermal stability expressed as $Tm_{50(40)}$-value than the ketoreductase of comparative SEQ ID NO:1; and/or
(ii) exhibit a higher thermal stability expressed as $Tm_{50(10)}$-value than the ketoreductase of comparative SEQ ID NO:1; and/or
(iii) exhibits an improved thermal stability expressed as residual activity after 15 minutes at 42° C. over the comparative SEQ ID NO: 1, and/or
(iv) exhibits an increased activity, in particular specific activity, in the oxidation of alcohol substrates to ketone or aldehyde products over the comparative SEQ ID NO: 1; and/or (v) exhibits an increased activity, in particular specific activity, the reduction of ketone or aldehyde substrates to alcohol products over the comparative SEQ ID NO: 1; and/or (vi) exhibits an increased ratio of oxidation activity over reduction activity for the conversion of ketone or aldehyde substrates to alcohol products or vice versa; and/or (vi) exhibits an increased ratio of reduction activity over oxidation activity for the conversion of ketone or aldehyde substrates to alcohol products or vice versa over the comparative SEQ ID NO: 1; or (vii) exhibits a decreased ratio of reduction activity over oxidation activity for the conversion of ketone or aldehyde substrates to alcohol products or vice versa over the comparative SEQ ID NO: 1.

Ketoreductases according to the invention may also exhibit a high stereospecificity, and/or a high activity in various solvents optionally containing cosubstrates such as isopropanol.

For the purpose of the description, the functional properties of the ketoreductase according to the invention are preferably measured under standard conditions with standard substrates and optionally compared with the respective properties of other ketoreductases, e.g. according to comparative SEQ ID NO:3, under the same conditions. Preferably, unless expressly stated otherwise, said standard substrates are selected from the group consisting of ethyl acetoacetate/ethyl-3-hydroxybutyrate, cyclohexanone/cyclohexanol, acetone/isopropanol, ethyl-4-chloro-3-hydroxybutanoate (COBE), and 1-(4-chlorophenyl)ethanol (4-CAP); and said standard conditions are as outlined in the experimental section.

For the purpose of the specification, stereoselectivity is the property of a chemical reaction in which a single reactant is converted into an unequal mixture of stereoisomers during the non-stereospecific creation of a new stereocenter or during the non-stereospecific transformation of a pre-existing one. The selectivity typically arises from differences in steric effects and electronic effects in the mechanistic pathways leading to the different products. Preferably, the conversion of a substrate into a chiral product under catalysis of the ketoreductase according to the invention provides the desired chiral product with an enantiomeric excess of at least 50% ee, more preferably at least 75% ee, still more preferably at least 90% ee, yet more preferably at least 95% ee, even more preferably at least 96% ee, even more preferably at least 97% ee, most preferably at least 98% ee, and in particular at least 99% ee. A high stereoselectivity describes the ability of an enzyme to selectively oxidize one enantiomer from a mixture of (R)- and (S)-enantiomers of secondary alcohols to a prochiral ketone without significant conversion of the other enantiomer, or selectively reduce a prochiral ketone to just one enantiomer ((R)- or (S)) of the secondary alcohol product without significant production of the other enantiomer. The stereoselectivity can be determined by analyzing the reaction mixture using analytical chiral chromatography e.g. gas chromatography (GC) or high-performance liquid chromatography (HPLC) using an appropriate column with a chiral stationary phase, able to separate the different enantiomers For the purpose of the specification, stereospecificity is the property of a reaction mechanism that leads to different stereoisomeric reaction products from different stereoisomeric reactants, or which operates on only one (or a subset) of the stereoisomers. Preferably, the conversion of a chiral substrate into another chiral product under catalysis of the ketoreductase according to the invention provides the desired chiral product with a diastereomeric excess of at least 50% ee, more preferably at least 75% ee, still more preferably at least 90% ee, yet more preferably at least 95% ee, even more preferably at least 96% ee, even more preferably at least 97% ee, most preferably at least 98% ee, and in particular at least 99% ee.

For the purpose of the specification, regioselectivity is the property of specifically converting a specific functionality out of a group of various alternative functionalities of the same type without at the same time also converting the other functionalities. Examples of substrates having more than a single convertible functionality include but are not limited to rhamnono-1,5-lactone, mevalonolactone, glucanolactone, saccharides, and the like. Thus, for the purpose of specification, a high regioselectivity describes the ability of an enzyme to selectively oxidize just one of two or more alcohol-groups to the corresponding carbonyl product or selectively reduce just one of two or more carbonyl groups to the corresponding alcohol product without significantly oxidizing or reducing the other groups. The regioselectivity can be determined using analytical chromatographic methods like gas chromatography (GC) or high-performance liquid chromatography (HPLC) employing a suitable column and separation protocol to separate the different possible products. By comparison to analytical standards the produced products can be identified. Alternatively also mass spectroscopy or nuclear magnetic resonance (NMR) spectroscopy can be used for product identification.

For the purpose of the specification, activity in conversion of a substrate to a product means the conversion rate, preferably the initial conversion rate, at which the enzyme converts such substrate to a product under certain reaction conditions. Preferably, the activity is a specific activity, in which the enzymatic activity is related to a second, usually quantitative parameter, indicating the effectiveness of the enzyme in respect to such secondary parameter. Generally used secondary parameters may be the weight of (lyophilized) enzyme (per gram enzyme), the weight of purified (lyophilized) enzyme (per gram purified enzyme), or per cell culture volume used in production and purification of the enzyme (per culture volume). A ketoreductase lyophilizate may be obtained e.g. by disruption of the cells as described in example 2 (see below) and subsequent lyophilization of the crude extract.

For the purpose of specification, the pH-related activity of an enzyme describes the relative activity, preferably relative specific activity, of an enzyme at different pH values. Preferably, the pH profile of an enzyme provides a broad range of activity at various pH values. The relative activity at different pH values can be expressed as the "pH-related activity ratio", which may be described as a pH-related activity ratio (in percent) of an activity at a pH value (1) and a pH value (2). The optimum pH value is the pH value at which the enzyme exhibits its highest specific activity. It is desirable, that enzyme exhibit a high pH-related activity over a broad pH range. Specifically, many ketoreductases exhibit higher specific activity values for oxidation reactions at slightly alkaline pH values over neutral or slightly acidic pH values, and higher specific activity values for reductive reactions at slightly acidic/neutral pH values over slightly alkaline pH values. Preferably, ketoreductases exhibit a high pH-related activity for oxidation reactions at slightly acidic and neutral pH values. The "pH-related activity ratio" according to the invention relates to higher ratio (as percentage) of the specific activity at pH7 versus pH9, or alternatively at pH7.5 versus pH9, respectively, wherein the specific activity of a certain ketoreductase for a substrate at pH 9 is defined as a 100% value, and the percentage of the specific activity of the same ketoreductase for the same substrate at pH 7, or pH 7.5 respectively, describes the pH-related activity ratio.

For the purpose of specification, the cofactor preference describes the relative activity, preferably relative specific activity, of an enzyme, specifically of a ketoreductase, in converting a given substrate to a product in presence of the cofactors NAD/NADH or NADP/NADPH. For some applications no preference of one over the other cofactor NADH or NADPH is necessary/mandatory. For certain reactions, however, a preference in using a specific cofactor is desirable. Accordingly, it is advantageous to provide ketoreductases with a high cofactor preference, which may be either a preference for $NAD^+$/NADH or a preference for $NADP^+$/NADPH. The cofactor preference at a given reaction can be expressed as percentage of the specific activity of a cofactor (1) in comparison to the cofactor (2). Preferably, the ketoreductase according to the invention of inventive SEQ ID NO: 1 exhibits cofactor preference ratio for NADPH/NADP of 37.3 for ethyl acetoacetate, and of 3.3 for COBE.

Preferably, the ketoreductase according to the invention is capable of reducing or oxidizing a substrate at a high specific activity, preferably at a specific activity of 0.001-100 U/mg, more preferably 0.01-50 U/mg, 0.01-25 U/mg, 0.01-10 U/mg, 0.01-7.5 U/mg, 0.01-6 U/mg, 0.01-5.5 U/mg, 0.01-5 U/mg, 0.01-4.5 U/mg, 0.01-4.4 U/mg, 0.01-4.3 U/mg, 0.01-4.2 U/mg, 0.02-4.2 U/mg, 0.03-4.2 U/mg, 0.03-4.1 U/mg, even more preferably 0.1-50 U/mg, 0.1-25 U/mg, 0.1-10 U/mg, 0.1-7.5 U/mg, 0.1-6 U/mg, 0.1-5.5 U/mg, 0.1-5 U/mg, 0.1-4.5 U/mg, 0.1-4.4 U/mg, 0.1-4.3 U/mg, 0.1-4.2 U/mg, 0.1-4.2 U/mg, 0.1-4.2 U/mg, 0.1-4.1 U/mg, even more preferably 0.3-50 U/mg, 0.3-25 U/mg, 0.3-10 U/mg, 0.3-7.5 U/mg, 0.3-6 U/mg, 0.3-5.5 U/mg, 0.3-5 U/mg, 0.3-4.5 U/mg, 0.3-4.4 U/mg, 0.3-4.3 U/mg, 0.3-4.2 U/mg, 0.3-4.2 U/mg, 0.3-4.2 U/mg, 0.3-4.1 U/mg, yet more preferably 0.5-50 U/mg, 0.5-25 U/mg, 0.5-10 U/mg, 0.5-7.5 U/mg, 0.5-6 U/mg, 0.5-5.5 U/mg, 0.5-5 U/mg, 0.5-4.5 U/mg, 0.5-4.4 U/mg, 0.5-4.3 U/mg, 0.5-4.2 U/mg, 0.5-4.2 U/mg, 0.5-4.2 U/mg, 0.5-4.1 U/mg lyophilizate of ketoreductase. Substrates in the meaning of the invention are primary or secondary alcohols, aldehydes or ketones that are converted by a ketoreductase according to the invention.

Preferably, the ketoreductase according to the invention is capable of reducing or oxidizing a substrate in the presence of NADPH at a high specific activity, preferably at a specific activity of 0.01-100 U/mg, 0.01-50 U/mg, 0.01-25 U/mg, 0.01-10 U/mg, 0.01-7.5 U/mg, 0.01-6 U/mg, 0.01-5.5 U/mg, 0.01-5 U/mg, more preferably 0.1-100 U/mg, 0.1-50 U/mg, 0.1-25 U/mg, 0.1-10 U/mg, 0.1-7.5 U/mg, 0.1-6 U/mg, 0.1-5.5 U/mg, 0.1-5 U/mg, more preferably 1-100 U/mg, 1-50 U/mg, 1-25 U/mg, 1-10 U/mg, 1-7.5 U/mg, 1-6 U/mg, 1-5.5 U/mg, 1-5 U/mg, even more preferably 2-100 U/mg, 2-50 U/mg, 2-25 U/mg, 2-10 U/mg, 2-7.5 U/mg, 2-6 U/mg, 2-5.5 U/mg, 2-5 U/mg, and most preferably, 2.4-4.1 U/mg, Substrates in the meaning of the invention are primary or secondary alcohols, aldehydes or ketones that are converted by a ketoreductase according to the invention. Specifically, the ketoreductase according to the invention is capable of reducing ethyl acetoacetate in the presence of NADPH at a specific activity of 4.1 U/mg lyophilizate of ketoreductase, of reducing cyclohexanone in the presence of NADPH at a specific activity of 3.2 U/mg lyophilizate of ketoreductase, and of reducing 4-CAP in the presence of NADPH at a specific activity of 2.4 U/mg lyophilizate of ketoreductase.

Preferably, the ketoreductase according to the invention is capable of reducing ethyl acetoacetate at a high specific activity, preferably at a specific activity of 0.01-100 U/mg, more preferably, 0.01-50 U/mg, 0.01-25 U/mg, 0.01-10 U/mg, 0.01-7.5 U/mg, 0.01-6 U/mg, 0.01-5.5 U/mg, 0.01-5 U/mg, more preferably of 0.1-100 U/mg, 0.1-50 U/mg, 0.1-25 U/mg, 0.1-10 U/mg, 0.1-7.5 U/mg, 0.1-6 U/mg, 0.1-5.5 U/mg, 0.1-5 U/mg, even more preferably of 0.2-100 U/mg, 0.2-50 U/mg, 0.2-25 U/mg, 0.2-10 U/mg, 0.2-7.5 U/mg, 0.2-6 U/mg, 0.2-5.5 U/mg, 0.2-5 U/mg, yet more preferably of 0.3-100 U/mg, 0.3-50 U/mg, 0.3-25 U/mg, 0.3-10 U/mg, 0.3-7.5 U/mg, 0.3-6 U/mg, 0.3-5.5 U/mg, 0.3-5 U/mg, more preferably 0.1-4.5 U/mg, more preferably 0.11-4.5 U/mg, more preferably 0.15-4.5 U/mg, more preferably 0.2-4.5 U/mg, more preferably 0.1-4.3 U/mg, more preferably 0.15-4.3 U/mg, more preferably 0.2-4.3 U/mg, more preferably 0.1-4.2 U/mg, more preferably 0.1-4.2 U/mg, more preferably 0.1-4.1 U/mg, more preferably 0.11-4.2 U/mg, most preferably 0.11-4.1 U/mg lyophilizate of ketoreductase. Specifically, the ketoreductase according to the invention is capable of reducing ethyl acetoacetate at a specific activity of 4.1 U/mg lyophilizate of ketoreductase in the presence of NADPH, and at a specific activity of 0.11 U/mg lyophilizate of ketoreductase in the presence of NADH.

Preferably, the ketoreductase according to the invention is capable of reducing 4-CAP at a high specific activity, preferably at a specific activity of 0.001-100 U/mg, more preferably, 0.01-50 U/mg, more preferably 0.01-25 U/mg, more preferably 0.01-10 U/mg, more preferably 0.01-7.5 U/mg, more preferably 0.01-5 U/mg, more preferably 0.01-4 U/mg, more preferably 0.01-3 U/mg, more preferably 0.05-3 U/mg, more preferably 0.1-3 U/mg, more preferably 0.2-2.9 U/mg, more preferably 0.25-2.8 U/mg, more preferably 0.5-2.7 U/mg, more preferably 1-2.6 U/mg, more preferably 1-2.5 U/mg, more preferably 1-2.4 U/mg, more preferably 2-2.4 U/mg, most preferably 2.2.-2.4 Uhng lyophilizate of ketoreductase. Specifically, the ketoreductase according to the invention is capable of reducing 4-CAP at a specific activity of 2.4 U/mg lyophilizate of ketoreductase in the presence of NADPH.

Preferably, the ketoreductase according to the invention is capable of reducing cyclohexanone at a high specific activity, preferably at a specific activity of 0.01-100 U/mg, preferably of 0.1-100 U/mg, 0.5-100 U/mg, more preferably, 0.5-50 U/mg, more preferably 0.5-25 U/mg, more preferably 0.5-10 U/mg, more preferably 0.5-7.5 U/mg, more preferably 0.5-5 U/mg, more preferably 1-5 U/mg, more preferably 1.5-5 U/mg, more preferably 2-5 U/mg, more preferably 2-4 U/mg, more preferably 2-3.9 U/mg, more preferably 2.5-3.8 U/mg, more preferably 3-3.7 U/mg, more preferably 3-3.6 U/mg, more preferably 3-3.5 U/mg, more preferably 3-3.4 U/mg, more preferably 3-3.3 U/mg, most preferably 3.2 U/mg lyophilizate of ketoreductase. Specifically, the ketoreductase according to the invention is capable of reducing cyclohexanone at a specific activity of 3.2 U/mg lyophilizate of ketoreductase in the presence of NADPH.

Preferably, the ketoreductase according to the invention is capable of reducing COBE at a high specific activity, preferably at a specific activity of 0.01-100 U/mg, more preferably 0.06-50 U/mg, 0.08-50 U/mg, more preferably 0.08-25 U/mg, more preferably 0.8-10 U/mg, more preferably 0.08-5 U/mg, more preferably 0.08-2.5 U/mg, more preferably 0.08-1 U/mg, more preferably 0.08-0.9 U/mg, more preferably 0.08-0.8 U/mg, more preferably 0.08-0.7 U/mg, more preferably 0.08-0.6 U/mg, more preferably 0.08-0.5 U/mg, more preferably 0.08-0.4 U/mg, more preferably 0.09-0.4 U/mg, and most preferably 0.09-0.3 U/mg lyophilizate of ketoreductase. Specifically, the ketoreductase according to the invention is capable of reducing COBE at a specific activity of 0.3 U/mg lyophilizate of ketoreductase in the presence of NADPH and at a specific activity of 0.09 U/mg lyophilizate of ketoreductase in the presence of NADH.

Preferably, the ketoreductase according to the invention is capable of oxidizing ethyl-3-hydroxybutyrate at a high specific activity, preferably at a specific activity of 0.03-100 U/mg, more preferably, 0.05-50 U/mg, more preferably 0.05-25 U/mg, more preferably 0.05-10 U/mg, more preferably 0.06-5 U/mg, more preferably 0.06-2.5 U/mg, more preferably 0.07-1 U/mg, more preferably 0.07-0.9 U/mg, more preferably 0.07-0.8 U/mg, more preferably 0.07-0.7 U/mg, more preferably 0.07-0.6 U/mg, more preferably 0.07-0.5 U/mg, more preferably 0.07-0.4 U/mg, more preferably 0.07-0.3 U/mg, more preferably 0.08-0.25 U/mg, and most preferably 0.09-0.22 U/mg lyophilizate of ketoreductase. Specifically, the ketoreductase according to the invention is capable of oxidizing ethyl-3-hydroxybutyrate at a high specific activity at pH 7 of 0.07-0.1 U/mg, most preferably at 0.09 U/mg lyophilizate of ketoreductase, and at a high specific activity at pH 9 of 0.07-0.25 U/mg, more preferably of 0.1-0.25 U/mg, of 0.15-0.25 U/mg, of 0.2-0.25 U/mg, and most preferably at 0.22 U/mg lyophilizate of ketoreductase.

Preferably, the ketoreductase according to the invention is capable of oxidizing cyclohexanol at a high specific activity, preferably at a specific activity of 0.25-100 U/mg, more preferably 0.26-50 U/mg, 0.26-25 U/mg, 0.26-10 U/mg, 0.27-5 U/mg, 0.28-2.5 U/mg, 0.29-2.5 U/mg, 0.29-1 U/mg, 0.29-0.9 U/mg, 0.29-0.8 U/mg, more preferably 0.29-0.7 U/mg, more preferably 0.3-0.6 U/mg, and most preferably 0.31-0.5 U/mg lyophilizate of ketoreductase. Specifically, the ketoreductase according to the invention is capable of oxidizing cyclohexanol at a high specific activity at pH 7.5 of 0.3-0.5 U/mg, most preferably at 0.31 U/mg lyophilizate of ketoreductase, and at a high specific activity at pH 9 of 0.3-1 U/mg, more preferably of 0.3-0.8 U/mg, of 0.3-0.7 U/mg, of 0.3-0.6 U/mg, and most preferably at 0.5 U/mg lyophilizate of ketoreductase.

Preferably, the ketoreductase according to the invention is capable of oxidizing isopropanol at pH 7 at a high specific activity, preferably at a specific activity of 0.02-10 U/mg, 0.02-5 U/mg, 0.02-2 U/mg, 0.02-1 U/mg, 0.02-0.5 U/mg, 0.02-0.25 U/mg, 0.02-0.1 U/mg, 0.02-0.09 U/mg, 0.02-0.08 U/mg, 0.02-0.07 U/mg, 0.02-0.06 U/mg, 0.03-0.05 U/mg, and most preferably 0.03 U/mg lyophilizate of ketoreductase.

Preferably, the ketoreductase according to the invention is capable of oxidizing isopropanol at pH 9 at a high specific activity, preferably at a specific activity of 0.04-10 U/mg, 0.04-5 U/mg, 0.04-2 U/mg, 0.04-1 U/mg, 0.04-0.5 U/mg, 0.04-0.25 U/mg, 0.04-0.1 U/mg, 0.04-0.09 U/mg, 0.04-0.08 U/mg, 0.04-0.07 U/mg, 0.04-0.06 U/mg, and most preferably 0.05 U/mg lyophilizate of ketoreductase.

For determination of oxidation activity with respect to a given substrate, the ketoreductase according to the invention is preferably incubated in a buffer containing the substrate (50-100 mM or 20% (v/v)), and a cofactor, for example 0.25 mM of NAD(P)$^+$ at 30° C. The oxidation activity is determined by measuring the change of absorbance at 340 nm resulting from NAD(P)$^+$ change.

For determination of reduction activity with respect to a given substrate, the ketoreductase according to the invention is preferably incubated in a buffer containing the substrate (50-100 mM or 20% (v/v)), and a cofactor, for example 0.25 mM of NAD(P)H at 30° C. The reduction activity is determined by measuring the change of absorbance at 340 nm resulting from NAD(P)H change.

Suitable cosubstrates established for cofactor regeneration in a ketoreductase reaction may be selected according their specific activity, preferably from the group consisting of isopropyl alcohol, 2-butanol, 2-pentanol, 2-hexanol and 2-heptanol.

Other suitable methods for cofactor regeneration in a ketoreductase may be enzymatic systems to be coupled with the ketoreductase of the invention. In particular, NAD(P)H-oxidases (NOX) can be used for oxidation of NAD(P)H to NAD(P)$^+$ using oxygen as a co-substrate. NOX systems are of particular interest for processes involving NADPH as a cofactor, as certain NOX systems are characterized by a cofactor preference of NADP$^+$ over NAD$^+$.

Preferably, the ketoreductases according to the invention exhibit a high stability in cosubstrates, preferably in isopropyl alcohol, 2-butanol, 2-pentanol, 2-hexanol and/or 2-heptanol. Preferably, after 6h pre-incubation of the ketoreductase at 30° C. in 50% aqueous cosubstrate, preferably isopropyl alcohol, the ketoreductase exhibits a residual activity of at least 1%, more preferably at least 10% or at least 20%, still more preferably at least 30% or at least 40%, yet more preferably at least 50% or at least 60%, even more preferably at least 70% or at least 80%, most preferably at least 85% or at least 90%, in particular at least 95% or at least 99%, relative to its activity before pre-incubation. In this regard, residual activity in the meaning of this invention describes the remaining ketoreductase activity of an enzyme after pre-incubation with a cosubstrate compared to the activity after pre-incubation without the cosubstrate. For determination of stability in cosubstrate, including e.g. isopropyl alcohol, the ketoreductase according to the invention is pre-incubated in a buffer, preferably at pH 7 or pH 9, containing 50% cosubstrate, e.g. isopropyl alcohol, at 30° C. for 6h, and the enzyme activity of the ketoreductase is compared to an enzyme pre-incubated without cosubstrate. The residual activity of the ketoreductase according the invention is 100%, when both enzyme activities are identical; i.e. when there is no loss of activity as compared to the activity under pre-incubation without cosubstrate.

An efficient conversion of cosubstrates by the ketoreductase and the ketoreductase stability in cosubstrate are of particular relevance for the setup of efficient industrial processes for the reduction of keto or aldehyde substrates to secondary or primary alcohols. The stability of the ketoreductases of the invention in cosubstrate and their capability of conversion of cosubstrates according the invention is also of relevance for the reverse conversion of primary and secondary alcohols to aldehyde and keto substrates.

For the purpose of specification, a high thermal stability describes the ability of an enzyme to resist irreversible inactivation after exposure to a specified elevated temperature over a given period of time. Residual activity of an enzyme incubated at the elevated temperature for a certain time is calculated as relative of the enzyme activity to a sample of the enzyme that has not been incubated at the elevated temperature. The enzyme activity can be determined in principle by using any activity assay. For the purpose of this invention thermal stability was determined by measuring and describing one or more of the following characteristics:

The $Tm_{50(40)}$-value: For the purpose of this invention, the $Tm_{50(40)}$-value is the temperature at which after 15 min of incubation of a 40 mg/ml solution of lyophilized enzyme in Tris/HCl-buffer (50 mM, pH 7, 2 mM MgCl$_2$) the ketoreductase enzyme possesses 50% of its initial activity. The initial activity is the activity of the respective enzyme without temperature treatment, i.e. with 15 min incubation at room temperature. The enzyme activity can be determined in principle by using any activity assay. In this invention the assays for the determination of oxidation or reduction activity as specified in the examples have been used, which are made part to the description.

The Tm$_{50(10)}$ value: For the purpose of this invention, the Tm$_{50(10)}$-value is the temperature at which after 15 min of incubation of a crude extract corresponding to an OD$_{600}$ of 10 the ketoreductase enzyme possesses 50% of its initial activity. The initial activity is the activity of the respective enzyme without temperature treatment, i.e. with 15 min incubation at room temperature. The enzyme activity can be determined in principle by using any activity assay. In this invention the assays for the determination of oxidation or reduction activity as specified in the examples have been used, which are made part to the description.

Residual activity: For the purpose of this invention, residual activity after 15 min/42° C. is defined as the activity of a ketoreductase enzyme after incubation for 15 min at 42° C. compared to its activity without incubation at 42° C. The residual activity is calculated by dividing the activity after incubation at 42° C. for 15 min by the activity without incubation at 42° C. and multiplying the value by 100 to obtain the residual activity value in percent. The enzyme activity can be determined in principle by using any activity assay. For the purpose of this invention the assays as described in the examples have been used, which are made part to the description.

In some embodiments the ketoreductases according to the invention exhibit a superior oxidation and reduction activity, preferably a superior specific oxidation and reduction activity, a superior thermal stability, and/or stereoselectivity resulting from sequence differences to the comparative SEQ ID NO:3.

For comparative purposes of the specification, it is referred to comparative SEQ ID NO:3 as being "comparative" meaning that beyond the disclosure of WO 2013/102619, wherein it is referred to as the sequence with the identification no. 10, no further change into any sequence position has been performed on comparative SEQ ID NO:3.

A superior specific activity according to the invention relates to a specific activity of a ketoreductase according to the invention which is higher than the specific activity of the ketoreductase of comparative SEQ ID NO:3. Preferably, the specific activity of the ketoreductase according to the invention is at least 10%, at least 50%, at least 100%, at least 1.4 times, at least 1.5 times, at least 2 times, at least 2.5 times, at least 3 times, at least 3.5 times, at least 4 times, at least 4.5 times, at least 5 times, at least 5.5 times, at least 6 times, at least 6.5 times, at least 7 times, at least 7.5 times, at least 8 times, at least 8.5 times, at least 9 times, at least 9.5 times, at least 10 times, at least 14 times, at least 20 times, at least 46 times, at least 50 times, at least 100 times, at least 200 times, at least 300 times, at least 500 times, at least 700 times, at least 250 times, at least 10.000 times, or at least 100.000 times higher than the specific activity of the ketoreductase of comparative SEQ ID NO:3. The improved specific activity may also mean that the ketoreductase according to the invention does exhibit a certain activity towards the desired substrate, whereas the ketoreductase of comparative SEQ ID NO:3 has no significant activity towards said substrate.

A superior "pH-related activity ratio" according to the invention relates to a pH-related activity ratio of a ketoreductase according to the invention which is higher than the pH-related activity ratio of comparative SEQ ID NO:3. Preferably, the value of the pH-related activity ratio of the ketoreductase according to the invention is at least 35%, at least 36% at least 37%, at least 38%, at least 39%, at least 40%, at least 41%, at least 42% at least 43%, at least 44%, at least 45%, at least 46%, at least 47%, at least 48%, at least 49%, at least 50%, at least 51%, at least 52% at least 53%, at least 54%, at least 55%, at least 56%, at least 57%, at least 58%, at least 59%, at least 60%, at least 61%, at least 62% at least 63%, at least 64%, at least 65%, at least 66%, at least 67%, at least 68%, at least 69%, at least 70%, at least 75%, at least 80%, or at least 90%. Specifically, the value of the pH-related activity ratio of the ketoreductase according to the invention for the substrate ethyl-3-hydroxybutyrate is preferably between 35% and 70%, more preferable between 37% and 60%, and most preferably is at 41%, the value of the pH-related activity ratio of the ketoreductase according to the invention for the substrate cyclohexanol is preferably between 35% and 80%, more preferable between 45% and 75%, and most preferably is at 62%, and the value of the pH-related activity ratio of the ketoreductase according to the invention for the substrate isopropanol is preferably between 40% and 80%, more preferable between 50% and 75%, and most preferably is at 60%.

A superior thermal stability according to the invention relates to a higher residual specific activity of the ketoreductase according to the invention after a certain time period at a given temperature, for example incubation for at least 15 minutes at 46° C., in comparison with the ketoreductase of comparative SEQ ID NO:3. Alternatively, an improved thermal stability according to this invention can relate to the same residual specific activity of an ketoreductase according to the invention in comparison with the ketoreductase of comparative SEQ ID NO:3, but after incubation for the same time at a higher temperature, or for a longer time at the same temperature. Preferably, the thermal stability provided by the ketoreductase according to the invention corresponds to a Tm$_{50(40)}$-value of at least 40° C., of at least 41° C., of at least 42° C., of at least 43° C., of at least 44° C., of at least 45° C., of at least 46° C., of at least 47° C., of at least 48° C., of at least 49° C., of at least 50° C., of at least 55° C., of at least 60° C., of at least 65° C., of at least 70° C., or of at least 72° C. It is also preferable according to the invention, that the ketoreductase according to the invention exhibits a thermal stability which corresponds to a Tm$_{50(40)}$-value which in comparison to the Tm$_{50(40)}$-value of comparative SEQ ID NO:3 is increased by at least 1° C., by at least 1° C. to 2° C., by at least 1° C. to 3° C., by at least 1° C. to 4° C., by at least 1° C. to 5° C., by at least 1° C. to 6° C., by at least 1° C. to 7° C., by at least 1° C. to 8° C., by at least 1° C. to 9° C., by at least 1° C. to 10° C., by at least 1° C. to 15° C., by at least 1° C. to 20° C., by at least 1° C. to 25° C., by at least 1° C. to 30° C., by at least 1° C. to 35° C., by at least 1° C. to 40° C., by at least 1° C. to 45° C., by at least 1° C. to 50° C., or by at least 1° C. to 55° C.; preferably by at least 2° C. to 3° C., by at least 2° C. to 4° C., by at least 2° C. to 5° C., by at least 2° C. to 6° C., by at least 2° C. to 7° C., by at least 2° C. to 8° C., by at least 2° C. to 9° C., by at least 2° C. to 10° C., by at least 2° C. to 15° C.m, and by at least 2° C. to 20° C., by at least 2° C. to 25° C., by at least 2° C. to 30° C., by at least 2° C. to 35° C., by at least 2° C. to 40° C., by at least 2° C. to 45° C., or by at least 2° C. to 50° C.; more preferably by at least 3° C. to 4° C., by at least 3° C. to 5° C., by at least 3° C. to 6° C., by at least 3° C. to 7° C., by at least 3° C. to 8° C., by at least 3° C. to 9° C., by at least 3° C. to 10° C., by at least 3° C. to 15° C., by at least 3° C. to 20° C., by at least 3° C. to 25° C., by at least 3° C. to 30° C., by at least 3° C. to 35° C., by at least 3° C. to 40° C., by at least 3° C. to 45° C., or by at least 3° C. to 50° C.; even more preferably by at least 4° C. to 5° C., by at least 4° C. to 6° C., by at least 4° C. to 7° C., by at least 4° C. to 8° C., by at least 4° C. to 9° C., by at least 4° C. to 10° C., and by at least 4° C. to 15° C., by at least 4° C. to 20° C., by at least 4° C. to 25° C., by at least 4° C. to 30° C., by at least 4° C. to 35° C., by at least 4° C. to 40° C., by at least 4° C. to 45° C.; even more preferably by at least 5° C. to 6° C., by at least 5° C. to 7° C., by at least 5° C. to 8° C., by at least 5° C. to 9° C., or by at least 5° C. to 10° C., by at least 5° C. to 15° C., by at least 5° C. to 20° C., by at least 5° C. to 25° C., by at least 5° C. to 30° C., by at least 5° C. to 35° C., by at least 5° C. to 40° C.; yet more preferably by at least 6° C. to 7° C., by at least 6° C. to 8° C., by at least 6° C. to 9° C., or by at least 6° C. to 10° C., by at least 6° C. to 15° C., by at least 6° C. to 20° C., by at least 6° C. to 25° C., by at least 6° C. to 30° C., by at least 6° C. to 35° C.; and most preferably at least 30° C.

In a certain embodiment, the ketoreductase according to the invention exhibits a thermal stability which corresponds to a $Tm_{50(40)}$-value which in comparison to the $Tm_{50(40)}$-value of comparative SEQ ID No:3 is increased by at least 1° C., by at least 2° C., by at least 3° C., by at least 4° C., by at least 5° C., by at least 6° C., by at least 7° C., by at least 8° C., by at least 9° C., by at least 10° C., by at least 15° C., by at least 20° C., by at least 25° C., or by at least 30° C.

A superior stereoselectivity according to the invention relates to an enantiomeric excess of the product provided by means of the ketoreductase according to the invention which is higher than the enantiomeric excess of the product provided by means of the ketoreductase of comparative SEQ ID NO:3. Preferably, the enantiomeric excess provided by the ketoreductase according to the invention of inventive SEQ ID NO: 1 is at least 20% ee, at least 30% ee, at least 40% ee, at least 50% ee, at least 60% ee, at least 70% ee, at least 80% ee, at least 90% ee, at least 91% ee, at least 92% ee, at least 93% ee, at least 94% ee, at least 95% ee, at least 96% ee, at least 97% ee, at least 98% ee, or at least 99% ee. It is also preferable according to the invention, that the ketoreductase of the invention of inventive SEQ ID NO: 1 provides an enantiomeric excess which is increased over the comparative SEQ ID NO:3 by at least 0.1% ee, at least 0.5% ee, at least 1% ee, at least 1.5% ee, at least 2% ee, at least 2.5% ee, at least 3% ee, at least 3.5% ee, at least 4% ee, or at least 4.5% ee.

A superior specific activity of the ketoreductase according to the invention compared to the ketoreductase of comparative SEQ ID NO:3 is preferably determined under standardized reaction conditions, typically at 30° C. in buffered aqueous solution, containing substrate, cofactor, optional supplements and ketoreductase. The buffer is preferably selected from the group consisting of 10-200 mM Tris/HCl at pH 7-9 containing 2 mM $MgCl_2$, 10-200 mM sodium phosphate/NaOH at pH 6-8, or 10-200 mM triethanolamine/HCl at pH 7-9. The cofactor NAD(P)H for the reductive reaction or NAD(P) for the oxidative reaction is preferably added to a final concentration ranging from 0.05 to 10 mM. Optional other supplements are preferably selected from the group consisting of 1-5% Triton™ X-100 (v/v), and 0.5 to 10% DMSO (v/v). The ketoreductase is preferably added as crude extract supernatant. The crude extract is obtained by disruption of the expression host containing the ketoreductase and subsequent centrifugation to separate the cell debris and the ketoreductase containing supernatant of the crude extract. The specific activity is preferably determined by measuring product formation, depletion of the reduced cofactor NADPH or NADH, preferably NADPH, and/or substrate depletion. In case the specific activity is determined by measuring product formation or substrate depletion, a cofactor regeneration system (isopropanol, GDH/glucose, or NOX) may be applied in the standard reaction. No cofactor regeneration system is applied, in case the specific activity is determined by measuring depletion of the reduced cofactor NADPH or NADH, preferably NADPH. In case a cofactor regeneration system is applied the reduced cofactor NADPH or NADH, preferably NADPH, can be substituted by the oxidized cofactor $NAD^+$ or $NADP^+$, preferably $NADP^+$, which is reduced by the cofactor regeneration system.

A superior thermal stability of the ketoreductase according to the invention compared to the ketoreductase of comparative SEQ ID NO:3 is preferably determined by incubation of the ketoreductase containing crude extract for 15 minutes at a given temperature (preferably the temperature, at which the ketoreductase of comparative SEQ ID NO:3 exhibits a residual activity of 10%) in a PCR cycler. Afterwards the crude extract is incubated on ice for 30 minutes. Insoluble proteins are separated by centrifugation and the supernatant is analyzed regarding its remaining ketoreductase activity in a standard ketoreductase assay. In this standard assay a suitable substrate for the ketoreductase is converted by the ketoreductase with concomitant oxidation of NADPH to $NADP^+$. The increase of NADPH is monitored by measuring the absorption at 340 nm in a standard photometer. The assay is carried out under standardized reaction conditions, i. e. typically at 30° C. in buffered aqueous solution, containing substrate (e.g. ethyl acetoacetate), cofactor and ketoreductase. The ketoreductase is preferably added as crude extract supernatant. The crude extract is obtained by disruption of the expression host containing the ketoreductase and subsequent centrifugation to separate the cell debris and the ketoreductase containing supernatant of the crude extract. The buffer is preferably selected from the group consisting of 10-200 mM Tris/HCl at pH 7-9 containing 2 mM $MgCl_2$, 10-200 mM sodium phosphate/NaOH at pH 6-8, or 10-200 mM triethanolamine/HCl at pH 7-9. The cofactor $NADP^+$ is preferably added to a final concentration ranging from 0.05 to 10 mM. The ketoreductase is preferably added as crude extract supernatant. The crude extract is obtained by disruption of the expression host containing the ketoreductase and subsequent centrifugation to separate the cell debris and the ketoreductase containing supernatant of the crude extract.

A superior stereoselectivity of the ketoreductase according to the invention compared to the ketoreductase of comparative SEQ ID NO:3 is preferably determined under standardized reaction conditions as described above for the determination of the improved specific activity. A chiral analytic is applied to analyze the product formed in the reaction.

Preferably, the ketoreductases according to the invention are capable of reducing any aldehyde substrate or are capable of stereoselectively and/or regioselectively reducing any keto substrate.

Preferably, the ketoreductase according to the invention besides an improved specific activity, thermal stability, and/or stereoselectivity compared to the ketoreductase of comparative SEQ ID NO:3 furthermore exhibits a high cosubstrate activity and/or cosubstrate stability, in particular a high stability and/or activity with isopropyl alcohol, 2-butanol, 2-pentanol, 2-hexanol, or 2-heptanol.

Preferably, the ketoreductase according to the invention exhibits a thermal stability that is higher than the thermal stability of the ketoreductase of comparative SEQ ID NO:3. Preferably, the ketoreductase according to the invention exhibits an improved $Tm_{50(40)}$-value which is elevated by 1° C. to 40° C., preferably 1° C. to 30° C., more preferably 1° C. to 20° C., even more preferably 3° C. to 15° C., and most preferably 7° C. compared to the ketoreductase of comparative SEQ ID NO:3, and more preferably exhibits an improved $Tm_{50(40)}$-value which is elevated by 1° C. to 60° C., preferably 1° C. to 50° C., more preferably 1° C. to 40° C., even more preferably 3° C. to 35° C., and most preferably 30° C. compared to the ketoreductase of comparative SEQ ID NO:3.

The ketoreductase is preferably added as crude extract supernatant. The crude extract is obtained by disruption of the expression host containing the ketoreductase and subsequent centrifugation to separate the cell debris and the ketoreductase containing supernatant of the crude extract.

Another aspect of the invention relates to a method for the stereoselective reduction of a keto substrate to a secondary alcohol or the stereoselective oxidation of one enantiomer of a chiral alcohol to a prochiral ketone comprising the step of reacting the keto substrate and a suitable cofactor in the presence of a ketoreductase according to the invention. Preferably, said suitable cofactor is NADH or NADPH for the reduction reaction or $NAD^+$ or NADP for the oxidation reaction. All preferred embodiments that have been defined above with respect to the ketoreductase according to the invention also apply to the method according to the invention and thus, are not reiterated hereinafter.

Another aspect of the invention relates to a method for reducing aldehydes to primary alcohols comprising the step of reacting the aldehyde and a suitable cofactor in the presence of a ketoreductase according to the invention. Preferably, said suitable cofactor is NADH or NADPH. All preferred embodiments that have been defined above with respect to the ketoreductase according to the invention also apply to the method according to the invention and thus, are not reiterated hereinafter.

Preferably, the method involves to concomitant conversion of a cosubstrate for cofactor regeneration by the respective ketoreductase at a high specific activity, such cosubstrates preferably being selected according their specific activity from the group consisting of isopropyl alcohol, 2-butanol, 2-pentanol, 2-hexanol, and 2-heptanol, and most preferably converting isopropyl alcohol to acetone at a high specific activity. In a preferred embodiment of the method according to the invention, the oxidized cofactor $NAD(P)^+$ is regenerated by use of NADPH:NADH oxidase (NOX), e.g. from *Lactobacillus sanfranciscensis* (Lountos et al., Acta Cryst. (2004), D60, 2044-2047), and a suitable cosubstrate, e.g. isopropyl alcohol.

Another aspect of the invention relates to a method for stereoselective oxidation of secondary alcohols to keto products comprising the step of reacting the secondary alcohol and a suitable cofactor in the presence of a ketoreductase according to the invention. Preferably, said suitable cofactor is $NAD^+$ or $NADP^+$. All preferred embodiments that have been defined above with respect to the ketoreductase according to the invention also apply to the method according to the invention and thus, are not reiterated hereinafter.

Another aspect of the invention relates to a method for oxidizing primary alcohols to aldehydes comprising the step of reacting the primary alcohol and a suitable cofactor in the presence of a ketoreductase according to the invention. Preferably, said suitable cofactor is $NAD^+$ or $NADP^+$. All preferred embodiments that have been defined above with respect to the ketoreductase according to the invention also apply to the method according to the invention and thus, are not reiterated hereinafter.

Preferably, the method involves to concomitant conversion of a cosubstrate for cofactor regeneration by the respective ketoreductase at a high specific activity, such cosubstrates preferably being selected according their specific activity from the group consisting of isopropyl alcohol, 2-butanol, 2-pentanol, 2-hexanol, and 2-heptanol, and most preferably converting isopropyl alcohol to acetone at a high specific activity. In a preferred embodiment of the method according to the invention, the reduced cofactor NAD(P)H is regenerated by use of NADPH:NADH oxidase (NOX), e.g. from *Lactobacillus sanfranciscensis* (Lountos et al., Acta Cryst. (2004), D60, 2044-2047), and a suitable cosubstrate, e.g. acetone.

Preferably, in the method according to the invention for the stereoselective reduction of keto substrates to secondary alcohols, and for the reduction of aldehyde substrates to primary alcohols, respectively, the aldehyde substrate and the keto substrate may be any aldehyde substrate or any keto substrate, preferably an aldehyde substrate according to formula (I) or a keto substrate according to formula (I).

All preferred embodiments that have been defined above with respect to the keto substrates and the aldehyde substrates according to the invention also apply to the method according to the invention and thus, are not reiterated hereinafter.

Another aspect of the invention relates to a method for oxidizing aldehyde substrates to carboxylic acids comprising the step of reacting the aldehyde substrate and a suitable cofactor in the presence of a ketoreductase according to the invention. Preferably, said suitable cofactor is $NAD^+$ or $NADP^+$. All preferred embodiments that have been defined above with respect to the ketoreductase according to the invention also apply to the method according to the invention and thus, are not reiterated hereinafter.

Preferably, the aldehyde substrate is of general formula (V)

wherein Z is selected from
saturated or unsaturated, unsubstituted or mono- or polysubstituted, branched or unbranched $C_1$-$C_{12}$ aliphatic residues;
saturated or unsaturated, unsubstituted or mono- or polysubstituted $C_3$-$C_{12}$ cycloaliphatic residues, optionally being bridged to the CO-moiety through a saturated or unsaturated, unsubstituted or mono- or polysubstituted $C_1$-$C_{12}$-aliphatic residue;
saturated or unsaturated, unsubstituted or mono- or polysubstituted $C_1$-$C_{12}$ heterocycloaliphatic residues, optionally being bridged to the CO-moiety through a saturated or unsaturated, unsubstituted or mono- or polysubstituted $C_1$-$C_{12}$-aliphatic residue;

unsubstituted or mono- or polysubstituted $C_6$-$C_{10}$-aromatic residues, optionally being bridged to the CO-moiety through a saturated or unsaturated, unsubstituted or mono- or polysubstituted $C_1$-$C_{12}$-aliphatic residue; or unsubstituted or mono- or polysubstituted $C_1$-$C_{12}$ heteroaromatic residues, optionally being bridged to the CO-moiety through a saturated or unsaturated, unsubstituted or mono- or polysubstituted $C_1$-$C_{12}$-aliphatic residue;

and wherein mono- or polysubstituted means independently substituted with one or more functional groups selected from —F, —Cl, —Br, —$C_{1-12}$-alkyl, —$C_{1-12}$-alkyl-F, —$C_{1-12}$-alkyl-Cl, —$C_{1-12}$-alkyl-Br, —OH, =O, —O$C_{1-12}$-alkyl, —O$C_{6-10}$-aryl, —O-heteroaryl, —OCO$C_{1-12}$-alkyl, —OCO$C_{6-10}$-aryl, —OCO-heteroaryl, —SH, —S$C_{1-12}$-alkyl, —S$C_{6-10}$-aryl, —S-heteroaryl, —S(=O)$_{1-2}$OH, —NO, —NO$_2$, —N$_3$, —NH$_2$, —NH($C_{1-12}$-alkyl), —N($C_{1-12}$-alkyl)$_2$, —NH($C_{6-10}$-aryl), —N($C_{6-10}$-aryl)$_2$, —NH(heteroaryl), —N(heteroaryl)$_2$, —CN, —CHO, —CO$_2$H, CO—$C_{1-2}$-alkyl, —CO—$C_{6-10}$-aryl and —CO-heteroaryl; and wherein heterocycloaliphatic or heteroaromatic means cyclic structures that have atoms of at least two different elements as members of its ring(s), whereas the heteroatoms are preferably selected from the group consisting of the elements S, O, N, and B.

Preferably, the method involves to concomitant conversion of a cosubstrate for cofactor regeneration by the respective ketoreductase at a high specific activity, such cosubstrates preferably being selected according their specific activity from the group consisting of isopropyl alcohol, 2-butanol, 2-pentanol, 2-hexanol, and 2-heptanol, and most preferably converting isopropyl alcohol to acetone at a high specific activity. In a preferred embodiment of the method according to the invention, the reduced cofactor NAD(P)H is regenerated by use of NADPH:NADH oxidase (NOX), e.g. from *Lactobacillus sanfranciscensis* (Lountos et al., Acta Cryst. (2004), D60, 2044-2047), and a suitable cosubstrate, e.g. acetone.

Thus, the present invention also relates to a method for the
preparation of a secondary alcohol involving the preferably stereoselective reduction of a keto substrate to said secondary alcohol;
preparation of a primary alcohol involving the reduction of an aldehyde substrate to said primary alcohol;
preparation of a keto product involving the oxidation of a secondary alcohol substrate to said keto product;
preparation of an aldehyde involving the oxidation of a primary alcohol substrate to said aldehyde; and/or
preparation of a carboxylic acid involving the oxidation of an aldehyde substrate to said carboxylic acid;
wherein the method comprises the step of reacting the substrate and a suitable cofactor in the presence of a ketoreductase according to the invention. For a reduction reaction catalyzed by ketoreductase (reduction of keto substrate to corresponding secondary alcohol, reduction of aldehyde to corresponding primary alcohol) the suitable cofactor is required in its reduced form as electron donor. For an oxidation reaction catalyzed by ketoreductase (oxidation of secondary alcohol to corresponding ketone, oxidation of primary alcohol to corresponding aldehyde, oxidation of aldehyde to corresponding carboxylic acid) the suitable cofactor is required in its oxidized form as electron acceptor.

When the substrate is chiral, the reaction may proceed stereoselectively and/or regioselectively and thus, may be used e.g. for kinetic racemic resolution.

In setting up processes, e. g. reduction of ketones, in a preparative scale, the method according to the invention can be performed under consideration of specific further reaction conditions, considering one or more of the parameters selected from the following parameters: The preparative scale reduction can either be performed e.g. with isopropanol or with glucose/GDH for cofactor regeneration. The method according to the invention can be performed in an aqueous environment, in a non-aqueous environment, or in a 2-phase system. The method according to the invention can be carried out at pH values ranging from 4-11, and/or at temperatures between 5° C. and 90° C., and/or at substrate concentrations ranging from 1-800 g/L. The method according to the invention can be performed with free or with immobilized enzyme. The method according to the invention can be performed as batch process or with continuous removal of product. The method according to the invention can be performed with high substrate feed, and/or by binding (e. g. by adsorption) of product to a solid phase in the reaction vessel, and/or with the addition of water miscible solvents and/or under high shear forces.

Another aspect of the invention relates to a process for the preparation of a product, preferably of a chiral product, comprising
the method for the stereoselective reduction of a keto substrate to a secondary alcohol according to the invention;
the method for reducing aldehydes to primary alcohols according to the invention;
the method for stereoselective oxidation of secondary alcohols to keto products according to the invention;
the method for oxidizing primary alcohols to aldehydes according to the invention; and/or
the method for oxidizing aldehyde substrates to carboxylic acids according to the invention.

All preferred embodiments that have been defined above with respect to the various methods according to the invention including the ketoreductase according to the invention, the keto substrates according to the invention, the secondary alcohol substrates according to the invention, the aldehyde substrates according to the invention, the primary alcohol substrates according to the invention also apply to the process according to the invention and thus, are not reiterated hereinafter.

Another aspect of the invention relates to the use of a ketoreductase according to the invention for the stereoselective reduction of a keto substrate to a secondary alcohol.

Another aspect of the invention relates to the use of a ketoreductase according to the invention for the reduction of an aldehyde to a primary alcohol.

Another aspect of the invention relates to the use of a ketoreductase according to the invention for the oxidation of a secondary alcohol to a keto product.

Another aspect of the invention relates to the use of a ketoreductase according to the invention for the oxidation of a primary alcohol to an aldehyde product.

Another aspect of the invention relates to the use of a ketoreductase according to the invention for the oxidation of an aldehyde to a carboxylic acid.

Preferably, in the use according to the invention for the stereoselective reduction of keto substrates to secondary alcohols, and for the reduction of aldehyde substrates to primary alcohols, respectively, the aldehyde substrate and the keto substrate may be any aldehyde substrate or any keto substrate, preferably an aldehyde substrate according to formula (I) or a keto substrate according to formula (I).

All preferred embodiments that have been defined above with respect to the keto substrates and the aldehyde substrates according to the invention also apply to the method according to the invention and thus, are not reiterated hereinafter.

The following examples further illustrate the invention but are not to be construed as limiting its scope.

Example 1—Detection of the New Ketoreductase Gene Corresponding to Inventive SEQ ID NO:1

The gene of the new ketoreductase with SEQ ID NO:2 was identified in a PCR-based genome screening for new ketoreductases from *Candida magnoliae* DSMZ 70638 using degenerate PCR primers. Surprisingly a segment of the gene corresponding to the new ketoreductase of inventive SEQ ID NO: 1 was found and cloned, representing a yet unknown new ketoreductase according to the invention. By using refined PCR-primer the full open reading frame of the ketoreductase gene as shown in SEQ ID:No2 was identified, which encodes for the newly identified ketoreductase of the invention inventive SEQ ID NO: 1.

Example 2—Expression of the New Ketoreductase Genes to SEQ ID NO:2 and SEQ ID NO:5

The gene of the newly found ketoreductase SEQ ID NO 2 encoding for the ketoreductase of the invention (inventive SEQ ID NO: 1), and the ketoreductase gene SEQ ID NO:5, encoding for ketoreductase corresponding to the comparative SEQ ID NO:3, were cloned into the expression vector pLEIA17 (derivative of pRSF-1b, Novagen). The resulting plasmids were used for transformation of *E. coli* BL21(DE3) cells. SEQ ID NO:5 is a codon-optimized DNA variant of SEQ ID NO:4; both DNA sequences, SEQ ID NO:4 and SEQ ID NO:5, encode for the same ketoreductase enzyme sequence of SEQ ID NO:3.

For expression of the ketoreductase genes SEQ ID NO:2 and SEQ ID NO:5, cells were cultivated in ZYM505 medium (F. William Studier, Protein Expression and Purification 41 (2005) 207-234) supplemented with kanamycin (50 mg/1l) at 37° C. Expression of the gene was induced at logarithmic phase by IPTG (0.1 mM) and carried out at 30° C. for 16-18 hours.

Cells were harvested by centrifugation (3220×g, 20 min, 4° C.) and disrupted with cell lysis buffer (50 mM Tris-HCl pH 7.0; 2 mM MgCl2, 1× CelLytic B (Sigma); DNA nuclease 0.02 U, lysozyme 0.5 mg/ml). The crude extracts were separated from cell debris by centrifugation (3220×g 30 min, 4° C.). The supernatant was sterile-filtrated over a 0.2 μm-membrane filter and freeze dried. A brownish powder was obtained.

The crude extract supernatant and the insoluble cell debris were investigated regarding the level of ketoreductase enzyme content via denaturing SDS-PAGE. Approx. 75% of the overexpressed protein of inventive SEQ ID NO: 1 was found in the crude extract supernatant, while 25% were found in the insoluble fraction. From comparative SEQ ID NO:3 ketoreductase enzyme just 50% of the overexpressed protein was found in the soluble fraction and 50% in the insoluble cell debris.

Example 3—Reduction Activity for Ethyl Acetoacetate, Cyclohexanone, COBE, 2-Heptanone, 4-CAP Initial activities for the reduction of ethyl acetoacetate, Cyclohexanone, COBE, 2-Heptanone, 4-CAP by the ketoreductases of inventive SEQ ID NO: 1 and comparative SEQ ID NO:3 were measured photometrically, by monitoring the decrease in absorbance at 340 nm resulting from the oxidation of NADH or NADPH. One unit corresponds to the oxidation of 1 μmol NADH or NADPH per minute.

For reduction activity measurements, 100 mM ethyl acetoacetate or 50 mM of COBE or 4-CAP or 2-Heptanone or Cyclohexanone were used in Tris-HCl buffer (50 mM, pH 7.0, 2 mM MgCl$_2$) with 0.5 mM NADH or NADPH. Stock solutions of 20 mg/ml from the lyophilisates of every tested ketoreductase, corresponding to inventive SEQ ID NO: 1 and comparative SEQ ID NO:3, respectively, were prepared and diluted for the activity assay depending on the individual activity with the different substrates (typically 1:2.5 up to 1:100). The experimental results are shown in the Table below.

It becomes clear from the comparative data that the ketoreductase according to the invention (inventive SEQ ID NO:1) has a substantially improved reduction activity (Units/mg lyophilisate) compared to the ketoreductase of comparative SEQ ID NO:3.

The ketoreductase of inventive SEQ ID NO:1 exhibits a strong cofactor preference of NADPH over NADH (e.g. cofactor preference ratio: for ethyl acetoacetate: 37.3; for COBE: 3.3)

The experimental results are compiled in the following table:

| Substrate | Cofactor | SEQ-ID NO: 1 [U/mg] | SEQ-ID NO: 3 [U/mg] | Improvement Factor SEQ-ID NO: 1/SEQ-ID NO: 3 |
| --- | --- | --- | --- | --- |
| ethyl acetoacetate | NADPH | 4.1 | 0.09 | 46 |
| ethyl acetoacetate | NADH | 0.11 | n.d.* | |
| cyclohexanone | NADPH | 3.2 | 0.45 | 7 |
| COBE | NADPH | 0.3 | 0.05 | 5 |
| COBE | NADH | 0.09 | n.d.* | |
| 4-CAP | NADPH | 2.4 | 0.17 | 14 |
| 4-CAP | NADH | n.d.* | n.d.* | |

*not detectable, activity below detection limit

Example 4—Oxidation Activity for Ethyl-3-Hydroxybutyrate, Cyclohexanol, Isopropanol; pH Profile For oxidation activity measurements, initial activities for the oxidation of ethyl-3-hydroxybutyrate, cyclohexanol and isopropanol were measured photometrically, by measuring the increase in absorbance at 340 nm resulting from the oxidation of NADP$^+$. One unit corresponds to the oxidation of 1 μmol NADH per minute.

100 mM ethyl-3-hydroxybutyrate or 50 mM cyclohexanol or 20% (v/v) isopropanol were used either in potassium phosphate buffer (50 mM, pH 7.0) or in Tris/HCl puffer (50 mM, pH 9.0, MgCl$_2$). Stock solution of 20 mg/ml Stock solutions of 20 mg/ml from the lyophilisate of every tested ketoreductase, corresponding to inventive SEQ ID NO:1 and comparative SEQ ID NO:3, respectively, were prepared and diluted for the activity assay depending on the individual activity with the different substrates (typically 1:1 to 1:10).

It becomes clear from the comparative data that the ketoreductase according to the invention (inventive SEQ ID NO: 1) has a substantially improved oxidation activity compared to the ketoreductase of comparative SEQ ID NO:3. Furthermore, the inventive ketoreductase of inventive SEQ ID NO: 1 shows over the comparative SEQ ID NO:3 a superior pH profile at lower pH values (pH 7.0 or 7.5, respectively) than at higher pH (pH 9.0), which is reflected in a higher "improvement factor" at pH 7.0 in comparison to pH 9.0 as indicated in the upper table below, wherein "improvement factor" describes the activity ratio of SEQ ID NO:1 over comparative SEQ ID NO:3 under assay conditions with respective pH values. As another way to express the superior pH profile of inventive SEQ ID NO: 1, the lower Table below shows the "activity percentage" of the oxidation activity of a respective enzyme at pH 7 (or 7.5, respectively) compared to its activity at pH 9. While the comparative ketoreductase of comparative SEQ ID NO:3 shows activity percentages of 27% and 33% for cyclohexanol and isopropanol, the inventive ketoreductase of inventive SEQ ID NO:1 shows activity percentages of 60% or 62% for the same substrates. This indicates that the ketoreductase according to the invention (inventive SEQ ID NO:1) is substantially improved for oxidations at neutral to slightly acidic conditions.

The experimental results are compiled in the following tables:

| Substrate | pH-Value | SEQ-ID NO: 1 [U/mg] | SEQ-ID NO: 3 [U/mg] | Improvement Factor SEQ-ID NO: 1/SEQ-ID NO: 33 |
|---|---|---|---|---|
| ethyl-3-hydroxybutyrate | 7.0 | 0.09 | n.d.* | >9 |
|  | 9.0 | 0.22 | 0.02 | 9.3 |
| cyclohexanol | 7.5 | 0.31 | 0.06 | 4.9 |
|  | 9.0 | 0.50 | 0.22 | 2.3 |
| isopropanol | 7.0 | 0.03 | 0.01 | 3.3 |
|  | 9.0 | 0.05 | 0.03 | 1.4 |

*not detectable, activity below detection limit

| Activity Percentage: activity rate Substrate | pH-Value | SEQ-ID NO: 1 [U/mg] | pH-related activity ratio Activity$_{pH\,9}$/Activity$_{pH\,7/7.5}$ [%] | SEQ-ID NO: 3 [U/mg] | pH-related activity ratio Activity$_{pH\,9}$/Activity$_{pH\,7/7.5}$ [%] |
|---|---|---|---|---|---|
| ethyl-3-hydroxybutyrate | 7.0 | 0.09 | 41% | n.d.* | n.d.* |
|  | 9.0 | 0.22 |  | 0.02 |  |
| Cyclohexanol | 7.5 | 0.31 | 62% | 0.06 | 27% |
|  | 9.0 | 0.50 |  | 0.22 |  |
| Isopropanol | 7.0 | 0.03 | 60% | 0.01 | 33% |
|  | 9.0 | 0.05 |  | 0.03 |  |

The experimental results as shown in the two tables above reveal that the ketoreductase according to the invention (inventive SEQ ID NO:1) has a substantially improved oxidation activity at different pH values (Units/mg lyophilizate) compared to the ketoreductase of comparative SEQ ID NO:3, with a lower decrease of initial activity (higher "activity percentage") at neutral pH (pH 7 and pH 7.5, respectively) compared to its initial activity at pH 9.

Example 5—Stereoselectivity

Analytical biotransformations were performed with 4 mg/ml of the ketoreductases according to inventive SEQ ID NO: 1 and comparative SEQ ID NO:3. For cofactor recycling a glucose dehydrogenase (GDH) system was used comprising of 0.1 mg/ml GDH-03 (commercial product from c-LEcta GmbH, Germany) and 150 mM glucose for constant reduction of NADP+ to NADPH. The reaction was performed in potassium phosphate buffer (50 mM, pH 7.0, 2 mM MgCl2) with 1 mM NADP+ and 50 mM of 2-heptanone or 4-CAP or COBE. The reaction mixture was incubated for 24h at 200 rpm and 30° C. The reaction mixture was extracted using five volumes of MTBE (2-Methoxy-2-methylpropan). The organic phase was used for chiral GC analysis. The Ivadex-3 GC-column (IVA-Analysentechnik, chiral phase: Diacetyltertbutylsilyl beta-cyclodextrin, length 25m, ID 0.25 mm, film 0.25 μm) was used on a Shimadzu GC2010 with FID-detector. The enantiomers were identified by comparison to analytical standard substrates. The enantiomeric access was calculated from the peak areas of the enantiomers.

The experimental results are compiled in the following:

| [%ee] (R-pos/S-neg) | 4-CAP (1-(4-chloro-phenyl)ethanol) | 2-heptanone | COBE (ethyl-4-chloro-3-hydroxy-butanoate) |
|---|---|---|---|
| comparative SEQ ID NO: 3 | −98% ee | −90% ee | 91% ee |
| inventive SEQ ID NO: 1 | −99% ee | −97% ee | 98% ee |

It becomes clear from the above comparative data that the ketoreductase according to the invention (inventive SEQ ID NO: 1) has a substantially higher stereoselectivity compared to the ketoreductase of comparative SEQ ID NO:3 with all tested substrates.

Example 6—Tm-Value-Tm$_{50(40)}$

The thermostability of the ketoreductases according to inventive SEQ ID NO: 1 and comparative SEQ ID NO:3 were measured after incubation of a 40 mg/ml solution of the respective enzyme at different temperatures for 15 min. The I value is defined to be the temperature at which after 15 min of incubation of a 40 mg/ml solution 50% of residual activity still remains, compared to a sample stored at 25° C. The activity was measured photometric detection using ethyl acetoacetate as described in Example 1.

The experimental results are shown in FIG. 1.

It becomes clear from the comparative data that the ketoreductase according to the invention (inventive SEQ ID NO: 1) has a substantially improved half maximum melting temperature (Tm$_{50(40)}$) of +7° C. compared to the ketoreductase of comparative SEQ ID NO:3. The half maximum melting temperature is the temperature at which the respective ketoreductase still has 50% residual activity compared to its activity at 25° C. Therefore, the ketoreductase according to the invention (inventive SEQ ID NO: 1) has a substantially improved activity at higher temperatures compared to the ketoreductase of comparative SEQ ID NO:3.

Example 7—Reduction Activity Towards Ethyl Acetoacetate of SEQ ID NO: 1 and Variants Molecular biology methods: Variants of SEQ ID NO: 1 were created by standard site-directed mutagenesis technologies as known in the state of the art.

Initial activities for the reduction of ethyl acetoacetate by ketoreductases were measured photometrically by monitoring the decrease in absorbance at 340 nm resulting from the oxidation of NADPH. One unit corresponds to the oxidation of 1 µmol NADPH per minute.

For reduction activity measurement, 100 mM ethyl acetoacetate was used in Tris-HCl buffer (50 mM, pH 7.0, 2 mM MgCl2) with 2 mM NADPH at 30° C. The crude cell extract was diluted for the activity assay depending on the individual activity and the screening format. The characterization of selected enzymes was measured in cuvettes. The high-throughput screening was performed in 96-well microtiter plates.

Example 8—Reduction Activity Towards Cyclohexanone of SEQ ID NO: 1 and Variants Initial activities for the reduction of cyclohexanone by ketoreductases were measured by monitoring the decrease in absorbance at 340 nm resulting from the oxidation of NADPH. One unit corresponds to the oxidation of 1 µmol NADPH per minute. The crude cell extract was diluted for the activity assay depending on the individual activity.

For reduction activity measurement, 50 mM cyclohexanone was used in potassium phosphate buffer (50 mM, pH 7.0) with 0.5 mM NADPH at 30° C.

The experimental results are compiled in the following:

| SEQ ID NO: | Cyclohexanon activity U/mL culture | x-fold improvement in cyclohexanon activity compared to SEQ ID NO: 1 | cyclohexanon activity in % compared to SEQ ID NO: 1 |
|---|---|---|---|
| SEQ ID NO: 1 | 20.1 | 1.0 | 100 |
| SEQ ID NO: 18 | 21.2 | 1.1 | 105 |
| SEQ ID NO: 38 | 25.5 | 1.3 | 127 |
| SEQ ID NO: 39 | 39.1 | 2.0 | 195 |
| SEQ ID NO: 91 | 16.2 | 0.8 | 81 |
| SEQ ID NO: 92 | 14.2 | 0.7 | 71 |
| SEQ ID NO: 162 | 29.8 | 1.5 | 148 |
| SEQ ID NO: 163 | 36.6 | 1.8 | 183 |
| SEQ ID NO: 164 | 15.8 | 0.8 | 79 |
| SEQ ID NO: 165 | 22.0 | 1.1 | 110 |
| SEQ ID NO: 166 | 25.5 | 1.3 | 127 |
| SEQ ID NO: 167 | 21.2 | 1.1 | 105 |
| SEQ ID NO: 168 | 22.5 | 1.1 | 112 |
| SEQ ID NO: 169 | 35.0 | 1.7 | 175 |
| SEQ ID NO: 170 | 21.7 | 1.1 | 108 |
| SEQ ID NO: 171 | 62.9 | 3.1 | 314 |
| SEQ ID NO: 172 | 96.0 | 4.8 | 479 |
| SEQ ID NO: 173 | 27.5 | 1.4 | 137 |
| SEQ ID NO: 174 | 15.9 | 0.8 | 79 |
| SEQ ID NO: 175 | 12.6 | 0.6 | 63 |
| SEQ ID NO: 176 | 40.2 | 2.0 | 200 |
| SEQ ID NO: 177 | 33.3 | 1.7 | 166 |
| SEQ ID NO: 178 | 8.3 | 0.4 | 41 |

Some variants exhibit a lower cyclohexanone activity in comparison to SEQ ID NO: 1, but irrespective thereof provide improved red/ox ratios as exemplified in Example 10.

Example 9—Oxidation Activity Towards Cyclohexanol of SEQ ID NO: 1 and Variants Initial activities for the oxidation of cyclohexanol by ketoreductases were measured by monitoring the increase in absorbance at 340 nm resulting from the reduction of NADP+. One unit corresponds to the oxidation of 1 µmol NADP+ per minute. The crude cell extracts were diluted for the activity assay depending on its individual activity.

For oxidation activity measurement, 50 mM cyclohexanone was used in potassium phosphate buffer (50 mM, pH 7.0) with 1 mM NADP+ at 30° C.

The high-throughput screening was performed in 96-well microtiter plates. In the high-throughput screening, values of more than a 5-fold improvement to SEQ ID NO: 1 cannot be accurately measured and are given as ≥5.

The experimental results from high throughput screening are compiled in the following:

| SEQ ID NO: | x-fold improvement in cyclohexanol activity compared to SEQ ID NO: 1 | cyclohexanol activity in % compared to SEQ ID NO: 1 |
|---|---|---|
| SEQ ID NO: 7 | 1.4 | 140 |
| SEQ ID NO: 8 | ≥5.0 | ≥500 |
| SEQ ID NO: 9 | 1.3 | 134 |
| SEQ ID NO: 11 | ≥5.0 | ≥500 |
| SEQ ID NO: 13 | 1.3 | 135 |
| SEQ ID NO: 14 | 1.5 | 153 |
| SEQ ID NO: 15 | 1.4 | 137 |
| SEQ ID NO: 16 | 1.4 | 144 |
| SEQ ID NO: 17 | 1.7 | 169 |
| SEQ ID NO: 19 | 1.6 | 164 |
| SEQ ID NO: 20 | 1.4 | 137 |
| SEQ ID NO: 21 | 1.3 | 131 |
| SEQ ID NO: 22 | 1.3 | 129 |
| SEQ ID NO: 23 | 1.1 | 113 |
| SEQ ID NO: 27 | 1.2 | 123 |
| SEQ ID NO: 28 | 1.4 | 139 |
| SEQ ID NO: 29 | 1.2 | 122 |
| SEQ ID NO: 30 | 1.4 | 138 |
| SEQ ID NO: 32 | ≥5.0 | ≥500 |
| SEQ ID NO: 40 | 1.6 | 162 |
| SEQ ID NO: 41 | 1.2 | 123 |
| SEQ ID NO: 44 | 1.5 | 150 |
| SEQ ID NO: 48 | 1.1 | 111 |
| SEQ ID NO: 55 | 1.2 | 115 |
| SEQ ID NO: 63 | 1.6 | 162 |
| SEQ ID NO: 73 | 1.2 | 122 |
| SEQ ID NO: 75 | 1.2 | 117 |
| SEQ ID NO: 78 | 1.2 | 122 |
| SEQ ID NO: 80 | 1.2 | 117 |
| SEQ ID NO: 84 | 1.3 | 127 |
| SEQ ID NO: 89 | 4.1 | 411 |
| SEQ ID NO: 90 | 2.4 | 238 |
| SEQ ID NO: 93 | 1.3 | 128 |
| SEQ ID NO: 143 | 1.3 | 130 |

The detailed activity characterization of selected enzymes was measured in cuvettes.

The corresponding experimental results are compiled in the following:

| SEQ ID NO: | Cyclohexanol activity U/mL culture | x-fold improvement in cyclohexanol activity compared to SEQ ID NO: 1 | cyclohexanol activity in % compared to SEQ ID NO: 1 |
|---|---|---|---|
| SEQ ID NO: 1 | 0.8 | 1.0 | 100 |
| SEQ ID NO: 18 | 1.4 | 1.7 | 169 |
| SEQ ID NO: 38 | 6.1 | 7.3 | 733 |
| SEQ ID NO: 39 | 4.6 | 5.6 | 557 |
| SEQ ID NO: 91 | 1.5 | 1.8 | 176 |
| SEQ ID NO: 92 | 1.2 | 1.4 | 145 |
| SEQ ID NO: 162 | 7.4 | 8.9 | 893 |
| SEQ ID NO: 163 | 3.2 | 3.8 | 381 |

-continued

| SEQ ID NO: | Cyclohexanol activity U/mL culture | x-fold improvement in cyclohexanol activity compared to SEQ ID NO: 1 | cyclohexanol activity in % compared to SEQ ID NO: 1 |
|---|---|---|---|
| SEQ ID NO: 164 | 5.1 | 6.1 | 614 |
| SEQ ID NO: 165 | 0.9 | 1.1 | 105 |
| SEQ ID NO: 166 | 9.4 | 11.3 | 1133 |
| SEQ ID NO: 167 | 5.4 | 6.4 | 645 |
| SEQ ID NO: 168 | 0.6 | 0.8 | 77 |
| SEQ ID NO: 169 | 0.5 | 0.6 | 56 |
| SEQ ID NO: 170 | 0.6 | 0.7 | 68 |
| SEQ ID NO: 171 | 4.5 | 5.4 | 535 |
| SEQ ID NO: 172 | 6.8 | 8.2 | 822 |
| SEQ ID NO: 173 | 0.2 | 0.3 | 28 |
| SEQ ID NO: 174 | 2.1 | 2.5 | 254 |
| SEQ ID NO: 175 | 2.4 | 2.9 | 286 |
| SEQ ID NO: 176 | 3.2 | 3.9 | 386 |
| SEQ ID NO: 177 | 5.8 | 7.0 | 697 |
| SEQ ID NO: 178 | 1.4 | 1.7 | 165 |

Some variants exhibit a lower cyclohexanol activity in comparison to SEQ ID NO: 1, but irrespective thereof provide improved red/ox ratios as exemplified in Example 10.

Example 10—Determination of the Red/Ox Ratio for SEQ ID NO:1 Variants

Ketoreductases usually show a much higher activity for the reduction of the oxidized form of a specific substrate than for the oxidation of its reduced form. Therefore, a ketoreductase with improved oxidative properties is much desired for certain applications.

The ratio between reduction and oxidation activity was calculated from the initial reduction activity towards cyclohexanone (see Example 8) divided by the oxidation activity of cyclohexanol (see Example 9). The lower the calculated ratio is, the more preferred is the oxidative activity of the respective variant.

The experimental results are compiled in the following:

| SEQ ID NO: | ratio red/ox | x-fold compared to SEQ ID NO: 1 |
|---|---|---|
| SEQ ID NO: 1 | 24.1 | 1.00 |
| SEQ ID NO: 18 | 15.1 | 0.62 |
| SEQ ID NO: 38 | 4.2 | 0.17 |
| SEQ ID NO: 39 | 8.4 | 0.35 |
| SEQ ID NO: 91 | 11.1 | 0.46 |
| SEQ ID NO: 92 | 11.8 | 0.49 |
| SEQ ID NO: 162 | 4.0 | 0.17 |
| SEQ ID NO: 163 | 11.6 | 0.48 |
| SEQ ID NO: 164 | 3.1 | 0.13 |
| SEQ ID NO: 165 | 25.1 | 1.04 |
| SEQ ID NO: 166 | 2.7 | 0.11 |
| SEQ ID NO: 167 | 3.9 | 0.16 |
| SEQ ID NO: 168 | 35.4 | 1.47 |
| SEQ ID NO: 169 | 75.0 | 3.11 |
| SEQ ID NO: 170 | 38.5 | 1.60 |
| SEQ ID NO: 171 | 14.1 | 0.59 |
| SEQ ID NO: 172 | 14.0 | 0.58 |
| SEQ ID NO: 173 | 117.1 | 4.86 |
| SEQ ID NO: 174 | 7.5 | 0.31 |
| SEQ ID NO: 175 | 5.3 | 0.22 |
| SEQ ID NO: 176 | 12.5 | 0.52 |
| SEQ ID NO: 177 | 5.7 | 0.24 |
| SEQ ID NO: 178 | 6.0 | 0.25 |

The ratio between reduction and oxidation activity is indicative for enzyme preferences for selecting enzymes depending on applications requiring either oxidation or reduction.

Example 11—Screening for Improved Thermostability in High Throughout Screening

The improvement of thermostability is highly desirable for biocatalytic processes. More stable enzymes can tolerate higher temperatures without degradation. Additionally, more stable enzymes usually stay active over a longer period of time at moderate temperatures, are more tolerant for organic co-solvents or high substrate or product concentrations. This usually leads to a higher process performance of stabilized enzyme variants over less stable enzymes.

To identify more stable enzyme variants during high-throughput screenings, the residual activity of the enzyme variants was measured after incubation of the crude extracts diluted to an OD of 10 at 42° C. for 15 min using the reduction assay towards ethyl acetoacetate as described in Example 5 and compared to the activity of a sample, that has not undergone thermal treatment. The residual activity is expressed as the remaining activity after thermal treatment compared to the initial activity, expressed in percent. The wild-type enzyme of SEQ ID NO:1 usually showed a residual activity between 10-25%. More stable enzymes were identified if they show higher residual activity after incubation at the indicated temperature.

The experimental results are compiled in the following:

| SEQ ID NO: | % residual activity |
|---|---|
| SEQ ID NO: 7 | 60 |
| SEQ ID NO: 12 | 50 |
| SEQ ID NO: 13 | 49 |
| SEQ ID NO: 19 | 83 |
| SEQ ID NO: 23 | 100 |
| SEQ ID NO: 24 | 42 |
| SEQ ID NO: 25 | 100 |
| SEQ ID NO: 26 | 100 |
| SEQ ID NO: 27 | 100 |
| SEQ ID NO: 28 | 100 |
| SEQ ID NO: 29 | 57 |
| SEQ ID NO: 35 | 100 |
| SEQ ID NO: 40 | 100 |
| SEQ ID NO: 41 | 100 |
| SEQ ID NO: 46 | 35 |
| SEQ ID NO: 47 | 40 |
| SEQ ID NO: 49 | 57 |
| SEQ ID NO: 50 | 43 |
| SEQ ID NO: 52 | 60 |
| SEQ ID NO: 55 | 37 |
| SEQ ID NO: 56 | 38 |
| SEQ ID NO: 58 | 56 |
| SEQ ID NO: 60 | 66 |
| SEQ ID NO: 64 | 76 |
| SEQ ID NO: 65 | 74 |
| SEQ ID NO: 69 | 38 |
| SEQ ID NO: 70 | 100 |
| SEQ ID NO: 71 | 37 |
| SEQ ID NO: 72 | 67 |
| SEQ ID NO: 73 | 63 |
| SEQ ID NO: 74 | 58 |
| SEQ ID NO: 75 | 65 |
| SEQ ID NO: 76 | 55 |
| SEQ ID NO: 79 | 48 |
| SEQ ID NO: 81 | 53 |
| SEQ ID NO: 82 | 89 |
| SEQ ID NO: 83 | 60 |
| SEQ ID NO: 84 | 57 |
| SEQ ID NO: 88 | 30 |
| SEQ ID NO: 89 | 52 |

| SEQ ID NO: | % residual activity |
|---|---|
| SEQ ID NO: 90 | 30 |
| SEQ ID NO: 93 | 68 |
| SEQ ID NO: 96 | 41 |
| SEQ ID NO: 104 | 38 |
| SEQ ID NO: 106 | 31 |
| SEQ ID NO: 110 | 30 |
| SEQ ID NO: 115 | 33 |
| SEQ ID NO: 116 | 39 |
| SEQ ID NO: 123 | 37 |
| SEQ ID NO: 124 | 32 |
| SEQ ID NO: 125 | 51 |
| SEQ ID NO: 126 | 43 |
| SEQ ID NO: 127 | 44 |
| SEQ ID NO: 131 | 34 |
| SEQ ID NO: 133 | 42 |
| SEQ ID NO: 135 | 50 |
| SEQ ID NO: 136 | 36 |
| SEQ ID NO: 137 | 33 |
| SEQ ID NO: 143 | 34 |
| SEQ ID NO: 144 | 35 |
| SEQ ID NO: 145 | 39 |
| SEQ ID NO: 146 | 31 |
| SEQ ID NO: 147 | 49 |
| SEQ ID NO: 159 | 31 |
| SEQ ID NO: 161 | 40 |

Example 12—Measuring the Tm-Value $Tm_{50(10)}$

The thermostability of selected ketoreductase variants was measured after incubation of crude extracts of an $OD_{600}=10$ at different temperatures for 15 minutes. The $Tm_{50(10)}$ value is defined to be the temperature at which after 15 minutes of incubation of a crude extract corresponding to an $OD_{600}$ of 10, 50% of residual activity still remains, compared to a sample stored on ice. The activity was measured as described in Example 5.

The experimental results are compiled in the following:

| SEQ ID NO: | $Tni_{50(10)}$[° C.] |
|---|---|
| SEQ ID NO: 1 | 40.9 |
| SEQ ID NO: 36 | 46.9 |
| SEQ ID NO: 38 | 50.5 |
| SEQ ID NO: 67 | 44.6 |
| SEQ ID NO: 68 | 42.0 |
| SEQ ID NO: 91 | 45.3 |
| SEQ ID NO: 92 | 50.0 |
| SEQ ID NO: 162 | 54.8 |
| SEQ ID NO: 163 | 42.9 |
| SEQ ID NO: 165 | 45.5 |
| SEQ ID NO: 166 | 60.5 |
| SEQ ID NO: 167 | 57.4 |
| SEQ ID NO: 169 | 47.2 |
| SEQ ID NO: 171 | 55.5 |
| SEQ ID NO: 172 | 58.0 |
| SEQ ID NO: 173 | 51.5 |
| SEQ ID NO: 174 | 48.0 |
| SEQ ID NO: 175 | 49.3 |
| SEQ ID NO: 176 | 61.2 |
| SEQ ID NO: 177 | 61.2 |
| SEQ ID NO: 178 | 53.2 |
| SEQ ID NO: 179 | 66.5 |
| SEQ ID NO: 180 | 64.5 |
| SEQ ID NO: 181 | 65.5 |
| SEQ ID NO: 182 | 66.5 |

Example 13—Ethyl Acetoacetate Activity

Initial activities for the reduction of ethyl acetoacetate of several ketoreductase variants was tested as described in Example 3 using NADPH as a cofactor.

The experimental results are compiled in the following:

| SEQ ID NO: | ethyl acetoacetate U/mg | Improvement Factor to SEQ ID NO: 3 |
|---|---|---|
| SEQ ID NO: 174 | 0.80 | 9 |
| SEQ ID NO: 178 | 0.94 | 10 |
| SEQ ID NO: 179 | 0.71 | 8 |
| SEQ ID NO: 180 | 0.33 | 4 |
| SEQ ID NO: 181 | 0.36 | 4 |
| SEQ ID NO: 182 | 0.32 | 4 |

```
SEQ ID NO 1:
Met Thr Ser Ser Ser Ser Pro Ser Leu Asn Ala Leu Va  Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
```

-continued

```
            130                 135                 140
Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
                195                 200                 205

Leu Pro Ile Asn Gly Trp Ile Glu Val Asp Ala Ile Ala Asp Ala Val
            210                 215                 220

Thr Tyr Leu Val Lys Ser Lys Asn Val Thr Gly Thr Thr Val Ser Val
225                 230                 235                 240

Asp Asn Gly Tyr Cys Ala
                245
```

SEQ ID NO 2 (encodes SEQ ID NO: 1):

```
atgacgtcct cctcttctcc ctccttgaac gctctggtca cgggcggcag ccgcggcatt     60
ggcgaggcca tttccatgca gctggccgcc gagggctaca gcgtcacaat tgcgtctcgc    120
gggctcgagc agctcgaggc cgtgaaggca aagctgccca ttgtgaagca gggccagacg    180
caccacgtgt ggcagctcga tctcagtgat gtcgaggccg ccggctcctt caagggtgcg    240
ccgctgccgg ccagcagcta cgacgtgttt gtgagcaatg ccggcatttc tcagttctcg    300
ccgattgcgg agcacgccga cgcggattgg cagaacatgc tgaccgtgaa cctgacggcg    360
ccgattgcgc tcacgaaggc cgtcgtgaag gcaatcagcg acaagccgcg ccagacgcct    420
gcgcacatca tcttcatctc gacgggcctg tcgaagcgcg gcgccccaat ggttggcgtc    480
tacagcgcct cgaaggccgg catcgacggg ttcatgcgct cgctggcccg cgagctcggc    540
ccgaagggca tcaacgtgaa ctgcgtgagc cccggcgtga caaggacgag catggccgag    600
ggcatcgacc ccagcatgtt cgaccttcct atcaacgggt ggattgaggt cgacgcgatc    660
gccgacgcgg tcacgtacct cgtgaagtcg aaaaacgtca cgggcacgac cgtttccgtc    720
gacaacggct actgcgccta a                                              741
```

SEQ ID NO 3:

```
Met Asn Ala Leu Val Thr Gly Gly Ser Arg Gly Ile Gly Glu Ala Val
1               5                  10                  15

Ser Ile Gln Leu Ala Ser Gln Gly Tyr Gly Val Thr Ile Ala Ser Arg
                20                  25                  30

Gly Val Glu Gln Leu Glu Ala Val Lys Ala Lys Leu Pro Val Val Lys
            35                  40                  45

Gln Gly Gln Thr His His Val Trp Gln Leu Asp Leu Ser Asp Val Glu
        50                  55                  60

Ala Ala Gly Ser Phe Lys Gly Ala Pro Leu Pro Ala Ser Ser Tyr Asp
65                  70                  75                  80

Val Phe Val Ser Asn Ala Gly Ile Ala Gln Phe Ser Pro Ile Ala Glu
                85                  90                  95

His Ala Asp Ala Asp Trp Gln Asn Met Leu Thr Val Asn Leu Thr Ala
            100                 105                 110

Pro Ile Ala Leu Thr Lys Ala Val Val Lys Ala Ile Ser Asp Lys Pro
        115                 120                 125

Arg Glu Thr Pro Ala His Ile Ile Phe Ile Ser Thr Gly Leu Ser Lys
    130                 135                 140

Arg Gly Ala Pro Met Val Gly Val Tyr Ser Ala Ser Lys Ala Gly Ile
145                 150                 155                 160
```

Asp Gly Phe Met Arg Ser Leu Ala Arg Glu Leu Gly Pro Lys Gly Ile
            165                 170                 175

Asn Val Asn Cys Val Ser Pro Gly Val Thr Arg Thr Ala Ile Ser Asp
        180                 185                 190

Gly Val Asp Pro Ser Met Phe Asp Leu Pro Ile Ser Gly Trp Ile Glu
    195                 200                 205

Val Asp Ala Ile Ala Asp Ala Val Thr Tyr Leu Val Lys Ser Lys Asn
210                 215                 220

Val Thr Gly Ala Ile Leu Val Val Asp Asn Gly Phe Ser Thr
225                 230                 235

SEQ ID NO 4 (encoding SEQ ID NO: 3):
atgaacgctc tagtgacggg tggcagtcgt ggcattggcg aggccgtttc cattcaattg      60
gcttcgcagg gctacggcgt cacaattgca tctcgcggcg ttgagcagct cgaggccgta     120
aaggcgaagc tgcccgttgt gaagcagggc cagacgcacc acgtgtggca gctcgacttg     180
agcgacgtcg aggcggccgg ctccttcaag ggtgcgcccc tgccggccag cagctacgac     240
gtgtttgtga gcaatgccgg cattgctcag ttctcgccga ttgcggaaca cgccgacgcg     300
gactggcaaa acatgctgac cgtgaacctg acggcgccga tcgccctcac gaaggcggtc     360
gtgaaggcca tcagcgacaa gccgcgcgag acgccggccc atatcatttt catctcaacg     420
ggcctatcga gcgcggcgc tccgatggtc ggtgtctaca gcgcttcaaa ggccggtatc     480
gacggattca tgcgctcgct ggcccgcgag ctcggcccaa agggcatcaa cgtgaactgc     540
gtcagccccg gagtgacaag gacggccatt ccgatggtg tggaccccag catgttcgac     600
ctgcctatca gcgggtggat cgaggtcgac gccattgccg acgccgttac gtacctcgtg     660
aagtcgaaga cgtcacggg cgcgatcctc gtagtcgaca cggcttctc gacgtag        717

SEQ ID NO 5 (encoding SEQ ID NO: 3, codon optimized):
atgaatgcgc tggttacggg cggatctcgc ggtattggcg aagctgtgag catccagctg      60
gcatcacagg ggtatggcgt tacgattgcc tctcgtggcg tggaacaact ggaagcggta     120
aaagccaaac ttcccgtagt caaacagggg caaacacacc atgtgtggca actggacttg     180
tcggatgtag aagcggctgg aagcttcaaa ggtgcaccct accagcgag ttcgtatgac      240 gtgtttgtgt ccaatgctgg gattgcccag ttttcgccga ttgcggaaca tgctgatgca     300
gactggcaga acatgctgac cgtcaatctg accgcaccga ttgcgctcac caaggcagtc     360
gttaaagcca tctccgacaa accacgggaa actcctgctc acatcatctt cattagcacc     420
ggactgtcaa aacgcggtgc accgatggtt ggtgtctact cagccagcaa agccggcatc     480
gatggcttca tgcgctctct ggcccgtgag ttaggcccga aaggcatcaa cgtgaattgc     540
gttagcccgg gtgtcactcg taccgcgatt gcgatggtg tggatccgag tatgtttgat     600
ctccctatca gtggttggat tgaggtagac gcgattgccg atgcggttac ctacttggtg     660
aagtcgaaga acgttacagg tgcgattctt gtggtggata cggctttttc cacgtaa       717

---

What we claim is:

1. A ketoreductase comprising an amino acid sequence, wherein the amino acid sequence has a sequence identity of at least 77% with SEQ ID NO: 1 and differs from SEQ ID NO: 1 by at least one residue change in a position located in a sequence section of SEQ ID NO: 1 selected from the group of:

sequence section SS-01 ranging from position 1 to position 10;
sequence section SS-02 ranging from position 11 to position 20;
sequence section SS-03 ranging from position 21 to position 30;
sequence section SS-04 ranging from position 31 to position 40;
sequence section SS-06 ranging from position 51 to position 60;
sequence section SS-07 ranging from position 61 to position 70;
sequence section SS-08 ranging from position 71 to position 80;
sequence section SS-10 ranging from position 91 to position 100;
sequence section SS-11 ranging from position 101 to position 110;
sequence section SS-12 ranging from position 111 to position 120;
sequence section SS-13 ranging from position 121 to position 130;
sequence section SS-14 ranging from position 131 to position 140;
sequence section SS-15 ranging from position 141 to position 150;
sequence section SS-16 ranging from position 151 to position 160;
sequence section SS-17 ranging from position 161 to position 170;
sequence section SS-18 ranging from position 171 to position 180;
sequence section SS-19 ranging from position 181 to position 190;
sequence section SS-20 ranging from position 191 to position 200;
sequence section SS-21 ranging from position 201 to position 210;
sequence section SS-22 ranging from position 211 to position 220;
sequence section SS-23 ranging from position 221 to position 230;
sequence section SS-24 ranging from position 231 to position 240; and sequence section SS-25 ranging from position 241 to position 246, wherein when the at least one residue change is in position L9, then L9 is changed to L9A, L9R, L9N, L9D, L9C, L9Q, L9E, L9G, L9H, L9I, L9K, L9F, L9P, L9S, L9T, L9W, L9Y, or L9V;

in position I24, then I24 is changed to I24A, I24L, I24M, I24Y, I24S, or I24T;

in position M26, then M26 is changed to M26A, M26R, M26N, M26D, M26C, M26Q, M26E, M26G, M26H, M26L, M26K, M26F, M26P, M26S, M26T, M26W, M26Y, or M26V:

in position A30, then A30 is changed to A30R, A30N, A30D, A30C, A30Q, A30E, A30G, A30H, A30I, A30L, A30K, A30M, A30F, A30P, A30T, A30W, A30Y, or A30V;

in position E31, then E31 is changed to E31A, E31R, E31N, E31D, E31C, E31G, E31H, E31I, E31L, E31K, E31M, E31F, E31P, E31S, E31T, E31W, E31Y, or E31V;

in position S34, then S34 is changed to S34I, S34F, S34T, S34N, S34D, S34H, S34K, or S34R;

in position I54, then I54 is changed to I54A, I54R, I54N, I54D, I54C, I54Q, I54E, I54G, I54H, I54L, I54K, I54M, I54F, I54P, I54S, I54T, I54W, or I54Y;

in position S97, then S97 is changed to S97R, S97N, S97D, S97C, S97Q, S97E, S97G, S97H, S97I, S97L, S97K, S97M, S97F, S97P, S97T, S97W, S97Y, or S97V;

in position Q138, then Q138 is changed to Q138A, Q138R, Q138N, Q138D, Q138C, Q138G, Q138H, Q138I, Q138L, Q138K, Q138M, Q138F, Q138P, Q138S, Q138T, Q138W, Q138Y, or Q138V;

in position S197, then S197 is changed to S197P, S197N, S197Q, S197D, S197E, S197K, S197R, or S197H;

in position M198, then M198 is changed to M198A, M198L, M198T, M198N, M198Q, or M198D;

in position A199, then A199 is changed to A199R, A199N, A199D, A199C, A199Q, A199E, A199G, A199H, A199I, A199L, A199K, A199M, A199F, A199P, A199T, A199W, A199Y, or A199V;

in position E200, then E200 is changed to E200A, E200R, E200N, E200C, E200Q, E200G, E200H, E200I, E200L, E200K, E200M, E200F, E200P, E200S, E200T, E200W, E200Y, or E200V:

in position I202, then I202 is changed to I202A, I202R, I202N, I202D, I202C, I202Q, I202E, I202G, I202H, I202L, I202K, I202M, I202F, I202P, I202S, I202T, I202W, or I202Y;

in position N212, then N212 is changed to N212A, N212R, N212D, N212C, N212Q, N212E, N212G, N212H, N212I, N212L, N212K, N212M, N212F, N212P, N212T, N212W, N212Y, or N212V;

in position T236, then T236 is changed to T236R, T236N, T236D, T236C, T236Q, T236E, T236G, T236H, T236I, T236L, T236K, T236M, T236F, T236P, T236S, T236W, T236Y, or T236V:

in position T237, then T237 is changed to T237A, T237V, T237L, T237M, T237G, T237S, T237C, T237N, T237D, T237E, or T237H;

in position V238, then V238 is changed to V238A, V238R, V238N, V238D, V238C, V238Q, V238E, V238G, V238H, V238I, V238K, V238M, V238F, V238P, V238S, V238T, V238W, or V238Y;

in position S239, then S239 is changed to S239A, S239R, S239N, S239D, S239C, S239Q, S239E, S239G, S239H, S239I, S239L, S239K, S239M, S239F, S239P, S239T, S239W, or S239Y;

in position Y244, then Y244 is changed to Y244A, Y244R, Y244N, Y244D, Y244C, Y244Q, Y244E, Y244G, Y244H, Y244I, Y244L, Y244K, Y244M, Y244P, Y244S, Y244T, Y244W, or Y244V;

in position C245, then C245 is changed to C245A, C245R, C245N, C245D, C245Q, C245E, C245G, C245H, C245I, C245L, C245K, C245M, C245F, C245P, C245T, C245W, C245Y, or C245V; and in position A246, then A246 is changed to A246R, A246N, A246D, A246C, A246Q, A246E, A246G, A246H, A246I, A246L, A246K, A246M, A246F, A246P, A246S, A246W, A246Y, or A246V.

2. The ketoreductase according to claim 1, wherein when the at least one residue change is in position L9, then L9 is changed to L9C, L9R, L9K, L9Q, or L9G;

in position M26, then M26 is changed to M26R;

in position A30, then A30 is changed to A30R;

in position E31, then E31 is changed to E31N;

in position I54, then I54 is changed to I54R;

in position S97, then S97 is changed to S97W, S97V, S97C, S97F, or S97M;

in position Q138, then Q138 is changed to Q138A, Q138T, or Q138S;

in position A199, then A199 is changed to A199C;

in position E200, then E200 is changed to E200P, E200V, or E200A;

in position N212, then N212 is changed to N212K, N212P, or N212A;

in position T236, then T236 is changed to T236S;

in position V238, then V238 is changed to V238F;

in position S239, then S239 is changed to S239F;

in position Y244, then Y244 is changed to Y244L;

in position C245, then C245 is changed to C245F; and in position A246, then A246 is changed to A246F.

3. The ketoreductase according to claim 1, wherein the amino acid sequence in comparison to comparative SEQ ID NO: 1 exhibits one or more properties selected from the group consisting of:

(i) an improved thermal stability, expressed as $Tm_{50(40)}$-value, as $Tm_{50(10)}$-value, and/or expressed as residual activity after 15 minutes at 42° C. compared to the comparative SEQ ID NO:1;

(ii) an increased activity, in particular specific activity, in the oxidation of alcohol substrates to ketone or aldehyde products;

(iii) an increased activity, in particular specific activity, in the reduction of ketone or aldehyde substrates to alcohol products;

(iv) an increased ratio of oxidation activity over reduction activity for the conversion of ketone or aldehyde substrates to alcohol products or vice versa;

(v) an increased ratio of reduction activity over oxidation activity for the conversion of ketone or aldehyde substrates to alcohol products or vice versa; and (vi) a decreased ratio of reduction activity over oxidation activity for the conversion of ketone or aldehyde substrates to alcohol products or vice versa.

4. The ketoreductase according to claim 1, wherein the amino acid sequence differs from the ketoreductase of SEQ ID NO:1 by at least one residue change in a sequence section SS-01 of SEQ ID NO:1, wherein said sequence section SS-01 ranges from position 1 of SEQ ID NO:1 to position 10 of SEQ ID NO:1; from position 3 of SEQ ID NO:1 to position 10 of SEQ ID NO:1; or the at least one residue change corresponds to a change in one or more or all positions selected from the group consisting of S3, S4, S8, L9, and N10.

5. The ketoreductase according to claim 1, which is capable of reducing a keto substrate of general formula (I)

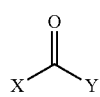

(I)

to a secondary alcohol;
or reducing an aldehyde substrate of general formula (I')

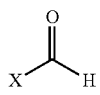

(I')

to a primary alcohol;
wherein X and Y are each independently selected from
saturated or unsaturated, unsubstituted or mono- or polysubstituted, branched or unbranched $C_1$-$C_{12}$ aliphatic residues;
saturated or unsaturated, unsubstituted or mono- or polysubstituted $C_3$-$C_{12}$ cycloaliphatic residues, optionally being bridged to the CO-moiety through a saturated or unsaturated, unsubstituted or mono- or poly substituted $C_1$-$C_{12}$-aliphatic residue;
saturated or unsaturated, unsubstituted or mono- or poly substituted $C_1$-$C_{12}$ heterocycloaliphatic residues, optionally being bridged to the CO-moiety through a saturated or unsaturated, unsubstituted or mono- or polysubstituted $C_1$-$C_{12}$-aliphatic residue;
unsubstituted or mono- or polysubstituted $C_6$-$C_{10}$-aromatic residues, optionally being bridged to the CO-moiety through a saturated or unsaturated, unsubstituted or mono- or poly substituted $C_1$-$C_{12}$-aliphatic residue; or
unsubstituted or mono- or polysubstituted $C_1$-$C_{12}$ heteroaromatic residues, optionally being bridged to the CO-moiety through a saturated or unsaturated, unsubstituted or mono- or poly substituted $C_1$-$C_{12}$-aliphatic residue;
or wherein X and Y together with the carbon atom to which they are attached may form a saturated or unsaturated, unsubstituted or mono- or polysubstituted $C_3$-$C_{12}$ cycloaliphatic residue, or a saturated or unsaturated, unsubstituted or mono- or polysubstituted $C_1$-$C_{12}$ heterocycloaliphatic residue;
and wherein mono- or polysubstituted means independently substituted with one or more functional groups selected from —F, —Cl, —Br, —$C_{1-12}$-alkyl, —$C_{1-12}$-alkyl-F, —$C_{1-12}$-alkyl-Cl, —$C_{1-12}$-alkyl-Br, —OH, =O, —O$C_{1-12}$-alkyl, —O$C_{6-10}$-aryl, —O-heteroaryl, —OCO$C_{1-12}$-alkyl, —OCO$C_{6-10}$-aryl, —OCO-heteroaryl, —SH, —S$C_{1-12}$-alkyl, —S$C_{6-10}$-aryl, —S-heteroaryl, —S(=O)$_{1-2}$ OH, —NO, —NO$_2$, —N$_3$, —NH$_2$, —NH($C_{1-12}$-alkyl), —N($C_{1-12}$-alkyl)$_2$, —NH($C_{6-10}$-aryl), —N($C_{6-10}$-aryl)$_2$, —NH(heteroaryl), —N(heteroaryl)$_2$, —CN, —CHO, —CO$_2$H, CO—$C_{1-2}$-alkyl, —CO—$C_{6-10}$-aryl and —CO-heteroaryl;
and wherein heterocycloaliphatic or heteroaromatic means cyclic structures that have atoms of at least two different elements as members of its ring(s), whereas the heteroatoms are preferably selected from the group consisting of the elements S, O, N, and B.

6. The ketoreductase according to claim 1, which is capable of oxidizing a secondary alcohol of the general formula (II)

(II)

to a ketone;
or a primary alcohol of the general formula (II')

(II')

to an aldehyde;
wherein X and Y are each independently selected from
saturated or unsaturated, unsubstituted or mono- or polysubstituted, branched or unbranched $C_1$-$C_{12}$ aliphatic residues;
saturated or unsaturated, unsubstituted or mono- or polysubstituted $C_3$-$C_{12}$ cycloaliphatic residues, optionally being bridged to the CO-moiety through a saturated or unsaturated, unsubstituted or mono- or polysubstituted $C_1$-$C_{12}$-aliphatic residue;
saturated or unsaturated, unsubstituted or mono- or polysubstituted $C_1$-$C_{12}$ heterocycloaliphatic residues, optionally being bridged to the CO-moiety through a saturated or unsaturated, unsubstituted or mono- or polysubstituted $C_1$-$C_{12}$-aliphatic residue;
unsubstituted or mono- or polysubstituted $C_6$-$C_{10}$-aromatic residues, optionally being bridged to the CO-moiety through a saturated or unsaturated, unsubstituted or mono- or polysubstituted $C_1$-$C_{12}$-aliphatic residue; or
unsubstituted or mono- or polysubstituted $C_1$-$C_{12}$ heteroaromatic residues, optionally being bridged to the CO-moiety through a saturated or unsaturated, unsubstituted or mono- or polysubstituted $C_1$-$C_{12}$-aliphatic residue;
or wherein X and Y together with the carbon atom to which they are attached may form a saturated or unsaturated, unsubstituted or mono- or polysubstituted $C_3$-$C_{12}$ cycloaliphatic residue, or a saturated or unsaturated, unsubstituted or mono- or polysubstituted $C_1$-$C_{12}$ heterocycloaliphatic residue;
and wherein mono- or polysubstituted means independently substituted with one or more functional groups selected from —F, —Cl, —Br, —$C_{1-12}$-alkyl, —$C_{1-12}$-alkyl-F, —$C_{1-12}$-alkyl-Cl, —$C_{1-12}$-alkyl-Br, —OH, =O, —O$C_{1-12}$-alkyl, —O$C_{6-10}$-aryl, —O-heteroaryl, —OCO$C_{1-12}$-alkyl, —OCO$C_{6-10}$-aryl, —OCO-heteroaryl, —SH, —S$C_{1-12}$-alkyl, —S$C_{6-10}$-aryl, —S-heteroaryl, —S(=O)$_{1-2}$ OH, —NO, —NO$_2$, —N$_3$, —NH$_2$, —NH($C_{1-12}$-alkyl), —N($C_{1-12}$-alkyl)$_2$, —NH($C_{6-10}$-aryl), —N($C_{6-10}$-aryl)$_2$, —NH(heteroaryl), —N(heteroaryl)$_2$, —CN, —CHO, —CO$_2$H, CO—$C_{1-2}$-alkyl, —CO—$C_{6-10}$-aryl and —CO-heteroaryl;

and wherein heterocycloaliphatic or heteroaromatic means cyclic structures that have atoms of at least two different elements as members of its ring(s), whereas the heteroatoms are preferably selected from the group consisting of the elements S, O, N, and B.

7. A method for reduction of a keto substrate to a secondary alcohol;

reduction of an aldehyde substrate to a primary alcohol;

oxidation of a secondary alcohol substrate to a keto product;

oxidation of a primary alcohol substrate to an aldehyde; and/or oxidation of an aldehyde substrate to a carboxylic acid;

wherein the method comprises reacting the substrate and a suitable cofactor in presence of a ketoreductase according to claim 2.

8. The method according to claim 7, wherein the substrate is a keto substrate of general formula (I)

an aldehyde substrate of general formula (I')

wherein X and Y are each independently selected from
saturated or unsaturated, unsubstituted or mono- or polysubstituted, branched or unbranched $C_1$-$C_{12}$ aliphatic residues;
saturated or unsaturated, unsubstituted or mono- or polysubstituted $C_3$-$C_{12}$ cycloaliphatic residues, optionally being bridged to the CO-moiety through a saturated or unsaturated, unsubstituted or mono- or polysubstituted $C_1$-$C_{12}$-aliphatic residue;
saturated or unsaturated, unsubstituted or mono- or polysubstituted $C_1$-$C_{12}$ heterocycloaliphatic residues, optionally being bridged to the CO-moiety through a saturated or unsaturated, unsubstituted or mono- or polysubstituted $C_1$-$C_{12}$-aliphatic residue;
unsubstituted or mono- or polysubstituted $C_6$-$C_{10}$-aromatic residues, optionally being bridged to the CO-moiety through a saturated or unsaturated, unsubstituted or mono- or polysubstituted $C_1$-$C_{12}$-aliphatic residue; or
unsubstituted or mono- or polysubstituted $C_1$-$C_{12}$ heteroaromatic residues, optionally being bridged to the CO-moiety through a saturated or unsaturated, unsubstituted or mono- or polysubstituted $C_1$-$C_{12}$-aliphatic residue;
or wherein X and Y together with the carbon atom to which they are attached may form a saturated or unsaturated, unsubstituted or mono- or polysubstituted $C_3$-$C_{12}$ cycloaliphatic residue, or a saturated or unsaturated, unsubstituted or mono- or polysubstituted $C_1$-$C_{12}$ heterocycloaliphatic residue;
and wherein mono- or polysubstituted means independently substituted with one or more functional groups selected from —F, —Cl, —Br, —$C_{1-12}$-alkyl, —$C_{1-12}$-alkyl-F, —$C_{1-12}$-alkyl-Cl, —$C_{1-12}$-alkyl-Br, —OH, =O, —O$C_{1-12}$-alkyl, —O$C_{6-10}$-aryl, —O-heteroaryl, —OCO$C_{1-12}$-alkyl, —OCO$C_{6-10}$-aryl, —OCO-heteroaryl, —SH, —S$C_{1-12}$-alkyl, —S$C_{6-10}$-aryl, —S-heteroaryl, —S(=O)$_{1-2}$ OH, —NO, —NO$_2$, —N$_3$, —NH$_2$, —NH($C_{1-12}$-alkyl), —N($C_{1-12}$-alkyl)$_2$, —NH($C_{6-10}$-aryl), —N($C_{6-10}$-aryl)$_2$, —NH(heteroaryl), —N(heteroaryl)$_2$, —CN, —CHO, —CO$_2$H, CO—$C_{1-2}$-alkyl, —CO—$C_{6-10}$-aryl and —CO-heteroaryl;
and wherein heterocycloaliphatic or heteroaromatic means cyclic structures that have atoms of at least two different elements as members of its ring(s), whereas the heteroatoms are preferably selected from the group consisting of the elements S, O, N, and B.

9. The method according to claim 7, wherein the substrate is a secondary alcohol of the general formula (II)

or a primary alcohol of the general formula (II')

wherein X and Y are each independently selected from
saturated or unsaturated, unsubstituted or mono- or polysubstituted, branched or unbranched $C_1$-$C_{12}$ aliphatic residues;
saturated or unsaturated, unsubstituted or mono- or polysubstituted $C_3$-$C_{12}$ cycloaliphatic residues, optionally being bridged to the CO-moiety through a saturated or unsaturated, unsubstituted or mono- or poly substituted $C_1$-$C_{12}$-aliphatic residue;
saturated or unsaturated, unsubstituted or mono- or poly substituted $C_1$-$C_{12}$ heterocycloaliphatic residues, optionally being bridged to the CO-moiety through a saturated or unsaturated, unsubstituted or mono- or polysubstituted $C_1$-$C_{12}$-aliphatic residue;
unsubstituted or mono- or polysubstituted $C_6$-$C_{10}$-aromatic residues, optionally being bridged to the CO-moiety through a saturated or unsaturated, unsubstituted or mono- or polysubstituted $C_1$-$C_{12}$-aliphatic residue; or
unsubstituted or mono- or polysubstituted $C_1$-$C_{12}$ heteroaromatic residues, optionally being bridged to the CO-moiety through a saturated or unsaturated, unsubstituted or mono- or polysubstituted $C_1$-$C_{12}$-aliphatic residue;
or wherein X and Y together with the carbon atom to which they are attached may form a saturated or unsaturated, unsubstituted or mono- or polysubstituted $C_3$-$C_{12}$ cycloaliphatic residue, or a saturated or unsaturated, unsubstituted or mono- or polysubstituted $C_1$-$C_{12}$ heterocycloaliphatic residue;
and wherein mono- or polysubstituted means independently substituted with one or more functional groups selected from —F, —Cl, —Br, —$C_{1-12}$-alkyl, —$C_{1-12}$-alkyl-F, —$C_{1-12}$-alkyl-Cl, —$C_{1-12}$-alkyl-Br, —OH, =O, —OC$_{1-12}$-alkyl, —OC$_{6-10}$-aryl, —O-heteroaryl, —OCOC$_{1-12}$-alkyl, —OCOC$_{6-10}$-aryl, —OCO-heteroaryl, —SH, —SC$_{1-12}$-alkyl, —SC$_{6-10}$-aryl, —S-heteroaryl, —S(=O)$_{1-2}$ OH, —NO, —NO$_2$, —N$_3$, —NH$_2$, —NH(C$_{1-12}$-alkyl), —N(C$_{1-12}$-alkyl)$_2$, —NH (C$_{6-10}$-aryl), —N(C$_{6-10}$-aryl)$_2$, —NH(heteroaryl), —N(heteroaryl)$_2$, —CN, —CHO, —CO$_2$H, CO—C$_{1-2}$-alkyl, —CO—C$_{6-10}$-aryl and —CO-heteroaryl;

and wherein heterocycloaliphatic or heteroaromatic means cyclic structures that have atoms of at least two different elements as members of its ring(s), whereas the heteroatoms are preferably selected from the group consisting of the elements S, O, N, and B.

10. The ketoreductase according to claim 1, wherein the amino acid sequence differs from the ketoreductase of SEQ ID NO:1 by at least one residue change in a sequence section SS-02 of SEQ ID NO:1, wherein
said sequence section SS-02 ranges from position 11 of SEQ ID NO:1 to position 20 of SEQ ID NO:1;
from position 11 of SEQ ID NO:1 to position 16 of SEQ ID NO:1;-or the at least one residue change corresponds to a change in one or more or all positions selected from A11 and V13.

11. The ketoreductase according to claim 1, wherein the amino acid sequence differs from the ketoreductase of SEQ ID NO:1 by at least one residue change in a sequence section SS-03 of SEQ ID NO:1, wherein said sequence section SS-03 ranges from position 21 of SEQ ID NO:1 to position 30 of SEQ ID NO:1; from position 22 of SEQ ID NO:1 to position 30 of SEQ ID NO:1;
or the at least one residue change corresponds to a change in one or more or all positions selected from E22, S25, M26, and A30.

12. The ketoreductase according to claim 1, wherein the amino acid sequence differs from the ketoreductase of SEQ ID NO:1 by at least one residue change in a sequence section SS-04 of SEQ ID NO:1, wherein said sequence section SS-04 ranges from position 31 of SEQ ID NO:1 to position 40 of SEQ ID NO:1.

13. The ketoreductase according to claim 12, wherein said sequence section SS-04 ranges from position 31 of SEQ ID NO:1 to position 39 of SEQ ID NO:1 or differs from the ketoreductase of SEQ ID NO:1 in one or more or all positions selected from E31, A38, and S39.

14. The ketoreductase according to claim 1, wherein the amino acid sequence differs from the ketoreductase of SEQ ID NO:1 by at least one residue change in a sequence section SS-06 of SEQ ID NO:1, wherein said sequence section SS-06 ranges from position 51 of SEQ ID NO:1 to position 60 of SEQ ID NO:1; from position 54 of SEQ ID NO:1 to position 60 of SEQ ID NO:1;
or the at least one residue change corresponds to a change in one or more or all positions selected from I54, V55, K56, Q57, and T60.

15. The ketoreductase according to claim 1, wherein the amino acid sequence differs from the ketoreductase of SEQ ID NO:1 by at least one residue change in a sequence section SS-07 of SEQ ID NO:1, wherein said sequence section SS-07 ranges from position 61 of SEQ ID NO:1 to position 70 of SEQ ID NO:1; from position 63 of SEQ ID NO:1 to position 70 of SEQ ID NO:1; or the at least one residue change corresponds to a change in one or more or all positions selected from S69, and D70.

16. The ketoreductase according to claim 1, wherein the amino acid sequence differs from the ketoreductase of SEQ ID NO:1 by at least one residue change in a sequence section SS-08 of SEQ ID NO:1, wherein said sequence section SS-08 ranges from position 71 of SEQ ID NO:1 to position 80 of SEQ ID NO:1; from position 75 of SEQ ID NO:1 to position 77 of SEQ ID NO:1;
or the at least one residue change corresponds to a change in one or more or all positions selected from G75, S76, and F77.

17. The ketoreductase according to claim 1, wherein the amino acid sequence differs from the ketoreductase of SEQ ID NO:1 by at least one residue change in a sequence section SS-09 of SEQ ID NO:1, wherein said sequence section SS-09 ranges from position 81 of SEQ ID NO:1 to position 90 of SEQ ID NO:1; or from position 82 of SEQ ID NO:1 to position 89 of SEQ ID NO:1.

18. The ketoreductase according to claim 1, wherein the amino acid sequence differs from the ketoreductase of SEQ ID NO:1 by at least one residue change in a sequence section SS-10 of SEQ ID NO:1, wherein said sequence section SS-10 ranges from position 91 of SEQ ID NO:1 to position 100 of SEQ ID NO:1; from position 92 of SEQ ID NO:1 to position 100 of SEQ ID NO:1; or the at least one residue change corresponds to a change in one or more or all positions selected from S92, S97, Q98, F99, and S100.

19. The ketoreductase according to claim 1, wherein the amino acid sequence differs from the ketoreductase of SEQ ID NO:1 by at least one residue change in a sequence section SS-11 of SEQ ID NO:1, wherein said sequence section SS-11 ranges from position 101 of SEQ ID NO:1 to position 110 of SEQ ID NO:1; from position 101 of SEQ ID NO:1 to position 109 of SEQ ID NO:1; or the at least one residue change corresponds to a change in one or more or all positions selected from P101, A106, A108, and D109.

20. The ketoreductase according to claim 1, wherein the amino acid sequence differs from the ketoreductase of SEQ ID NO:1 by at least one residue change in a sequence section SS-12 of SEQ ID NO:1, wherein said sequence section SS-12 ranges from position 111 of SEQ ID NO:1 to position 120 of SEQ ID NO:1; from position 112 of inventive SEQ ID NO:1 to position 120 of inventive SEQ ID NO:1; or the at least one residue change corresponds to a change in one or more or all positions selected from N112, M113, L114, T119, and A120.

21. The ketoreductase according to claim 1, wherein the amino acid sequence differs from the ketoreductase of SEQ ID NO:1 by at least one residue change in a sequence section SS-13 of SEQ ID NO:1, wherein said sequence section SS-13 ranges from position 121 of SEQ ID NO:1 to position 130 of SEQ ID NO:1; from position 121 of inventive SEQ ID NO:1 to position 127 of inventive SEQ ID NO:1; or the at least one residue change corresponds to a change in one or more or all positions selected from P121, and A127.

22. The ketoreductase according to claim 1, wherein the amino acid sequence differs from the ketoreductase of SEQ ID NO:1 by at least one residue change in a sequence section SS-14 of SEQ ID NO:1, wherein said sequence section SS-14 ranges from position 131 of SEQ ID NO:1 to position 140 of SEQ ID NO:1; from position 132 of-SEQ ID NO:1 to position 139 of SEQ ID NO:1; or the at least one residue change corresponds to a change in one or more or all positions selected from I132, S133, P136, Q138, and T139.

23. The ketoreductase according to claim 1, wherein the amino acid sequence differs from the ketoreductase of SEQ ID NO:1 by at least one residue change in a sequence section SS-15 of SEQ ID NO:1, wherein said sequence section SS-15 ranges from position 141 of SEQ ID NO:1 to position 150 of SEQ ID NO:1; from position 141 of SEQ ID NO:1 to position 149 of SEQ ID NO:1; or the at least one residue change corresponds to a change in one or more or all positions selected from A141, G147, T148, and G149.

24. The ketoreductase according to claim 1, wherein the amino acid sequence differs from the ketoreductase of SEQ ID NO:1 by at least one residue change in a sequence section SS-16 of SEQ ID NO:1, wherein said sequence section SS-16 ranges from position 151 of SEQ ID NO:1 to position 160 of SEQ ID NO:1; from position 151 of inventive SEQ ID NO:1 to position 159 of inventive SEQ ID NO:1; or the at least one residue change corresponds to a change in one or more or all positions selected from S151, K152, A155, M157, V158, and G159.

25. The ketoreductase according to claim 1, wherein the amino acid sequence differs from the ketoreductase of SEQ ID NO:1 by at least one residue change in a sequence section SS-17 of SEQ ID NO:1, wherein said sequence section SS-17 ranges from position 161 of SEQ ID NO:1 to position 170 of SEQ ID NO:1; from position 168 of SEQ ID NO:1 to position 170 of SEQ ID NO:1; or the at least one residue change corresponds to a change in one or more or all positions selected from D169.

26. The ketoreductase according to claim 1, wherein the amino acid sequence differs from the ketoreductase of SEQ ID NO:1 by at least one residue change in a sequence section SS-18 of SEQ ID NO:1, wherein said sequence section SS-18 ranges from position 171 of SEQ ID NO:1 to position 180 of SEQ ID NO:1; from position 172 of SEQ ID NO:1 to position 177 of SEQ ID NO:1; or the at least one residue change corresponds to a change in one or more or all positions selected from M172.

27. The ketoreductase according to claim 1, wherein the amino acid sequence differs from the ketoreductase of-SEQ ID NO:1 by at least one residue change in a sequence section SS-19 of SEQ ID NO:1, wherein said sequence section SS-19 ranges from position 181 of SEQ ID NO:1 to position 190 of SEQ ID NO:1; from position 181 of SEQ ID NO:1 to position 185 of SEQ ID NO:1; or the at least one residue change corresponds to a change in one or more or all positions selected from P181, K182, and N185.

28. The ketoreductase according to claim 1, wherein the amino acid sequence differs from the ketoreductase of SEQ ID NO:1 by at least one residue change in a sequence section SS-20 of SEQ ID NO:1, wherein said sequence section SS-20 ranges from position 191 of SEQ ID NO:1 to position 200 of SEQ ID NO:1; from position 194 of SEQ ID NO:1 to position 200 of SEQ ID NO:1; or the at least one residue change corresponds to a change in one or more or all positions selected from T194, A199, and E200.

29. The ketoreductase according to claim 1, wherein the amino acid sequence differs from the ketoreductase of SEQ ID NO:1 by at least one residue change in a sequence section SS-21 of inventive SEQ ID NO:1, wherein said sequence section SS-21 ranges from position 201 of SEQ ID NO:1 to position 210 of SEQ ID NO:1; from position 202 of inventive SEQ ID NO:1 to position 210 of inventive SEQ ID NO:1; or the at least one residue change corresponds to a change in one or more or all positions selected from I202, P204, M206, D208, L209 and P210.

30. The ketoreductase according to claim 1, wherein the amino acid sequence differs from the ketoreductase of SEQ ID NO:1 by at least one residue change in a sequence section SS-22 of SEQ ID NO:1, wherein said sequence section SS-22 ranges from position 211 of SEQ ID NO:1 to position 220 of SEQ ID NO:1; from position 212 of inventive SEQ ID NO:1 to position 220 of inventive SEQ ID NO:1; or the at least one residue change corresponds to a change in one or more or all positions selected from N212, G213, W214, I215, V217, and I220.

31. The ketoreductase according to claim 1, wherein the amino acid sequence differs from the ketoreductase of SEQ ID NO:1 by at least one residue change in a sequence section SS-23 of SEQ ID NO:1, wherein said sequence section SS-23 ranges from position 221 of SEQ ID NO:1 to position 230 of SEQ ID NO:1; from position 225 of SEQ ID NO:1 to position 227 of SEQ ID NO:1; or the at least one residue change corresponds to a change in one or more or all positions selected from T225, and L227.

32. The ketoreductase according to claim 1, wherein the amino acid sequence differs from the ketoreductase of SEQ ID NO:1 by at least one residue change in a sequence section SS-24 of SEQ ID NO:1, wherein said sequence section SS-24 ranges from position 231 of SEQ ID NO:1 to position 240 of SEQ ID NO:1; from position 232 of SEQ ID NO:1 to position 239 of SEQ ID NO:1; or the at least one residue change corresponds to a change in one or more or all positions selected from N232, G235, T236, T237, V238, and S239.

33. The ketoreductase according to claim 1, wherein the amino acid sequence differs from the ketoreductase of SEQ ID NO:1 by at least one residue change in a sequence section SS-25 of SEQ ID NO:1, wherein said sequence section SS-25 ranges from position 241 of SEQ ID NO:1 to position 246 of SEQ ID NO:1; from position 243 of SEQ ID NO:1 to position 246 of SEQ ID NO:1; or the at least one residue change corresponds to a change in one or more or all positions selected from G243, Y244, C245, and A246.

34. The ketoreductase of claim 1, wherein the ketoreductase differs from the ketoreductase of inventive SEQ ID NO:1 by at least two, at least three, at least four, at least five, or at least six residue changes in one or more sequence sections SS-01 to SS-25.

35. The ketoreductase according to claim 1, wherein when the at least one residue change is in position S97, then S97 is changed to S97V or S97C.

36. The ketoreductase according to claim 1, wherein when the at least one residue change is in position S97, then S97 is changed to S97C.

37. The ketoreductase according to claim 1, wherein the amino acid sequence has at least 93% sequence identity with the amino acid sequence of SEQ ID NO:1.

38. The ketoreductase according to claim 1,
wherein when the at least one residue change is
in position S3, then S3 is changed to S3A, S3R, S3N, S3D, S3C, S3Q, S3E, S3G, S3H, S3I, S3L, S3K, S3M, S3F, S3P, S3T, S3W, S3Y, or S3V;
in position S4, then S4 is changed to S4A, S4R, S4N, S4D, S4C, S4Q, S4E, S4G, S4H, S4I, S4L, S4K, S4M, S4F, S4P, S4T, S4W, S4Y, or S4V;
in position S8, then S8 is changed to S8A, S8R, S8N, S8D, S8C, S8Q, S8E, S8G, S8H, S8I, S8L, S8K, S8M, S8F, S8P, S8T, S8W, S8Y, or S8V;
in position N10, then N10 is changed to N10A, N10R, N10D, N10C, N10Q, N10E, N10G, N10H, N10I, N10L, N10K, N10M, N10F, N10P, N10S, N10T, N10W, N10Y, or N10V;
in position A11, then A11 is changed to A11R, A11N, A11D, A11C, A11Q, A11E, A11G, A11H, A11I, A11L, A11K, A11M, A11F, A11P, A11S, A11T, A11W, A11Y, or A11V;

in position V13, then V13 is changed to V13A, V13R, V13N, V13D, V13C, V13Q, V13E, V13G, V13H, V13I, V13L, V13K, V13M, V13F, V13P, V13S, V13T, V13W, or V13Y;

in position E22, then E22 is changed to E22A, E22R, E22N, E22D, E22C, E22Q, E22G, E22H, E22I, E22L, E22K, E22M, E22F, E22P, E22S, E22T, E22W, E22Y, or E22V;

in position I24, then I24 is changed to I24A, I24L, I24M, I24Y, I24S, or I24T;

in position S25, then S25 is changed to S25A, S25R, S25N, S25D, S25C, S25Q, S25E, S25G, S25H, S25I, S25L, S25K, S25M, S25F, S25P, S25T, S25W, S25Y, or S25V in position S34, then S34 is changed to S34I, S34F, S34T, S34N, S34D, S34H, S34K, or S34R;

in position A38, then A38 is changed to A38R, A38N, A38D, A38C, A38Q, A38E, A38G, A38H, A38I, A38L, A38K, A38M, A38F, A38P, A38S, A38T, A38W, A38Y, or A38V;

in position S39, then S39 is changed to S39A, S39R, S39N, S39D, S39C, S39Q, S39E, S39G, S39H, S39I, S39L, S39K, S39M, S39F, S39P, S39T, S39W, S39Y, or S39V;

in position L42, then L42 is changed to L42A, L42R, L42N, L42D, L42C, L42Q, L42E, L42G, L42H, L42I, L42K, L42M, L42F, L42P, L42S, L42T, L42W, or L42Y;

in position V55, then V55 is changed to V55A, V55R, V55N, V55D, V55C, V55Q, V55E, V55G, V55H, V55I, V55L, V55K, V55M, V55F, V55P, V55S, V55T, V55W, or V55Y;

in position K56, then K56 is changed to K56A, K56R, K56N, K56D, K56C, K56Q, K56E, K56G, K56H, K56I, K56L, K56M, K56F, K56P, K56S, K56T, K56W, K56Y, or K56V;

in position Q57, then Q57 is changed to Q57A, Q57R, Q57N, Q57D, Q57C, Q57E, Q57G, Q57H, Q57I, Q57L, Q57K, Q57M, Q57F, Q57P, Q57S, Q57T, Q57W, Q57Y, or Q57V;

in position T60, then T60 is changed to T60A, T60R, T60N, T60D, T60C, T60Q, T60E, T60G, T60H, T60I, T60L, T60K, T60M, T60F, T60P, T60S, T60W, T60Y, or T60V;

in position S69, then S69 is changed to S69A, S69R, S69N, S69D, S69C, S69Q, S69E, S69G, S69H, S69I, S69L, S69K, S69M, S69F, S69P, S69T, S69W, S69Y, or S69V;

in position D70, then D70 is changed to D70A, D70R, D70N, D70C, D70Q, D70E, D70G, D70H, D70I, D70L, D70K, D70M, D70F, D70P, D70S, D70T, D70W, D70Y, or D70V;

in position G75, then G75 is changed to G75A, G75R, G75N, G75D, G75C, G75Q, G75E, G75H, G75I, G75L, G75K, G75M, G75F, G75P, G75S, G75T, G75W, G75Y, or G75V;

in position S76, then S76 is changed to S76A, S76R, S76N, S76D, S76C, S76Q, S76E, S76G, S76H, S76I, S76L, S76K, S76M, S76F, S76P, S76T, S76W, S76Y, or S76V;

in position F77, then F77 is changed to F77A, F77R, F77N, F77D, F77C, F77Q, F77E, F77G, F77H, F77I, F77L, F77K, F77M, F77P, F77S, F77T, F77W, F77Y, or F77V;

in position S92, then S92 is changed to S92A, S92R, S92N, S92D, S92C, S92Q, S92E, S92G, S92H, S92I, S92L, S92K, S92M, S92F, S92P, S92T, S92W, S92Y, or S92V;

in position S97, then S97 is changed to S97R, S97N, S97D, S97C, S97Q, S97E, S97G, S97H, S97I, S97L, S97K, S97M, S97F, S97P, S97T, S97W, S97Y, or S97V;

in position Q98, then Q98 is changed to Q98A, Q98R, Q98N, Q98D, Q98C, Q98E, Q98G, Q98H, Q98I, Q98L, Q98K, Q98M, Q98F, Q98P, Q98S, Q98T, Q98W, Q98Y, or Q98V;

in position F99, then F99 is changed to F99A, F99R, F99N, F99D, F99C, F99Q, F99E, F99G, F99H, F99I, F99L, F99K, F99M, F99P, F99S, F99T, F99W, F99Y, or F99V;

in position S100, then S100 is changed to S100A, S100R, S100N, S100D, S100C, S100Q, S100E, S100G, S100H, S100I, S100L, S100K, S100M, S100F, S100P, S100T, S100W, S100Y, or S100V;

in position P101, then P101 is changed to P101A, P101R, P101N, P101D, P101C, P101Q, P101E, P101G, P101H, P101I, P101L, P101K, P101M, P101F, P101S, P101T, P101W, P101Y, or P101V;

in position A106, then A106 is changed to A106R, A106N, A106D, A106C, A106Q, A106E, A106G, A106H, A106I, A106L, A106K, A106M, A106F, A106P, A106S, A106T, A106W, A106Y, or A106V;

in position A108, then A108 is changed to A108R, A108N, A108D, A108C, A108Q, A108E, A108G, A108H, A108I, A108L, A108K, A108M, A108F, A108P, A108S, A108T, A108W, A108Y, or A108V;

in position D109, then D109 is changed to D109A, D109R, D109N, D109C, D109Q, D109E, D109G, D109H, D109I, D109L, D109K, D109M, D109F, D109P, D109S, D109T, D109W, D109Y, or D109V;

in position N112, then N112 is changed to N112A, N112R, N112D, N112C, N112Q, N112E, N112G, N112H, N112I, N112L, N112K, N112M, N112F, N112P, N112S, N112T, N112W, N112Y, or N112V;

in position M113, then M113 is changed to M113A, M113R, M113N, M113D, M113C, M113Q, M113E, M113G, M113H, M113I, M113L, M113K, M113F, M113P, M113S, M113T, M113W, M113Y, or M113V;

in position L114, then L114 is changed to L114A, L114R, L114N, L114D, L114C, L114Q, L114E, L114G, L114H, L114I, L114K, L114M, L114F, L114P, L114S, L114T, L114W, L114Y, or L114V;

in position T119, then T119 is changed to T119A, T119R, T119N, T119D, T119C, T119Q, T119E, T119G, T119H, T119I, T119L, T119K, T119M, T119F, T119P, T119S, T119W, T119Y, or T119V;

in position A120, then A120 is changed to A120R, A120N, A120D, A120C, A120Q, A120E, A120G, A120H, A120I, A120L, A120K, A120M, A120F, A120P, A120S, A120T, A120W, A120Y, or A120V;

in position P121, then P121 is changed to P121A, P121R, P121N, P121D, P121C, P121Q, P121E, P121G, P121H, P121I, P121L, P121K, P121M, P121F, P121S, P121T, P121W, P121Y, or P121V;

in position A127, then A127 is changed to A127R, A127N, A127D, A127C, A127Q, A127E, A127G, A127H, A127I, A127L, A127K, A127M, A127F, A127P, A127S, A127T, A127W, A127Y, or A127V;

in position I132, then I132 is changed to I132A, I132R, I132N, I132D, I132C, I132Q, I132E, I132G, I132H, I132L, I132K, I132M, I132F, I132P, I132S, I132T, I132W, I132Y, or I132V;

in position S133, then S133 is changed to S133A, S133R, S133N, S133D, S133C, S133Q, S133E, S133G, S133H, S133I, S133L, S133K, S133M, S133F, S133P, S133T, S133W, S133Y, or S133V;

in position P136, then P136 is changed to P136A, P136R, P136N, P136D, P136C, P136Q, P136E, P136G, P136H, P136I, P136L, P136K, P136M, P136F, P136S, P136T, P136W, P136Y, or P136V;

in position T139, then T139 is changed to T139A, T139R, T139N, T139D, T139C, T139Q, T139E, T139G, T139H, T139I, T139L, T139K, T139M, T139F, T139P, T139S, T139W, T139Y, or T139V;

in position A141, then A141 is changed to A141R, A141N, A141D, A141C, A141Q, A141E, A141G, A141H, A141I, A141L, A141K, A141M, A141F, A141P, A141S, A141T, A141W, A141Y, or A141V;

in position G147, then G147 is changed to G147A, G147R, G147N, G147D, G147C, G147Q, G147E, G147H, G147I, G147L, G147K, G147M, G147F, G147P, G147S, G147T, G147W, G147Y, or G147V;

in position T148, then T148 is changed to T148A, T148R, T148N, T148D, T148C, T148Q, T148E, T148G, T148H, T148I, T148L, T148K, T148M, T148F, T148P, T148S, T148W, T148Y, or T148V;

in position G149, then G149 is changed to G149A, G149R, G149N, G149D, G149C, G149Q, G149E, G149H, G149I, G149L, G149K, G149M, G149F, G149P, G149S, G149T, G149W, G149Y, or G149V;

in position S151, then S151 is changed to S151A, S151R, S151N, S151D, S151C, S151Q, S151E, S151G, S151H, S151I, S151L, S151K, S151M, S151F, S151P, S151T, S151W, S151Y, or S151V;

in position K152, then K152 is changed to K152A, K152R, K152N, K152D, K152C, K152Q, K152E, K152G, K152H, K152I, K152L, K152M, K152F, K152P, K152S, K152T, K152W, K152Y, or K152V;

in position A155, then A155 is changed to A155R, A155N, A155D, A155C, A155Q, A155E, A155G, A155H, A155I, A155L, A155K, A155M, A155F, A155P, A155S, A155T, A155W, A155Y, or A155V;

in position M157, then M157 is changed to M157A, M157R, M157N, M157D, M157C, M157Q, M157E, M157G, M157H, M157I, M157L, M157K, M157F, M157P, M157S, M157T, M157W, M157Y, or M157V;

in position V158, then V158 is changed to V158A, V158R, V158N, V158D, V158C, V158Q, V158E, V158G, V158H, V158I, V158L, V158K, V158M, V158F, V158P, V158S, V158T, V158W, or V158Y;

in position G159, then G159 is changed to G159A, G159R, G159N, G159D, G159C, G159Q, G159E, G159H, G159I, G159L, G159K, G159M, G159F, G159P, G159S, G159T, G159W, G159Y, or G159V;

in position D169, then D169 is changed to D169A, D169R, D169N, D169C, D169Q, D169E, D169G, D169H, D169I, D169L, D169K, D169M, D169F, D169P, D169S, D169T, D169W, D169Y, or D169V;

in position M172, then M172 is changed to M172A, M172R, M172N, M172D, M172C, M172Q, M172E, M172G, M172H, M172I, M172L, M172K, M172F, M172P, M172S, M172T, M172W, M172Y, or M172V;

in position P181, then P181 is changed to P181A, P181R, P181N, P181D, P181C, P181Q, P181E, P181G, P181H, P181I, P181L, P181K, P181M, P181F, P181S, P181T, P181W, P181Y, or P181V;

in position K182, then K182 is changed to K182A, K182R, K182N, K182D, K182C, K182Q, K182E, K182G, K182H, K182I, K182L, K182M, K182F, K182P, K182S, K182T, K182W, K182Y, or K182V;

in position N185, then N185 is changed to N185A, N185R, N185D, N185C, N185Q, N185E, N185G, N185H, N185I, N185L, N185K, N185M, N185F, N185P, N185S, N185T, N185W, N185Y, or N185V;

in position T194, then T194 is changed to T194A, T194R, T194N, T194D, T194C, T194Q, T194E, T194G, T194H, T194I, T194L, T194K, T194M, T194F, T194P, T194S, T194W, T194Y, or T194V;

in position S197, then S197 is changed to S197P, S197N, S197Q, S197D, S197E, S197K, S197R, or S197H;

in position M198, then M198 is changed to M198A, M198L, M198T, M198N, M198Q, or M198D;

in position I202, then I202 is changed to I202A, I202R, I202N, I202D, I202C, I202Q, I202E, I202G, I202H, I202L, I202K, I202M, I202F, I202P, I202S, I202T, I202W, or I202Y;

in position P204, then P204 is changed to P204A, P204R, P204N, P204D, P204C, P204Q, P204E, P204G, P204H, P204I, P204L, P204K, P204M, P204F, P204S, P204T, P204W, P204Y, or P204V;

in position M206, then M206 is changed to M206A, M206R, M206N, M206D, M206C, M206Q, M206E, M206G, M206H, M206I, M206L, M206K, M206F, M206P, M206S, M206T, M206W, M206Y, or M206V;

in position D208, then D208 is changed to D208A, D208R, D208N, D208C, D208Q, D208E, D208G, D208H, D208I, D208L, D208K, D208M, D208F, D208P, D208S, D208T, D208W, D208Y, or D208V;

in position L209, then L209 is changed to L209A, L209R, L209N, L209D, L209C, L209Q, L209E, L209G, L209H, L209I, L209K, L209M, L209F, L209P, L209S, L209T, L209W, L209Y, or L209V;

in position P210, then P210 is changed to P210A, P210R, P210N, P210D, P210C, P210Q, P210E, P210G, P210H, P210I, P210L, P210K, P210M, P210F, P210S, P210T, P210W, P210Y, or P210V;

in position G213, then G213 is changed to G213A, G213R, G213N, G213D, G213C, G213Q, G213E, G213H, G213I, G213L, G213K, G213M, G213F, G213P, G213S, G213T, G213W, G213Y, or G213V; or in position W214, then W214 is changed to W214A, W214R, W214N, W214D, W214C, W214Q, W214E, W214G, W214H, W214I, W214L, W214K, W214M, W214F, W214P, W214S, W214T, W214Y, or W214V;

in position I215, then I215 is changed to I215A, I215R, I215N, I215D, I215C, I215Q, I215E, I215G, I215H, I215L, I215K, I215M, I215F, I215P, I215S, I215T, I215W, I215Y, or I215V;

in position V217, then V217 is changed to V217A, V217R, V217N, V217D, V217C, V217Q, V217E, V217G, V217H, V217I, V217L, V217K, V217M, V217F, V217P, V217S, V217T, V217W, or V217Y;

in position I220, then I220 is changed to I220A, I220R, I220N, I220D, I220C, I220Q, I220E, I220G, I220H, I220L, I220K, I220M, I220F, I220P, I220S, I220T, I220W, I220Y, or I220V;

in position T225, then T225 is changed to T225A, T225R, T225N, T225D, T225C, T225Q, T225E, T225G, T225H, T225I, T225L, T225K, T225M, T225F, T225P, T225S, T225W, T225Y, or T225V;

in position L227, then L227 is changed to L227A, L227R, L227N, L227D, L227C, L227Q, L227E, L227G, L227H, L227I, L227K, L227M, L227F, L227P, L227S, L227T, L227W, L227Y, or L227V;

in position N232, then N232 is changed to N232A, N232R, N232D, N232C, N232Q, N232E, N232G, N232H, N232I, N232L, N232K, N232M, N232F, N232P, N232S, N232T, N232W, N232Y, or N232V;

in position G235, then G235 is changed to G235A, G235R, G235N, G235D, G235C, G235Q, G235E, G235H, G235I, G235L, G235K, G235M, G235F, G235P, G235S, G235T, G235W, G235Y, or G235V;

in position T237, then T237 is changed to T237A, T237R, T237N, T237D, T237C, T237Q, T237E, T237G, T237H, T237L, T237K, T237M, T237F, T237P, T237S, T237W, T237Y, or T237V; or in position G243, then G243 is changed to G243A, G243R, G243N, G243D, G243C, G243Q, G243E, G243H, G243I, G243L, G243K, G243M, G243F, G243P, G243S, G243T, G243W, G243Y, or G243V.

39. The ketoreductase according to claim 1, wherein when the at least one residue change is in position S3, then S3 is changed to S3I;
in position S4, then S4 is changed to S4N;
in position S8, then S8 is changed to S8A;
in position N10, then N10 is changed to N10G;
in position A11, then A11 is changed to A11V or A11C;
in position V13, then V13 is changed to V13G;
in position E22, then E22 is changed to E22K;
in position S25, then S25 is changed to S25A;
in position A38, then A38 is changed to A38M;
in position S39, then S39 is changed to S39G or S39A;
in position L42, then L32 is changed to L42Y;
in position V55, then V55 is changed to V55I or V55C;
in position K56, then K56 is changed to K56M;
in position Q57, then Q57 is changed to Q57P or Q57A;
in position T60, then T60 is changed to T60C, T60N, or T60A;
in position S69, then S69 is changed to S69V or S69A;
in position D70, then D70 is changed to D70C or D70S;
in position G75, then G75 is changed to G75L;
in position S76, then S76 is changed to S76M, S76C, S76L, or S76G;
in position F77, then F77 is changed to F77L;
in position S92, then S92 is changed to S92M and S92G;
in position S97, then S97 is changed to S97V or S97C;
in position Q98, then Q98 is changed to Q98E;
in position F99, then F99 is changed to F99R;
in position S100, then S100 is changed to S100R;
in position P101, then P101 is changed to P101F, P101H, or P101W;
in position A106, then A106 is changed to A106C or A106E;
in position A108, then A108 is changed to A108P;
in position D109, then D109 is changed to D109G or D109R;
in position N112, then N112 is changed to N112T;
in position M113, then M113 is changed to M113V;
in position L114, then L114 is changed to L114V or L114I;
in position T119, then T119 is changed to T119L;
in position A120, then A120 is changed to A120G;
in position P121, then P121 is changed to P121V, or P121A;
in position A127, then A127 is changed to A127K, A127C, A127G, or A127Q;

in position I132, then I132 is changed to I132V, I132W, or I132F;
in position S133, then S133 is changed to S133M, S133L, S133A, S133Q, or S133V;
in position P136, then P136 is changed to P136V or P136G;
in position T139, then T139 is changed to T139V, T139F, or, T139K;
in position A141, then A141 is changed to A141S;
in position G147, then G147 is changed to G147C;
in position T148, then T148 is changed to T148S;
in position G149, then G149 is changed to G149C, G149V, G149M, G149 I or G149S;
in position S151, then S151 is changed to S151A;
in position K152, then K152 is changed to K152A;
in position A155, then A155 is changed to A155W or A155H;
in position M157, then M157 is changed to M157F, M157R, M157G, M157C, M157E, M157D or M157K;
in position V158, then V158 is changed to V158M;
in position G159, then G159 is changed to G159S or G159A;
in position D169, then D169 is changed to D169E;
in position M172, then M172 is changed to M172C;
in position P181, then P181 is changed to P181V, P181W, or P181L;
in position K182, then K182 is changed to K182I;
in position N185, then N185 is changed to N185R;
in position T194, then T194 is changed to T194V;
in position P204, then P204 is changed to P204L;
in position M206, then M206 is changed to M206T, M206D, M206G, or M206A;
in position D208, then D208 is changed to D208H, D208C, or D208N;
in position L209, then L209 is changed to L209C;
in position P210, then P210 is changed to P210C;
in position G213, then G213 is changed to G213D;
in position W214, then W214 is changed to W214G;
in position I215, then I215 is changed to I215T;
in position V217, then V217 is changed to V217N or V217P;
in position I220, then I220 is changed to I220V;
in position T225, then T225 is changed to T225M or T225I;
in position L227, then L227 is changed to L227V;
in position N232, then N232 is changed to N232Y or N232F;
in position G235, then G235 is changed to G235F;
in position G243, then G243 is changed to G243V; and
in position Y244, then Y244 is changed to Y244L.

40. The ketoreductase according to claim 1 comprising one or more substitutions at position(s) selected from the group consisting of S3, S4, S8, L9, N10, A11, V13, E22, I24, S25, M26, A30, E31, S34, A38, S39, L42, I54, V55, K56, Q57, T60, S69, D70, G75, S76, F77, S92, S97, Q98, F99, S100, P101, A106, A108, D109, N112, M113, L114, T119, A120, P121, A127, I132, S133, P136, Q138, T139, A141, G147, T148, G149, S151, K152, A155, M157, V158, G159, D169, M172, P181, K182, N185, T194, S197, M198, A199, E200, I202, P204, M206, D208, L209, P210, N212, G213, W214, I215, V217, I220, T225, L227, N232, G235, T236, T237, V238, S239, G243, Y244, C245, and A246.

41. The ketoreductase according to claim 40 comprising one or more substitutions at position(s) selected from the group consisting of S97, F99, S100, P121, G147, G149, M206, P210, and Y244.

* * * * *

UNITED STATES PATENT AND TRADEMARK OFFICE
CERTIFICATE OF CORRECTION

PATENT NO. : 11,286,466 B2
APPLICATION NO. : 16/740728
DATED : March 29, 2022
INVENTOR(S) : Koepke et al.

It is certified that error appears in the above-identified patent and that said Letters Patent is hereby corrected as shown below:

In the Specification

In Column 9, Line 20, delete "M," and insert -- M1, --, therefor.

In Column 9, Line 21, delete "LA," and insert -- L4, --, therefor.

In Column 9, Line 22, delete "G1, 112," and insert -- G11, I12, --, therefor.

In Column 10, Line 46, delete "Homepage Other" and insert -- Homepage. Other --, therefor.

In Column 12, Line 6, delete "Gin," and insert -- Gln, --, therefor.

In Column 14, Line 24, delete "M1MSSSSPSM," and insert -- M1MTSSSPSM, --, therefor.

In Column 15, Line 15, delete "V34E." and insert -- V34E, --, therefor.

In Column 15, Line 27, delete "A89R." and insert -- A89R, --, therefor.

In Column 19, Line 53, delete "a identity" and insert -- an identity --, therefor.

In Column 36, Line 49, delete "Y244L" and insert -- Y244L. --, therefor.

In Column 53, Lines 53-54, delete "a aldotetrose" and insert -- an aldotetrose --, therefor.

In Column 53, Line 54, delete "a aldohexose" and insert -- an aldohexose --, therefor.

In Column 57, Line 52, delete "enantiomer," and insert -- enantiomer; --, therefor.

In Column 57, Line 60, delete "enantiomers" and insert -- enantiomers. --, therefor.

Signed and Sealed this
Twentieth Day of September, 2022

Katherine Kelly Vidal
*Director of the United States Patent and Trademark Office*

CERTIFICATE OF CORRECTION (continued)
U.S. Pat. No. 11,286,466 B2

In Column 58, Line 1, delete "an diastereomeric" and insert -- a diastereomeric --, therefor.

In Column 59, Line 9, delete "NAD/NADH or NADP/NADPH." and insert -- NAD$^+$/NADH or NADP$^+$/NADPH. --, therefor.

In Column 67, Line 32, delete "NADP" and insert -- NADP$^+$ --, therefor.

In Column 68, Line 29, delete "formula (I)" and insert -- formula (I') --, therefor.

In Column 70, Line 67, delete "formula (I)" and insert -- formula (I') --, therefor.

In Column 72, Line 26, delete "COBE: 3.3)" and insert -- COBE: 3.3). --, therefor.

In the Claims

In Column 351, in Claim 1, Line 12, delete "M26V:" and insert -- M26V; --, therefor.

In Column 351, in Claim 1, Line 46, delete "E200V:" and insert -- E200V; --, therefor.

In Column 351, in Claim 1, Line 58, delete "T236V:" and insert -- T236V; --, therefor.

In Column 361, in Claim 38, Line 15, delete "S25V" and insert -- S25V; --, therefor.

SEQUENCE LISTING

<160> NUMBER OF SEQ ID NOS: 182

<210> SEQ ID NO 1
<211> LENGTH: 246
<212> TYPE: PRT
<213> ORGANISM: Artificial Sequence
<220> FEATURE:
<223> OTHER INFORMATION: Synthetic

<400> SEQUENCE: 1

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
            195                 200                 205

Leu Pro Ile Asn Gly Trp Ile Glu Val Asp Ala Ile Ala Asp Ala Val
210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 2
<211> LENGTH: 741
<212> TYPE: DNA
<213> ORGANISM: Artificial Sequence
<220> FEATURE:
<223> OTHER INFORMATION: Synthetic: encoding SEQ ID NO:1

<400> SEQUENCE: 2
atgacgtcct cctcttctcc ctccttgaac gctctggtca cgggcggcag ccgcggcatt      60
ggcgaggcca tttccatgca gctggccgcc gagggctaca gcgtcacaat tgcgtctcgc     120
gggctcgagc agctcgaggc cgtgaaggca aagctgccca ttgtgaagca gggccagacg     180
caccacgtgt ggcagctcga tctcagtgat gtcgaggccg ccggctcctt caagggtgcg     240
ccgctgccgg ccagcagcta cgacgtgttt gtgagcaatg ccggcatttc tcagttctcg     300
ccgattgcgg agcacgccga cgcggattgg cagaacatgc tgaccgtgaa cctgacggcg     360
ccgattgcgc tcacgaaggc cgtcgtgaag gcaatcagcg acaagccgcg ccagacgcct     420
gcgcacatca tcttcatctc gacgggcctg tcgaagcgcg gcgccccaat ggttggcgtc     480
tacagcgcct cgaaggccgg catcgacggg ttcatgcgct cgctggcccg cgagctcggc     540
ccgaagggca tcaacgtgaa ctgcgtgagc cccggcgtga caaggacgag catggccgag     600

```
ggcatcgacc ccagcatgtt cgaccttcct atcaacgggt ggattgaggt cgacgcgatc    660
gccgacgcgg tcacgtacct cgtgaagtcg aaaaacgtca cgggcacgac cgtttccgtc    720
gacaacggct actgcgccta a                                              741
```

<210> SEQ ID NO 3
<211> LENGTH: 238
<212> TYPE: PRT
<213> ORGANISM: Artificial Sequence
<220> FEATURE:
<223> OTHER INFORMATION: Synthetic: artificial, comparative

<400> SEQUENCE: 3

```
Met Asn Ala Leu Val Thr Gly Gly Ser Arg Gly Ile Gly Glu Ala Val
1               5                   10                  15

Ser Ile Gln Leu Ala Ser Gln Gly Tyr Gly Val Thr Ile Ala Ser Arg
            20                  25                  30

Gly Val Glu Gln Leu Glu Ala Val Lys Ala Lys Leu Pro Val Val Lys
        35                  40                  45

Gln Gly Gln Thr His His Val Trp Gln Leu Asp Leu Ser Asp Val Glu
    50                  55                  60

Ala Ala Gly Ser Phe Lys Gly Ala Pro Leu Pro Ala Ser Ser Tyr Asp
65                  70                  75                  80

Val Phe Val Ser Asn Ala Gly Ile Ala Gln Phe Ser Pro Ile Ala Glu
                85                  90                  95

His Ala Asp Ala Asp Trp Gln Asn Met Leu Thr Val Asn Leu Thr Ala
            100                 105                 110

Pro Ile Ala Leu Thr Lys Ala Val Val Lys Ala Ile Ser Asp Lys Pro
        115                 120                 125

Arg Glu Thr Pro Ala His Ile Ile Phe Ile Ser Thr Gly Leu Ser Lys
    130                 135                 140

Arg Gly Ala Pro Met Val Gly Val Tyr Ser Ala Ser Lys Ala Gly Ile
145                 150                 155                 160

Asp Gly Phe Met Arg Ser Leu Ala Arg Glu Leu Gly Pro Lys Gly Ile
                165                 170                 175

Asn Val Asn Cys Val Ser Pro Gly Val Thr Arg Thr Ala Ile Ser Asp
            180                 185                 190

Gly Val Asp Pro Ser Met Phe Asp Leu Pro Ile Ser Gly Trp Ile Glu
        195                 200                 205

Val Asp Ala Ile Ala Asp Ala Val Thr Tyr Leu Val Lys Ser Lys Asn
    210                 215                 220

Val Thr Gly Ala Ile Leu Val Val Asp Asn Gly Phe Ser Thr
225                 230                 235
```

<210> SEQ ID NO 4
<211> LENGTH: 717
<212> TYPE: DNA
<213> ORGANISM: Artificial Sequence
<220> FEATURE:
<223> OTHER INFORMATION: Synthetic: encoding SEQ ID NO:3

<400> SEQUENCE: 4

```
atgaacgctc tagtgacggg tggcagtcgt ggcattggcg aggccgtttc cattcaattg     60
gcttcgcagg gctacggcgt cacaattgca tctcgcggcg ttgagcagct cgaggccgta    120
aaggcgaagc tgcccgttgt gaagcagggc cagacgcacc acgtgtggca gctcgacttg    180
agcgacgtcg aggcggccgg ctccttcaag ggtgcgcccc tgccggccag cagctacgac    240
```

```
gtgtttgtga gcaatgccgg cattgctcag ttctcgccga ttgcggaaca cgccgacgcg    300
gactggcaaa acatgctgac cgtgaacctg acggcgccga tcgccctcac gaaggcggtc    360
gtgaaggcca tcagcgacaa gccgcgcgag acgccggccc atatcatttt catctcaacg    420
ggcctatcga agcgcggcgc tccgatggtc ggtgtctaca gcgcttcaaa ggccggtatc    480
gacggattca tgcgctcgct ggcccgcgag ctcggcccaa agggcatcaa cgtgaactgc    540 gtcagcccg  gagtgacaag gacggccatt tccgatggtg tggacccag  catgttcgac    600 ctgcctatca gcgggtggat cgaggtcgac gccattgccg acgccgttac gtacctcgtg    660
aagtcgaaga acgtcacggg cgcgatcctc gtagtcgaca acggcttctc gacgtag      717
```

<210> SEQ ID NO 5
<211> LENGTH: 717
<212> TYPE: DNA
<213> ORGANISM: Artificial Sequence
<220> FEATURE:
<223> OTHER INFORMATION: Synthetic: encoding SEQ ID NO:3, codon
      optimized

<400> SEQUENCE: 5

```
atgaatgcgc tggttacggg cggatctcgc ggtattggcg aagctgtgag catccagctg    60
gcatcacagg ggtatggcgt tacgattgcc tctcgtggcg tggaacaact ggaagcggta    120
aaagccaaac ttcccgtagt caaacagggg caaacacacc atgtgtggca actggacttg    180
tcggatgtag aagcggctgg aagcttcaaa ggtgcaccct accagcgag  ttcgtatgac    240 gtgtttgtgt ccaatgctgg gattgcccag ttttcgccga ttgcggaaca tgctgatgca    300
gactggcaga acatgctgac cgtcaatctg accgcaccga ttgcgctcac caaggcagtc    360
gttaaagcca ctccgacaa accacgggaa actcctgctc acatcatctt cattagcacc    420
ggactgtcaa aacgcggtgc accgatggtt ggtgtctact cagccagcaa agccggcatc    480
gatggcttca tgcgctctct ggcccgtgag ttaggcccga aaggcatcaa cgtgaattgc    540
gttagcccgg gtgtcactcg taccgcgatt agcgatggtg tggatccgag tatgtttgat    600
ctccctatca gtggttggat tgaggtagac gcgattgccg atgcggttac ctacttggtg    660
aagtcgaaga acgttacagg tgcgattctt gtggtggata acggctttc  cacgtaa      717
```

<210> SEQ ID NO 6
<211> LENGTH: 246
<212> TYPE: PRT
<213> ORGANISM: Artificial Sequence
<220> FEATURE:
<223> OTHER INFORMATION: Synthetic

<400> SEQUENCE: 6

```
Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95
```

```
Ser Gln Phe Ser Pro Ile Ala Glu His Ala Asp Ala Asp Trp Gln Asn
            100                 105                 110
Met Leu Thr Val Asn Leu Thr Ala Pro Ile Ala Leu Thr Lys Ala Val
        115                 120                 125
Val Lys Ala Ile Ser Asp Lys Pro Arg Gln Thr Pro Ala His Ile Ile
    130                 135                 140
Phe Ile Ser Thr Gly Leu Ser Lys Arg Gly Ala Pro Met Val Gly Val
145                 150                 155                 160
Tyr Ser Ala Ser Lys Ala Gly Ile Asp Gly Phe Met Arg Ser Leu Ala
                165                 170                 175
Arg Glu Leu Gly Pro Lys Gly Ile Asn Val Asn Cys Val Ser Pro Gly
            180                 185                 190
Val Thr Arg Thr Ser Met Ala Glu Gly Ile Asp Pro Ser Met Phe Asp
        195                 200                 205
Leu Pro Ile Asn Gly Trp Ile Glu Val Asp Ala Val Ala Asp Ala Val
    210                 215                 220
Thr Tyr Leu Val Lys Ser Lys Asn Val Thr Gly Thr Thr Val Ser Val
225                 230                 235                 240
Asp Asn Gly Tyr Cys Ala
                245

<210> SEQ ID NO 7
<211> LENGTH: 246
<212> TYPE: PRT
<213> ORGANISM: Artificial Sequence
<220> FEATURE:
<223> OTHER INFORMATION: Synthetic

<400> SEQUENCE: 7

Met Thr Ser Ser Ser Pro Ser Leu Asn Ala Leu Val Thr Gly Gly
1               5                   10                  15
Ser Arg Gly Ile Gly Glu Ala Ile Ser Met Gln Leu Ala Ala Glu Gly
                20                  25                  30
Tyr Ser Val Thr Ile Ala Ser Arg Gly Leu Glu Gln Leu Glu Ala Val
            35                  40                  45
Lys Ala Lys Leu Pro Ile Val Lys Gln Gly Gln Thr His His Val Trp
    50                  55                  60
Gln Leu Asp Leu Ser Asp Val Glu Ala Ala Gly Ser Phe Lys Gly Ala
65                  70                  75                  80
Pro Leu Pro Ala Ser Ser Tyr Asp Val Phe Val Ser Asn Ala Gly Ile
                85                  90                  95
Ser Gln Phe Ser Pro Ile Ala Glu His Ala Asp Ala Asp Trp Gln Asn
            100                 105                 110
Met Leu Thr Val Asn Leu Thr Ala Pro Ile Ala Leu Thr Lys Ala Val
        115                 120                 125
Val Lys Ala Ile Ser Asp Lys Pro Arg Gln Thr Pro Ala His Ile Ile
    130                 135                 140
Phe Ile Ser Thr Gly Leu Ser Lys Arg Gly Ala Pro Met Val Gly Val
145                 150                 155                 160
Tyr Ser Ala Ser Lys Ala Gly Ile Asp Gly Phe Met Arg Ser Leu Ala
                165                 170                 175
Arg Glu Leu Gly Pro Lys Gly Ile Asn Val Asn Cys Val Ser Pro Gly
            180                 185                 190
Val Thr Arg Thr Ser Met Ala Glu Gly Ile Asp Pro Ser Met Phe Asp
        195                 200                 205
```

Leu Pro Ile Asn Gly Trp Ile Glu Val Asp Ala Ile Ala Asp Ala Val
            210                 215                 220

Thr Tyr Leu Val Lys Ser Lys Asn Val Thr Gly Thr Thr Val Ser Val
225                 230                 235                 240

Asp Asn Gly Phe Cys Ala
                245

<210> SEQ ID NO 8
<211> LENGTH: 246
<212> TYPE: PRT
<213> ORGANISM: Artificial Sequence
<220> FEATURE:
<223> OTHER INFORMATION: Synthetic

<400> SEQUENCE: 8

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
                20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Leu Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 9
<211> LENGTH: 246
<212> TYPE: PRT
<213> ORGANISM: Artificial Sequence
<220> FEATURE:
<223> OTHER INFORMATION: Synthetic

<400> SEQUENCE: 9

Met Thr Ser Ser Ser Pro Ser Leu Asn Ala Leu Val Thr Gly Gly
1               5                   10                  15

```
Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
 50                  55                  60

Gln Leu Asp Leu Ser Asp Val Glu Ala Ala Gly Ser Phe Lys Gly Ala
 65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe His
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 10
<211> LENGTH: 246
<212> TYPE: PRT
<213> ORGANISM: Artificial Sequence
<220> FEATURE:
<223> OTHER INFORMATION: Synthetic

<400> SEQUENCE: 10

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
 50                  55                  60

Gln Leu Asp Leu Ser Asp Val Glu Ala Ala Gly Ser Phe Lys Gly Ala
 65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
            115                 120                 125
```

```
Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Asp Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 11
<211> LENGTH: 246
<212> TYPE: PRT
<213> ORGANISM: Artificial Sequence
<220> FEATURE:
<223> OTHER INFORMATION: Synthetic

<400> SEQUENCE: 11

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
                20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Cys
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240
```

Asp Asn Gly Tyr Cys Ala
                245

<210> SEQ ID NO 12
<211> LENGTH: 246
<212> TYPE: PRT
<213> ORGANISM: Artificial Sequence
<220> FEATURE:
<223> OTHER INFORMATION: Synthetic

<400> SEQUENCE: 12

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
        50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
        130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Val Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 13
<211> LENGTH: 246
<212> TYPE: PRT
<213> ORGANISM: Artificial Sequence
<220> FEATURE:
<223> OTHER INFORMATION: Synthetic

<400> SEQUENCE: 13

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val

```
                35                  40                  45
Lys Ala Lys Leu Pro Ile Val Lys Gln Gly Gln Thr His His Val Trp
 50                  55                  60

Gln Leu Asp Leu Ser Asp Val Glu Ala Ala Gly Ser Phe Lys Gly Ala
 65                  70                  75                  80

Pro Leu Pro Ala Ser Ser Tyr Asp Val Phe Val Ser Asn Ala Gly Ile
                 85                  90                  95

Ser Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
                115                 120                 125

Val Lys Ala Ile Ser Asp Lys Pro Arg Gln Thr Pro Ala His Ile Ile
                130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
                180                 185                 190

Val Thr Arg Thr Ser Met Cys Glu Gly Ile Asp Pro Ser Met Phe Asp
                195                 200                 205

Leu Pro Ile Asn Gly Trp Ile Glu Val Asp Ala Ile Ala Asp Ala Val
                210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 14
<211> LENGTH: 246
<212> TYPE: PRT
<213> ORGANISM: Artificial Sequence
<220> FEATURE:
<223> OTHER INFORMATION: Synthetic

<400> SEQUENCE: 14

Met Thr Ser Ser Ser Pro Ser Leu Asn Ala Leu Val Thr Gly Gly
 1               5                  10                  15

Ser Arg Gly Ile Gly Glu Ala Ile Ser Met Gln Leu Ala Ala Glu Gly
                 20                  25                  30

Tyr Ser Val Thr Ile Ala Ser Arg Gly Leu Glu Gln Leu Glu Ala Val
                 35                  40                  45

Lys Ala Lys Leu Pro Ile Val Lys Gln Gly Gln Thr His His Val Trp
 50                  55                  60

Gln Leu Asp Leu Ser Asp Val Glu Ala Ala Gly Ser Phe Lys Gly Ala
 65                  70                  75                  80

Pro Leu Pro Ala Ser Ser Tyr Asp Val Phe Val Ser Asn Ala Gly Ile
                 85                  90                  95

Ser Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
                115                 120                 125

Val Lys Ala Ile Ser Asp Lys Pro Arg Gln Thr Pro Ala His Ile Ile
                130                 135                 140

Phe Ile Ser Thr Gly Leu Ser Lys Arg Gly Ala Pro Met Val Gly Val
```

```
            145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
                180                 185                 190

Val Thr Arg Thr Ser Met Ala Glu Gly Ile Asp Pro Ser Met Phe Asp
            195                 200                 205

Leu Pro Ile Asn Gly Trp Ile Glu Asn Asp Ala Ile Ala Asp Ala Val
        210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 15
<211> LENGTH: 246
<212> TYPE: PRT
<213> ORGANISM: Artificial Sequence
<220> FEATURE:
<223> OTHER INFORMATION: Synthetic

<400> SEQUENCE: 15

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
                20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
        50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
        130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
                180                 185                 190

Val Thr Arg Thr Ser Met Ala Pro Gly Ile Asp Pro Ser Met Phe Asp
            195                 200                 205

Leu Pro Ile Asn Gly Trp Ile Glu Val Asp Ala Ile Ala Asp Ala Val
        210                 215                 220

Thr Tyr Leu Val Lys Ser Lys Asn Val Thr Gly Thr Thr Val Ser Val
225                 230                 235                 240

Asp Asn Gly Tyr Cys Ala
                245
```

```
<210> SEQ ID NO 16
<211> LENGTH: 246
<212> TYPE: PRT
<213> ORGANISM: Artificial Sequence
<220> FEATURE:
<223> OTHER INFORMATION: Synthetic

<400> SEQUENCE: 16

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
                20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Val Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 17
<211> LENGTH: 246
<212> TYPE: PRT
<213> ORGANISM: Artificial Sequence
<220> FEATURE:
<223> OTHER INFORMATION: Synthetic

<400> SEQUENCE: 17

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
                20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
50                  55                  60
```

```
Gln Leu Asp Leu Ser Asp Val Glu Ala Ala Gly Ser Phe Lys Gly Ala
 65                  70                  75                  80

Pro Leu Pro Ala Ser Ser Tyr Asp Val Phe Val Ser Asn Ala Gly Ile
                 85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Thr Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 18
<211> LENGTH: 246
<212> TYPE: PRT
<213> ORGANISM: Artificial Sequence
<220> FEATURE:
<223> OTHER INFORMATION: Synthetic

<400> SEQUENCE: 18

Met Thr Ser Ser Ser Pro Ser Leu Asn Ala Leu Val Thr Gly Gly
 1               5                  10                  15

Ser Arg Gly Ile Gly Glu Ala Ile Ser Met Gln Leu Ala Ala Glu Gly
                 20                  25                  30

Tyr Ser Val Thr Ile Ala Ser Arg Gly Leu Glu Gln Leu Glu Ala Val
             35                  40                  45

Lys Ala Lys Leu Pro Ile Val Lys Gln Gly Gln Thr His His Val Trp
 50                  55                  60

Gln Leu Asp Leu Ser Asp Val Glu Ala Ala Gly Ser Phe Lys Gly Ala
 65                  70                  75                  80

Pro Leu Pro Ala Ser Ser Tyr Asp Val Phe Val Ser Asn Ala Gly Ile
                 85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175
```

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Asp Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 19
<211> LENGTH: 246
<212> TYPE: PRT
<213> ORGANISM: Artificial Sequence
<220> FEATURE:
<223> OTHER INFORMATION: Synthetic

<400> SEQUENCE: 19

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Gly Phe Asp
        195                 200                 205

Leu Pro Ile Asn Gly Trp Ile Glu Val Asp Ala Ile Ala Asp Ala Val
    210                 215                 220

Met Tyr Leu Val Lys Ser Lys Asn Val Thr Gly Thr Thr Val Ser Val
225                 230                 235                 240

Asp Asn Gly Tyr Cys Ala
                245

<210> SEQ ID NO 20
<211> LENGTH: 246
<212> TYPE: PRT
<213> ORGANISM: Artificial Sequence
<220> FEATURE:

<223> OTHER INFORMATION: Synthetic

<400> SEQUENCE: 20

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Ala Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 21
<211> LENGTH: 246
<212> TYPE: PRT
<213> ORGANISM: Artificial Sequence
<220> FEATURE:
<223> OTHER INFORMATION: Synthetic

<400> SEQUENCE: 21

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Val Gly Ile Asp Pro Ser Met Phe Asp
            195                 200                 205

Leu Pro Ile Asn Gly Trp Ile Glu Val Asp Ala Ile Ala Asp Ala Val
        210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 22
<211> LENGTH: 246
<212> TYPE: PRT
<213> ORGANISM: Artificial Sequence
<220> FEATURE:
<223> OTHER INFORMATION: Synthetic

<400> SEQUENCE: 22

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Ala Gly Ile Asp Pro Ser Met Phe Asp
            195                 200                 205

```
Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245
```

<210> SEQ ID NO 23
<211> LENGTH: 246
<212> TYPE: PRT
<213> ORGANISM: Artificial Sequence
<220> FEATURE:
<223> OTHER INFORMATION: Synthetic

<400> SEQUENCE: 23

```
Met Thr Ser Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Pro Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245
```

<210> SEQ ID NO 24
<211> LENGTH: 246
<212> TYPE: PRT
<213> ORGANISM: Artificial Sequence
<220> FEATURE:
<223> OTHER INFORMATION: Synthetic

<400> SEQUENCE: 24

```
Met Thr Ser Ser Ser Ser Pro Ser Leu Asn Ala Leu Val Thr Gly Gly
```

```
1               5                   10                  15
Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
 50                 55                  60

Gln Leu Asp Leu Ser Asp Val Glu Ala Ala Gly Ser Phe Lys Gly Ala
 65                 70                  75                  80

Pro Leu Pro Ala Ser Ser Tyr Asp Val Phe Val Ser Asn Ala Gly Ile
            85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
 130                135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
            165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
            195                 200                 205

Leu Pro Ile Asn Gly Trp Ile Glu Val Asp Ala Ile Ala Asp Ala Val
            210                 215                 220

Ile Tyr Leu Val Lys Ser Lys Asn Val Thr Gly Thr Thr Val Ser Val
225                 230                 235                 240

Asp Asn Gly Tyr Cys Ala
            245
```

<210> SEQ ID NO 25
<211> LENGTH: 246
<212> TYPE: PRT
<213> ORGANISM: Artificial Sequence
<220> FEATURE:
<223> OTHER INFORMATION: Synthetic

<400> SEQUENCE: 25

```
Met Thr Ser Ser Ser Pro Ser Leu Asn Ala Leu Val Thr Gly Gly
 1              5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
 50                 55                  60

Gln Leu Asp Leu Ser Asp Val Glu Ala Ala Gly Ser Phe Lys Gly Ala
 65                 70                  75                  80

Pro Leu Pro Ala Ser Ser Tyr Asp Val Phe Val Ser Asn Ala Gly Ile
            85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
```

```
            115                 120                 125
Val Lys Ala Ile Ser Asp Lys Pro Arg Gln Thr Pro Ala His Ile Ile
        130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Val Val Lys Ser Lys Asn Val Thr Gly Thr Thr Val Ser Val
225                 230                 235                 240

Asp Asn Gly Tyr Cys Ala
                245

<210> SEQ ID NO 26
<211> LENGTH: 246
<212> TYPE: PRT
<213> ORGANISM: Artificial Sequence
<220> FEATURE:
<223> OTHER INFORMATION: Synthetic

<400> SEQUENCE: 26

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Tyr Val Thr Gly Thr Thr Val Ser Val
```

```
225                 230                 235                 240

Asp Asn Gly Tyr Cys Ala
                245

<210> SEQ ID NO 27
<211> LENGTH: 246
<212> TYPE: PRT
<213> ORGANISM: Artificial Sequence
<220> FEATURE:
<223> OTHER INFORMATION: Synthetic

<400> SEQUENCE: 27

Met Thr Ser Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Phe Val Thr Gly Thr Thr Val Ser Val
225                 230                 235                 240

Asp Asn Gly Tyr Cys Ala
                245

<210> SEQ ID NO 28
<211> LENGTH: 246
<212> TYPE: PRT
<213> ORGANISM: Artificial Sequence
<220> FEATURE:
<223> OTHER INFORMATION: Synthetic

<400> SEQUENCE: 28

Met Thr Ser Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30
```

-continued

```
Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
 50                  55                  60

Gln Leu Asp Leu Ser Asp Val Glu Ala Ala Gly Ser Phe Lys Gly Ala
 65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
                180                 185                 190

Val Thr Arg Thr Ser Met Ala Glu Gly Ile Asp Pro Ser Met Phe Asp
            195                 200                 205

Leu Pro Ile Asn Gly Trp Ile Glu Val Asp Ala Ile Ala Asp Ala Val
        210                 215                 220

Thr Tyr Leu Val Lys Ser Lys Asn Val Thr Gly Ser Thr Val Ser Val
225                 230                 235                 240

Asp Asn Gly Tyr Cys Ala
                245

<210> SEQ ID NO 29
<211> LENGTH: 246
<212> TYPE: PRT
<213> ORGANISM: Artificial Sequence
<220> FEATURE:
<223> OTHER INFORMATION: Synthetic

<400> SEQUENCE: 29

Met Thr Ser Ser Ser Pro Ser Leu Asn Ala Leu Val Thr Gly Gly
 1               5                  10                  15

Ser Arg Gly Ile Gly Glu Ala Ile Ser Met Gln Leu Ala Ala Glu Gly
                20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
 50                  55                  60

Gln Leu Asp Leu Ser Asp Val Glu Ala Ala Gly Ser Phe Lys Gly Ala
 65                  70                  75                  80

Pro Leu Pro Ala Ser Ser Tyr Asp Val Phe Val Ser Asn Ala Gly Ile
                85                  90                  95

Ser Gln Phe Glu Pro Ile Ala Glu His Ala Asp Ala Asp Trp Gln Thr
                100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
130                 135                 140
```

```
Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
            195                 200                 205

Leu Pro Ile Asn Gly Trp Ile Glu Val Asp Ala Ile Ala Asp Ala Val
            210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 30
<211> LENGTH: 246
<212> TYPE: PRT
<213> ORGANISM: Artificial Sequence
<220> FEATURE:
<223> OTHER INFORMATION: Synthetic

<400> SEQUENCE: 30

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
                20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Gln Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
            130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
            195                 200                 205

Leu Pro Ile Asn Gly Trp Ile Glu Val Asp Ala Ile Ala Asp Ala Val
            210                 215                 220

Thr Tyr Leu Val Lys Ser Lys Asn Val Thr Gly Thr Thr Val Ser Val
225                 230                 235                 240

Asp Asn Gly Tyr Cys Ala
                245
```

<210> SEQ ID NO 31
<211> LENGTH: 246
<212> TYPE: PRT
<213> ORGANISM: Artificial Sequence
<220> FEATURE:
<223> OTHER INFORMATION: Synthetic

<400> SEQUENCE: 31

```
Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
                35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Gly Trp Gln Asn
                100                 105                 110

Met Leu Thr Val Asn Leu Thr Ala Pro Ile Ala Leu Thr Lys Ala Val
                115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
                180                 185                 190

Val Thr Arg Thr Ser Met Ala Glu Gly Ile Asp Pro Ser Met Phe Asp
            195                 200                 205

Leu Pro Ile Asn Gly Trp Ile Glu Val Asp Ala Ile Ala Asp Ala Val
        210                 215                 220

Thr Tyr Leu Val Lys Ser Lys Asn Val Thr Gly Thr Thr Val Ser Val
225                 230                 235                 240

Asp Asn Gly Tyr Cys Ala
                245
```

<210> SEQ ID NO 32
<211> LENGTH: 246
<212> TYPE: PRT
<213> ORGANISM: Artificial Sequence
<220> FEATURE:
<223> OTHER INFORMATION: Synthetic

<400> SEQUENCE: 32

```
Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
                35                  40                  45

Lys Ala Lys Leu Pro Ile Val Lys Gln Gly Gln Thr His His Val Trp
    50                  55                  60
```

```
Gln Leu Asp Leu Ser Asp Val Glu Ala Ala Gly Ser Phe Lys Gly Ala
 65                  70                  75                  80

Pro Leu Pro Ala Ser Ser Tyr Asp Val Phe Val Ser Asn Ala Gly Ile
                 85                  90                  95

Ser Gln Phe Arg Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 33
<211> LENGTH: 246
<212> TYPE: PRT
<213> ORGANISM: Artificial Sequence
<220> FEATURE:
<223> OTHER INFORMATION: Synthetic

<400> SEQUENCE: 33

Met Thr Ser Ser Ser Pro Ser Leu Asn Ala Leu Val Thr Gly Gly
 1               5                  10                  15

Ser Arg Gly Ile Gly Glu Ala Ile Ser Met Gln Leu Ala Ala Glu Gly
                 20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
 65                  70                  75                  80

Pro Leu Pro Ala Ser Ser Tyr Asp Val Phe Val Ser Asn Ala Gly Ile
                 85                  90                  95

Ser Gln Phe Ser Phe Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175
```

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
            195                 200                 205

Leu Pro Ile Asn Gly Trp Ile Glu Val Asp Ala Ile Ala Asp Ala Val
            210                 215                 220

Thr Tyr Leu Val Lys Ser Lys Asn Val Thr Gly Thr Thr Val Ser Val
225                 230                 235                 240

Asp Asn Gly Tyr Cys Ala
            245

<210> SEQ ID NO 34
<211> LENGTH: 246
<212> TYPE: PRT
<213> ORGANISM: Artificial Sequence
<220> FEATURE:
<223> OTHER INFORMATION: Synthetic

<400> SEQUENCE: 34

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
            85                  90                  95

Ser Gln Phe Ser His Ile Ala Glu His Ala Asp Ala Asp Trp Gln Asn
            100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
            130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
            165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
            195                 200                 205

Leu Pro Ile Asn Gly Trp Ile Glu Val Asp Ala Ile Ala Asp Ala Val
            210                 215                 220

Thr Tyr Leu Val Lys Ser Lys Asn Val Thr Gly Thr Thr Val Ser Val
225                 230                 235                 240

Asp Asn Gly Tyr Cys Ala
            245

<210> SEQ ID NO 35
<211> LENGTH: 246
<212> TYPE: PRT
<213> ORGANISM: Artificial Sequence
<220> FEATURE:
<223> OTHER INFORMATION: Synthetic

<400> SEQUENCE: 35

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
                35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Trp Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 36
<211> LENGTH: 246
<212> TYPE: PRT
<213> ORGANISM: Artificial Sequence
<220> FEATURE:
<223> OTHER INFORMATION: Synthetic

<400> SEQUENCE: 36

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
                35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile

```
                    85                  90                  95
Ser Gln Arg Ser Pro Ile Ala Glu His Ala Asp Ala Asp Trp Gln Asn
                100                 105                 110
Met Leu Thr Val Asn Leu Thr Ala Pro Ile Ala Leu Thr Lys Ala Val
                115                 120                 125
Val Lys Ala Ile Ser Asp Lys Pro Arg Gln Thr Pro Ala His Ile Ile
            130                 135                 140
Phe Ile Ser Thr Gly Leu Ser Lys Arg Gly Ala Pro Met Val Gly Val
145                 150                 155                 160
Tyr Ser Ala Ser Lys Ala Gly Ile Asp Gly Phe Met Arg Ser Leu Ala
                165                 170                 175
Arg Glu Leu Gly Pro Lys Gly Ile Asn Val Asn Cys Val Ser Pro Gly
            180                 185                 190
Val Thr Arg Thr Ser Met Ala Glu Gly Ile Asp Pro Ser Met Phe Asp
        195                 200                 205
Leu Pro Ile Asn Gly Trp Ile Glu Val Asp Ala Ile Ala Asp Ala Val
    210                 215                 220
Thr Tyr Leu Val Lys Ser Lys Asn Val Thr Gly Thr Thr Val Ser Val
225                 230                 235                 240
Asp Asn Gly Tyr Cys Ala
                245

<210> SEQ ID NO 37
<211> LENGTH: 246
<212> TYPE: PRT
<213> ORGANISM: Artificial Sequence
<220> FEATURE:
<223> OTHER INFORMATION: Synthetic

<400> SEQUENCE: 37

Met Thr Ser Ser Ser Pro Ser Leu Asn Ala Leu Val Thr Gly Gly
1               5                   10                  15
Ser Arg Gly Ile Gly Glu Ala Ile Ser Met Gln Leu Ala Ala Glu Gly
                20                  25                  30
Tyr Ser Val Thr Ile Ala Ser Arg Gly Leu Glu Gln Leu Glu Ala Val
            35                  40                  45
Lys Ala Lys Leu Pro Ile Val Lys Gln Gly Gln Thr His His Val Trp
        50                  55                  60
Gln Leu Asp Leu Ser Asp Val Glu Ala Ala Gly Ser Phe Lys Gly Ala
65                  70                  75                  80
Pro Leu Pro Ala Ser Ser Tyr Asp Val Phe Val Ser Asn Ala Gly Ile
                85                  90                  95
Ser Gln Phe Ser Pro Ile Ala Glu His Ala Asp Ala Asp Trp Gln Asn
                100                 105                 110
Met Leu Thr Val Asn Leu Thr Ala Pro Ile Ala Leu Thr Lys Ala Val
                115                 120                 125
Val Lys Ala Val Ser Asp Lys Pro Arg Gln Thr Pro Ala His Ile Ile
            130                 135                 140
Phe Ile Ser Thr Gly Leu Ser Lys Arg Gly Ala Pro Met Val Gly Val
145                 150                 155                 160
Tyr Ser Ala Ser Lys Ala Gly Ile Asp Gly Phe Met Arg Ser Leu Ala
                165                 170                 175
Arg Glu Leu Gly Pro Lys Gly Ile Asn Val Asn Cys Val Ser Pro Gly
            180                 185                 190
Val Thr Arg Thr Ser Met Ala Glu Gly Ile Asp Pro Ser Met Phe Asp
```

```
                    195                 200                 205
Leu Pro Ile Asn Gly Trp Ile Glu Val Asp Ala Ile Ala Asp Ala Val
    210                 215                 220
Thr Tyr Leu Val Lys Ser Lys Asn Val Thr Gly Thr Thr Val Ser Val
225                 230                 235                 240
Asp Asn Gly Tyr Cys Ala
                245

<210> SEQ ID NO 38
<211> LENGTH: 246
<212> TYPE: PRT
<213> ORGANISM: Artificial Sequence
<220> FEATURE:
<223> OTHER INFORMATION: Synthetic

<400> SEQUENCE: 38

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
                20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
    130                 135                 140

Phe Ile Ser Thr Cys Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
    195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 39
<211> LENGTH: 246
<212> TYPE: PRT
<213> ORGANISM: Artificial Sequence
<220> FEATURE:
<223> OTHER INFORMATION: Synthetic

<400> SEQUENCE: 39
```

```
Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
 50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
130                 135                 140

Phe Ile Ser Thr Val Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
210                 215                 220

Thr Tyr Leu Val Lys Ser Lys Asn Val Thr Gly Thr Thr Val Ser Val
225                 230                 235                 240

Asp Asn Gly Tyr Cys Ala
                245
```

<210> SEQ ID NO 40
<211> LENGTH: 246
<212> TYPE: PRT
<213> ORGANISM: Artificial Sequence
<220> FEATURE:
<223> OTHER INFORMATION: Synthetic

<400> SEQUENCE: 40

```
Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
 50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110
```

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
    130                 135                 140

Phe Ile Ser Thr Ser Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
    195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 41
<211> LENGTH: 246
<212> TYPE: PRT
<213> ORGANISM: Artificial Sequence
<220> FEATURE:
<223> OTHER INFORMATION: Synthetic

<400> SEQUENCE: 41

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
            115                 120                 125

Val Lys Ala Trp Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
    195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Val Ser Val
225                 230                 235                 240

Asp Asn Gly Tyr Cys Ala
            245

<210> SEQ ID NO 42
<211> LENGTH: 246
<212> TYPE: PRT
<213> ORGANISM: Artificial Sequence
<220> FEATURE:
<223> OTHER INFORMATION: Synthetic

<400> SEQUENCE: 42

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Val Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
            195                 200                 205

Leu Pro Ile Asn Gly Trp Ile Glu Val Asp Ala Ile Ala Asp Ala Val
210                 215                 220

Thr Tyr Leu Val Lys Ser Lys Asn Val Thr Gly Thr Val Ser Val
225                 230                 235                 240

Asp Asn Gly Tyr Cys Ala
            245

<210> SEQ ID NO 43
<211> LENGTH: 246
<212> TYPE: PRT
<213> ORGANISM: Artificial Sequence
<220> FEATURE:
<223> OTHER INFORMATION: Synthetic

<400> SEQUENCE: 43

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
 50                  55                  60

Gln Leu Asp Leu Ser Asp Val Glu Ala Ala Gly Ser Phe Lys Gly Ala
 65                  70                  75                  80

Pro Leu Pro Ala Ser Ser Tyr Asp Val Phe Val Ser Asn Ala Gly Ile
                 85                  90                  95

Ser Gln Phe Cys Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
            195                 200                 205

Leu Pro Ile Asn Gly Trp Ile Glu Val Asp Ala Ile Ala Asp Ala Val
        210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 44
<211> LENGTH: 246
<212> TYPE: PRT
<213> ORGANISM: Artificial Sequence
<220> FEATURE:
<223> OTHER INFORMATION: Synthetic

<400> SEQUENCE: 44

Met Thr Ser Ser Ser Pro Ser Leu Asn Ala Leu Val Thr Gly Gly
 1               5                  10                  15

Ser Arg Gly Ile Gly Glu Ala Ile Ser Met Gln Leu Ala Ala Glu Gly
                 20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
 50                  55                  60

Gln Leu Asp Leu Ser Asp Val Glu Ala Ala Gly Ser Phe Lys Gly Ala
 65                  70                  75                  80

Pro Leu Pro Ala Ser Ser Tyr Asp Val Phe Val Ser Asn Ala Gly Ile
                 85                  90                  95

Ser Gln Phe Ser Pro Ile Ala Glu His Ala Asp Ala Arg Trp Gln Asn
                100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
            245

<210> SEQ ID NO 45
<211> LENGTH: 246
<212> TYPE: PRT
<213> ORGANISM: Artificial Sequence
<220> FEATURE:
<223> OTHER INFORMATION: Synthetic

<400> SEQUENCE: 45

Met Thr Ser Ser Ser Pro Ser Gly Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
            245

<210> SEQ ID NO 46
<211> LENGTH: 246
<212> TYPE: PRT
<213> ORGANISM: Artificial Sequence
<220> FEATURE:
<223> OTHER INFORMATION: Synthetic

<400> SEQUENCE: 46

```
Met Thr Ser Ser Ser Pro Ser Met Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245
```

<210> SEQ ID NO 47
<211> LENGTH: 246
<212> TYPE: PRT
<213> ORGANISM: Artificial Sequence
<220> FEATURE:
<223> OTHER INFORMATION: Synthetic

<400> SEQUENCE: 47

```
Met Thr Ser Ser Ser Pro Ser Leu Gly Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
```

```
            50                  55                  60
Gln Leu Asp Leu Ser Asp Val Glu Ala Ala Gly Ser Phe Lys Gly Ala
 65                  70                  75                  80

Pro Leu Pro Ala Ser Ser Tyr Asp Val Phe Val Ser Asn Ala Gly Ile
                 85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245
```

<210> SEQ ID NO 48
<211> LENGTH: 246
<212> TYPE: PRT
<213> ORGANISM: Artificial Sequence
<220> FEATURE:
<223> OTHER INFORMATION: Synthetic

<400> SEQUENCE: 48

```
Met Thr Ser Ser Ser Pro Ser Leu Asn Ala Leu Val Thr Gly Cys
 1               5                  10                  15

Ser Arg Gly Ile Gly Glu Ala Ile Ser Met Gln Leu Ala Ala Glu Gly
                20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
 50                  55                  60

Gln Leu Asp Leu Ser Asp Val Glu Ala Ala Gly Ser Phe Lys Gly Ala
 65                  70                  75                  80

Pro Leu Pro Ala Ser Ser Tyr Asp Val Phe Val Ser Asn Ala Gly Ile
                 85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
```

```
                165                 170                 175
Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 49
<211> LENGTH: 246
<212> TYPE: PRT
<213> ORGANISM: Artificial Sequence
<220> FEATURE:
<223> OTHER INFORMATION: Synthetic

<400> SEQUENCE: 49

Met Thr Ser Ser Ser Pro Ser Arg Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 50
<211> LENGTH: 246
<212> TYPE: PRT
```

-continued

<213> ORGANISM: Artificial Sequence
<220> FEATURE:
<223> OTHER INFORMATION: Synthetic

<400> SEQUENCE: 50

```
Met Thr Ser Ser Ser Pro Ser Lys Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
        210                 215                 220

Thr Tyr Leu Val Lys Ser Lys Asn Val Thr Gly Thr Thr Val Ser Val
225                 230                 235                 240

Asp Asn Gly Tyr Cys Ala
                245
```

<210> SEQ ID NO 51
<211> LENGTH: 246
<212> TYPE: PRT
<213> ORGANISM: Artificial Sequence
<220> FEATURE:
<223> OTHER INFORMATION: Synthetic

<400> SEQUENCE: 51

```
Met Thr Ser Ser Ser Pro Ser Gln Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Ser Phe Lys Gly Ala
65                  70                  75                  80
```

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
        130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
            195                 200                 205

Leu Pro Ile Asn Gly Trp Ile Glu Val Asp Ala Ile Ala Asp Ala Val
        210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 52
<211> LENGTH: 246
<212> TYPE: PRT
<213> ORGANISM: Artificial Sequence
<220> FEATURE:
<223> OTHER INFORMATION: Synthetic

<400> SEQUENCE: 52

Met Thr Ser Ser Ser Pro Ser Leu Asn Ala Leu Val Thr Gly Gly
1               5                   10                  15

Ser Arg Gly Ile Gly Glu Ala Ile Ala Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
        130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

```
Val Thr Arg Thr Ser Met Ala Glu Gly Ile Asp Pro Ser Met Phe Asp
            195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 53
<211> LENGTH: 246
<212> TYPE: PRT
<213> ORGANISM: Artificial Sequence
<220> FEATURE:
<223> OTHER INFORMATION: Synthetic

<400> SEQUENCE: 53

Met Thr Ser Ser Ser Pro Ser Leu Asn Ala Leu Val Thr Gly Gly
1               5                   10                  15

Ser Arg Gly Ile Gly Lys Ala Ile Ser Met Gln Leu Ala Ala Glu Gly
                20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
 50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 54
<211> LENGTH: 246
<212> TYPE: PRT
<213> ORGANISM: Artificial Sequence
<220> FEATURE:
<223> OTHER INFORMATION: Synthetic

<400> SEQUENCE: 54
```

-continued

```
Met Thr Ser Ser Ser Pro Ser Leu Asn Ala Leu Val Thr Gly Gly
1               5                   10                  15

Ser Arg Gly Ile Gly Glu Ala Ile Ser Arg Gln Leu Ala Ala Glu Gly
            20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
            195                 200                 205

Leu Pro Ile Asn Gly Trp Ile Glu Val Asp Ala Ile Ala Asp Ala Val
            210                 215                 220

Thr Tyr Leu Val Lys Ser Lys Asn Val Thr Gly Thr Thr Val Ser Val
225                 230                 235                 240

Asp Asn Gly Tyr Cys Ala
                245
```

```
<210> SEQ ID NO 55
<211> LENGTH: 246
<212> TYPE: PRT
<213> ORGANISM: Artificial Sequence
<220> FEATURE:
<223> OTHER INFORMATION: Synthetic

<400> SEQUENCE: 55
```

```
Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Arg Glu Gly
            20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110
```

```
Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
        130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 56
<211> LENGTH: 246
<212> TYPE: PRT
<213> ORGANISM: Artificial Sequence
<220> FEATURE:
<223> OTHER INFORMATION: Synthetic

<400> SEQUENCE: 56

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Asn Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
210                 215                 220
```

```
Thr Tyr Leu Val Lys Ser Lys Asn Val Thr Gly Thr Thr Val Ser Val
225                 230                 235                 240

Asp Asn Gly Tyr Cys Ala
            245

<210> SEQ ID NO 57
<211> LENGTH: 246
<212> TYPE: PRT
<213> ORGANISM: Artificial Sequence
<220> FEATURE:
<223> OTHER INFORMATION: Synthetic

<400> SEQUENCE: 57

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Met Ser Arg Gly Leu Glu Gln Leu Glu Ala Val
        35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
            245

<210> SEQ ID NO 58
<211> LENGTH: 246
<212> TYPE: PRT
<213> ORGANISM: Artificial Sequence
<220> FEATURE:
<223> OTHER INFORMATION: Synthetic

<400> SEQUENCE: 58

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
```

```
                20                  25                  30

Tyr Ser Val Thr Ile Ala Gly Arg Gly Leu Glu Gln Leu Glu Ala Val
            35                  40                  45

Lys Ala Lys Leu Pro Ile Val Lys Gln Gly Gln Thr His His Val Trp
        50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 59
<211> LENGTH: 246
<212> TYPE: PRT
<213> ORGANISM: Artificial Sequence
<220> FEATURE:
<223> OTHER INFORMATION: Synthetic

<400> SEQUENCE: 59

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Tyr Glu Gln Leu Glu Ala Val
        35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
```

```
            130                 135                 140
Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
                180                 185                 190

Val Thr Arg Thr Ser Met Ala Glu Gly Ile Asp Pro Ser Met Phe Asp
            195                 200                 205

Leu Pro Ile Asn Gly Trp Ile Glu Val Asp Ala Ile Ala Asp Ala Val
            210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 60
<211> LENGTH: 246
<212> TYPE: PRT
<213> ORGANISM: Artificial Sequence
<220> FEATURE:
<223> OTHER INFORMATION: Synthetic

<400> SEQUENCE: 60

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
                20                  25                  30

Tyr Ser Val Thr Ile Ala Ala Arg Gly Leu Glu Gln Leu Glu Ala Val
                35                  40                  45

Lys Ala Lys Leu Pro Ile Val Lys Gln Gly Gln Thr His His Val Trp
            50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
                180                 185                 190

Val Thr Arg Thr Ser Met Ala Glu Gly Ile Asp Pro Ser Met Phe Asp
            195                 200                 205

Leu Pro Ile Asn Gly Trp Ile Glu Val Asp Ala Ile Ala Asp Ala Val
            210                 215                 220

Thr Tyr Leu Val Lys Ser Lys Asn Val Thr Gly Thr Thr Val Ser Val
225                 230                 235                 240

Asp Asn Gly Tyr Cys Ala
```

-continued

```
<210> SEQ ID NO 61
<211> LENGTH: 246
<212> TYPE: PRT
<213> ORGANISM: Artificial Sequence
<220> FEATURE:
<223> OTHER INFORMATION: Synthetic

<400> SEQUENCE: 61

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
            35                  40                  45

Lys Ala Lys Leu Pro Arg Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
            195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 62
<211> LENGTH: 246
<212> TYPE: PRT
<213> ORGANISM: Artificial Sequence
<220> FEATURE:
<223> OTHER INFORMATION: Synthetic

<400> SEQUENCE: 62

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
            35                  40                  45
```

```
Lys Ala Lys Leu Pro Val Val Lys Gln Gly Gln Thr His His Val Trp
 50                  55                  60

Gln Leu Asp Leu Ser Asp Val Glu Ala Ala Gly Ser Phe Lys Gly Ala
 65                  70                  75                  80

Pro Leu Pro Ala Ser Ser Tyr Asp Val Phe Val Ser Asn Ala Gly Ile
                 85                  90                  95

Ser Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
                115                 120                 125

Val Lys Ala Ile Ser Asp Lys Pro Arg Gln Thr Pro Ala His Ile Ile
        130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
                180                 185                 190

Val Thr Arg Thr Ser Met Ala Glu Gly Ile Asp Pro Ser Met Phe Asp
            195                 200                 205

Leu Pro Ile Asn Gly Trp Ile Glu Val Asp Ala Ile Ala Asp Ala Val
        210                 215                 220

Thr Tyr Leu Val Lys Ser Lys Asn Val Thr Gly Thr Thr Val Ser Val
225                 230                 235                 240

Asp Asn Gly Tyr Cys Ala
                245
```

<210> SEQ ID NO 63
<211> LENGTH: 246
<212> TYPE: PRT
<213> ORGANISM: Artificial Sequence
<220> FEATURE:
<223> OTHER INFORMATION: Synthetic

<400> SEQUENCE: 63

```
Met Thr Ser Ser Ser Pro Ser Leu Asn Ala Leu Val Thr Gly Gly
 1               5                  10                  15

Ser Arg Gly Ile Gly Glu Ala Ile Ser Met Gln Leu Ala Ala Glu Gly
                 20                  25                  30

Tyr Ser Val Thr Ile Ala Ser Arg Gly Leu Glu Gln Leu Glu Ala Val
             35                  40                  45

Lys Ala Lys Leu Pro Ile Ile Lys Gln Gly Gln Thr His His Val Trp
 50                  55                  60

Gln Leu Asp Leu Ser Asp Val Glu Ala Ala Gly Ser Phe Lys Gly Ala
 65                  70                  75                  80

Pro Leu Pro Ala Ser Ser Tyr Asp Val Phe Val Ser Asn Ala Gly Ile
                 85                  90                  95

Ser Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
                115                 120                 125

Val Lys Ala Ile Ser Asp Lys Pro Arg Gln Thr Pro Ala His Ile Ile
        130                 135                 140

Phe Ile Ser Thr Gly Leu Ser Lys Arg Gly Ala Pro Met Val Gly Val
145                 150                 155                 160
```

-continued

Tyr Ser Ala Ser Lys Ala Gly Ile Asp Gly Phe Met Arg Ser Leu Ala
            165                 170                 175

Arg Glu Leu Gly Pro Lys Gly Ile Asn Val Asn Cys Val Ser Pro Gly
        180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
        210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 64
<211> LENGTH: 246
<212> TYPE: PRT
<213> ORGANISM: Artificial Sequence
<220> FEATURE:
<223> OTHER INFORMATION: Synthetic

<400> SEQUENCE: 64

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Met Asn Ala Gly Ile
                85                  90                  95

Ser Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
        130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
        210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 65
<211> LENGTH: 246

<212> TYPE: PRT
<213> ORGANISM: Artificial Sequence
<220> FEATURE:
<223> OTHER INFORMATION: Synthetic

<400> SEQUENCE: 65

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
                35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Gly Asn Ala Gly Ile
                85                  90                  95

Ser Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
                115                 120                 125

Val Lys Ala Ile Ser Asp Lys Pro Arg Gln Thr Pro Ala His Ile Ile
130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
                180                 185                 190

Val Thr Arg Thr Ser Met Ala Glu Gly Ile Asp Pro Ser Met Phe Asp
                195                 200                 205

Leu Pro Ile Asn Gly Trp Ile Glu Val Asp Ala Ile Ala Asp Ala Val
                210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 66
<211> LENGTH: 246
<212> TYPE: PRT
<213> ORGANISM: Artificial Sequence
<220> FEATURE:
<223> OTHER INFORMATION: Synthetic

<400> SEQUENCE: 66

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
                35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Ser Phe Lys Gly Ala
65                  70                  75                  80

```
Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Phe Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 67
<211> LENGTH: 246
<212> TYPE: PRT
<213> ORGANISM: Artificial Sequence
<220> FEATURE:
<223> OTHER INFORMATION: Synthetic

<400> SEQUENCE: 67

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
                20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Val Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190
```

```
Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 68
<211> LENGTH: 246
<212> TYPE: PRT
<213> ORGANISM: Artificial Sequence
<220> FEATURE:
<223> OTHER INFORMATION: Synthetic

<400> SEQUENCE: 68

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Glu Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 69
<211> LENGTH: 246
<212> TYPE: PRT
<213> ORGANISM: Artificial Sequence
<220> FEATURE:
<223> OTHER INFORMATION: Synthetic
```

-continued

```
<400> SEQUENCE: 69

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Leu Ala Pro Ile Ala Leu Thr Lys Ala Val
        115                 120                 125

Val Lys Ala Ile Ser Asp Lys Pro Arg Gln Thr Pro Ala His Ile Ile
130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
        210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 70
<211> LENGTH: 246
<212> TYPE: PRT
<213> ORGANISM: Artificial Sequence
<220> FEATURE:
<223> OTHER INFORMATION: Synthetic

<400> SEQUENCE: 70

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
```

```
            100                 105                 110
Met Leu Thr Val Asn Leu Thr Ala Ala Ile Ala Leu Thr Lys Ala Val
            115                 120                 125

Val Lys Ala Ile Ser Asp Lys Pro Arg Gln Thr Pro Ala His Ile Ile
            130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
                180                 185                 190

Val Thr Arg Thr Ser Met Ala Glu Gly Ile Asp Pro Ser Met Phe Asp
                195                 200                 205

Leu Pro Ile Asn Gly Trp Ile Glu Val Asp Ala Ile Ala Asp Ala Val
            210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 71
<211> LENGTH: 246
<212> TYPE: PRT
<213> ORGANISM: Artificial Sequence
<220> FEATURE:
<223> OTHER INFORMATION: Synthetic

<400> SEQUENCE: 71

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
                20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
                100                 105                 110

Met Leu Thr Val Asn Leu Thr Ala Ala Ile Ala Leu Thr Lys Ala Val
            115                 120                 125

Val Lys Ala Ile Met Asp Lys Pro Arg Gln Thr Pro Ala His Ile Ile
            130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
                180                 185                 190

Val Thr Arg Thr Ser Met Ala Glu Gly Ile Asp Pro Ser Met Phe Asp
                195                 200                 205

Leu Pro Ile Asn Gly Trp Ile Glu Val Asp Ala Ile Ala Asp Ala Val
```

```
            210                 215                 220
Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 72
<211> LENGTH: 246
<212> TYPE: PRT
<213> ORGANISM: Artificial Sequence
<220> FEATURE:
<223> OTHER INFORMATION: Synthetic

<400> SEQUENCE: 72

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
                20                  25                  30

Tyr Ser Val Thr Ile Ala Ser Arg Gly Leu Glu Gln Leu Glu Ala Val
                35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
                115                 120                 125

Val Lys Ala Ile Ser Asp Lys Pro Arg Gln Thr Pro Ala His Ile Ile
130                 135                 140

Phe Ile Ser Thr Gly Leu Ser Lys Arg Gly Ala Pro Phe Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
                180                 185                 190

Val Thr Arg Thr Ser Met Ala Glu Gly Ile Asp Pro Ser Met Phe Asp
                195                 200                 205

Leu Pro Ile Asn Gly Trp Ile Glu Val Asp Ala Ile Ala Asp Ala Val
                210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 73
<211> LENGTH: 246
<212> TYPE: PRT
<213> ORGANISM: Artificial Sequence
<220> FEATURE:
<223> OTHER INFORMATION: Synthetic

<400> SEQUENCE: 73

Met Thr Ser Ser Ser Pro Ser Leu Asn Ala Leu Val Thr Gly Gly
1               5                   10                  15
```

```
Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
 50                  55                  60

Gln Leu Asp Leu Ser Asp Val Glu Ala Ala Gly Ser Phe Lys Gly Ala
 65                  70                  75                  80

Pro Leu Pro Ala Ser Ser Tyr Asp Val Phe Val Ser Asn Ala Gly Ile
                 85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
130                 135                 140

Phe Ile Ser Thr Gly Leu Ser Lys Arg Gly Ala Pro Arg Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 74
<211> LENGTH: 246
<212> TYPE: PRT
<213> ORGANISM: Artificial Sequence
<220> FEATURE:
<223> OTHER INFORMATION: Synthetic

<400> SEQUENCE: 74

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
 50                  55                  60

Gln Leu Asp Leu Ser Asp Val Glu Ala Ala Gly Ser Phe Lys Gly Ala
 65                  70                  75                  80

Pro Leu Pro Ala Ser Ser Tyr Asp Val Phe Val Ser Asn Ala Gly Ile
                 85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125
```

```
Val Lys Ala Ile Ser Asp Lys Pro Arg Gln Thr Pro Ala His Ile Ile
130                 135                 140

Phe Ile Ser Thr Gly Leu Ser Lys Arg Gly Ala Pro Gly Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
                180                 185                 190

Val Thr Arg Thr Ser Met Ala Glu Gly Ile Asp Pro Ser Met Phe Asp
                195                 200                 205

Leu Pro Ile Asn Gly Trp Ile Glu Val Asp Ala Ile Ala Asp Ala Val
        210                 215                 220

Thr Tyr Leu Val Lys Ser Lys Asn Val Thr Gly Thr Thr Val Ser Val
225                 230                 235                 240

Asp Asn Gly Tyr Cys Ala
                245
```

<210> SEQ ID NO 75
<211> LENGTH: 246
<212> TYPE: PRT
<213> ORGANISM: Artificial Sequence
<220> FEATURE:
<223> OTHER INFORMATION: Synthetic

<400> SEQUENCE: 75

```
Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
                20                  25                  30

Tyr Ser Val Thr Ile Ala Ser Arg Gly Leu Glu Gln Leu Glu Ala Val
                35                  40                  45

Lys Ala Lys Leu Pro Ile Val Lys Gln Gly Gln Thr His His Val Trp
        50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
                115                 120                 125

Val Lys Ala Ile Ser Asp Lys Pro Arg Gln Thr Pro Ala His Ile Ile
130                 135                 140

Phe Ile Ser Thr Gly Leu Ala Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
                180                 185                 190

Val Thr Arg Thr Ser Met Ala Glu Gly Ile Asp Pro Ser Met Phe Asp
                195                 200                 205

Leu Pro Ile Asn Gly Trp Ile Glu Val Asp Ala Ile Ala Asp Ala Val
        210                 215                 220

Thr Tyr Leu Val Lys Ser Lys Asn Val Thr Gly Thr Thr Val Ser Val
225                 230                 235                 240
```

Asp Asn Gly Tyr Cys Ala
            245

<210> SEQ ID NO 76
<211> LENGTH: 246
<212> TYPE: PRT
<213> ORGANISM: Artificial Sequence
<220> FEATURE:
<223> OTHER INFORMATION: Synthetic

<400> SEQUENCE: 76

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
130                 135                 140

Phe Ile Ser Thr Gly Leu Ser Lys Arg Gly Ala Pro Gly Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
            195                 200                 205

Leu Pro Ile Asn Gly Trp Thr Glu Val Asp Ala Ile Ala Asp Ala Val
            210                 215                 220

Thr Tyr Leu Val Lys Ser Lys Asn Val Thr Gly Thr Thr Val Ser Val
225                 230                 235                 240

Asp Asn Val Tyr Phe Phe
            245

<210> SEQ ID NO 77
<211> LENGTH: 246
<212> TYPE: PRT
<213> ORGANISM: Artificial Sequence
<220> FEATURE:
<223> OTHER INFORMATION: Synthetic

<400> SEQUENCE: 77

Met Thr Ser Ser Ser Pro Ser Gly Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
            35                  40                  45

```
Lys Ala Lys Leu Pro Ile Val Lys Gln Gly Gln Thr His His Val Trp
 50                  55                  60

Gln Leu Asp Leu Ser Asp Val Glu Ala Ala Gly Ser Phe Lys Gly Ala
 65                  70                  75                  80

Pro Leu Pro Ala Ser Ser Tyr Asp Val Phe Val Ser Asn Ala Gly Ile
                 85                  90                  95

Ser Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
                115                 120                 125

Val Lys Ala Ile Ser Asp Lys Pro Arg Gln Thr Pro Ala His Ile Ile
                130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
                180                 185                 190

Val Thr Arg Thr Ser Met Ala Glu Gly Ile Asp Pro Ser Met Phe Asp
                195                 200                 205

Leu Pro Ile Asn Gly Trp Ile Glu Val Asp Ala Ile Ala Asp Ala Val
                210                 215                 220

Thr Tyr Leu Val Lys Ser Lys Asn Val Thr Gly Thr Thr Val Ser Val
225                 230                 235                 240

Asp Asn Gly Tyr Cys Ala
                245
```

<210> SEQ ID NO 78
<211> LENGTH: 246
<212> TYPE: PRT
<213> ORGANISM: Artificial Sequence
<220> FEATURE:
<223> OTHER INFORMATION: Synthetic

<400> SEQUENCE: 78

```
Met Thr Ser Ser Ser Pro Ser Leu Asn Ala Leu Val Thr Gly Gly
 1               5                  10                  15

Ser Arg Gly Ile Gly Glu Ala Ile Ser Met Gln Leu Ala Ala Glu Gly
                 20                  25                  30

Tyr Ser Val Thr Ile Ala Ser Arg Gly Leu Glu Gln Leu Glu Ala Val
                 35                  40                  45

Lys Ala Lys Leu Pro Ile Val Lys Gln Gly Gln Thr His His Val Trp
 50                  55                  60

Gln Leu Asp Leu Ser Asp Val Glu Ala Ala Gly Ser Phe Lys Gly Ala
 65                  70                  75                  80

Pro Leu Pro Ala Ser Ser Tyr Asp Val Phe Val Ser Asn Ala Gly Ile
                 85                  90                  95

Ser Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
                115                 120                 125

Val Lys Ala Ile Ser Asp Lys Pro Arg Gln Thr Pro Ala His Ile Ile
                130                 135                 140

Phe Ile Ser Thr Gly Leu Ser Lys Arg Gly Ala Pro Met Val Gly Val
145                 150                 155                 160
```

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Gly Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 79
<211> LENGTH: 246
<212> TYPE: PRT
<213> ORGANISM: Artificial Sequence
<220> FEATURE:
<223> OTHER INFORMATION: Synthetic

<400> SEQUENCE: 79

Met Thr Ser Ser Ser Pro Ser Leu Asn Ala Leu Val Thr Gly Gly
1               5                   10                  15

Ser Arg Gly Ile Gly Glu Ala Ile Ala Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asn
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 80

```
<211> LENGTH: 246
<212> TYPE: PRT
<213> ORGANISM: Artificial Sequence
<220> FEATURE:
<223> OTHER INFORMATION: Synthetic

<400> SEQUENCE: 80
```

| Met | Thr | Ser | Ser | Ser | Pro | Ser | Leu | Asn | Ala | Leu | Val | Thr | Gly | Gly |
|---|---|---|---|---|---|---|---|---|---|---|---|---|---|---|
| 1 | | | | 5 | | | | | 10 | | | | | 15 |

| Ser | Arg | Gly | Ile | Gly | Glu | Ala | Ile | Ser | Arg | Gln | Leu | Ala | Ala | Glu | Gly |
|---|---|---|---|---|---|---|---|---|---|---|---|---|---|---|---|
| | | | 20 | | | | | 25 | | | | | 30 | | |

| Tyr | Ser | Val | Thr | Ile | Ala | Ser | Arg | Gly | Leu | Glu | Gln | Leu | Glu | Ala | Val |
|---|---|---|---|---|---|---|---|---|---|---|---|---|---|---|---|
| | | | 35 | | | | | 40 | | | | | 45 | | |

| Lys | Ala | Lys | Leu | Pro | Ile | Val | Lys | Gln | Gly | Gln | Thr | His | His | Val | Trp |
|---|---|---|---|---|---|---|---|---|---|---|---|---|---|---|---|
| | 50 | | | | | 55 | | | | | 60 | | | | |

| Gln | Leu | Asp | Leu | Ser | Asp | Val | Glu | Ala | Ala | Gly | Ser | Phe | Lys | Gly | Ala |
|---|---|---|---|---|---|---|---|---|---|---|---|---|---|---|---|
| 65 | | | | | 70 | | | | | 75 | | | | | 80 |

| Pro | Leu | Pro | Ala | Ser | Ser | Tyr | Asp | Val | Phe | Val | Ser | Asn | Ala | Gly | Ile |
|---|---|---|---|---|---|---|---|---|---|---|---|---|---|---|---|
| | | | | 85 | | | | | 90 | | | | | 95 | |

| Ser | Gln | Phe | Ser | Pro | Ile | Ala | Glu | His | Ala | Asp | Ala | Asp | Trp | Gln | Asn |
|---|---|---|---|---|---|---|---|---|---|---|---|---|---|---|---|
| | | | | 100 | | | | | 105 | | | | | 110 | |

| Met | Leu | Thr | Val | Asn | Leu | Thr | Ala | Pro | Ile | Ala | Leu | Thr | Lys | Ala | Val |
|---|---|---|---|---|---|---|---|---|---|---|---|---|---|---|---|
| | | | 115 | | | | | 120 | | | | | 125 | | |

| Val | Lys | Ala | Ile | Ser | Asp | Lys | Pro | Arg | Gln | Thr | Pro | Ala | His | Ile | Ile |
|---|---|---|---|---|---|---|---|---|---|---|---|---|---|---|---|
| | 130 | | | | | 135 | | | | | 140 | | | | |

| Phe | Ile | Ser | Thr | Gly | Leu | Ser | Lys | Arg | Gly | Ala | Pro | Met | Val | Gly | Val |
|---|---|---|---|---|---|---|---|---|---|---|---|---|---|---|---|
| 145 | | | | | 150 | | | | | 155 | | | | | 160 |

| Tyr | Ser | Ala | Ser | Lys | Ala | Gly | Ile | Asp | Gly | Phe | Met | Arg | Ser | Leu | Ala |
|---|---|---|---|---|---|---|---|---|---|---|---|---|---|---|---|
| | | | | 165 | | | | | 170 | | | | | 175 | |

| Arg | Glu | Leu | Gly | Pro | Lys | Gly | Ile | Asn | Val | Asn | Cys | Val | Ser | Pro | Gly |
|---|---|---|---|---|---|---|---|---|---|---|---|---|---|---|---|
| | | | 180 | | | | | 185 | | | | | 190 | | |

| Val | Thr | Arg | Thr | Ser | Met | Ala | Glu | Gly | Ile | Asp | Pro | Ser | Met | Phe | Asp |
|---|---|---|---|---|---|---|---|---|---|---|---|---|---|---|---|
| | | 195 | | | | | 200 | | | | | 205 | | | |

| Leu | Pro | Ile | Asn | Gly | Trp | Ile | Glu | Val | Asp | Ala | Ile | Ala | Asp | Ala | Val |
|---|---|---|---|---|---|---|---|---|---|---|---|---|---|---|---|
| | 210 | | | | | 215 | | | | | 220 | | | | |

| Thr | Tyr | Leu | Val | Lys | Ser | Lys | Asn | Val | Thr | Phe | Thr | Ile | Phe | Phe | Val |
|---|---|---|---|---|---|---|---|---|---|---|---|---|---|---|---|
| 225 | | | | | 230 | | | | | 235 | | | | | 240 |

| Asp | Asn | Gly | Tyr | Cys | Ala |
|---|---|---|---|---|---|
| | | | | 245 | |

```
<210> SEQ ID NO 81
<211> LENGTH: 246
<212> TYPE: PRT
<213> ORGANISM: Artificial Sequence
<220> FEATURE:
<223> OTHER INFORMATION: Synthetic

<400> SEQUENCE: 81
```

| Met | Thr | Ser | Ser | Ser | Pro | Ser | Leu | Asn | Ala | Leu | Val | Thr | Gly | Gly |
|---|---|---|---|---|---|---|---|---|---|---|---|---|---|---|
| 1 | | | | 5 | | | | | 10 | | | | | 15 |

| Ser | Arg | Gly | Ile | Gly | Glu | Ala | Ile | Ser | Met | Gln | Leu | Ala | Ala | Glu | Gly |
|---|---|---|---|---|---|---|---|---|---|---|---|---|---|---|---|
| | | | 20 | | | | | 25 | | | | | 30 | | |

| Tyr | Ser | Val | Thr | Ile | Ala | Ser | Arg | Gly | Leu | Glu | Gln | Leu | Glu | Ala | Val |
|---|---|---|---|---|---|---|---|---|---|---|---|---|---|---|---|
| | | | 35 | | | | | 40 | | | | | 45 | | |

| Lys | Ala | Lys | Leu | Pro | Ile | Val | Lys | Gln | Gly | Gln | Thr | His | His | Val | Trp |
|---|---|---|---|---|---|---|---|---|---|---|---|---|---|---|---|
| | 50 | | | | | 55 | | | | | 60 | | | | |

| Gln | Leu | Asp | Leu | Ser | Asp | Val | Glu | Ala | Ala | Gly | Ser | Phe | Lys | Gly | Ala |
|---|---|---|---|---|---|---|---|---|---|---|---|---|---|---|---|

```
Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Cys Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 82
<211> LENGTH: 246
<212> TYPE: PRT
<213> ORGANISM: Artificial Sequence
<220> FEATURE:
<223> OTHER INFORMATION: Synthetic

<400> SEQUENCE: 82

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Glu Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
```

180             185             190
Val Thr Arg Thr Ser Met Ala Glu Gly Ile Asp Pro Ser Met Phe Asp
                195                 200                 205

Leu Pro Ile Asn Gly Trp Ile Glu Val Asp Ala Ile Ala Asp Ala Val
            210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 83
<211> LENGTH: 246
<212> TYPE: PRT
<213> ORGANISM: Artificial Sequence
<220> FEATURE:
<223> OTHER INFORMATION: Synthetic

<400> SEQUENCE: 83

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
                20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
        50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
        130                 135                 140

Phe Ile Ser Thr Gly Leu Ser Lys Arg Gly Ala Pro Lys Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 84
<211> LENGTH: 246
<212> TYPE: PRT
<213> ORGANISM: Artificial Sequence
<220> FEATURE:
<223> OTHER INFORMATION: Synthetic

<400> SEQUENCE: 84

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
130                 135                 140

Phe Ile Ser Ser Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 85
<211> LENGTH: 246
<212> TYPE: PRT
<213> ORGANISM: Artificial Sequence
<220> FEATURE:
<223> OTHER INFORMATION: Synthetic

<400> SEQUENCE: 85

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Cys Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 86
<211> LENGTH: 246
<212> TYPE: PRT
<213> ORGANISM: Artificial Sequence
<220> FEATURE:
<223> OTHER INFORMATION: Synthetic

<400> SEQUENCE: 86

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Glu Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220
Thr Tyr Leu Val Lys Ser Lys Asn Val Thr Gly Thr Thr Val Ser Val
225                 230                 235                 240
Asp Asn Gly Tyr Cys Ala
                245

<210> SEQ ID NO 87
<211> LENGTH: 246
<212> TYPE: PRT
<213> ORGANISM: Artificial Sequence
<220> FEATURE:
<223> OTHER INFORMATION: Synthetic

<400> SEQUENCE: 87

Met Thr Ser Ser Ser Pro Ser Leu Asn Ala Leu Val Thr Gly Gly
1               5                   10                  15
Ser Arg Gly Ile Gly Glu Ala Ile Ser Met Gln Leu Ala Ala Glu Gly
                20                  25                  30
Tyr Ser Val Thr Ile Ala Ser Arg Gly Leu Glu Gln Leu Glu Ala Val
            35                  40                  45
Lys Ala Lys Leu Pro Ile Val Lys Gln Gly Gln Thr His His Val Trp
    50                  55                  60
Gln Leu Asp Leu Ser Asp Val Glu Ala Ala Gly Ser Phe Lys Gly Ala
65                  70                  75                  80
Pro Leu Pro Ala Ser Ser Tyr Asp Val Phe Val Ser Asn Ala Gly Ile
                85                  90                  95
Ser Gln Phe Ser Pro Ile Ala Glu His Ala Asp Pro Asp Trp Gln Asn
            100                 105                 110
Met Leu Thr Val Asn Leu Thr Ala Pro Ile Ala Leu Thr Lys Ala Val
        115                 120                 125
Val Lys Ala Ile Ser Asp Lys Pro Arg Gln Thr Pro Ala His Ile Ile
    130                 135                 140
Phe Ile Ser Thr Gly Leu Ser Lys Arg Gly Ala Pro Met Val Gly Val
145                 150                 155                 160
Tyr Ser Ala Ser Lys Ala Gly Ile Asp Gly Phe Met Arg Ser Leu Ala
                165                 170                 175
Arg Glu Leu Gly Pro Lys Gly Ile Asn Val Asn Cys Val Ser Pro Gly
            180                 185                 190
Val Thr Arg Thr Ser Met Ala Glu Gly Ile Asp Pro Ser Met Phe Asp
        195                 200                 205
Leu Pro Ile Asn Gly Trp Ile Glu Val Asp Ala Ile Ala Asp Ala Val
    210                 215                 220
Thr Tyr Leu Val Lys Ser Lys Asn Val Thr Gly Thr Thr Val Ser Val
225                 230                 235                 240
Asp Asn Gly Tyr Cys Ala
                245

<210> SEQ ID NO 88
<211> LENGTH: 246
<212> TYPE: PRT
<213> ORGANISM: Artificial Sequence
<220> FEATURE:
<223> OTHER INFORMATION: Synthetic

<400> SEQUENCE: 88

Met Thr Ser Ser Ser Pro Ser Leu Asn Ala Leu Val Thr Gly Gly
1               5                   10                  15

```
Ser Arg Gly Ile Gly Glu Ala Ile Ser Met Gln Leu Ala Ala Glu Gly
             20                  25                  30

Tyr Ser Val Thr Ile Ala Ser Arg Gly Leu Glu Gln Leu Glu Ala Val
             35                  40                  45

Lys Ala Lys Leu Pro Ile Val Lys Gln Gly Gln Thr His His Val Trp
 50                  55                  60

Gln Leu Asp Leu Ser Asp Val Glu Ala Ala Gly Ser Phe Lys Gly Ala
 65                  70                  75                  80

Pro Leu Pro Ala Ser Ser Tyr Asp Val Phe Val Ser Asn Ala Gly Ile
                 85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
130                 135                 140

Phe Ile Ser Thr Gly Leu Ser Lys Arg Gly Ala Pro Met Val Ser Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
                180                 185                 190

Val Thr Arg Thr Ser Met Ala Glu Gly Ile Asp Pro Ser Met Phe Asp
                195                 200                 205

Leu Pro Ile Asn Gly Trp Ile Glu Val Asp Ala Ile Ala Asp Ala Val
            210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 89
<211> LENGTH: 246
<212> TYPE: PRT
<213> ORGANISM: Artificial Sequence
<220> FEATURE:
<223> OTHER INFORMATION: Synthetic

<400> SEQUENCE: 89

Met Thr Ser Ser Ser Pro Ser Leu Asn Ala Leu Val Thr Gly Gly
 1               5                  10                  15

Ser Arg Gly Ile Gly Glu Ala Ile Ser Met Gln Leu Ala Ala Glu Gly
             20                  25                  30

Tyr Ser Val Thr Ile Ala Ser Arg Gly Leu Glu Gln Leu Glu Ala Val
             35                  40                  45

Lys Ala Lys Leu Pro Ile Val Lys Gln Gly Gln Thr His His Val Trp
 50                  55                  60

Gln Leu Asp Leu Ser Asp Val Glu Ala Ala Gly Ser Phe Lys Gly Ala
 65                  70                  75                  80

Pro Leu Pro Ala Ser Ser Tyr Asp Val Phe Val Ser Asn Ala Gly Ile
                 85                  90                  95

Ala Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
            115                 120                 125
```

Val Lys Ala Ile Ser Asp Lys Pro Arg Gln Thr Pro Ala His Ile Ile
130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
                180                 185                 190

Val Thr Arg Thr Ser Met Ala Glu Gly Ile Asp Pro Ser Met Phe Asp
                195                 200                 205

Leu Pro Ile Asn Gly Trp Ile Glu Val Asp Ala Ile Ala Asp Ala Val
                210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 90
<211> LENGTH: 246
<212> TYPE: PRT
<213> ORGANISM: Artificial Sequence
<220> FEATURE:
<223> OTHER INFORMATION: Synthetic

<400> SEQUENCE: 90

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
                20                  25                  30

Tyr Ser Val Thr Ile Ala Ser Arg Gly Leu Glu Gln Leu Glu Ala Val
                35                  40                  45

Lys Ala Lys Leu Pro Ile Val Lys Gln Gly Gln Thr His His Val Trp
                50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Trp Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
                115                 120                 125

Val Lys Ala Ile Ser Asp Lys Pro Arg Gln Thr Pro Ala His Ile Ile
130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
                180                 185                 190

Val Thr Arg Thr Ser Met Ala Glu Gly Ile Asp Pro Ser Met Phe Asp
                195                 200                 205

Leu Pro Ile Asn Gly Trp Ile Glu Val Asp Ala Ile Ala Asp Ala Val
                210                 215                 220

Thr Tyr Leu Val Lys Ser Lys Asn Val Thr Gly Thr Thr Val Ser Val
225                 230                 235                 240

Asp Asn Gly Tyr Cys Ala
            245

<210> SEQ ID NO 91
<211> LENGTH: 246
<212> TYPE: PRT
<213> ORGANISM: Artificial Sequence
<220> FEATURE:
<223> OTHER INFORMATION: Synthetic

<400> SEQUENCE: 91

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
    50                  55                  60

Gln Leu Asp Leu Ser Asp Val Glu Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Val Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
            245

<210> SEQ ID NO 92
<211> LENGTH: 246
<212> TYPE: PRT
<213> ORGANISM: Artificial Sequence
<220> FEATURE:
<223> OTHER INFORMATION: Synthetic

<400> SEQUENCE: 92

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val

```
            35                  40                  45
Lys Ala Lys Leu Pro Ile Val Lys Gln Gly Gln Thr His His Val Trp
 50                  55                  60

Gln Leu Asp Leu Ser Asp Val Glu Ala Ala Gly Ser Phe Lys Gly Ala
 65                  70                  75                  80

Pro Leu Pro Ala Ser Ser Tyr Asp Val Phe Val Ser Asn Ala Gly Ile
                 85                  90                  95

Cys Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 93
<211> LENGTH: 246
<212> TYPE: PRT
<213> ORGANISM: Artificial Sequence
<220> FEATURE:
<223> OTHER INFORMATION: Synthetic

<400> SEQUENCE: 93

Met Thr Ser Ser Ser Pro Ser Leu Asn Ala Leu Val Thr Gly Gly
 1               5                  10                  15

Ser Arg Gly Ile Gly Glu Ala Ile Ser Met Gln Leu Ala Ala Glu Gly
                 20                  25                  30

Tyr Ser Val Thr Ile Ala Ser Arg Gly Leu Glu Gln Leu Glu Ala Val
             35                  40                  45

Lys Ala Lys Leu Pro Ile Val Lys Gln Gly Gln Thr His His Val Trp
 50                  55                  60

Gln Leu Asp Leu Ser Asp Val Glu Ala Ala Gly Ser Phe Lys Gly Ala
 65                  70                  75                  80

Pro Leu Pro Ala Ser Ser Tyr Asp Val Phe Val Ser Asn Ala Gly Ile
                 85                  90                  95

Met Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
```

```
            145                 150                 155                 160
Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
                180                 185                 190

Val Thr Arg Thr Ser Met Ala Glu Gly Ile Asp Pro Ser Met Phe Asp
                195                 200                 205

Leu Pro Ile Asn Gly Trp Ile Glu Val Asp Ala Ile Ala Asp Ala Val
                210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 94
<211> LENGTH: 246
<212> TYPE: PRT
<213> ORGANISM: Artificial Sequence
<220> FEATURE:
<223> OTHER INFORMATION: Synthetic

<400> SEQUENCE: 94

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
                20                  25                  30

Tyr Ser Val Thr Ile Ala Ser Arg Gly Leu Glu Gln Leu Glu Ala Val
                35                  40                  45

Lys Ala Lys Leu Pro Ile Cys Lys Gln Gly Gln Thr His His Val Trp
                50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
                115                 120                 125

Val Lys Ala Ile Ser Asp Lys Pro Arg Gln Thr Pro Ala His Ile Ile
                130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
                180                 185                 190

Val Thr Arg Thr Ser Met Ala Glu Gly Ile Asp Pro Ser Met Phe Asp
                195                 200                 205

Leu Pro Ile Asn Gly Trp Ile Glu Val Asp Ala Ile Ala Asp Ala Val
                210                 215                 220

Thr Tyr Leu Val Lys Ser Lys Asn Val Thr Gly Thr Thr Val Ser Val
225                 230                 235                 240

Asp Asn Gly Tyr Cys Ala
                245
```

-continued

```
<210> SEQ ID NO 95
<211> LENGTH: 246
<212> TYPE: PRT
<213> ORGANISM: Artificial Sequence
<220> FEATURE:
<223> OTHER INFORMATION: Synthetic

<400> SEQUENCE: 95

Met Thr Ser Asn Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 96
<211> LENGTH: 246
<212> TYPE: PRT
<213> ORGANISM: Artificial Sequence
<220> FEATURE:
<223> OTHER INFORMATION: Synthetic

<400> SEQUENCE: 96

Met Thr Ser Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Lys Gln Leu Glu Ala Val
        35                  40                  45

Lys Ala Lys Leu Pro Ile Val Lys Gln Gly Gln Thr His His Val Trp
    50                  55                  60
```

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
            130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
            195                 200                 205

Leu Pro Ile Asn Gly Trp Ile Glu Val Asp Ala Ile Ala Asp Ala Val
            210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 97
<211> LENGTH: 246
<212> TYPE: PRT
<213> ORGANISM: Artificial Sequence
<220> FEATURE:
<223> OTHER INFORMATION: Synthetic

<400> SEQUENCE: 97

Met Thr Ser Ser Ser Pro Ser Leu Asn Val Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
            130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
        210                 215                 220

Thr Tyr Leu Val Lys Ser Lys Asn Val Thr Gly Thr Thr Val Ser Val
225                 230                 235                 240

Asp Asn Gly Tyr Cys Ala
            245

<210> SEQ ID NO 98
<211> LENGTH: 246
<212> TYPE: PRT
<213> ORGANISM: Artificial Sequence
<220> FEATURE:
<223> OTHER INFORMATION: Synthetic

<400> SEQUENCE: 98

Met Thr Ile Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
        210                 215                 220

Thr Tyr Leu Val Lys Ser Lys Asn Val Thr Gly Thr Thr Val Ser Val
225                 230                 235                 240

Asp Asn Gly Tyr Cys Ala
            245

<210> SEQ ID NO 99
<211> LENGTH: 246
<212> TYPE: PRT
<213> ORGANISM: Artificial Sequence
<220> FEATURE:

<223> OTHER INFORMATION: Synthetic

<400> SEQUENCE: 99

Met Thr Ser Ser Ser Pro Ala Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 100
<211> LENGTH: 246
<212> TYPE: PRT
<213> ORGANISM: Artificial Sequence
<220> FEATURE:
<223> OTHER INFORMATION: Synthetic

<400> SEQUENCE: 100

Met Thr Ser Ser Ser Pro Ser Leu Asn Cys Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

```
Ser Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
        130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
        210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 101
<211> LENGTH: 246
<212> TYPE: PRT
<213> ORGANISM: Artificial Sequence
<220> FEATURE:
<223> OTHER INFORMATION: Synthetic

<400> SEQUENCE: 101

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
        130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205
```

-continued

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Val Ser Val
225                 230                 235                 240

Asp Asn Gly Tyr Cys Ala
                245

<210> SEQ ID NO 102
<211> LENGTH: 246
<212> TYPE: PRT
<213> ORGANISM: Artificial Sequence
<220> FEATURE:
<223> OTHER INFORMATION: Synthetic

<400> SEQUENCE: 102

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
                20                  25                  30

Tyr Ser Val Thr Ile Ala Ser Arg Gly Leu Glu Thr Leu Glu Ala Val
            35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Val Ser Val
225                 230                 235                 240

Asp Asn Gly Tyr Cys Ala
                245

<210> SEQ ID NO 103
<211> LENGTH: 246
<212> TYPE: PRT
<213> ORGANISM: Artificial Sequence
<220> FEATURE:
<223> OTHER INFORMATION: Synthetic

<400> SEQUENCE: 103

Met Thr Ser Ser Ser Pro Ser Leu Asn Ala Leu Val Thr Gly Gly

```
            1               5                  10                  15
        Ser Arg Gly Ile Gly Glu Ala Ile Ser Met Gln Leu Ala Ala Glu Gly
                        20                  25                  30

Tyr Ser Val Thr Ile Ala Ser Arg Gly Leu Glu Gln Leu Glu Ala Val
                        35                  40                  45

Arg Ala Lys Leu Pro Ile Val Lys Gln Gly Gln Thr His His Val Trp
                    50                  55                  60

Gln Leu Asp Leu Ser Asp Val Glu Ala Ala Gly Ser Phe Lys Gly Ala
         65                  70                  75                  80

Pro Leu Pro Ala Ser Ser Tyr Asp Val Phe Val Ser Asn Ala Gly Ile
                            85                  90                  95

Ser Gln Phe Ser Pro Ile Ala Glu His Ala Asp Ala Asp Trp Gln Asn
                       100                 105                 110

Met Leu Thr Val Asn Leu Thr Ala Pro Ile Ala Leu Thr Lys Ala Val
                       115                 120                 125

Val Lys Ala Ile Ser Asp Lys Pro Arg Gln Thr Pro Ala His Ile Ile
                  130                 135                 140

Phe Ile Ser Thr Gly Leu Ser Lys Arg Gly Ala Pro Met Val Gly Val
        145                 150                 155                 160

Tyr Ser Ala Ser Lys Ala Gly Ile Asp Gly Phe Met Arg Ser Leu Ala
                            165                 170                 175

Arg Glu Leu Gly Pro Lys Gly Ile Asn Val Asn Cys Val Ser Pro Gly
                        180                 185                 190

Val Thr Arg Thr Ser Met Ala Glu Gly Ile Asp Pro Ser Met Phe Asp
                        195                 200                 205

Leu Pro Ile Asn Gly Trp Ile Glu Val Asp Ala Ile Ala Asp Ala Val
                    210                 215                 220

Thr Tyr Leu Val Lys Ser Lys Asn Val Thr Gly Thr Thr Val Ser Val
        225                 230                 235                 240

Asp Asn Gly Tyr Cys Ala
                        245

<210> SEQ ID NO 104
<211> LENGTH: 246
<212> TYPE: PRT
<213> ORGANISM: Artificial Sequence
<220> FEATURE:
<223> OTHER INFORMATION: Synthetic

<400> SEQUENCE: 104

Met Thr Ser Ser Ser Pro Ser Leu Asn Ala Leu Val Thr Gly Gly
         1               5                  10                  15

Ser Arg Gly Ile Gly Glu Ala Ile Ser Met Gln Leu Ala Ala Glu Gly
                        20                  25                  30

Tyr Ser Val Thr Ile Ala Ser Arg Gly Leu Glu Glu Leu Glu Ala Val
                        35                  40                  45

Lys Ala Lys Leu Pro Ile Val Lys Gln Gly Gln Thr His His Val Trp
                    50                  55                  60

Gln Leu Asp Leu Ser Asp Val Glu Ala Ala Gly Ser Phe Lys Gly Ala
         65                  70                  75                  80

Pro Leu Pro Ala Ser Ser Tyr Asp Val Phe Val Ser Asn Ala Gly Ile
                            85                  90                  95

Ser Gln Phe Ser Pro Ile Ala Glu His Ala Asp Ala Asp Trp Gln Asn
                       100                 105                 110

Met Leu Thr Val Asn Leu Thr Ala Pro Ile Ala Leu Thr Lys Ala Val
```

```
                115                 120                 125
Val Lys Ala Ile Ser Asp Lys Pro Arg Gln Thr Pro Ala His Ile Ile
            130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 105
<211> LENGTH: 246
<212> TYPE: PRT
<213> ORGANISM: Artificial Sequence
<220> FEATURE:
<223> OTHER INFORMATION: Synthetic

<400> SEQUENCE: 105

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Lys Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
```

Asp Asn Gly Tyr Cys Ala
            245

<210> SEQ ID NO 106
<211> LENGTH: 246
<212> TYPE: PRT
<213> ORGANISM: Artificial Sequence
<220> FEATURE:
<223> OTHER INFORMATION: Synthetic

<400> SEQUENCE: 106

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Arg Leu Glu Ala Val
        35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
            245

<210> SEQ ID NO 107
<211> LENGTH: 246
<212> TYPE: PRT
<213> ORGANISM: Artificial Sequence
<220> FEATURE:
<223> OTHER INFORMATION: Synthetic

<400> SEQUENCE: 107

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
            35                  40                  45

Lys Ala Lys Leu Pro Ile Val Met Gln Gly Gln Thr His His Val Trp
 50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
            195                 200                 205

Leu Pro Ile Asn Gly Trp Ile Glu Val Asp Ala Ile Ala Asp Ala Val
            210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 108
<211> LENGTH: 246
<212> TYPE: PRT
<213> ORGANISM: Artificial Sequence
<220> FEATURE:
<223> OTHER INFORMATION: Synthetic

<400> SEQUENCE: 108

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
            35                  40                  45

Lys Ala Lys Leu Pro Ile Val Lys Pro Gly Gln Thr His His Val Trp
 50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
130                 135                 140

```
Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 109
<211> LENGTH: 246
<212> TYPE: PRT
<213> ORGANISM: Artificial Sequence
<220> FEATURE:
<223> OTHER INFORMATION: Synthetic

<400> SEQUENCE: 109

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
                20                  25                  30

Tyr Ser Val Thr Ile Ala Ser Arg Gly Leu Glu Gln Leu Glu Ala Val
            35                  40                  45

Lys Ala Lys Leu Pro Ile Val Lys Ala Gly Gln Thr His His Val Trp
        50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
        130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245
```

<210> SEQ ID NO 110
<211> LENGTH: 246
<212> TYPE: PRT
<213> ORGANISM: Artificial Sequence
<220> FEATURE:
<223> OTHER INFORMATION: Synthetic

<400> SEQUENCE: 110

```
Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
                20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Cys His His Val Trp
50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245
```

<210> SEQ ID NO 111
<211> LENGTH: 246
<212> TYPE: PRT
<213> ORGANISM: Artificial Sequence
<220> FEATURE:
<223> OTHER INFORMATION: Synthetic

<400> SEQUENCE: 111

```
Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
                20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Asn His His Val Trp
50                  55                  60
```

```
Gln Leu Asp Leu Ser Asp Val Glu Ala Ala Gly Ser Phe Lys Gly Ala
 65                  70                  75                  80

Pro Leu Pro Ala Ser Ser Tyr Asp Val Phe Val Ser Asn Ala Gly Ile
             85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 112
<211> LENGTH: 246
<212> TYPE: PRT
<213> ORGANISM: Artificial Sequence
<220> FEATURE:
<223> OTHER INFORMATION: Synthetic

<400> SEQUENCE: 112

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Ala His His Val Trp
    50                  55                  60

Gln Leu Asp Leu Ser Asp Val Glu Ala Ala Gly Ser Phe Lys Gly Ala
 65                  70                  75                  80

Pro Leu Pro Ala Ser Ser Tyr Asp Val Phe Val Ser Asn Ala Gly Ile
             85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175
```

```
Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 113
<211> LENGTH: 246
<212> TYPE: PRT
<213> ORGANISM: Artificial Sequence
<220> FEATURE:
<223> OTHER INFORMATION: Synthetic

<400> SEQUENCE: 113

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 114
<211> LENGTH: 246
<212> TYPE: PRT
<213> ORGANISM: Artificial Sequence
```

<220> FEATURE:
<223> OTHER INFORMATION: Synthetic

<400> SEQUENCE: 114

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
                35                  40                  45

Lys Ala Lys Leu Pro Ile Val Lys Gln Gly Gln Thr His His Val Trp
    50                  55                  60

Gln Leu Asp Leu Val Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 115
<211> LENGTH: 246
<212> TYPE: PRT
<213> ORGANISM: Artificial Sequence
<220> FEATURE:
<223> OTHER INFORMATION: Synthetic

<400> SEQUENCE: 115

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
                35                  40                  45

Lys Ala Lys Leu Pro Ile Val Lys Gln Gly Gln Thr His His Val Trp
    50                  55                  60

Gln Leu Asp Leu Ser Cys Val Glu Ala Ala Gly Ser Phe Lys Gly Ala
65                  70                  75                  80

Pro Leu Pro Ala Ser Ser Tyr Asp Val Phe Val Ser Asn Ala Gly Ile

```
                    85                  90                  95
Ser Gln Phe Ser Pro Ile Ala Glu His Ala Asp Ala Asp Trp Gln Asn
                100                 105                 110
Met Leu Thr Val Asn Leu Thr Ala Pro Ile Ala Leu Thr Lys Ala Val
                115                 120                 125
Val Lys Ala Ile Ser Asp Lys Pro Arg Gln Thr Pro Ala His Ile Ile
130                 135                 140
Phe Ile Ser Thr Gly Leu Ser Lys Arg Gly Ala Pro Met Val Gly Val
145                 150                 155                 160
Tyr Ser Ala Ser Lys Ala Gly Ile Asp Gly Phe Met Arg Ser Leu Ala
                165                 170                 175
Arg Glu Leu Gly Pro Lys Gly Ile Asn Val Asn Cys Val Ser Pro Gly
                180                 185                 190
Val Thr Arg Thr Ser Met Ala Glu Gly Ile Asp Pro Ser Met Phe Asp
                195                 200                 205
Leu Pro Ile Asn Gly Trp Ile Glu Val Asp Ala Ile Ala Asp Ala Val
                210                 215                 220
Thr Tyr Leu Val Lys Ser Lys Asn Val Thr Gly Thr Thr Val Ser Val
225                 230                 235                 240
Asp Asn Gly Tyr Cys Ala
                245
```

<210> SEQ ID NO 116
<211> LENGTH: 246
<212> TYPE: PRT
<213> ORGANISM: Artificial Sequence
<220> FEATURE:
<223> OTHER INFORMATION: Synthetic

<400> SEQUENCE: 116

```
Met Thr Ser Ser Ser Pro Ser Leu Asn Ala Leu Val Thr Gly Gly
1               5                   10                  15
Ser Arg Gly Ile Gly Glu Ala Ile Ser Met Gln Leu Ala Ala Glu Gly
                20                  25                  30
Tyr Ser Val Thr Ile Ala Ser Arg Gly Leu Glu Gln Leu Glu Ala Val
                35                  40                  45
Lys Ala Lys Leu Pro Ile Val Lys Gln Gly Gln Thr His His Val Trp
50                  55                  60
Gln Leu Asp Leu Ser Ser Val Glu Ala Ala Gly Ser Phe Lys Gly Ala
65                  70                  75                  80
Pro Leu Pro Ala Ser Ser Tyr Asp Val Phe Val Ser Asn Ala Gly Ile
                85                  90                  95
Ser Gln Phe Ser Pro Ile Ala Glu His Ala Asp Ala Asp Trp Gln Asn
                100                 105                 110
Met Leu Thr Val Asn Leu Thr Ala Pro Ile Ala Leu Thr Lys Ala Val
                115                 120                 125
Val Lys Ala Ile Ser Asp Lys Pro Arg Gln Thr Pro Ala His Ile Ile
130                 135                 140
Phe Ile Ser Thr Gly Leu Ser Lys Arg Gly Ala Pro Met Val Gly Val
145                 150                 155                 160
Tyr Ser Ala Ser Lys Ala Gly Ile Asp Gly Phe Met Arg Ser Leu Ala
                165                 170                 175
Arg Glu Leu Gly Pro Lys Gly Ile Asn Val Asn Cys Val Ser Pro Gly
                180                 185                 190
Val Thr Arg Thr Ser Met Ala Glu Gly Ile Asp Pro Ser Met Phe Asp
```

```
                    195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 117
<211> LENGTH: 246
<212> TYPE: PRT
<213> ORGANISM: Artificial Sequence
<220> FEATURE:
<223> OTHER INFORMATION: Synthetic

<400> SEQUENCE: 117

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
    50                  55                  60

Gln Leu Asp Leu Ala Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 118
<211> LENGTH: 246
<212> TYPE: PRT
<213> ORGANISM: Artificial Sequence
<220> FEATURE:
<223> OTHER INFORMATION: Synthetic

<400> SEQUENCE: 118
```

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Met Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 119
<211> LENGTH: 246
<212> TYPE: PRT
<213> ORGANISM: Artificial Sequence
<220> FEATURE:
<223> OTHER INFORMATION: Synthetic

<400> SEQUENCE: 119

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Cys Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

```
Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
    195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 120
<211> LENGTH: 246
<212> TYPE: PRT
<213> ORGANISM: Artificial Sequence
<220> FEATURE:
<223> OTHER INFORMATION: Synthetic

<400> SEQUENCE: 120

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Leu Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
    195                 200                 205

Leu Pro Ile Asn Gly Trp Ile Glu Val Asp Ala Ile Ala Asp Ala Val
    210                 215                 220
```

```
Thr Tyr Leu Val Lys Ser Lys Asn Val Thr Gly Thr Val Ser Val
225                 230                 235                 240

Asp Asn Gly Tyr Cys Ala
                245
```

<210> SEQ ID NO 121
<211> LENGTH: 246
<212> TYPE: PRT
<213> ORGANISM: Artificial Sequence
<220> FEATURE:
<223> OTHER INFORMATION: Synthetic

<400> SEQUENCE: 121

```
Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
                20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
210                 215                 220

Thr Tyr Leu Val Lys Ser Lys Asn Val Thr Gly Thr Val Ser Val
225                 230                 235                 240

Asp Asn Gly Tyr Cys Ala
                245
```

<210> SEQ ID NO 122
<211> LENGTH: 246
<212> TYPE: PRT
<213> ORGANISM: Artificial Sequence
<220> FEATURE:
<223> OTHER INFORMATION: Synthetic

<400> SEQUENCE: 122

```
Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
                20                  25                  30
```

```
Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
 50                  55                  60

Gln Leu Asp Leu Ser Asp Val Glu Ala Ala Gly Ser Leu Lys Gly Ala
 65                  70                  75                  80

Pro Leu Pro Ala Ser Ser Tyr Asp Val Phe Val Ser Asn Ala Gly Ile
                 85                  90                  95

Ser Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
            195                 200                 205

Leu Pro Ile Asn Gly Trp Ile Glu Val Asp Ala Ile Ala Asp Ala Val
            210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 123
<211> LENGTH: 246
<212> TYPE: PRT
<213> ORGANISM: Artificial Sequence
<220> FEATURE:
<223> OTHER INFORMATION: Synthetic

<400> SEQUENCE: 123

Met Thr Ser Ser Ser Pro Ser Leu Asn Ala Leu Val Thr Gly Gly
 1               5                  10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
 50                  55                  60

Gln Leu Asp Leu Ser Asp Val Glu Ala Ala Leu Ser Phe Lys Gly Ala
 65                  70                  75                  80

Pro Leu Pro Ala Ser Ser Tyr Asp Val Phe Val Ser Asn Ala Gly Ile
                 85                  90                  95

Ser Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
130                 135                 140
```

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 124
<211> LENGTH: 246
<212> TYPE: PRT
<213> ORGANISM: Artificial Sequence
<220> FEATURE:
<223> OTHER INFORMATION: Synthetic

<400> SEQUENCE: 124

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Cys Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 125
<211> LENGTH: 246
<212> TYPE: PRT
<213> ORGANISM: Artificial Sequence
<220> FEATURE:
<223> OTHER INFORMATION: Synthetic

<400> SEQUENCE: 125

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
                20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Lys Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 126
<211> LENGTH: 246
<212> TYPE: PRT
<213> ORGANISM: Artificial Sequence
<220> FEATURE:
<223> OTHER INFORMATION: Synthetic

<400> SEQUENCE: 126

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
                20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp

```
                50                  55                  60
Gln Leu Asp Leu Ser Asp Val Glu Ala Ala Gly Ser Phe Lys Gly Ala
 65                  70                  75                  80

Pro Leu Pro Ala Ser Ser Tyr Asp Val Phe Val Ser Asn Ala Gly Ile
                 85                  90                  95

Ser Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
                115                 120                 125

Val Lys Ala Ile Ser Asp Lys Pro Arg Gln Thr Pro Ala His Ile Ile
130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
                180                 185                 190

Val Thr Arg Thr Ser Met Ala Glu Gly Ile Asp Pro Ser Met Phe Asp
                195                 200                 205

Leu Pro Ile Pro Gly Trp Ile Glu Val Asp Ala Ile Ala Asp Ala Val
                210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 127
<211> LENGTH: 246
<212> TYPE: PRT
<213> ORGANISM: Artificial Sequence
<220> FEATURE:
<223> OTHER INFORMATION: Synthetic

<400> SEQUENCE: 127

Met Thr Ser Ser Ser Pro Ser Leu Asn Ala Leu Val Thr Gly Gly
 1               5                  10                  15

Ser Arg Gly Ile Gly Glu Ala Ile Ser Met Gln Leu Ala Ala Glu Gly
                 20                  25                  30

Tyr Ser Val Thr Ile Ala Ser Arg Gly Leu Glu Gln Leu Glu Ala Val
                 35                  40                  45

Lys Ala Lys Leu Pro Ile Val Lys Gln Gly Gln Thr His His Val Trp
 50                  55                  60

Gln Leu Asp Leu Ser Asp Val Glu Ala Ala Gly Ser Phe Lys Gly Ala
 65                  70                  75                  80

Pro Leu Pro Ala Ser Ser Tyr Asp Val Phe Val Ser Asn Ala Gly Ile
                 85                  90                  95

Ser Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
                115                 120                 125

Val Lys Ala Ile Ser Asp Lys Pro Arg Gln Thr Pro Ala His Ile Ile
130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
```

165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Ala Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 128
<211> LENGTH: 246
<212> TYPE: PRT
<213> ORGANISM: Artificial Sequence
<220> FEATURE:
<223> OTHER INFORMATION: Synthetic

<400> SEQUENCE: 128

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Lys Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 129
<211> LENGTH: 246
<212> TYPE: PRT

<213> ORGANISM: Artificial Sequence
<220> FEATURE:
<223> OTHER INFORMATION: Synthetic

<400> SEQUENCE: 129

```
Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Cys Val
                115                 120                 125

Val Lys Ala Ile Ser Asp Lys Pro Arg Gln Thr Pro Ala His Ile Ile
130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
                180                 185                 190

Val Thr Arg Thr Ser Met Ala Glu Gly Ile Asp Pro Ser Met Phe Asp
            195                 200                 205

Leu Pro Ile Asn Gly Trp Ile Glu Val Asp Ala Ile Ala Asp Ala Val
            210                 215                 220

Thr Tyr Leu Val Lys Ser Lys Asn Val Thr Gly Thr Thr Val Ser Val
225                 230                 235                 240

Asp Asn Gly Tyr Cys Ala
                245
```

<210> SEQ ID NO 130
<211> LENGTH: 246
<212> TYPE: PRT
<213> ORGANISM: Artificial Sequence
<220> FEATURE:
<223> OTHER INFORMATION: Synthetic

<400> SEQUENCE: 130

```
Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Ser Phe Lys Gly Ala
65                  70                  75                  80
```

```
Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Gly Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 131
<211> LENGTH: 246
<212> TYPE: PRT
<213> ORGANISM: Artificial Sequence
<220> FEATURE:
<223> OTHER INFORMATION: Synthetic

<400> SEQUENCE: 131

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Val Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190
```

```
Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 132
<211> LENGTH: 246
<212> TYPE: PRT
<213> ORGANISM: Artificial Sequence
<220> FEATURE:
<223> OTHER INFORMATION: Synthetic

<400> SEQUENCE: 132

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
                20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Gln Val
            115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
    195                 200                 205

Leu Pro Ile Asn Gly Trp Ile Glu Val Asp Ala Ile Ala Asp Ala Val
        210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 133
<211> LENGTH: 246
<212> TYPE: PRT
<213> ORGANISM: Artificial Sequence
<220> FEATURE:
<223> OTHER INFORMATION: Synthetic

<400> SEQUENCE: 133
```

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
            115                 120                 125

Val Lys Ala Ile Leu Asp Lys Pro Arg Gln Thr Pro Ala His Ile Ile
130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
            195                 200                 205

Leu Pro Ile Asn Gly Trp Ile Glu Val Asp Ala Ile Ala Asp Ala Val
210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 134
<211> LENGTH: 246
<212> TYPE: PRT
<213> ORGANISM: Artificial Sequence
<220> FEATURE:
<223> OTHER INFORMATION: Synthetic

<400> SEQUENCE: 134

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

```
Met Leu Thr Val Asn Leu Thr Ala Pro Ile Ala Leu Thr Lys Ala Val
            115                 120                 125

Val Lys Ala Ile Ala Asp Lys Pro Arg Gln Thr Pro Ala His Ile Ile
        130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 135
<211> LENGTH: 246
<212> TYPE: PRT
<213> ORGANISM: Artificial Sequence
<220> FEATURE:
<223> OTHER INFORMATION: Synthetic

<400> SEQUENCE: 135

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
            115                 120                 125

Val Lys Ala Ile Gln Asp Lys Pro Arg Gln Thr Pro Ala His Ile Ile
        130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
210                 215                 220
```

Thr Tyr Leu Val Lys Ser Lys Asn Val Thr Gly Thr Thr Val Ser Val
225                 230                 235                 240

Asp Asn Gly Tyr Cys Ala
            245

<210> SEQ ID NO 136
<211> LENGTH: 246
<212> TYPE: PRT
<213> ORGANISM: Artificial Sequence
<220> FEATURE:
<223> OTHER INFORMATION: Synthetic

<400> SEQUENCE: 136

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
                35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Met Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
            245

<210> SEQ ID NO 137
<211> LENGTH: 246
<212> TYPE: PRT
<213> ORGANISM: Artificial Sequence
<220> FEATURE:
<223> OTHER INFORMATION: Synthetic

<400> SEQUENCE: 137

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly

```
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Val Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 138
<211> LENGTH: 246
<212> TYPE: PRT
<213> ORGANISM: Artificial Sequence
<220> FEATURE:
<223> OTHER INFORMATION: Synthetic

<400> SEQUENCE: 138

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Val Arg Gln Thr Pro Ala His Ile Ile
```

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 139
<211> LENGTH: 246
<212> TYPE: PRT
<213> ORGANISM: Artificial Sequence
<220> FEATURE:
<223> OTHER INFORMATION: Synthetic

<400> SEQUENCE: 139

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Ala Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala

-continued

245

<210> SEQ ID NO 140
<211> LENGTH: 246
<212> TYPE: PRT
<213> ORGANISM: Artificial Sequence
<220> FEATURE:
<223> OTHER INFORMATION: Synthetic

<400> SEQUENCE: 140

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Thr Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 141
<211> LENGTH: 246
<212> TYPE: PRT
<213> ORGANISM: Artificial Sequence
<220> FEATURE:
<223> OTHER INFORMATION: Synthetic

<400> SEQUENCE: 141

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

```
Lys Ala Lys Leu Pro Ile Val Lys Gln Gly Gln Thr His His Val Trp
 50                  55                  60

Gln Leu Asp Leu Ser Asp Val Glu Ala Ala Gly Ser Phe Lys Gly Ala
 65                  70                  75                  80

Pro Leu Pro Ala Ser Ser Tyr Asp Val Phe Val Ser Asn Ala Gly Ile
                 85                  90                  95

Ser Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
            115                 120                 125

Val Lys Ala Ile Ser Asp Lys Gly Arg Gln Thr Pro Ala His Ile Ile
        130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 142
<211> LENGTH: 246
<212> TYPE: PRT
<213> ORGANISM: Artificial Sequence
<220> FEATURE:
<223> OTHER INFORMATION: Synthetic

<400> SEQUENCE: 142

Met Thr Ser Ser Ser Pro Ser Leu Asn Ala Leu Val Thr Gly Gly
 1               5                  10                  15

Ser Arg Gly Ile Gly Glu Ala Ile Ser Met Gln Leu Ala Ala Glu Gly
                 20                  25                  30

Tyr Ser Val Thr Ile Ala Ser Arg Gly Leu Glu Gln Leu Glu Ala Val
             35                  40                  45

Lys Ala Lys Leu Pro Ile Val Lys Gln Gly Gln Thr His His Val Trp
 50                  55                  60

Gln Leu Asp Leu Ser Asp Val Glu Ala Ala Gly Ser Phe Lys Gly Ala
 65                  70                  75                  80

Pro Leu Pro Ala Ser Ser Tyr Asp Val Phe Val Ser Asn Ala Gly Ile
                 85                  90                  95

Ser Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Ser Thr Pro Ala His Ile Ile
        130                 135                 140

Phe Ile Ser Thr Gly Leu Ser Lys Arg Gly Ala Pro Met Val Gly Val
145                 150                 155                 160
```

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 143
<211> LENGTH: 246
<212> TYPE: PRT
<213> ORGANISM: Artificial Sequence
<220> FEATURE:
<223> OTHER INFORMATION: Synthetic

<400> SEQUENCE: 143

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
        130                 135                 140

Phe Ile Ser Thr Gly Leu Ser Lys Arg Gly Trp Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 144
<211> LENGTH: 246

```
<212> TYPE: PRT
<213> ORGANISM: Artificial Sequence
<220> FEATURE:
<223> OTHER INFORMATION: Synthetic

<400> SEQUENCE: 144
```

| Met<br>1 | Thr | Ser | Ser | Ser<br>5 | Pro | Ser | Leu | Asn | Ala<br>10 | Leu | Val | Thr | Gly | Gly<br>15 |

| Ser | Arg | Gly | Ile<br>20 | Gly | Glu | Ala | Ile | Ser<br>25 | Met | Gln | Leu | Ala | Ala<br>30 | Glu | Gly |

| Tyr | Ser | Val<br>35 | Thr | Ile | Ala | Ser | Arg<br>40 | Gly | Leu | Glu | Gln | Leu<br>45 | Glu | Ala | Val |

| Lys | Ala<br>50 | Lys | Leu | Pro | Ile | Val<br>55 | Lys | Gln | Gly | Gln | Thr<br>60 | His | His | Val | Trp |

| Gln<br>65 | Leu | Asp | Leu | Ser | Asp<br>70 | Val | Glu | Ala | Ala | Gly<br>75 | Ser | Phe | Lys | Gly | Ala<br>80 |

| Pro | Leu | Pro | Ala | Ser<br>85 | Ser | Tyr | Asp | Val | Phe<br>90 | Val | Ser | Asn | Ala | Gly<br>95 | Ile |

| Ser | Gln | Phe | Ser<br>100 | Pro | Ile | Ala | Glu | His<br>105 | Ala | Asp | Ala | Asp | Trp<br>110 | Gln | Asn |

| Met | Leu | Thr<br>115 | Val | Asn | Leu | Thr | Ala<br>120 | Pro | Ile | Ala | Leu | Thr<br>125 | Lys | Ala | Val |

| Val | Lys<br>130 | Ala | Ile | Ser | Asp | Lys<br>135 | Pro | Arg | Gln | Thr | Pro<br>140 | Ala | His | Ile | Ile |

| Phe | Ile<br>145 | Ser | Thr | Gly | Leu | Ser<br>150 | Lys | Arg | Gly | Ala | Pro<br>155 | Met | Met | Gly | Val<br>160 |

| Tyr | Ser | Ala | Ser | Lys<br>165 | Ala | Gly | Ile | Asp | Gly<br>170 | Phe | Met | Arg | Ser | Leu<br>175 | Ala |

| Arg | Glu | Leu | Gly<br>180 | Pro | Lys | Gly | Ile | Asn<br>185 | Val | Asn | Cys | Val | Ser<br>190 | Pro | Gly |

| Val | Thr | Arg<br>195 | Thr | Ser | Met | Ala | Glu<br>200 | Gly | Ile | Asp | Pro | Ser<br>205 | Met | Phe | Asp |

| Leu | Pro<br>210 | Ile | Asn | Gly | Trp | Ile<br>215 | Glu | Val | Asp | Ala | Ile<br>220 | Ala | Asp | Ala | Val |

| Thr<br>225 | Tyr | Leu | Val | Lys | Ser<br>230 | Lys | Asn | Val | Thr | Gly<br>235 | Thr | Thr | Val | Ser | Val<br>240 |

| Asp | Asn | Gly | Tyr | Cys<br>245 | Ala |

```
<210> SEQ ID NO 145
<211> LENGTH: 246
<212> TYPE: PRT
<213> ORGANISM: Artificial Sequence
<220> FEATURE:
<223> OTHER INFORMATION: Synthetic

<400> SEQUENCE: 145
```

| Met<br>1 | Thr | Ser | Ser | Ser<br>5 | Pro | Ser | Leu | Asn | Ala<br>10 | Leu | Val | Thr | Gly | Gly<br>15 |

| Ser | Arg | Gly | Ile<br>20 | Gly | Glu | Ala | Ile | Ser<br>25 | Met | Gln | Leu | Ala | Ala<br>30 | Glu | Gly |

| Tyr | Ser | Val<br>35 | Thr | Ile | Ala | Ser | Arg<br>40 | Gly | Leu | Glu | Gln | Leu<br>45 | Glu | Ala | Val |

| Lys | Ala<br>50 | Lys | Leu | Pro | Ile | Val<br>55 | Lys | Gln | Gly | Gln | Thr<br>60 | His | His | Val | Trp |

| Gln<br>65 | Leu | Asp | Leu | Ser | Asp<br>70 | Val | Glu | Ala | Ala | Gly<br>75 | Ser | Phe | Lys | Gly | Ala<br>80 |

```
Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Ala Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 146
<211> LENGTH: 246
<212> TYPE: PRT
<213> ORGANISM: Artificial Sequence
<220> FEATURE:
<223> OTHER INFORMATION: Synthetic

<400> SEQUENCE: 146

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190
```

```
Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 147
<211> LENGTH: 246
<212> TYPE: PRT
<213> ORGANISM: Artificial Sequence
<220> FEATURE:
<223> OTHER INFORMATION: Synthetic

<400> SEQUENCE: 147

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
                20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Glu Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 148
<211> LENGTH: 246
<212> TYPE: PRT
<213> ORGANISM: Artificial Sequence
<220> FEATURE:
<223> OTHER INFORMATION: Synthetic
```

```
<400> SEQUENCE: 148

Met Thr Ser Ser Ser Pro Ser Leu Asn Ala Leu Val Thr Gly Gly
 1               5                  10                  15

Ser Arg Gly Ile Gly Glu Ala Ile Ser Met Gln Leu Ala Ala Glu Gly
                20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
 50                  55                  60

Gln Leu Asp Leu Ser Asp Val Glu Ala Ala Gly Ser Phe Lys Gly Ala
 65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
               100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Cys Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 149
<211> LENGTH: 246
<212> TYPE: PRT
<213> ORGANISM: Artificial Sequence
<220> FEATURE:
<223> OTHER INFORMATION: Synthetic

<400> SEQUENCE: 149

Met Thr Ser Ser Ser Pro Ser Leu Asn Ala Leu Val Thr Gly Gly
 1               5                  10                  15

Ser Arg Gly Ile Gly Glu Ala Ile Ser Met Gln Leu Ala Ala Glu Gly
                20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
 50                  55                  60

Gln Leu Asp Leu Ser Asp Val Glu Ala Ala Gly Ser Phe Lys Gly Ala
 65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
```

```
            100                 105                 110
Met Leu Thr Val Asn Leu Thr Ala Pro Ile Ala Leu Thr Lys Ala Val
                115                 120                 125

Val Lys Ala Ile Ser Asp Lys Pro Arg Gln Thr Pro Ala His Ile Ile
        130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
            210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 150
<211> LENGTH: 246
<212> TYPE: PRT
<213> ORGANISM: Artificial Sequence
<220> FEATURE:
<223> OTHER INFORMATION: Synthetic

<400> SEQUENCE: 150

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Val Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
```

```
                210                 215                 220
Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 151
<211> LENGTH: 246
<212> TYPE: PRT
<213> ORGANISM: Artificial Sequence
<220> FEATURE:
<223> OTHER INFORMATION: Synthetic

<400> SEQUENCE: 151

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
                20                  25                  30

Tyr Ser Val Thr Ile Ala Ser Arg Gly Leu Glu Gln Leu Glu Ala Val
                35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
                115                 120                 125

Val Lys Ala Ile Ser Asp Lys Pro Arg Gln Thr Pro Ala His Ile Ile
130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Trp Lys Gly Ile Asn Val Asn Cys Val Ser Pro Gly
                180                 185                 190

Val Thr Arg Thr Ser Met Ala Glu Gly Ile Asp Pro Ser Met Phe Asp
                195                 200                 205

Leu Pro Ile Asn Gly Trp Ile Glu Val Asp Ala Ile Ala Asp Ala Val
                210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 152
<211> LENGTH: 246
<212> TYPE: PRT
<213> ORGANISM: Artificial Sequence
<220> FEATURE:
<223> OTHER INFORMATION: Synthetic

<400> SEQUENCE: 152

Met Thr Ser Ser Ser Pro Ser Leu Asn Ala Leu Val Thr Gly Gly
1               5                   10                  15
```

```
Ser Arg Gly Ile Gly Glu Ala Ile Ser Met Gln Leu Ala Ala Glu Gly
             20                  25                  30

Tyr Ser Val Thr Ile Ala Ser Arg Gly Leu Glu Gln Leu Glu Ala Val
         35                  40                  45

Lys Ala Lys Leu Pro Ile Val Lys Gln Gly Gln Thr His His Val Trp
 50                  55                  60

Gln Leu Asp Leu Ser Asp Val Glu Ala Ala Gly Ser Phe Lys Gly Ala
 65                  70                  75                  80

Pro Leu Pro Ala Ser Ser Tyr Asp Val Phe Val Ser Asn Ala Gly Ile
                 85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Leu Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 153
<211> LENGTH: 246
<212> TYPE: PRT
<213> ORGANISM: Artificial Sequence
<220> FEATURE:
<223> OTHER INFORMATION: Synthetic

<400> SEQUENCE: 153

Met Thr Ser Ser Ser Pro Ser Leu Asn Ala Leu Val Thr Gly Gly
 1               5                  10                  15

Ser Arg Gly Ile Gly Glu Ala Ile Ser Met Gln Leu Ala Ala Glu Gly
             20                  25                  30

Tyr Ser Val Thr Ile Ala Ser Arg Gly Leu Glu Gln Leu Glu Ala Val
         35                  40                  45

Lys Ala Lys Leu Pro Ile Val Lys Gln Gly Gln Thr His His Val Trp
 50                  55                  60

Gln Leu Asp Leu Ser Asp Val Glu Ala Ala Gly Ser Phe Lys Gly Ala
 65                  70                  75                  80

Pro Leu Pro Ala Ser Ser Tyr Asp Val Phe Val Ser Asn Ala Gly Ile
                 85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125
```

Val Lys Ala Ile Ser Asp Lys Pro Arg Gln Thr Pro Ala His Ile Ile
130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Ile Gly Ile Asn Val Asn Cys Val Ser Pro Gly
                180                 185                 190

Val Thr Arg Thr Ser Met Ala Glu Gly Ile Asp Pro Ser Met Phe Asp
                195                 200                 205

Leu Pro Ile Asn Gly Trp Ile Glu Val Asp Ala Ile Ala Asp Ala Val
                210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 154
<211> LENGTH: 246
<212> TYPE: PRT
<213> ORGANISM: Artificial Sequence
<220> FEATURE:
<223> OTHER INFORMATION: Synthetic

<400> SEQUENCE: 154

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
                20                  25                  30

Tyr Ser Val Thr Ile Ala Ser Arg Gly Leu Glu Gln Leu Glu Ala Val
                35                  40                  45

Lys Ala Lys Leu Pro Ile Val Lys Gln Gly Gln Thr His His Val Trp
            50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
                100                 105                 110

Met Val Thr Val Asn Leu Thr Ala Pro Ile Ala Leu Thr Lys Ala Val
                115                 120                 125

Val Lys Ala Ile Ser Asp Lys Pro Arg Gln Thr Pro Ala His Ile Ile
130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
                180                 185                 190

Val Thr Arg Thr Ser Met Ala Glu Gly Ile Asp Pro Ser Met Phe Asp
                195                 200                 205

Leu Pro Ile Asn Gly Trp Ile Glu Val Asp Ala Ile Ala Asp Ala Val
                210                 215                 220

Thr Tyr Leu Val Lys Ser Lys Asn Val Thr Gly Thr Thr Val Ser Val
225                 230                 235                 240

Asp Asn Gly Tyr Cys Ala
            245

<210> SEQ ID NO 155
<211> LENGTH: 246
<212> TYPE: PRT
<213> ORGANISM: Artificial Sequence
<220> FEATURE:
<223> OTHER INFORMATION: Synthetic

<400> SEQUENCE: 155

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
                20                  25                  30

Tyr Ser Val Thr Ile Ala Ser Arg Gly Leu Glu Gln Leu Glu Ala Val
                35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
                100                 105                 110

Met Ile Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
                180                 185                 190

Val Thr Arg Thr Ser Met Ala Glu Gly Ile Asp Pro Ser Met Phe Asp
            195                 200                 205

Leu Pro Ile Asn Gly Trp Ile Glu Val Asp Ala Ile Ala Asp Ala Val
        210                 215                 220

Thr Tyr Leu Val Lys Ser Lys Asn Val Thr Gly Thr Thr Val Ser Val
225                 230                 235                 240

Asp Asn Gly Tyr Cys Ala
            245

<210> SEQ ID NO 156
<211> LENGTH: 246
<212> TYPE: PRT
<213> ORGANISM: Artificial Sequence
<220> FEATURE:
<223> OTHER INFORMATION: Synthetic

<400> SEQUENCE: 156

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
                20                  25                  30

Tyr Ser Val Thr Ile Ala Ser Arg Gly Leu Glu Gln Leu Glu Ala Val
                35                  40                  45

```
Lys Ala Lys Leu Pro Ile Val Lys Gln Gly Gln Thr His His Val Trp
 50                  55                  60

Gln Leu Asp Leu Ser Asp Val Glu Ala Ala Gly Ser Phe Lys Gly Ala
 65                  70                  75                  80

Pro Leu Pro Ala Ser Ser Tyr Asp Val Phe Val Ser Asn Ala Gly Ile
                 85                  90                  95

Ser Gln Phe Ser Pro Ile Ala Glu His Ala Asp Ala Asp Trp Gln Asn
            100                 105                 110

Met Leu Thr Val Asn Leu Thr Gly Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 157
<211> LENGTH: 246
<212> TYPE: PRT
<213> ORGANISM: Artificial Sequence
<220> FEATURE:
<223> OTHER INFORMATION: Synthetic

<400> SEQUENCE: 157

Met Thr Ser Ser Ser Pro Ser Leu Asn Ala Leu Val Thr Gly Gly
 1               5                  10                  15

Ser Arg Gly Ile Gly Glu Ala Ile Ser Met Gln Leu Ala Ala Glu Gly
                20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
 50                  55                  60

Gln Leu Asp Leu Ser Asp Val Glu Ala Ala Gly Ser Phe Lys Gly Ala
 65                  70                  75                  80

Pro Leu Pro Ala Ser Ser Tyr Asp Val Phe Val Ser Asn Ala Gly Ile
                 85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Val Pro Ala His Ile Ile
    130                 135                 140

Phe Ile Ser Thr Gly Leu Ser Lys Arg Gly Ala Pro Met Val Gly Val
145                 150                 155                 160
```

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 158
<211> LENGTH: 246
<212> TYPE: PRT
<213> ORGANISM: Artificial Sequence
<220> FEATURE:
<223> OTHER INFORMATION: Synthetic

<400> SEQUENCE: 158

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Phe Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 159

<211> LENGTH: 246
<212> TYPE: PRT
<213> ORGANISM: Artificial Sequence
<220> FEATURE:
<223> OTHER INFORMATION: Synthetic

<400> SEQUENCE: 159

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
                35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Lys Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 160
<211> LENGTH: 246
<212> TYPE: PRT
<213> ORGANISM: Artificial Sequence
<220> FEATURE:
<223> OTHER INFORMATION: Synthetic

<400> SEQUENCE: 160

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
                35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala

```
                65                  70                  75                  80
Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
                115                 120                 125

Val Lys Ala Ile Ser Asp Lys Pro Arg Gln Thr Pro Ser His Ile Ile
                130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
                180                 185                 190

Val Thr Arg Thr Ser Met Ala Glu Gly Ile Asp Pro Ser Met Phe Asp
                195                 200                 205

Leu Pro Ile Asn Gly Trp Ile Glu Val Asp Ala Ile Ala Asp Ala Val
                210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 161
<211> LENGTH: 246
<212> TYPE: PRT
<213> ORGANISM: Artificial Sequence
<220> FEATURE:
<223> OTHER INFORMATION: Synthetic

<400> SEQUENCE: 161

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
                20                  25                  30

Tyr Ser Val Thr Ile Ala Ser Arg Gly Leu Glu Gln Leu Glu Ala Val
                35                  40                  45

Lys Ala Lys Leu Pro Ile Val Lys Gln Gly Gln Thr His His Val Trp
                50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
                115                 120                 125

Val Lys Ala Ile Ser Asp Lys Pro Arg Gln Thr Pro Ala His Ile Ile
                130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Arg Val Asn Cys Val Ser Pro Gly
```

```
                    180                 185                 190
Val Thr Arg Thr Ser Met Ala Glu Gly Ile Asp Pro Ser Met Phe Asp
                195                 200                 205

Leu Pro Ile Asn Gly Trp Ile Glu Val Asp Ala Ile Ala Asp Ala Val
            210                 215                 220

Thr Tyr Leu Val Lys Ser Lys Asn Val Thr Gly Thr Val Ser Val
225                 230                 235                 240

Asp Asn Gly Tyr Cys Ala
                245

<210> SEQ ID NO 162
<211> LENGTH: 246
<212> TYPE: PRT
<213> ORGANISM: Artificial Sequence
<220> FEATURE:
<223> OTHER INFORMATION: Synthetic: Variant

<400> SEQUENCE: 162

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Met Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Val Ser Val
225                 230                 235                 240

Asp Asn Gly Tyr Cys Ala
                245

<210> SEQ ID NO 163
<211> LENGTH: 246
<212> TYPE: PRT
<213> ORGANISM: Artificial Sequence
<220> FEATURE:
<223> OTHER INFORMATION: Synthetic: Variant
```

<400> SEQUENCE: 163

| | | | | | | | | | | | | | | |
|---|---|---|---|---|---|---|---|---|---|---|---|---|---|---|
Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Leu Cys Ala
                245

<210> SEQ ID NO 164
<211> LENGTH: 246
<212> TYPE: PRT
<213> ORGANISM: Artificial Sequence
<220> FEATURE:
<223> OTHER INFORMATION: Synthetic: Variant

<400> SEQUENCE: 164

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

```
Ser Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
        130                 135                 140

Phe Ile Ser Thr Ile Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Pro Ile Asn Gly Trp Ile Glu Val Asp Ala Ile Ala Asp Ala Val
210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 165
<211> LENGTH: 246
<212> TYPE: PRT
<213> ORGANISM: Artificial Sequence
<220> FEATURE:
<223> OTHER INFORMATION: Synthetic: Variant

<400> SEQUENCE: 165

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
        130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205
```

```
Leu Cys Ile Asn Gly Trp Ile Glu Val Asp Ala Ile Ala Asp Ala Val
            210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 166
<211> LENGTH: 246
<212> TYPE: PRT
<213> ORGANISM: Artificial Sequence
<220> FEATURE:
<223> OTHER INFORMATION: Synthetic: Variant

<400> SEQUENCE: 166

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
                20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Met Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Cys Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 167
<211> LENGTH: 246
<212> TYPE: PRT
<213> ORGANISM: Artificial Sequence
<220> FEATURE:
<223> OTHER INFORMATION: Synthetic: Variant

<400> SEQUENCE: 167

Met Thr Ser Ser Ser Pro Ser Leu Asn Ala Leu Val Thr Gly Gly
1               5                   10                  15
```

```
Ser Arg Gly Ile Gly Glu Ala Ile Ser Met Gln Leu Ala Ala Glu Gly
             20                  25                  30

Tyr Ser Val Thr Ile Ala Ser Arg Gly Leu Glu Gln Leu Glu Ala Val
         35                  40                  45

Lys Ala Lys Leu Pro Ile Val Lys Gln Gly Gln Thr His His Val Trp
 50                  55                  60

Gln Leu Asp Leu Ser Asp Val Glu Ala Ala Gly Ser Phe Lys Gly Ala
 65                  70                  75                  80

Pro Leu Pro Ala Ser Ser Tyr Asp Val Phe Val Ser Asn Ala Gly Ile
                 85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
130                 135                 140

Phe Ile Ser Thr Cys Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Cys Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 168
<211> LENGTH: 246
<212> TYPE: PRT
<213> ORGANISM: Artificial Sequence
<220> FEATURE:
<223> OTHER INFORMATION: Synthetic: Variant

<400> SEQUENCE: 168

Met Thr Ser Ser Ser Pro Ser Leu Asn Ala Leu Val Thr Gly Gly
 1               5                  10                  15

Ser Arg Gly Ile Gly Glu Ala Ile Ser Met Gln Leu Ala Ala Glu Gly
             20                  25                  30

Tyr Ser Val Thr Ile Ala Ser Arg Gly Leu Glu Gln Leu Glu Ala Val
         35                  40                  45

Lys Ala Lys Leu Pro Ile Val Lys Gln Gly Gln Thr His His Val Trp
 50                  55                  60

Gln Leu Asp Leu Ser Asp Val Glu Ala Ala Gly Ser Phe Lys Gly Ala
 65                  70                  75                  80

Pro Leu Pro Ala Ser Ser Tyr Asp Val Phe Val Ser Asn Ala Gly Ile
                 85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
            115                 120                 125
```

```
Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Ala Gly Ile Asp Pro Ser Asp Phe Asp
        195                 200                 205

Leu Cys Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 169
<211> LENGTH: 246
<212> TYPE: PRT
<213> ORGANISM: Artificial Sequence
<220> FEATURE:
<223> OTHER INFORMATION: Synthetic: Variant

<400> SEQUENCE: 169

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
                20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
        50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Arg Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Cys Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240
```

Asp Asn Gly Tyr Cys Ala
              245

<210> SEQ ID NO 170
<211> LENGTH: 246
<212> TYPE: PRT
<213> ORGANISM: Artificial Sequence
<220> FEATURE:
<223> OTHER INFORMATION: Synthetic: Variant

<400> SEQUENCE: 170

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Asp Phe Asp
            195                 200                 205

Leu Cys Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
              245

<210> SEQ ID NO 171
<211> LENGTH: 246
<212> TYPE: PRT
<213> ORGANISM: Artificial Sequence
<220> FEATURE:
<223> OTHER INFORMATION: Synthetic: Variant

<400> SEQUENCE: 171

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val

```
                35                  40                  45
Lys Ala Lys Leu Pro Ile Val Lys Gln Gly Gln Thr His His Val Trp
         50                  55                  60
Gln Leu Asp Leu Ser Asp Val Glu Ala Ala Gly Ser Phe Lys Gly Ala
 65                  70                  75                  80
Pro Leu Pro Ala Ser Ser Tyr Asp Val Phe Val Ser Asn Ala Gly Ile
                 85                  90                  95
Ser Gln Phe Arg Pro Ile Ala Glu His Ala Asp Ala Asp Trp Gln Asn
                100                 105                 110
Met Leu Thr Val Asn Leu Thr Ala Pro Ile Ala Leu Thr Lys Ala Val
            115                 120                 125
Val Lys Ala Ile Ser Asp Lys Pro Arg Gln Thr Pro Ala His Ile Ile
        130                 135                 140
Phe Ile Ser Thr Met Leu Ser Lys Arg Gly Ala Pro Met Val Gly Val
145                 150                 155                 160
Tyr Ser Ala Ser Lys Ala Gly Ile Asp Gly Phe Met Arg Ser Leu Ala
                165                 170                 175
Arg Glu Leu Gly Pro Lys Gly Ile Asn Val Asn Cys Val Ser Pro Gly
                180                 185                 190
Val Thr Arg Thr Ser Met Ala Ala Gly Ile Asp Pro Ser Met Phe Asp
            195                 200                 205
Leu Cys Ile Asn Gly Trp Ile Glu Val Asp Ala Ile Ala Asp Ala Val
        210                 215                 220
Thr Tyr Leu Val Lys Ser Lys Phe Val Thr Gly Thr Thr Val Ser Val
225                 230                 235                 240
Asp Asn Gly Tyr Cys Ala
                245

<210> SEQ ID NO 172
<211> LENGTH: 246
<212> TYPE: PRT
<213> ORGANISM: Artificial Sequence
<220> FEATURE:
<223> OTHER INFORMATION: Synthetic: Variant

<400> SEQUENCE: 172

Met Thr Ser Ser Ser Pro Ser Leu Asn Ala Leu Val Thr Gly Gly
 1               5                  10                  15
Ser Arg Gly Ile Gly Glu Ala Ile Ser Met Gln Leu Ala Ala Glu Gly
                 20                  25                  30
Tyr Ser Val Thr Ile Ala Ser Arg Gly Leu Glu Gln Leu Glu Ala Val
             35                  40                  45
Lys Ala Lys Leu Pro Ile Val Lys Gln Gly Gln Thr His His Val Trp
         50                  55                  60
Gln Leu Asp Leu Ser Asp Val Glu Ala Ala Gly Ser Phe Lys Gly Ala
 65                  70                  75                  80
Pro Leu Pro Ala Ser Ser Tyr Asp Val Phe Val Ser Asn Ala Gly Ile
                 85                  90                  95
Ser Gln Phe Arg Pro Ile Ala Glu His Ala Asp Ala Asp Trp Gln Asn
                100                 105                 110
Met Leu Thr Val Asn Leu Thr Ala Val Ile Ala Leu Thr Lys Ala Val
            115                 120                 125
Val Lys Ala Ile Ser Asp Lys Pro Arg Gln Thr Pro Ala His Ile Ile
        130                 135                 140
Phe Ile Ser Thr Met Leu Ser Lys Arg Gly Ala Pro Asp Val Gly Val
```

```
            145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Cys Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 173
<211> LENGTH: 246
<212> TYPE: PRT
<213> ORGANISM: Artificial Sequence
<220> FEATURE:
<223> OTHER INFORMATION: Synthetic: Variant

<400> SEQUENCE: 173

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
                20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
        50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Ser Gln Phe Arg Pro Ile Ala Glu His Ala Asp Ala Asp Trp Gln Asn
            100                 105                 110

Met Leu Thr Val Asn Leu Thr Ala Val Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Cys Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245
```

-continued

<210> SEQ ID NO 174
<211> LENGTH: 246
<212> TYPE: PRT
<213> ORGANISM: Artificial Sequence
<220> FEATURE:
<223> OTHER INFORMATION: Synthetic: Variant

<400> SEQUENCE: 174

```
Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Cys Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Asp Phe Asp
        195                 200                 205

Leu Cys Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245
```

<210> SEQ ID NO 175
<211> LENGTH: 246
<212> TYPE: PRT
<213> ORGANISM: Artificial Sequence
<220> FEATURE:
<223> OTHER INFORMATION: Synthetic: Variant

<400> SEQUENCE: 175

```
Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
50                  55                  60
```

```
Gln Leu Asp Leu Ser Asp Val Glu Ala Ala Gly Ser Phe Lys Gly Ala
 65                  70                  75                  80

Pro Leu Pro Ala Ser Ser Tyr Asp Val Phe Val Ser Asn Ala Gly Ile
                 85                  90                  95

Cys Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Ala Gly Ile Asp Pro Ser Asp Phe Asp
        195                 200                 205

Leu Cys Ile Asn Gly Trp Ile Glu Val Asp Ala Ile Ala Asp Ala Val
    210                 215                 220

Thr Tyr Leu Val Lys Ser Lys Asn Val Thr Gly Thr Thr Val Ser Val
225                 230                 235                 240

Asp Asn Gly Tyr Cys Ala
                245

<210> SEQ ID NO 176
<211> LENGTH: 246
<212> TYPE: PRT
<213> ORGANISM: Artificial Sequence
<220> FEATURE:
<223> OTHER INFORMATION: Synthetic: Variant

<400> SEQUENCE: 176

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
 65                 70                  75                  80

Pro Leu Pro Ala Ser Ser Tyr Asp Val Phe Val Ser Asn Ala Gly Ile
                 85                  90                  95

Cys Gln Phe Ser Pro Ile Ala Glu His Ala Asp Ala Asp Trp Gln Asn
            100                 105                 110

Met Leu Thr Val Asn Leu Thr Ala Val Ile Ala Leu Thr Lys Ala Val
        115                 120                 125

Val Lys Ala Ile Ser Asp Lys Pro Arg Gln Thr Pro Ala His Ile Ile
    130                 135                 140

Phe Ile Ser Thr Met Leu Ser Lys Arg Gly Ala Pro Asp Val Gly Val
145                 150                 155                 160

Tyr Ser Ala Ser Lys Ala Gly Ile Asp Gly Phe Met Arg Ser Leu Ala
                165                 170                 175
```

Arg Glu Leu Gly Pro Lys Gly Ile Asn Val Asn Cys Val Ser Pro Gly
                180                 185                 190

Val Thr Arg Thr Ser Met Ala Glu Gly Ile Asp Pro Ser Asp Phe Asp
            195                 200                 205

Leu Cys Ile Asn Gly Trp Ile Glu Val Asp Ala Ile Ala Asp Ala Val
        210                 215                 220

Thr Tyr Leu Val Lys Ser Lys Phe Val Thr Gly Thr Thr Val Ser Val
225                 230                 235                 240

Asp Asn Gly Tyr Cys Ala
                245

<210> SEQ ID NO 177
<211> LENGTH: 246
<212> TYPE: PRT
<213> ORGANISM: Artificial Sequence
<220> FEATURE:
<223> OTHER INFORMATION: Synthetic: Variant

<400> SEQUENCE: 177

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
                20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
        50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Cys Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
        130                 135                 140

Phe Ile Ser Thr Met Leu Ser Lys Arg Gly Ala Pro Asp Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Asp Phe Asp
        195                 200                 205

Leu Pro Ile Asn Gly Trp Ile Glu Val Asp Ala Ile Ala Asp Ala Val
    210                 215                 220

Thr Tyr Leu Val Lys Ser Lys Phe Val Thr Gly Thr Thr Val Ser Val
225                 230                 235                 240

Asp Asn Gly Tyr Cys Ala
                245

<210> SEQ ID NO 178
<211> LENGTH: 246
<212> TYPE: PRT
<213> ORGANISM: Artificial Sequence
<220> FEATURE:

<223> OTHER INFORMATION: Synthetic: Variant

<400> SEQUENCE: 178

```
Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
        35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Cys Gln Phe Ser Pro Ile Ala Glu His Ala Asp Ala Asp Trp Gln Asn
            100                 105                 110

Met Leu Thr Val Asn Leu Thr Ala Pro Ile Ala Leu Thr Lys Ala Val
        115                 120                 125

Val Lys Ala Ile Ser Asp Lys Pro Arg Gln Thr Pro Ala His Ile Ile
130                 135                 140

Phe Ile Ser Thr Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
        195                 200                 205

Leu Cys Ile Asn Gly Trp Ile Glu Val Asp Ala Ile Ala Asp Ala Val
210                 215                 220

Thr Tyr Leu Val Lys Ser Lys Asn Val Thr Gly Thr Thr Val Ser Val
225                 230                 235                 240

Asp Asn Gly Tyr Cys Ala
                245
```

<210> SEQ ID NO 179
<211> LENGTH: 246
<212> TYPE: PRT
<213> ORGANISM: Artificial Sequence
<220> FEATURE:
<223> OTHER INFORMATION: Synthetic: Variant

<400> SEQUENCE: 179

```
Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Lys Gln Leu Glu Ala Val
        35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95
```

```
Cys Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
130                 135                 140

Phe Ile Ser Ser Gly Leu Ser Lys Arg Gly Ala Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Val Arg Thr Ser Met Ala Glu Gly Ile Asp Pro Ser Met Phe Asp
            195                 200                 205

Leu Cys Ile Asn Gly Trp Ile Glu Val Asp Ala Ile Ala Asp Ala Val
            210                 215                 220

Thr Tyr Val Val Lys Ser Lys Asn Val Thr Gly Thr Thr Val Ser Val
225                 230                 235                 240

Asp Asn Gly Tyr Cys Ala
                245
```

<210> SEQ ID NO 180
<211> LENGTH: 246
<212> TYPE: PRT
<213> ORGANISM: Artificial Sequence
<220> FEATURE:
<223> OTHER INFORMATION: Synthetic: Variant

<400> SEQUENCE: 180

```
Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
            20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Cys Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
130                 135                 140

Phe Ile Ser Ser Gly Leu Ser Lys Arg Gly His Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
            195                 200                 205
```

-continued

Leu Cys Ile Asn Gly Trp Ile Glu Val Asp Ala Ile Ala Asp Ala Val
        210                 215                 220

Thr Tyr Val Val Lys Ser Lys Asn Val Thr Gly Thr Thr Val Ser Val
225                 230                 235                 240

Asp Asn Gly Tyr Cys Ala
                245

<210> SEQ ID NO 181
<211> LENGTH: 246
<212> TYPE: PRT
<213> ORGANISM: Artificial Sequence
<220> FEATURE:
<223> OTHER INFORMATION: Synthetic: Variant

<400> SEQUENCE: 181

Met Thr Ser Ser Ser Pro Ser Leu Asn Ala Leu Val Thr Gly Gly
1               5                   10                  15

Ser Arg Gly Ile Gly Glu Ala Ile Ser Met Gln Leu Ala Ala Glu Gly
                20                  25                  30

Tyr Ser Val Thr Ile Ala Ser Arg Gly Leu Glu Gln Leu Glu Ala Val
            35                  40                  45

Lys Ala Lys Leu Pro Ile Val Lys Gln Gly Gln Thr His His Val Trp
    50                  55                  60

Gln Leu Asp Leu Ser Asp Val Glu Ala Ala Gly Ser Phe Lys Gly Ala
65                  70                  75                  80

Pro Leu Pro Ala Ser Ser Tyr Asp Val Phe Val Ser Asn Ala Gly Ile
                85                  90                  95

Cys Gln Phe Ser Pro Ile Ala Glu His Ala Asp Ala Asp Trp Gln Asn
                100                 105                 110

Met Leu Thr Val Asn Leu Thr Ala Pro Ile Ala Leu Thr Lys Ala Val
            115                 120                 125

Val Lys Ala Ile Ser Asp Lys Pro Arg Gln Thr Pro Ala His Ile Ile
    130                 135                 140

Phe Ile Ser Ser Gly Leu Ser Lys Arg Gly His Pro Met Val Gly Val
145                 150                 155                 160

Tyr Ser Ala Ser Lys Ala Gly Ile Asp Gly Phe Met Arg Ser Leu Ala
                165                 170                 175

Arg Glu Leu Gly Pro Lys Gly Ile Asn Val Asn Cys Val Ser Pro Gly
            180                 185                 190

Val Thr Arg Thr Ser Met Ala Glu Gly Ile Asp Pro Ser Met Phe Asp
    195                 200                 205

Leu Cys Ile Asn Gly Trp Ile Glu Val Asp Ala Ile Ala Asp Ala Val
        210                 215                 220

Thr Tyr Val Val Lys Ser Lys Asn Val Thr Gly Thr Thr Val Ser Val
225                 230                 235                 240

Asp Asn Gly Phe Cys Ala
                245

<210> SEQ ID NO 182
<211> LENGTH: 246
<212> TYPE: PRT
<213> ORGANISM: Artificial Sequence
<220> FEATURE:
<223> OTHER INFORMATION: Synthetic: Variant

<400> SEQUENCE: 182

Met Thr Ser Ser Ser Ser Pro Ser Leu Asn Ala Leu Val Thr Gly Gly

-continued

```
1               5                   10                  15
Ser Arg Gly Ile Gly Glu Ala Ile Ser Met Gln Leu Ala Ala Glu Gly
            20                  25                  30
Tyr Ser Val Thr Ile Ala Ser Arg Gly Leu Lys Gln Leu Glu Ala Val
            35                  40                  45
Lys Ala Lys Leu Pro Ile Val Lys Gln Gly Gln Thr His His Val Trp
 50                  55                  60
Gln Leu Asp Leu Ser Asp Val Glu Ala Ala Gly Ser Phe Lys Gly Ala
 65                  70                  75                  80
Pro Leu Pro Ala Ser Ser Tyr Asp Val Phe Val Ser Asn Ala Gly Ile
            85                  90                  95
Cys Gln Phe Ser Pro Ile Ala Glu His Ala Asp Ala Asp Trp Gln Asn
            100                 105                 110
Met Leu Thr Val Asn Leu Thr Ala Pro Ile Ala Leu Thr Lys Ala Val
            115                 120                 125
Val Lys Ala Ile Ser Asp Lys Pro Arg Gln Thr Pro Ala His Ile Ile
 130                 135                 140
Phe Ile Ser Ser Gly Leu Ser Lys Arg Gly His Pro Met Val Gly Val
 145                150                 155                 160
Tyr Ser Ala Ser Lys Ala Gly Ile Asp Gly Phe Met Arg Ser Leu Ala
            165                 170                 175
Arg Glu Leu Gly Pro Lys Gly Ile Asn Val Asn Cys Val Ser Pro Gly
            180                 185                 190
Val Thr Arg Thr Ser Met Ala Glu Gly Ile Asp Pro Ser Met Phe Asp
            195                 200                 205
Leu Cys Ile Asn Gly Trp Ile Glu Val Asp Ala Ile Ala Asp Ala Val
 210                 215                 220
Thr Tyr Val Val Lys Ser Lys Asn Val Thr Gly Thr Thr Val Ser Val
 225                 230                 235                 240
Asp Asn Gly Phe Cys Ala
            245
```